US008101778B2

(12) United States Patent
Hangeland et al.

(10) Patent No.: US 8,101,778 B2
(45) Date of Patent: Jan. 24, 2012

(54) FIVE-MEMBERED HETEROCYCLES USEFUL AS SERINE PROTEASE INHIBITORS

(75) Inventors: Jon J. Hangeland, Morrisville, PA (US); Mimi L. Quan, Yardley, PA (US); Joanne M. Smallheer, Yardley, PA (US); Gregory S. Bisacchi, Newtown Highlands, MA (US); James R. Corte, Lawrenceville, NJ (US); Todd J. Friends, Bordentown, NJ (US); Zhong Sun, Hopewell, NJ (US); Karen A. Rossi, Newtown, PA (US); Cullen L. Cavallaro, Robbinsville, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 447 days.

(21) Appl. No.: 12/209,235

(22) Filed: Sep. 12, 2008

(65) Prior Publication Data
US 2009/0036438 A1 Feb. 5, 2009

Related U.S. Application Data

(62) Division of application No. 11/151,667, filed on Jun. 13, 2005, now Pat. No. 7,453,002.

(60) Provisional application No. 60/579,638, filed on Jun. 15, 2004, provisional application No. 60/684,127, filed on May 24, 2005.

(51) Int. Cl.
A61K 31/4178 (2006.01)
C07D 403/04 (2006.01)
(52) U.S. Cl. .................. 548/338.1; 514/397
(58) Field of Classification Search .............. 548/338.1
See application file for complete search history.

(56) References Cited

U.S. PATENT DOCUMENTS

| 6,069,162 | A | 5/2000 | Itoh et al. |
| 6,518,292 | B1 | 2/2003 | Robl et al. |
| 6,828,309 | B2 | 12/2004 | Striker |
| 7,129,264 | B2 | 10/2006 | Smallheer et al. |
| 7,138,412 | B2 | 11/2006 | Quan et al. |
| 7,429,604 | B2 | 9/2008 | Corte et al. |
| 7,459,564 | B2 | 12/2008 | Corte et al. |
| 2003/0232875 | A1 | 12/2003 | Bartlett et al. |
| 2004/0186151 | A1 | 9/2004 | Mjalli et al. |

FOREIGN PATENT DOCUMENTS

| JP | 2004-323516 A | 11/2004 |
| WO | WO96/16080 | 5/1996 |
| WO | WO97/45425 | 12/1997 |
| WO | WO98/27108 | 6/1998 |
| WO | WO99/64401 | 12/1999 |
| WO | WO00/00477 | 1/2000 |
| WO | WO00/25768 | 5/2000 |
| WO | WO01/26656 | 4/2001 |
| WO | WO01/27079 | 4/2001 |
| WO | WO01/32615 | 5/2001 |
| WO | WO01/51487 | 7/2001 |
| WO | WO01/62756 | 8/2001 |
| WO | WO01/66539 | 9/2001 |
| WO | WO02/10140 | 2/2002 |
| WO | WO02/069965 | 9/2002 |
| WO | WO01/32628 | 1/2003 |
| WO | WO03/000180 | 1/2003 |
| WO | WO03/035615 | 5/2003 |
| WO | WO03/076432 | 9/2003 |
| WO | WO2004/011445 | 2/2004 |
| WO | WO 2004/017908 A2 | 3/2004 |
| WO | WO2004/085439 | 3/2004 |
| WO | WO2004/056784 | 7/2004 |
| WO | WO2004/071448 | 8/2004 |
| WO | WO2004/101555 | 11/2004 |
| WO | WO2005/035510 | 4/2005 |

(Continued)

OTHER PUBLICATIONS

Ridker, Paul M, et al; "Long-Term, Low-Intensity Warfarin Therapy for the Prevention of Recurrent Venous Thromboembolism", N Engl J Med 2003; 348:1425-34.
Becker, Richard C, "Anticoagulation and the Heart", Journal of Thrombosis and Thrombolysis 12(1), 41-52, 2001.
Albers, Gregory W, "Antithrombotic Therapy for Prevention and Treatment of Ischemic Stroke", Journal of Thrombosis and Thrombolysis 12(1), 19-22, 2001.
Turpie, Alexander G.G., "Optimizing Prophylaxis of Venous Thromboembolism" Seminars in Thrombosis and Hemostasis, vol. 28, Supplement 2, 2002, pp. 25-32.

(Continued)

Primary Examiner — Laura L. Stockton
(74) Attorney, Agent, or Firm — Hong Liu

(57) ABSTRACT

The present invention provides a method for treating a thrombotic or an inflammatory disorder administering to a patient in need thereof a therapeutically effective amount of at least one compound of Formula (I) or Formula (V):

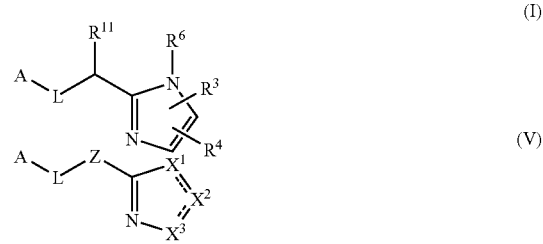

or a stereoisomer or pharmaceutically acceptable salt or solvate form thereof, wherein the variables A, L, Z, $R^3$, $R^4$, $R^6$, $R^{11}$, $X^1$, $X^2$, and $X^3$ are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors. This invention also provides compounds within the scope of Formula I and relates to pharmaceutical compositions comprising these compounds.

2 Claims, No Drawings

FOREIGN PATENT DOCUMENTS

| WO | WO2005/056550 | 6/2005 |
|----|---------------|--------|
| WO | WO2005/061496 | 7/2005 |
| WO | WO2005/082895 | 9/2005 |

OTHER PUBLICATIONS

Anderson Jr., Frederick A. et al., Prolonged Prophylaxis in Orthopedic Surgery: Insights from the United States, *Seminars in Thrombosis and Hemostasis*, vol. 28, Supplement 3, 2002, pp. 43-46.

Heit, John A., "Venous Thromboembolism Epidemiology: Implications for Prevention and Management", *Seminars in Thrombosis and Hemostasis*, vol. 28, Supplement 2, 2002, pp. 3-13.

Baettig, U. et al., "The design and synthesis of thrombin inhibitors: analogues of MD805 containing non-polar surrogates for arginine at the P1 position", Bioorganic & Med. Chem. Letters, vol. 10(14), (2000).

Wazir et al., "synthesis and anti-inflammatory activity of some substituted tetrazoles", Journal of the Indian Chemical Society, vol. 68(5), pp. 305-306 (1991).

Sheehan SM et al., "A four component coupling strategy for the synthesis of D-phenylglycinamide-derived non-covalent factor XA inhibitors", Bioorganic & Med. Chem. Letters, vol. 13(14), pp. 2255-2259 (2003).

Stanfield, M.K. et al., "Synthesis of phenistidine and derivatives", Journal of Organic Chemistry, vol. 30(5), pp. 1548-1550 (1965).

Crawford, et al., "The Preparation of Benziminazoles from α-Benzamido-acids and Peptides", J. Chem. Society, pp. 673-676 (1956).

Kilburn et al., "Solid-phase synthesis of substituted 2-aminomethylbenzimidazoles", Tetrahedron Letters, vol. 41, pp. 5419-5421 (2000).

Pantano et al., "Structural Versatility of Peptides from $C^{\alpha,\alpha}$-Disubstituted Glycines. Synthesis, Characterization, and Solution Conformational Analysis of Homopeptides from $C^{\alpha}$-Methyl-$C^{\alpha}$-benzylglycine, [(α-Me)Phe]$_n^1$", *Macromolecules*, vol. 26, pp. 1980-1984, 1993.

Meanwell, et al., "Nonprostanoid Prostacyclin Mimetics. 5. Structure-Activity Relationships Associated with [3-[4-(4,5-Diphenyl-2-oxazolyl)-5-oxazolyl]phenoxy]acetic Acid", *J. Med. Chem.*, vol. 36, pp. 3884-3903, 1993.

Galiani, D., "Activation of Factor IX by Factor XIa", *Trends in Cardiovascular Medicine*, vol. 10, No. 5, 2000, pp. 198-204.

Boma, B.N. et al., "Thrombin-Activatable Fibrinolysis Inhibitor (TAFI, Plasma Procarboxypeptidase B, Procarboxypeptidase R, Procarboxypeptidase U)", *Thrombosis. Research*, 2001, 101, pp. 329-354.

Gailani, D., "Gene Targeting in Hemostasis. Factor XI", *Frontiers in Bioscience*, 2001, 6, pp. d201-d207.

Gailani, D., et al., "A murine model of factor XI deficiency", *Blood Coagulation and Fibrinolysis*, 1997, vol. 8, pp. 134-144.

Minnema, M.C., et al., "Activation of Clotting Factors XI and IX in Patients with Acute Myocardial Infarction", *Arterioscler. Thromb. Vasc. Biol.*, 2000, 20, pp. 2489-2493.

Murakami, T., et al., "Evaluation of Factor XIa-$\alpha_1$—Antitrypsin in Plasma, a Contact Phase-Activated Coagulation Factor-Inhibitor Complex, in Patients With Coronary Artery Disease", *Arterioscler. Thromb. Vasc. Biol.*, 1995, 15, pp. 1107-1113.

Meijers, J.C.M., et al., "High Levels of Coagulation Factor XI as a Risk Factor for Venous Thrombosis", *N. Engl. J. Med.*, 2000, vol. 342, No. 10, pp. 696-701.

Walsh, P.N., "Platelets and Factor XI Bypass the Contact System of Blood Coagulation", *Thromb. Haemostasis*. 82(2), pp. 234-242, 1999.

Colman, R. Contact Activation Pathway: Inflammatory, Fibrinolytic, Anticoagulant, Antiadhesive, and Antiangiogenic Activities, *Hemostasis and thrombosis: basic principles and clinical practice*, Lippincott Williams & Wilkins, 2001, pp. 103-122.

Schmaier, A.H., "Contact Activation", *Thrombosis and Hemorrhage, Williams & Wilkins*, 1998, pp. 105-128.

CAS Registry No. 338410-51-8, Sep. 16, 2005.
CAS Registry No. 554407-78-2, Sep. 16, 2005.
CAS Registry No. 338410-59-6, Sep. 16, 2005.
CAS Registry No. 430452-18-9, Sep. 16, 2005.
CAS Registry No. 338410-55-2, Sep. 16, 2005.
CAS Registry No. 338410-76-7, Sep. 16, 2005.
CAS Registry No. 338410-56-3, Sep. 16, 2005.
CAS Registry No. 338410-71-2, Sep. 16, 2005.

Souillac, et al., Characterization of Delivery Systems, Differential Scanning Calorimetry in Encyclopedia of Controlled Drug Delivery, 1999, John Wiley & Sons, pp. 212-227.

Vippagunta et al., Advanced Drug Delivery Reviews, vol. 48, pp. 3-26 (2001).

Japanese Office Action—Mar. 2011 (English translation only).

FIVE-MEMBERED HETEROCYCLES USEFUL AS SERINE PROTEASE INHIBITORS

CROSS-REFERENCE TO RELATED APPLICATIONS

This application is a divisional of U.S. application Ser. No. 11/151,667, filed Jun. 13, 2005, now allowed, which claims the priority benefit of U.S. Provisional Application No. 60/579,638, filed Jun. 15, 2004 and the priority benefit of U.S. Provisional Application No. 60/684,127, filed May 24, 2005, all of which are expressly incorporated fully herein by reference.

FIELD OF THE INVENTION

The present invention provides a method for treating a thrombotic or an inflammatory disorder administering to a patient in need thereof a therapeutically effective amount of at least one compound of Formula (I) or Formula (V):

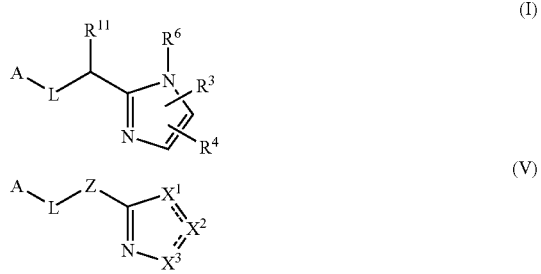

or a stereoisomer or pharmaceutically acceptable salt or solvate form thereof, wherein the variables A, L, Z, $R^3$, $R^4$, $R^6$, $R^{11}$, $X^1$, $X^2$, and $X^3$ are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors or dual inhibitors of fXIa and plasma kallikrein. This invention also relates to pharmaceutical compositions comprising these compounds and methods of using the same.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. Thromb. Haemostasis. 1999, 82, 234-242.) Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. Contact Activation Pathway, pages 103-122 in Hemostasis and Thrombosis, Lippincott Williams & Wilkins 2001; Schmaier A. H. Contact Activation, pages 105-128 in Thrombosis and Hemorrhage, 1998).

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D. Trends Cardiovasc. Med. 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. Thromb. Res. 2001, 101, 329-354.) Thus, inhibitors of factor XIa are expected to be anticoagulant and profibrinolytic.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g. oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailiani, D. *Frontiers in Bioscience* 2001, 6, 201-207; Gailiani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90$^{th}$ percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 µg/mL. The gene structure is similar to that of factor XI, overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in U.S. Patent Application Publication US20040235847A1 and US Patent Application Publication US20040220206A1.

Moreover, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

The present invention provides novel five-membered heterocycle derivatives, and analogues thereof, which are useful as selective inhibitors of serine protease enzymes, especially factor XIa and/or plasma kallikrein, or stereoisomers or pharmaceutically acceptable salts, solvates, or prodrugs thereof.

The present invention also provides processes and intermediates for making the compounds of the present invention or a stereoisomer or a pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a pharmaceutically acceptable salt, solvate or prodrug form thereof.

The present invention also provides a method for modulation of the coagulation cascade and/or the contact activation system comprising administering to a host in need of such treatment a therapeutically effective amount of at least one of the compounds of the present invention or a pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a pharmaceutically acceptable salt, solvate, or prodrug form thereof.

The present invention also provides a method for treating inflammatory diseases disorders comprising administering to a host in need of such treatment a therapeutically effective amount of at least one of the compounds of the present invention or a pharmaceutically acceptable salt, solvate, or prodrug form thereof.

The present invention also provides novel five-membered heterocycle derivatives, and analogues thereof, for use in therapy.

The present invention also provides the use of five-membered heterocycle derivatives, and analogues thereof, for the manufacture of a medicament for the treatment of a thromboembolic disorder.

The present invention also provides the use of five-membered heterocycle derivatives, and analogues thereof, for the manufacture of a medicament for the treatment of an inflammatory disorder.

These and other embodiments, which will become apparent during the following detailed description, have been achieved by the inventors' discovery that the presently claimed novel compounds of the present invention, or pharmaceutically acceptable salt or prodrug forms thereof, are effective factor XIa inhibitors and/or plasma kallikrein inhibitors.

DETAILED DESCRIPTION OF THE INVENTION

In a first aspect, the present invention includes, inter alia, a compound of Formula (I):

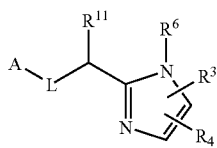

or its stereoisomers, tautomers, pharmaceutically acceptable salts, solvates, or prodrugs thereof, wherein:

A is $C_{3-10}$ carbocycle substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted with 0-1 $R^1$ and 0-3 $R^2$; provided when A is a heterocycle containing one or more nitrogen atoms, A is not attached to L via any of the nitrogen atoms on the A ring;

L is —C(O)$NR^{10}$—, —$NR^{10}$C(O)—, —$CH_2$C(O)$NR^{10}$—, —$CH_2NR^{10}$C(O)—, —C(O)$NR^{10}CH_2$—, —$NR^{10}$C(O)$CH_2$—, —$S(O)_2NR^{10}$—, —$NR^{10}S(O)_2$—, —$CH_2S(O)_2NR^{10}$—, —$CH_2NR^{10}S(O)_2$—, —$S(O)_2NR^{10}CH_2$—, —$NR^{10}S(O)_2CH_2$—, —$CH_2CH_2$—, —$CH_2NR^7$—, —$NR^7CH_2$—, —$CH_2CH_2NR^7$—, —$NR^7CH_2CH_2$—, —$CH_2NR^7CH_2$—, —$CH_2O$—, —$OCH_2$—, —$CH_2S(O)_p$—, —$S(O)_pCH_2$—, —$CH_2CH_2O$—, —$OCH_2CH_2$—, —$CH_2OCH_2$—, —$CH_2CH_2S(O)_p$—, —$S(O)_pCH_2CH_2$—, —$CH_2S(O)_pCH_2$—, —$CH_2C(O)$, —$CH_2C(O)CH_2$—, —$CH_2CH_2C(O)$—, —$C(O)CH_2CH_2$—, or —$C(O)CH_2$—;

$R^1$ is, independently at each occurrence, —$NH_2$, —NH($C_1$-$C_3$ alkyl), —N($C_1$-$C_3$ alkyl)$_2$, —C(=NH)$NH_2$, —C(O)$NR^8R^9$, —$S(O)_pNR^8R^9$, —(CH$_2$)$_r$$NR^7R^8$, —(CH$_2$)$_r$$NR^7CO_2R^a$, —$CH_2NH_2$, —$CH_2NH(C_{1-3}$ alkyl), —$CH_2N(C_{1-3}$ alkyl)$_2$, —$CH_2CH_2NH_2$, —$CH_2CH_2NH(C_1$-$C_3$ alkyl), —$CH_2CH_2N(C_{1-3}$ alkyl)$_2$, —CH($C_{1-4}$ alkyl)$NH_2$, —C($C_{1-4}$ alkyl)$_2NH_2$, —C(=$NR^{8a}$)$NR^7R^8$, —NHC(=$NR^{8a}$)$NR^7R^8$, =$NR^8$, —$NR^8CR^8$(=$NR^{8a}$), F, Cl, Br, I, OCF$_3$, CF$_3$, —(CH$_2$)$_r$OR$^a$, —(CH$_2$)$_r$SR$^a$, CN, 1-NH$_2$-1-cyclopropyl, or $C_{1-6}$ alkyl substituted with 0-1 $R^{1a}$;

$R^{1a}$ is H, —C(=$NR^{8a}$)$NR^7R^8$, —NHC(=$NR^{8a}$)$NR^7R^8$, —$NR^8$CH(=$NR^{8a}$), —$NR^7R^8$, —C(O)$NR^8R^9$, F, OCF$_3$, CF$_3$, OR$^a$, SR$^a$, CN, —$NR^9SO_2NR^8R^9$, —$NR^8SO_2R^c$, —$S(O)_p$—$C_{1-4}$ alkyl, —$S(O)_p$-phenyl, or —(CF$_2$)$_r$CF$_3$;

$R^2$ is, independently at each occurrence, H, =O, F, Cl, Br, I, OCF$_3$, CF$_3$, CHF$_2$, CN, NO$_2$, OR$^a$, SR$^a$, —C(O)R$^a$, —C(O)OR$^a$, —OC(O)R$^a$, —$NR^7R^8$, —C(O)$NR^7R^8$, —$NR^7C(O)R^b$, —$S(O)_2NR^8R^9$, —$NR^8S(O)_2R^c$, —$S(O)R^c$, —$S(O)_2R^c$, $C_{1-6}$ alkyl substituted with 0-2 $R^{2a}$, $C_{2-6}$ alkenyl substituted with 0-2 $R^{2a}$, $C_{2-6}$ alkynyl substituted with 0-2 $R^{2a}$, —(CH$_2$)$_r$—$C_{3-10}$ carbocycle substituted with 0-3 $R^{2b}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{2b}$;

$R^{2a}$ is, independently at each occurrence, H, F, Cl, Br, I, =O, =$NR^8$, CN, OCF$_3$, CF$_3$, OR$^a$, SR$^a$, —$NR^7R^8$, —C(O)$NR^8R^9$, —$NR^7C(O)R^b$, —$S(O)_pNR^8R^9$, —$NR^8SO_2R^c$, —$S(O)R^c$, or —$S(O)_2R^c$;

$R^{2b}$ is, independently at each occurrence, H, F, Cl, Br, I, =O, =$NR^8$, CN, NO$_2$, OR$^a$, SR$^a$, —C(O)R$^a$, —C(O)OR$^a$, —OC(O)R$^a$, —$NR^7R^8$, —C(O)$NR^7R^8$, —$NR^7C(O)R^b$, —$S(O)_2NR^8R^9$, —$S(O)_2R^c$, —$NR^8SO_2NR^8R^9$, —$NR^8SO_2R^c$, —(CF$_2$)$_r$CF$_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkoxy-;

alternately, when $R^1$ and $R^2$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^{2b}$;

$R^3$ is —(CH$_2$)$_r$C(O)$NR^8R^9$, —(CH$_2$)$_r$C(O)$NR^8$(CH$_2$)$_s$ CO$_2R^{3b}$, —(CH$_2$)$_r$CO$_2R^{3b}$, —(CH$_2$)$_r$—$C_{3-10}$ carbocycle substituted with 0-3 $R^{3a}$ and 0-1 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, OCF$_3$, CF$_3$, NO$_2$, CN, —(CH$_2$)$_r$OR$^{3b}$, —(CH$_2$)$_r$SR$^{3b}$, —(CH$_2$)$_r$$NR^7R^8$, C(=$NR^{8a}$)$NR^8R^9$, —NHC(=$NR^{8a}$)$NR^7R^8$, —$NR^8CR^8$(=$NR^{8a}$), —(CH$_2$)$_r$$NR^8C(O)R^{3b}$, =$NR^8$, —(CH$_2$)$_r$$NR^8C(O)R^{3b}$, —(CH$_2$)$_r$$NR^8C(O)_2R^{3b}$, —(CH$_2$)$_r$$S(O)_pNR^8R^9$, —(CH$_2$)$_r$$NR^8S(O)_pR^{3c}$, —$S(O)_pR^{3c}$, —$S(O)_pR^{3c}$, —C(O)—$C_1$-$C_4$ alkyl, —(CH$_2$)$_r$CO$_2R^{3b}$, —(CH$_2$)$_r$C(O)$NR^8R^9$, —(CH$_2$)$_r$OC(O)$NR^8R^9$, —NHCOCF$_3$, —NHSO$_2$CF$_3$, —SO$_2$$NHR^{3b}$, —SO$_2$$NHCOR^{3c}$, —SO$_2$$NHCO_2R^{3c}$, —CONHSO$_2R^{3c}$, —NHSO$_2R^{3c}$, —CONHOR$^{3b}$, $C_{1-4}$ haloalkyl, $C_{1-4}$ haloalkoxy-, $C_{1-6}$ alkyl substituted by $R^{3d}$, $C_{2-6}$ alkenyl substituted by $R^{3d}$, $C_{2-6}$ alkynyl substituted by $R^{3d}$, $C_{3-6}$ cycloalkyl substituted by 0-1 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are located on adjacent atoms, they can be taken together with the atoms to which they are attached to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, —(CH$_2$)$_r$OR$^a$, F, Cl, Br, CN, NO$_2$, —(CH$_2$)$_r$$NR^7R^8$, —C(O)R$^a$, —C(O)OR$^a$, —OC(O)R$^a$, —$NR^7C(O)R^b$, —C(O)$NR^8R^9$, —SO$_2NR^8R^9$, —$NR^8SO_2NR^8R^9$, —$NR^8SO_2R^c$, —$S(O)_pR^c$, —(CF$_2$)$_r$CF$_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and $S(O)_p$, wherein said heterocycle is substituted with 0-3 $R^d$;

$R^4$ is H, F, Cl, Br, I, OCF$_3$, CF$_3$, OR$^a$, SR$^a$, CN, NO$_2$, —C(O)R$^a$, —C(O)OR$^a$, —OC(O)R$^a$, —$NR^7R^8$, —C(O)$NR^8R^9$, —$NR^7C(O)R^b$, —$S(O)_pNR^8R^9$, —$NR^8S(O)_pR^c$, —$S(O)R^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —(CH$_2$)$_r$—$C_{3-10}$ carbocycle substituted with 0-3 $R^{4b}$, or —$(CH_2)_r$-5- to 10-membered heterocycle comprising carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-6}$ alkyl, $OR^a$, $SR^a$, $CF_3$, CN, $NO_2$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, —$NR^8S(O)_2R^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, $CF_3$, —$SO_2R^c$, —$NR^7R^8$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkoxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is H;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, or —$(CH_2)_r$-phenyl, or —$(CH_2)_r$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{8a}$ is, independently at each occurrence, H, OH, $C_{1-6}$ alkyl, $C_{1-4}$ alkoxy, $(C_{6-10}$ aryl)-$C_{1-4}$ alkoxy, —$(CH_2)_n$-phenyl, —$(CH_2)_n$-(5-10 membered heteroaryl), —$C(O)R^c$, —$C(O)_2R^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said phenyl, aryl, and heteroaryl is optionally substituted with 0-2 $R^f$;

$R^9$ is, independently at each occurrence, H, $C_{1-6}$ alkyl, or —$(CH_2)_r$-phenyl; wherein said alkyl and phenyl are optionally substituted with 0-2 $R^f$;

$R^{9a}$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-3 $R^{10a}$, $C_{2-6}$ alkenyl substituted with 0-3 $R^{10a}$, $C_{2-6}$ alkynyl substituted with 0-3 $R^{10a}$, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)OR^a$, —$NR^7R^8$, —$C(O)NR^7R^8$, —$NR^7C(O)R^b$, —$S(O)_pNR^8R^9$, —$NR^8SO_2R^c$—, —$S(O)R^c$, or —$S(O)_2R^c$;

$R^{11}$ is $C_{1-4}$ haloalkyl, —$(CH_2)_rC(O)NR^8R^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CR^{14}R^{15})_r$—$C_{3-10}$ carbocycle substituted with 0-3 $R^{11b}$, or —$(CR^{14}R^{15})_r$-5- to 10-membered heterocycle comprising carbon atoms and 1-4 heteroatoms selected from N, O, and $S(O)_p$, wherein said heterocycle is substituted with 0-3 $R^{11b}$;

$R^{11a}$ is, independently at each occurrence, H, =O, $C_{1-4}$ alkyl, $OR^a$, $CF_3$, $SR^a$, F, CN, $NO_2$, —$NR^7R^8$, —$C(O)NR^7R^8$, —$NR^7C(O)R^b$, —$S(O)_pNR^8R^9$, —$NR^8S(O)_pR^c$, —$C(O)R^a$, —$C(O)OR^a$, —$S(O)_pR^c$, $C_{3-6}$ cycloalkyl, $C_{1-4}$ haloalkyl, $C_{1-4}$ haloalkoxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$C(O)R^a$, —$C(O)OR^a$, —$SOR^c$, —$SO_2R^c$, —$NR^7R^8$, —$C(O)NR^7R^8$, —$NR^7C(O)R^b$, —$NR^8C(O)_2R^c$, —$S(O)_pNR^8R^9$, —$NR^8S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkoxy-, —$(CH_2)_r$—$C_{3-10}$ carbocycle substituted with 0-3 $R^d$, or —$(CH_2)_r$-5-10 membered heterocycle comprising: carbon atoms and 1-4 heteroatoms selected from N, O, and $S(O)_p$, wherein said heterocycle is substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{14}$ and $R^{15}$ are, independently at each occurrence, H, F, or $C_{1-4}$ alkyl;

alternatively, $R^{14}$ combines with $R^{15}$ to form =O;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10 membered heterocycle comprising: carbon atoms and 1-4 heteroatoms selected from N, O, and $S(O)_p$; wherein said cycloalkyl, aryl and heterocycle groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^d$, or —$(CH_2)_r$-5-10 membered heterocycle comprising: carbon atoms and 1-4 heteroatoms selected from N, O, and $S(O)_p$, wherein said heterocycle is substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, $(C_{6-10}$ aryl)-$C_{1-4}$ alkyl, or (5- to 10-membered heteroaryl)-$C_{1-4}$ alkyl, wherein said aryl and heteroaryl groups are optionally substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^8R^9$, —$C(O)R^a$, —$C(O)OR^a$, —$OC(O)R^a$, —$NR^8C(O)R^a$, —$C(O)NR^7R^8$, —$SO_2NR^8R^9$, $NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_r$—$OR^g$, F, Cl, Br, I, CN, $NO_2$, —$NR^{9a}R^{9a}$, —$C(O)R^g$, —C(O)OR$^g$, —NR$^{9a}$C(O)R$^g$, —C(O)NR$^{9a}$R$^{9a}$, —SO$_2$NR$^{9a}$R$^{9a}$, —NR$^{9a}$SO$_2$NR$^{9a}$R$^{9a}$, —NR$^{9a}$SO$_2$—C$_{1-4}$ alkyl, —NR$^{9a}$SO$_2$CF$_3$, —NR$^{9a}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2;
r, at each occurrence, is selected from 0, 1, 2, 3, and 4; and
s, at each occurrence, is selected from 1, 2, 3, and 4;
provided that:
(a). when L is —C(O)NH—, R$^3$ is not 2,4-dichlorophenyl, 4-nitrophenyl or pentafluorophenyl;
(b). when L is —C(O)NH—, R$^{11}$ is not —CH$_2$-(3-indolyl), —(CH$_2$)$_4$NHCO$_2$(t-Bu) or —(CH$_2$)$_4$NH$_2$.

In a second aspect, the present invention includes compounds of Formula (I), within the scope of the first aspect wherein:

L is —C(O)NR$^{10}$—, —NR$^{10}$C(O)—, —CH$_2$CONR$^{10}$—, or —NR$^{10}$COCH$_2$—;

R$^3$ is —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$-phenyl substituted with 0-3 R$^{3a}$ and 0-1 R$^{3d}$, —(CH$_2$)$_r$-naphthyl substituted with 0-3 R$^{3a}$ and 0-1 R$^{3d}$, —(CH$_2$)$_r$-indanyl substituted with 0-3 R$^{3a}$ and 0-1 R$^{3d}$, or —(CH$_2$)$_r$-5-10 membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^4$ is H, F, Cl, Br, I, OCF$_3$, CF$_3$, OR$^a$, SR$^a$, CN, NO$_2$, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

R$^{10}$ is, independently at each occurrence, H, C$_{1-6}$ alkyl substituted with 0-2 R$^{10a}$, —(CH$_2$)$_r$-phenyl substituted with 0-2 R$^d$, or —(CH$_2$)$_r$-5-10 membered heterocycle comprising carbon atoms and 1-4 heteroatoms selected from N, O, and S(O)$_p$, wherein said heterocycle is substituted with 0-2 R$^d$; and R$^{11}$ is C$_{1-4}$ haloalkyl, —(CH$_2$)$_r$—CONR$^8$R$^9$, C$_{1-6}$ alkyl substituted with 0-2 R$^{11a}$, C$_{2-6}$ alkenyl substituted with 0-2 R$^{11a}$, C$_{2-6}$ alkynyl substituted with 0-2 R$^{11a}$, —(CH$_2$)$_r$—C$_{3-10}$ carbocycle substituted with 0-3 R$^{11b}$, or —(CH$_2$)$_r$-5- to 10-membered heterocycle comprising carbon atoms and 1-4 heteroatoms selected from N, O, and S(O)$_p$, wherein said heterocycle is substituted with 0-3 R$^{11b}$.

In a third aspect, the present invention includes compounds of Formula (I), within the scope of the first aspect wherein:

R$^1$ is, independently at each occurrence, F, Cl, Me, Et, —NH$_2$, —C(=NH)NH$_2$, —C(O)NH$_2$, —CH$_2$NH$_2$, —CH$_2$CH$_2$NH$_2$, —CH$_2$NHCO$_2$Bn, —CH$_2$NHCO$_2$(t-Bu), —CH(Me)NH$_2$, —C(Me)$_2$NH$_2$, —NHEt, —NHCO$_2$(t-Bu), —NHCO$_2$Bn, —SO$_2$NH$_2$, OR$^a$, or —CH$_2$R$^{1a}$;

R$^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, —(CH$_2$)$_r$-phenyl substituted with 0-2 R$^{3a}$ and 0-1 R$^{3d}$, naphthyl substituted with 0-2 R$^{3a}$ and 0-1 R$^{3d}$, indanyl substituted with 0-2 R$^{3a}$ and 0-1 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-2 R$^{3a}$ and 0-1 R$^{3d}$;

R$^4$ is H, F, Cl, Br, CF$_3$, OMe, NH$_2$, CO$_2$H, CO$_2$Me, CO$_2$Et, —CONR$^8$R$^9$, C$_{1-6}$ alkyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

R$^{10}$ is, independently at each occurrence, H, Me, benzyl, phenethyl, —CH$_2$CH$_2$CO$_2$H, —CH$_2$CH$_2$CO$_2$Me, —CH$_2$CH$_2$CO$_2$Et, —CH$_2$CH$_2$CONH$_2$, or —CH$_2$CH$_2$CONHCH$_2$CH$_2$Ph; and R$^{11}$ is C$_{1-6}$ alkyl, —CH$_2$CONR$^8$R$^9$, —CH$_2$CH$_2$CONR$^8$R$^9$, —CH$_2$OBn, —CH$_2$SBn, —(CH$_2$)$_r$—C$_{3-7}$ cycloalkyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5-10 membered heterocycle comprising carbon atoms and 1-4 heteroatoms selected from N, O, and S(O)$_p$, wherein said heterocycle is substituted with 0-2 R$^{11b}$.

In a fourth aspect, the present invention includes a compound of Formula (II):

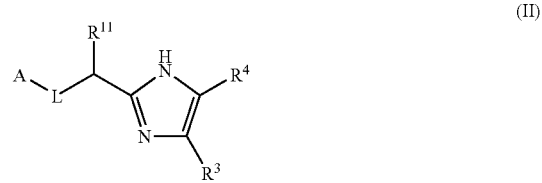

(II)

or its stereoisomers, tautomers, pharmaceutically acceptable salts, solvates, or prodrugs thereof, within the scope of the first aspect wherein:

A is substituted with 0-1 R$^1$ and 0-2 R$^2$ and selected from: C$_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

L is —C(O)NH— or —NHC(O)—;

R$^1$ is, independently at each occurrence, F, Cl, Me, Et, —NH$_2$, —C(=NH)NH$_2$, —C(O)NH$_2$, —CH$_2$NH$_2$, —CH$_2$NHCO$_2$Bn, —CH$_2$NHCO$_2$(t-Bu), —CH(Me)NH$_2$, —CMe$_2$NH$_2$, —NHEt, —NHCO$_2$(t-Bu), —NHCO$_2$Bn, —SO$_2$NH$_2$, OR$^a$, or —CH$_2$R$^{1a}$;

R$^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, phenyl substituted with 0-2 R$^{3a}$, naphthyl substituted with 0-2 R$^{3a}$, indanyl substituted with 0-2 R$^{3a}$, or a 5- to 10-membered heterocycle comprising: carbon atoms and 1-2 heteroatoms selected from N, O, and S(O)$_p$, wherein said heterocycle is substituted with 0-2 R$^{3a}$;

R$^4$ is H, F, Cl, Br, OMe, NH$_2$, CF$_3$, CO$_2$H, CO$_2$Me, CO$_2$Et, C$_{1-6}$ alkyl substituted with 0-2 R$^{4a}$, phenyl substituted with 0-2 R$^{4b}$, or 5-10 membered heterocycle comprising: carbon atoms and 1-4 heteroatoms selected from N, O, and S(O)$_p$, wherein said heterocycle is substituted with 0-2 R$^{4b}$;

R$^{11}$ is C$_{1-6}$ alkyl, —CH$_2$CONR$^8$R$^9$, —CH$_2$CH$_2$CONR$^8$R$^9$, —CH$_2$OBn, —CH$_2$SBn, —(CH$_2$)$_r$—C$_{3-7}$ cycloalkyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5- to 10-membered heteroaryl substituted with 0-2 R$^{11b}$ and selected from thiazolyl, oxazolyl, triazolyl, tetrazolyl, imidazolyl, pyridyl, pyrimidinyl, pyrazinyl, pyridazinyl, indolyl, isoindolyl, indolinyl, isoindolinyl, benzimidazolyl, benzothiazolyl, quinolinyl, isoquinolinyl, tetrahydroquinolinyl, and tetrahydroisoquinolinyl; and R$^{11b}$ is, independently at each occurrence, H, F, Cl, Br, CF$_3$, OMe, OEt, O(i-Pr), OCF$_3$, OCHF$_2$, CN, OPh, OBn, NO₂, —NH₂, —C(O)Rᵃ, —C(O)ORᵃ, —C(O)NR⁷R⁸, —NR⁷C(O)Rᵇ, —NR⁸C(O)₂Rᶜ, —S(O)ₚNR⁸R⁹, —NR⁸S(O)ₚRᶜ, —SO₂Rᶜ, C₁-C₄-alkyl, Ph, or Bn;

alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)ₚ and substituted with 0-2 R$^g$.

In a fifth aspect, the present invention includes a compound of Formula (II):

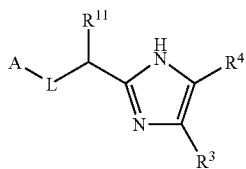

or its stereoisomers, tautomers, pharmaceutically acceptable salts, solvates, or prodrugs thereof, within the scope of the first aspect wherein:

A is 4-CH₂NH₂-cyclohexyl, 4-CO₂Me-cyclohexyl, 4-CONH₂-cyclohexyl, 4-NHCO₂(t-Bu)-cyclohexyl, 4-NHCO₂Bn-cyclohexyl, phenyl, 4-Me-phenyl, 3-OMe-phenyl, 4-CH₂NH₂-phenyl, 3-CONH₂-phenyl, 4-CONH₂-phenyl, 3-amidino-phenyl, 4-amidino-phenyl, 2-F-4-Me-phenyl, 2-Bn-4-CH₂NH₂-phenyl, 4-SO₂NH₂-phenyl, 2-F-5-OMe-phenyl, 2-F-4-Cl-phenyl, 2-F-4-CH₂NH₂-phenyl, 2-F-4-CONH₂-phenyl, 2-Cl-4-CONH₂-phenyl, 2-Et-4-CH₂NH₂-phenyl, 2-NHEt-4-CH₂NH₂-phenyl, 2-OMe-4-CONH₂-phenyl, 3-OMe-4-CONH₂-phenyl, 1,2,3,4-tetrahydronaphth-2-yl, 3-Cl-thien-2-yl, indol-5-yl, indol-6-yl, indazol-6-yl, 3-NH₂-indazol-6-yl, 3-NH₂-indazol-5-yl, 1-Me-3-NH₂-indazol-6-yl, 3-NH₂-benzisoxazol-6-yl, 1,2,3,4-tetrahydroisoquinolin-6-yl, 1,2,3,4-tetrahydroisoquinolin-3-yl, 2-COPh-1,2,3,4-tetrahydroisoquinolin-3-yl, 2-CO₂Bn-1,2,3,4-tetrahydroisoquinolin-3-yl, 1,2,3,4-tetrahydroisoquinolin-1-on-6-yl, 2H-isoquinolin-1-on-6-yl, isoquinolin-6-yl, 1-NH₂-isoquinolin-6-yl, 1-NH₂-3-Me-isoquinolin-6-yl, 1-NH₂-5,6,7,8-tetrahydroisoquinolin-6-yl, 4-NH₂-quinazolin-7-yl, 3H-quinazolin-4-on-7-yl,

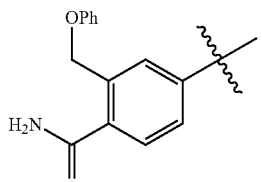

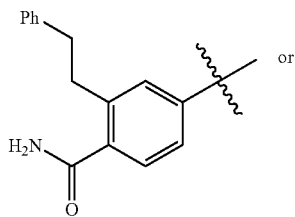

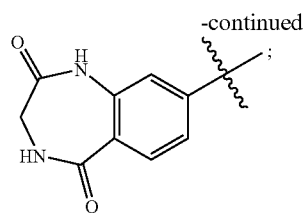

R³ is CO₂H, CO₂Me, —C(O)NHCH₂CO₂H, —C(O)NHCH₂CO₂Et, —C(O)NH₂, —C(O)NHMe, —C(O)NHBn, phenyl, phenethyl, —(CH=CH)-phenyl, 3-biphenyl, 4-biphenyl, 3,4-methylenedioxyphenyl, 1-naphthyl, 2-naphthyl, 3-NH₂-phenyl, 3-NMe₂-phenyl, 4-OPh-phenyl, 4-OBn-phenyl, 4-(t-butoxymethyl)-phenyl, 4-SO₂Me-phenyl, 3-CN-phenyl, 4-CN-phenyl, 3-F-phenyl, 4-F-phenyl, 3-Cl-phenyl, 4-Cl-phenyl, 3-Br-phenyl, 4-Br-phenyl, 3-OH-phenyl, 4-OH-phenyl, 2-OMe-phenyl, 3-OMe-phenyl, 4-OMe-phenyl, 3-CF₃-phenyl, 4-CF₃-phenyl, 3-CO₂H-phenyl, 4-CO₂H-phenyl, 3-CO₂Me-phenyl, 4-CO₂Me-phenyl, 3-CH₂CO₂H-phenyl, 4-CH₂CO₂H-phenyl, 4-CH₂CO₂Me-phenyl, 3-CH₂CO₂Et-phenyl, 4-CH₂CO₂Et-phenyl, 3-CONH₂-phenyl, 4-CONH₂-phenyl, 3-CH₂CONH₂-phenyl, 4-CH₂CONH₂-phenyl, 4-CONHMe-phenyl, 4-CONMe₂-phenyl, 4-amidino-phenyl, 3-NHCOMe-phenyl, 4-NHCOMe-phenyl, 4-NHCO₂Me-phenyl, 4-SO₂NH₂-phenyl, 3-NHSO₂Me-phenyl, 4-NHSO₂Me-phenyl, 2,4-diF-phenyl, 3-F-4-CN-phenyl, 3-CN-5-F-phenyl, 3-F-4-CONH₂-phenyl, 3-CO₂H-4-CN-phenyl, 3-NMe₂-4-CN-phenyl, 3-Ph-4-CONH₂-phenyl, 4-(2-oxo-1-piperidino)-phenyl, thiazol-2-yl, 4-CO₂Me-thiazol-2-yl, 4-CONH₂-thiazol-2-yl, 1-Bn-pyrazol-4-yl, 5-Ph-oxazol-2-yl, 5-CONH₂-thien-2-yl, 5-CO₂H-thien-2-yl, pyrid-2-yl, pyrid-3-yl, pyrid-4-yl, 6-NH₂-pyrid-3-yl, benzimidazol-2-yl, 1-Me-benzimidazol-2-yl, benzoxazol-2-yl, benzothiazol-2-yl, 3-NH₂-benzisoxazol-6-yl, 3-NH₂-benzisoxazol-5-yl, indazol-5-yl, indazol-6-yl, 3-NH₂-indazol-5-yl, 3-OH-indazol-5-yl, 3-NH₂-indazol-6-yl, 3-NH₂-4-F-indazol-6-yl, 3-NH₂-5-F-indazol-6-yl, 3-NH₂-7-F-indazol-6-yl, 4-imino-3,4-dihydro-2H-phthalazin-1-on-7-yl, 3-(5-tetrazolyl)-phenyl, 2,3-dihydroisoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, or 4-NH₂-quinazolin-7-yl;

R⁴ is H, Me, Br, Cl, CF₃, CO₂H, CO₂Me, CO₂Et, phenyl, 3-F-4-CN-phenyl, or 3-NH₂-6-indazolyl; and R¹¹ is Me, neopentyl, cyclohexylmethyl, —CH₂CH₂CONHBn, —CH₂CH₂CONH(CH₂CH₂Ph), —CH₂CH₂CON(Me)Bn, benzyl, phenethyl, 2-Me-benzyl, 3-Me-benzyl, 4-Me-benzyl, 2-F-benzyl, 3-F-benzyl, 4-F-benzyl, 2-Cl-benzyl, 3-Cl-benzyl, 4-Cl-benzyl, 2-Br-benzyl, 3-Br-benzyl, 4-Br-benzyl, 3-CF₃-benzyl, 4-CF₃-benzyl, 2-NH₂-benzyl, 3-NH₂-benzyl, 2-NO₂-benzyl, 3-NO₂-benzyl, 4-NO₂-benzyl, 3-OMe-benzyl, 4-OMe-benzyl, 3-OCF₂H-benzyl, 2-OCF₃-benzyl, 3-OCF₃-benzyl, 2-OPh-benzyl, 3-OPh-benzyl, 2-OBn-benzyl, 3-OBn-benzyl, 4-OBn-benzyl, 4-COPh-benzyl, 3-CO₂H-benzyl, 3-CO₂Me-benzyl, 3-NHAc-benzyl, 2-NHCOPh-benzyl, 2-NHCOBn-benzyl, 3-NHCOBn-benzyl, 3-N(Me)COPh-benzyl, 3-(—NHCOCH₂CH₂Ph)-benzyl, 2-NHSO₂Ph-benzyl, 3-NHSO₂Ph-benzyl, 3-[SO₂N(Me)Ph]-benzyl, 3-[N(Me)SO₂Ph]-benzyl, 3-[CONH(1-Bu)]-benzyl, 3-[CONH(t-Bu)]-benzyl, 3-[CONH(isopentyl)]-benzyl, 3-[CONH(2-Me-Ph)]-benzyl, 3-[CONH(3-Me-Ph)]-benzyl, 3-[CONH(4-Me-Ph)]-benzyl, 3-[CONH(4-F-Ph)]-benzyl, 3-[CONH(1-naphthyl)]-benzyl, 3-(CONHBn)-benzyl, 3-[CONH(4-Cl-Bn)]-benzyl, 3-[CONH(4-OMe-Bn)]-benzyl, 3-[CONHCH₂CH₂Ph]-benzyl, 3-[CONHCH₂CH₂(4-OMe-Ph)]-benzyl, 3-[CONHCH₂CH₂(2-Cl-Ph)]-benzyl, 3-[CONHCH₂CH₂(3-Cl-Ph)]-benzyl, 3-[CONHCH₂CH₂(4-

Cl-Ph)]-benzyl, 3-[CONH(CH$_2$)$_3$Ph]-benzyl, 3-[CONMe$_2$]-benzyl, 3-[CON(Me)(Et)]-benzyl, 3-[CON(Me)(i-Pr)]-benzyl, 3-[CON(Me)(1-Bu)]-benzyl, 3-[CON(Me)Ph]-benzyl, 3-[CON(Me)(3-Me-Ph)]-benzyl, 3-[CON(Me)(4-Me-Ph)]-benzyl, 3-[CON(Me)Bn]-benzyl, 3-[CON(Me)(3-Cl-Bn)]-benzyl, 3-[CON(Me)(4-Cl-Bn)]-benzyl, 3-[CON(Me)(CH$_2$CH$_2$Ph)]-benzyl, 3-[CON(Et)Ph]-benzyl, 3-[CO(1-piperidino)]-benzyl, 3-[CO(4-Ph-1-piperidino)]-benzyl, 3-[CO(1,2,3,4-tetrahydroisoquinolino)]-benzyl, 2-Ph-benzyl, 3-Ph-benzyl, 4-Ph-benzyl, 3-phenethyl-benzyl, —CH$_2$OBn, —CH$_2$SBn, 1-naphthylmethyl, 2-naphthylmethyl, thiazol-4-ylmethyl, pyrid-2-ylmethyl, pyrid-3-ylmethyl, pyrid-4-ylmethyl, 1-Bn-imidazol-4-ylmethyl, benzothiazol-2-ylmethyl,

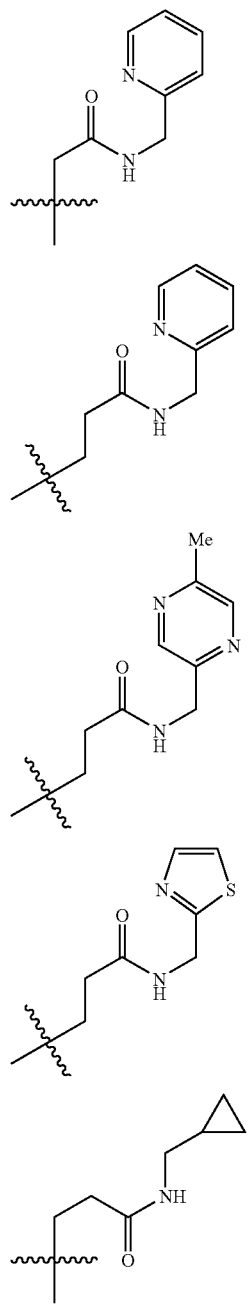

-continued

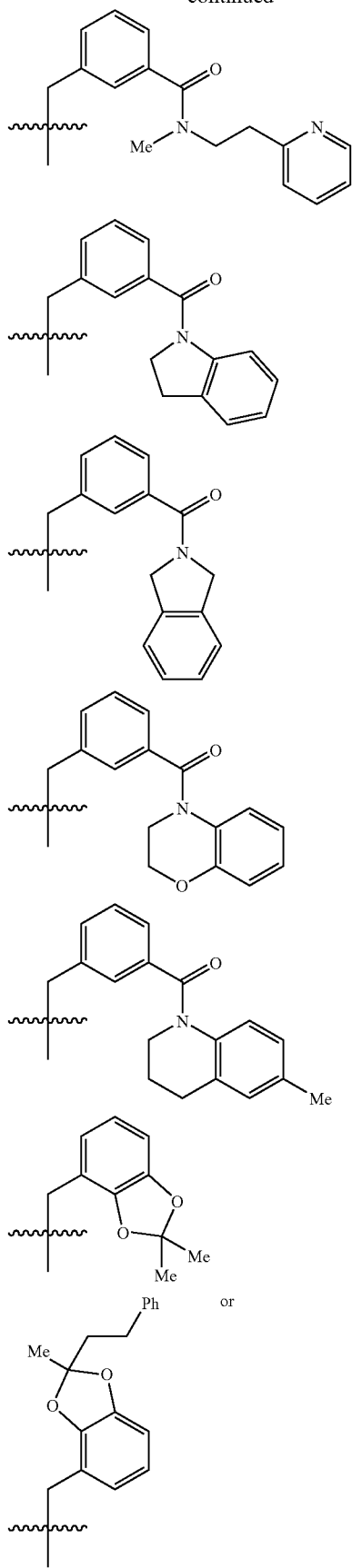

-continued

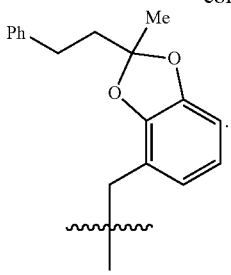

In a sixth aspect, the present invention includes a compound of Formula (II):

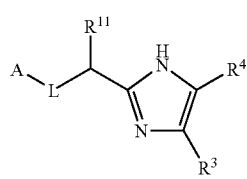
(II)

or its stereoisomers, tautomers, pharmaceutically acceptable salts, solvates, or prodrugs thereof, within the scope of the first aspect wherein:

$R^3$ is 3-$NH_2$-indazol-5-yl, 3-OH-indazol-5-yl, 3-$NH_2$-benzisoxazol-6-yl, 3-$NH_2$-benzisoxazol-5-yl, indazol-5-yl, indazol-6-yl, 3-$NH_2$-indazol-6-yl, 3-$NH_2$-4-F-indazol-6-yl, 3-$NH_2$-5-F-indazol-6-yl, 3-$NH_2$-7-F-indazol-6-yl, isoquinolin-5-yl, quinolin-5-yl, quinolin-8-yl, 2H-isoquinolin-1-on-6-yl, 2,4-diaminoquinazolin-7-yl, or 4-$NH_2$-quinazolin-7-yl.

In a seventh aspect, the present invention includes compounds of Formula (IIa) within the scope of the sixth aspect wherein:

L is —C(O)$NR^{10}$— or —$NR^{10}$C(O)—;

$R^1$ is, independently at each occurrence, F, Cl, Me, Et, —$NH_2$, —C(=NH)$NH_2$, —C(O)$NH_2$, —$CH_2NH_2$, —$CH_2CH_2NH_2$, —$CH_2NHCO_2Bn$, —$CH_2NHCO_2$(t-Bu), —CH(Me)$NH_2$, —C(Me)$_2NH_2$, —NHEt, —$NHCO_2$(t-Bu), —$NHCO_2Bn$, —$SO_2NH_2$, $OR^a$, or —$CH_2R^{1a}$;

$R^4$ is H, F, Cl, Br, OMe, $NH_2$, $CF_3$, $CO_2H$, $CO_2Me$, $CO_2Et$, —$CONR^8R^9$, $C_{1-6}$ alkyl substituted with 0-2 $R^{4a}$, phenyl substituted with 0-2 $R^{4b}$, or a 5-10 membered heterocycle comprising: carbon atoms and 1-4 heteroatoms selected from N, O, and $S(O)_p$, wherein said heterocycle is substituted with 0-3 $R^{4b}$;

$R^{10}$ is, independently at each occurrence, H, Me, benzyl, phenethyl, —$CH_2CH_2CO_2H$, —$CH_2CH_2CO_2Me$, —$CH_2CH_2CO_2Et$, —$CH_2CH_2CONH_2$, or —$CH_2CH_2CONHCH_2CH_2Ph$;

$R^{11}$ is $C_1$-$C_6$ alkyl, —$CH_2CONR^8R^9$, —$CH_2CH_2CONR^8R^9$, —$CH_2OBn$, —$CH_2SBn$, —$(CH_2)_r$-$C_{3-7}$ cycloalkyl substituted with 0-2 $R^{11b}$, —$(CH_2)_r$-phenyl substituted with 0-2 $R^{11b}$, —$(CH_2)_r$-naphthyl substituted with 0-2 $R^{11b}$, or —$(CH_2)_r$-5-10 membered heterocycle comprising carbon atoms and 1-4 heteroatoms selected from N, O, and $S(O)_p$, wherein said heterocycle is substituted with 0-2 $R^{11b}$; and $R^{11b}$ is, independently at each occurrence, H, F, Cl, Br, $CF_3$, OMe, OEt, O(i-Pr), $OCF_3$, $OCHF_2$, CN, OPh, OBn, $NO_2$, —$NH_2$, —C(O)$R^a$, —C(O)$OR^a$, —C(O)$NR^7R^8$, —$NR^7C(O)R^b$, —$N^8CO_2R^c$, —$S(O)_pNR^8R^9$, —$NR^8S(O)_pR^c$, —$SO_2R^c$, $C_1$-$C_4$-alkyl, Ph, or Bn.

In an eighth aspect, the present invention includes compounds of Formula (II), within the scope of the seventh aspect wherein:

A is substituted with 0-1 $R^1$ and 0-2 $R^2$ and selected from: $C_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl; and $R^{10}$ is H.

In a ninth aspect, the present invention includes compounds of Formula (II), within the scope of the eighth aspect wherein:

A is 4-$CH_2NH_2$-cyclohexyl, 4-$CO_2Me$-cyclohexyl, 4-$CONH_2$-cyclohexyl, 4-$NHCO_2$(t-Bu)-cyclohexyl, 4-$NHCO_2Bn$-cyclohexyl, phenyl, 4-Me-phenyl, 3-OMe-phenyl, 4-$CH_2NH_2$-phenyl, 3-$CONH_2$-phenyl, 4-$CONH_2$-phenyl, 3-amidino-phenyl, 4-amidino-phenyl, 2-F-4-Me-phenyl, 2-Bn-4-$CH_2NH_2$-phenyl, 4-$SO_2NH_2$-phenyl, 2-F-5-OMe-phenyl, 2-F-4-Cl-phenyl, 2-F-4-$CH_2NH_2$-phenyl, 2-F-4-$CONH_2$-phenyl, 2-Cl-4-$CONH_2$-phenyl, 2-Et-4-$CH_2NH_2$-phenyl, 2-NHEt-4-$CH_2NH_2$-phenyl, 2-OMe-4-$CONH_2$-phenyl, 3-OMe-4-$CONH_2$-phenyl, 1,2,3,4-tetrahydronaphth-2-yl, 3-Cl-thien-2-yl, indol-5-yl, indol-5-yl, indazol-5-yl, indazol-6-yl, 3-$NH_2$-indazol-6-yl, 3-$NH_2$-indazol-5-yl, 1-Me-3-$NH_2$-indazol-6-yl, 3-$NH_2$-benzisoxazol-6-yl, 1,2,3,4-tetrahydroisoquinolin-6-yl, 1,2,3,4-tetrahydroisoquinolin-3-yl, 2-COPh-1,2,3,4-tetrahydroisoquinolin-3-yl, 2-$CO_2Bn$-1,2,3,4-tetrahydroisoquinolin-3-yl, 1,2,3,4-tetrahydroisoquinolin-1-on-6-yl, 2H-isoquinolin-1-on-6-yl, isoquinolin-6-yl, 1-$NH_2$-isoquinolin-6-yl, 1-$NH_2$-3-Me-isoquinolin-6-yl, 1-$NH_2$-5,6,7,8-tetrahydroisoquinolin-6-yl, 4-$NH_2$-quinazolin-7-yl, 3H-quinazolin-4-on-7-yl,

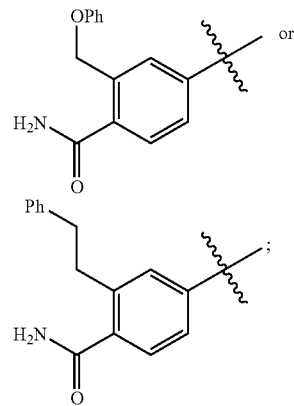

$R^4$ is H, Me, Br, Cl, $CF_3$, $CO_2H$, $CO_2Me$, $CO_2Et$, phenyl, 3-F-4-CN-phenyl, or 3-$NH_2$-6-indazolyl; and $R^{11}$ is Me, neopentyl, cyclohexylmethyl, —$CH_2CH_2CONHBn$, —$CH_2CH_2CONH(CH_2CH_2Ph)$, —$CH_2CH_2CON(Me)Bn$, benzyl, phenethyl, 2-Me-benzyl, 3-Me-benzyl, 4-Me-benzyl, 2-F-benzyl, 3-F-benzyl, 4-F-benzyl, 2-Cl-benzyl, 3-Cl-benzyl, 4-Cl-benzyl, 2-Br-benzyl, 3-Br-benzyl, 4-Br-benzyl, 3-$CF_3$-benzyl, 4-$CF_3$-benzyl, 2-$NH_2$-benzyl, 3-$NH_2$-benzyl, 2-$NO_2$-benzyl, 3-$NO_2$-benzyl, 4-$NO_2$-benzyl, 3-OMe-benzyl, 4-OMe-benzyl, 3-$OCF_2H$-benzyl, 2-$OCF_3$-benzyl, 3-$OCF_3$-benzyl, 2-OPhbenzyl, 3-OPh-benzyl, 2-OBn-benzyl, 3-OBn-benzyl, 4-OBn-benzyl, 4-COPh-benzyl, 3-CO₂H-benzyl, 3-CO₂Me-benzyl, 3-NHAc-benzyl, 2-NHCOPh-benzyl, 2-NHCOBn-benzyl, 3-NHCOBn-benzyl, 3-N(Me)COPh-benzyl, 3-(—NHCOCH₂CH₂Ph)-benzyl, 2-NHSO₂Ph-benzyl, 3-NHSO₂Ph-benzyl, 3-[SO₂N(Me)Ph]-benzyl, 3-[N(Me)SO₂Ph]-benzyl, 3-[CONH(1-Bu)]-benzyl, 3-[CONH(t-Bu)]-benzyl, 3-[CONH(isopentyl)]-benzyl, 3-[CONH(2-Me-Ph)]-benzyl, 3-[CONH(3-Me-Ph)]-benzyl, 3-[CONH(4-Me-Ph)]-benzyl, 3-[CONH(4-F-Ph)]-benzyl, 3-[CONH(1-naphthyl)]-benzyl, 3-(CONHBn)-benzyl, 3-[CONH(4-Cl-Bn)]-benzyl, 3-[CONH(4-OMe-Bn)]-benzyl, 3-[CONHCH₂CH₂Ph]-benzyl, 3-[CONHCH₂CH₂(4-OMe-Ph)]-benzyl, 3-[CONHCH₂CH₂(2-Cl-Ph)]-benzyl, 3-[CONHCH₂CH₂(3-Cl-Ph)]-benzyl, 3-[CONHCH₂CH₂(4-Cl-Ph)]-benzyl, 3-[CONH(CH₂)₃Ph]-benzyl, 3-[CONMe₂]-benzyl, 3-[CON(Me)(Et)]-benzyl, 3-[CON(Me)(i-Pr)]-benzyl, 3-[CON(Me)(1-Bu)]-benzyl, 3-[CON(Me)Ph]-benzyl, 3-[CON(Me)(3-Me-Ph)]-benzyl, 3-[CON(Me)(4-Me-Ph)]-benzyl, 3-[CON(Me)Bn]-benzyl, 3-[CON(Me)(3-Cl-Bn)]-benzyl, 3-[CON(Me)(4-Cl-Bn)]-benzyl, 3-[CON(Me)(CH₂CH₂Ph)]-benzyl, 3-[CON(Et)Ph]-benzyl, 3-[CO(1-piperidino)]-benzyl, 3-[CO(4-Ph-1-piperidino)]-benzyl, 3-[CO(1,2,3,4-tetrahydroisoquinolino)]-benzyl, 2-Ph-benzyl, 3-Ph-benzyl, 4-Ph-benzyl, 3-phenethyl-benzyl, —CH₂OBn, —CH₂SBn, 1-naphthylmethyl, 2-naphthylmethyl, thiazol-4-ylmethyl, pyrid-2-ylmethyl, pyrid-3-ylmethyl, pyrid-4-ylmethyl, 1-Bn-imidazol-4-ylmethyl, benzothiazol-2-ylmethyl,

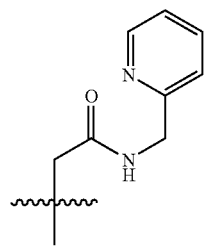

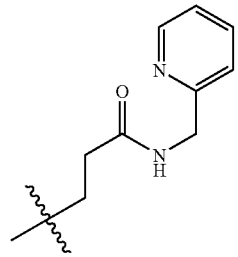

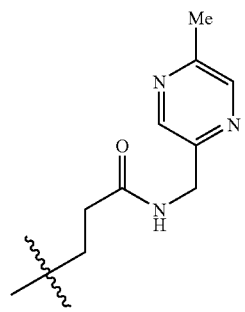

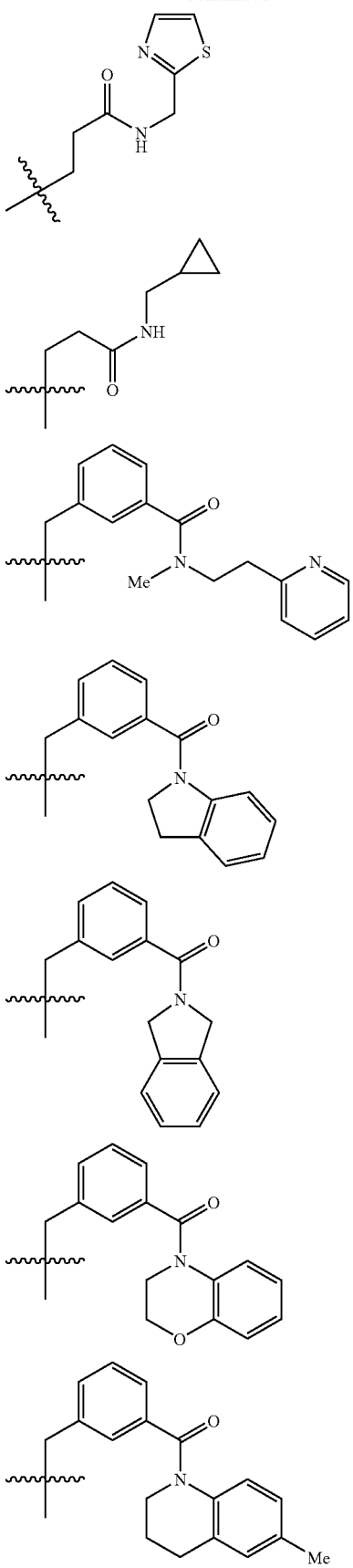

-continued

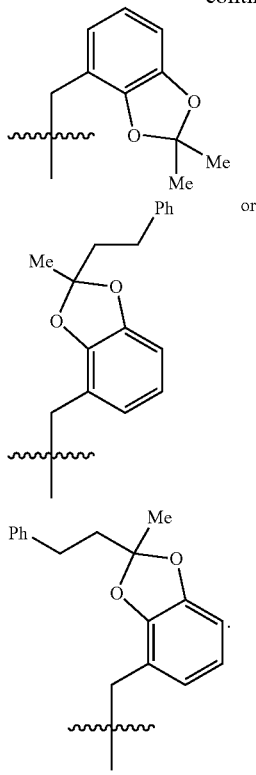

In a tenth aspect, the present invention includes compounds of Formula (II), within the scope of the eighth aspect wherein:

A is 4-$CH_2NH_2$-cyclohexyl, 4-$NHCO_2$(t-Bu)-cyclohexyl, 4-$NHCO_2$Bn-cyclohexyl, or 1-$NH_2$-5,6,7,8-tetrahydroisoquinolin-6-yl;

L is —C(O)NH— or NHC(O)—;

$R^3$ is indazol-5-yl, indazol-6-yl, 3-$NH_2$-indazol-5-yl, 3-OH-indazol-5-yl, 3-$NH_2$-indazol-6-yl, 3-$NH_2$-4-F-indazol-6-yl, 3-$NH_2$-5-F-indazol-6-yl, 3-$NH_2$-7-F-indazol-6-yl, or 4-$NH_2$-quinazolin-7-yl;

$R^4$ is H, Me, F, Br, Cl, or $CF_3$; and $R^{11}$ is benzyl substituted with 0-2 $R^{11b}$.

In an eleventh aspect, the present invention includes compounds of Formula (II), within the scope of the tenth aspect wherein:

A is 4-$CH_2NH_2$-cyclohexyl;

L is —C(O)NH—; and $R^3$ is 3-$NH_2$-indazol-6-yl or 4-$NH_2$-quinazolin-7-yl.

In a twelfth aspect, the present invention includes a compound of Formula (II):

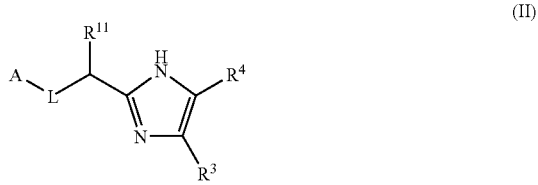

or its stereoisomers, tautomers, pharmaceutically acceptable salts, solvates, or prodrugs thereof, within the scope of the first aspect wherein:

A is substituted with 0-2 $R^1$ and 0-1 $R^2$ and selected from: $C_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

L is —C(O)$NR^{10}$— or —$NR^{10}$C(O)—;

$R^3$ is —$(CH_2)_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^4$ is H, F, Cl, Br, OMe, $NH_2$, $CF_3$, $CO_2H$, $CO_2Me$, $CO_2Et$, —$CONR^8R^9$, $C_{1-6}$ alkyl substituted with 0-2 $R^{4a}$, phenyl substituted with 0-2 $R^{4b}$, or a 5-10 membered heterocycle comprising: carbon atoms and 1-4 heteroatoms selected from N, O, and $S(O)_p$, wherein said heterocycle is substituted with 0-3 $R^{4b}$; and $R^{11}$ is benzyl substituted with 0-2 $R^{11b}$.

In another aspect, the present invention includes a compound of Formula (II), within the scope of the twelfth aspect wherein:

$R^3$ is —$(CH_2)_r$-9- to 10-membered bicyclic heterocycle comprising: carbon atoms and 1-4 heteroatoms selected from N, O, and $S(O)_p$, wherein said heterocycle is substituted with 0-3 $R^{3a}$.

In a thirteenth aspect, the present invention includes a compound of Formula (II):

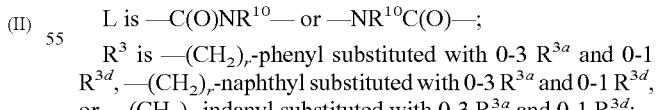

or its stereoisomers, tautomers, pharmaceutically acceptable salts, solvates, or prodrugs thereof, within the scope of the first aspect wherein:

A is substituted with 0-1 $R^1$ and 0-2 $R^2$ and selected from: $C_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

L is —C(O)$NR^{10}$— or —$NR^{10}$C(O)—;

$R^3$ is —$(CH_2)_r$-phenyl substituted with 0-3 $R^{3a}$ and 0-1 $R^{3d}$, —$(CH_2)_r$-naphthyl substituted with 0-3 $R^{3a}$ and 0-1 $R^{3d}$, or —$(CH_2)_r$-indanyl substituted with 0-3 $R^{3a}$ and 0-1 $R^{3d}$;

$R^4$ is, independently at each occurrence, H, Me, Br, Cl, $CF_3$, $CO_2H$, $CO_2Me$, $CO_2Et$, phenyl, 3-F-4-CN-phenyl, or 3-$NH_2$-6-indazolyl; and $R^{11}$ is benzyl substituted with 0-2 $R^{11b}$.

In another aspect, the present invention includes a compound of Formula (II), within the scope of the thirteenth aspect wherein:

$R^3$ is —$(CH_2)_r$-phenyl substituted with 0-3 $R^{3a}$.

In a fourteenth aspect, the present invention includes a compound of Formula (III):

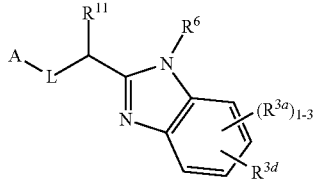

(III)

or its stereoisomers, tautomers, pharmaceutically acceptable salts, solvates, or prodrugs thereof, within the scope of the first aspect wherein:

$R^{3a}$ is, independently at each occurrence, =O, F, Cl, Br, Me, CN, OH, $NH_2$, OMe, O(t-Bu), OBn, $CF_3$, $CO_2H$, $CO_2Me$, —$CH_2CO_2H$, —$CH_2CO_2Me$, —$CH_2CO_2Et$, —NHCOMe, —$CONH_2$, —$CH_2CONH_2$, —CONHMe, —$CONMe_2$, —C(=NH)$NH_2$, —$NR^7R^8$, —$SO_2Me$, —$SO_2NH_2$, Ph, or 2-oxo-piperidin-1-yl;

$R^{3d}$ is H or $C_{1-4}$ alkyl;

$R^{10}$ is, independently at each occurrence, H, $C_{1-6}$ alkyl substituted with 0-2 $R^{10a}$, —(CH$_2$)$_r$-phenyl substituted with 0-2 $R^d$, or —(CH$_2$)$_r$-5-10 membered heterocycle comprising carbon atoms and 1-4 heteroatoms selected from N, O, and S(O)$_p$, wherein said heterocycle is substituted with 0-2 $R^d$; and $R^{11}$ is $C_{1-4}$ haloalkyl, —(CH$_2$)$_r$—CONR$^8$R$^9$, $C_{1-6}$ alkyl substituted with 0-2 $R^{11a}$, $C_{2-6}$ alkenyl substituted with 0-2 $R^{11a}$, $C_{2-6}$ alkynyl substituted with 0-2 $R^{11a}$, —(CH$_2$)$_r$—$C_{3-10}$ carbocycle substituted with 0-3 $R^{11b}$, or —(CH$_2$)$_r$-5-10 membered heterocycle comprising carbon atoms and 1-4 heteroatoms selected from N, O, and S(O)$_p$, wherein said heterocycle is substituted with 0-3 $R^{11b}$.

In a fifteenth aspect, the present invention includes compounds of Formula (III), within the scope of the fourteenth aspect wherein:

$R^1$ is, independently at each occurrence, —$NH_2$, —C(=NH)$NH_2$, —C(O)$NH_2$, —$CH_2NH_2$, —CH(Me)$NH_2$, —C(Me)$_2NH_2$, or —$CH_2CH_2NH_2$;

$R^{10}$ is H, Me, benzyl, or phenethyl; and $R^{11}$ is Me, —(CH$_2$)$_r$-phenyl substituted with 0-1 $R^{11b}$, or —(CH$_2$)$_r$-5-10 membered heteroaryl comprising carbon atoms and 1-4 heteroatoms selected from N, O, and S(O)$_p$, wherein said heterocycle is substituted with 0-1 $R^{11b}$.

In a sixteenth aspect, the present invention includes a compound of Formula (IV):

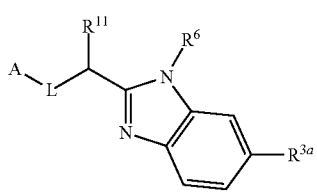

(IV)

or its stereoisomers, tautomers, pharmaceutically acceptable salts, solvates, or prodrugs thereof, within the scope of the first aspect wherein:

A is cyclohexyl substituted with 1 $R^1$, phenyl substituted with 1 $R^1$, pyridyl substituted with 1 $R^1$, naphthyl substituted with 1 $R^1$, benzisoxazole substituted with 1 $R^1$, or isoquinolinyl substituted with 0-1 $R^1$;

L is —C(O)NH—, —C(O)NMe, —C(O)N(benzyl)-, —C(O)N(phenethyl)-, —NHC(O)—, —CH$_2$C(O)NH—, —NHC(O)CH$_2$—, —C(O)NHCH$_2$—, or —NHC(O)CH$_2$—;

$R^1$ is, independently at each occurrence, —$NH_2$, —C(=NH)$NH_2$, —C(O)$NH_2$, or —$CH_2NH_2$;

$R^{3a}$ is F, Cl, Br, Me, CN, OMe, $CF_3$, $CO_2H$, $CO_2Me$, $CO_2Et$, —$CH_2CO_2H$, —$CH_2CO_2Me$, —$CH_2CO_2Et$, —$CONH_2$, —CONHMe, —CON(Me)$_2$, —$CH_2CONH_2$, or —C(=NH)$NH_2$;

$R^6$ is H;

$R^{10}$ is H, Me, benzyl, or phenethyl; and $R^{11}$ is Me, —(CH$_2$)$_r$-phenyl substituted with 0-1 $R^{11b}$, or —(CH$_2$)$_r$-5-10 membered heteroaryl substituted with 0-1 $R^{11b}$ and selected from thiazolyl, imidazolyl, pyridyl, and benzothiazolyl.

In a seventeenth aspect, the present invention includes compounds of Formula (IV), within the scope of the sixteenth aspect wherein:

A is 4-$CH_2NH_2$-cyclohexyl or 4-amidino-phenyl; and $R^{3a}$ is, independently at each occurrence, $CO_2H$, $CO_2Me$, —$CH_2CO_2H$, —$CH_2CO_2Et$, —$CONH_2$, or —$CH_2CONH_2$.

In an eighteenth aspect, the present invention provides, inter alia, a compound of Formula (V):

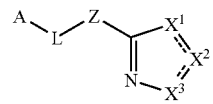

(V)

or its stereoisomers, tautomers, a pharmaceutically acceptable salts, solvates, or prodrugs thereof, wherein:

A is $C_{3-10}$ carbocycle substituted with 0-1 $R^1$ and 0-3 $R^2$, or a 5- to 12-membered heterocycle comprising: carbon atoms and 1-4 heteroatoms selected from N, O, and S(O)$_p$, wherein said heterocycle is substituted with 0-1 $R^1$ and 0-3 $R^2$; provided when A is a heterocycle containing one or more nitrogen atoms, A is not attached to L via any of the nitrogen atoms on the A ring;

$X^1$, $X^2$, and $X^3$ are independently $CR^3$, $CR^4$, $CR^4R^5$, O, S(O)$_p$, N, $NR^3$, $NR^6$, or C(O); provided that no S—S, S—O, or O—O bond is present in the ring;

provided that

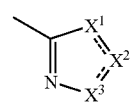

is other than

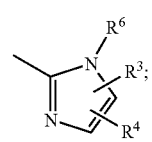

Z is —C($R^{11}$)($R^{12}$)—, —C($R^{11}$)($R^{12}$)—(CH$_2$)—, —$NR^{13}$—, or —$NR^{13}CH_2$—;

L is —C(O)$NR^{10}$—, —$NR^{10}C(O)$—, —$CH_2C(O)NR^{10}$—, —$CH_2NR^{10}C(O)$—, —C(O)$NR^{10}CH_2$—, —$NR^{10}C(O)CH_2$—, —S(O)$_2NR^{10}$—, —$NR^{10}S(O)_2$—, —$CH_2S(O)_2NR^{10}$—, —$CH_2NR^{10}S(O)_2$—, —S(O)$_2NR^{10}CH_2$—, —$NR^{10}S(O)_2CH_2$—, —$CH_2CH_2$—,

—CH$_2$CH$_2$CH$_2$—, —CH$_2$NR$^7$—, —NR$^7$CH$_2$—, —CH$_2$CH$_2$NR$^7$—, —NR$^7$CH$_2$CH$_2$, —CH$_2$NR$^7$CH$_2$—, —CH$_2$O—, —OCH$_2$—, —CH$_2$S(O)$_p$—, —S(O)$_p$CH$_2$—, —CH$_2$CH$_2$O—, —OCH$_2$CH$_2$—, —CH$_2$OCH$_2$—, —CH$_2$CH$_2$S(O)$_p$—, —S(O)$_p$CH$_2$CH$_2$—, —CH$_2$S(O)$_p$CH$_2$—, —CH$_2$C(O), —CH$_2$C(O)CH$_2$—, —CH$_2$CH$_2$C(O)—, —C(O)CH$_2$CH$_2$—, or —C(O)CH$_2$—;

R$^1$ is, independently at each occurrence, —NH$_2$, —NH(C$_{1-3}$ alkyl), —N(C$_{1-3}$ alkyl)$_2$, —C(=NH)NH$_2$, —C(O)NR$^8$R$^9$, —S(O)$_p$NR$^8$R$^9$, —(CH$_2$)$_r$NR$^7$R$^8$, —(CH$_2$)$_r$NR$^7$C(O)OR$^a$, —CH$_2$NH$_2$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —CH(C$_{1-4}$ alkyl)NH$_2$, —C(C$_{1-4}$ alkyl)$_2$NH$_2$, —C(=NR$^{8a}$)NR$^7$R$^8$, —NHC(=NR$^{8a}$)NR$^7$R$^8$, =NR$^8$, —NR$^8$CR$^8$(=NR$^{8a}$), F, Cl, Br, I, OCF$_3$, CF$_3$, —(CH$_2$)$_r$OR$^a$, —(CH$_2$)$_r$SR$^a$, CN, 1-NH$_2$-1-cyclopropyl, or C$_{1-6}$ alkyl substituted with 0-1 R$^{1a}$;

R$^{1a}$ is H, —C(=NR$^{8a}$)NR$^7$R$^8$, —NHC(=NR$^{8a}$)NR$^7$R$^8$, —NR$^8$CH(=NR$^{8a}$), —NR$^7$R$^8$, —C(O)NR$^8$R$^9$, F, OCF$_3$, CF$_3$, OR$^a$, SR$^a$, CN, —NR$^9$SO$_2$NR$^8$R$^9$, —NR$^8$SO$_2$R$^c$, —S(O)$_p$—C$_{1-4}$ alkyl, —S(O)$_p$-phenyl, or —(CF$_2$)$_r$CF$_3$;

R$^2$ is, independently at each occurrence, H, =O, F, Cl, Br, I, OCF$_3$, CF$_3$, CHF$_2$, CN, NO$_2$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_2$NR$^8$R$^9$, —NR$^8$S(O)$_2$R$^c$, —S(O)R$^c$, —S(O)$_2$R$^c$, C$_{1-6}$ alkyl substituted with 0-2 R$^{2a}$, C$_{2-6}$ alkenyl substituted with 0-2 R$^{2a}$, C$_{2-6}$ alkynyl substituted with 0-2 R$^{2a}$, —(CH$_2$)$_r$—C$_{3-10}$ carbocycle substituted with 0-3 R$^{2b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{2b}$;

R$^{2a}$ is, independently at each occurrence, H, F, Cl, Br, I, =O, =NR$^8$, CN, OCF$_3$, CF$_3$, OR$^a$, SR$^a$, —NR$^7$R$^8$, —C(O)NR$^8$R$^9$, —NR$^7$C(O)R$^b$, —S(O)$_p$NR$^8$R$^9$, —NR$^8$SO$_2$R$^c$, —S(O)R$^c$, or —S(O)$_2$R$^c$;

R$^{2b}$ is, independently at each occurrence, H, F, Cl, Br, I, =O, =NR$^8$, CN, NO$_2$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_2$NR$^8$R$^9$, —S(O)$_2$R$^c$, —NR$^8$SO$_2$NR$^8$R$^9$, —NR$^8$SO$_2$R$^c$, —(CF$_2$)$_r$CF$_3$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkoxy;

alternately, when R$^1$ and R$^2$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and S(O)$_p$, wherein said carbocycle or heterocycle is substituted with 0-2 R$^{2b}$;

R$^3$ is, independently at each occurrence, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$—C$_{3-10}$ carbocycle substituted with 0-3 R$^{3a}$ and 0-1 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^{3a}$ is, independently at each occurrence, =O, F, Cl, Br, I, OCF$_3$, CF$_3$, NO$_2$, CN, —(CH$_2$)$_r$OR$^{3b}$, —(CH$_2$)$_r$SR$^{3b}$, —(CH$_2$)$_r$NR$^7$R$^8$, C(=NR$^{8a}$)NR$^8$R$^9$, —NHC(=NR$^{8a}$)NR$^7$R$^8$, —NR$^8$CR$^8$(=NR$^{8a}$), —(CH$_2$)$_r$NR$^8$C(O)R$^{3b}$, =NR$^8$, —(CH$_2$)$_r$NR$^8$C(O)R$^{3b}$, —(CH$_2$)$_r$NR$^8$C(O)$_2$R$^{3b}$, —(CH$_2$)$_r$S(O)$_p$NR$^8$R$^9$, —(CH$_2$)$_r$NR$^8$S(O)$_p$R$^{3c}$, —S(O)$_p$R$^{3c}$, —S(O)$_p$R$^{3c}$, —C(O)—C$_{1-4}$ alkyl, —(CH$_2$)$_r$CO$_2$R$^{3b}$, —(CH$_2$)$_r$C(O)NR$^8$R$^9$, —(CH$_2$)$_r$OC(O)NR$^8$R$^9$, —NHCOCF$_3$, —NHSO$_2$CF$_3$, —SO$_2$NHR$^{3b}$, —SO$_2$NHCOR$^{3c}$, —SO$_2$NHCO$_2$R$^{3c}$, —CONHSO$_2$R$^{3c}$, —NHSO$_2$R$^{3c}$, —CONHOR$^{3b}$, C$_{1-4}$ haloalkyl, C$_{1-4}$ haloalkoxy-, C$_{1-6}$ alkyl substituted by R$^{3d}$, C$_{2-6}$ alkenyl substituted by R$^{3d}$, C$_{2-6}$ alkynyl substituted by R$^{3d}$, C$_{3-6}$ cycloalkyl substituted by 0-1 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

alternately, when two R$^{3a}$ groups are located on adjacent atoms, they can be taken together with the atoms to which they are attached to form a C$_{3-10}$ carbocycle substituted with 0-2 R$^{3d}$ or a 5- to 10-membered heterocycle comprising: carbon atoms and 1-4 heteroatoms selected from N, O, and S(O)$_p$, wherein said heterocycle is substituted with 0-2 R$^{3d}$;

R$^{3b}$ is, independently at each occurrence, H, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3c}$ is, independently at each occurrence, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3d}$ is, independently at each occurrence, H, =O, —(CH$_2$)$_r$OR$^a$, F, Cl, Br, CN, NO$_2$, —(CH$_2$)$_r$NR$^7$R$^8$, —C(O)R$^a$, —C(O)OR$^a$, —OC(O)R$^a$, —NR$^7$C(O)R$^b$, —C(O)NR$^8$R$^9$, —SO$_2$NR$^8$R$^9$, —NR$^8$SO$_2$NR$^8$R$^9$, —NR$^8$SO$_2$R$^c$, —S(O)$_p$R$^c$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, wherein said heterocycle is substituted with 0-3 R$^d$;

R$^4$ is, independently at each occurrence, H, =O, F, Cl, Br, I, OCF$_3$, CF$_3$, OR$^a$, SR$^a$, CN, NO$_2$, —C(O)R$^a$, —C(O)OR$^a$, —OC(O)R$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, —(CH$_2$)$_r$—C$_{3-10}$ carbocycle substituted with 0-3 R$^{4b}$, or —(CH$_2$)$_r$-5- to 10-membered heterocycle comprising carbon atoms and 1-4 heteroatoms selected from N, O, and S(O)$_p$, wherein said heterocycle is substituted with 0-3 R$^{4b}$;

R$^{4a}$ is, independently at each occurrence, H, F, =O, C$_{1-6}$ alkyl, OR$^a$, SR$^a$, CF$_3$, CN, NO$_2$, —C(O)R$^a$, —C(O)OR$^a$, —OC(O)R$^a$, —NR$^7$R$^8$, —C(O)NR$^8$R$^9$, —NR$^7$C(O)R$^b$, —S(O)$_p$NR$^8$R$^9$, —NR$^8$S(O)$_2$R$^c$, —S(O)R$^c$, or —S(O)$_2$R$^c$;

R$^{4b}$ is, independently at each occurrence, H, =O, =NR$^8$, F, Cl, Br, I, OR$^a$, SR$^a$, CN, NO$_2$, CF$_3$, —SO$_2$R$^c$, —NR$^7$R$^8$, —C(O)R$^a$, —C(O)OR$^a$, —OC(O)R$^a$, —NR$^7$R$^8$, —C(O)NR$^8$R$^9$, —NR$^7$C(O)R$^b$, —S(O)$_p$NR$^8$R$^9$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkoxy-;

alternately, R$^3$ and R$^4$ groups when located on adjacent atoms, can be taken together to form a C$_{3-10}$ carbocycle substituted with 0-2 R$^{3d}$ or a 5- to 10-membered heterocycle comprising: carbon atoms and 1-4 heteroatoms selected from N, O, and S(O)$_p$, wherein said heterocycle is substituted with 0-2 R$^{3d}$;

R$^5$ is, independently at each occurrence, H, F, OCF$_3$, CF$_3$, OR$^a$, SR$^a$, CN, NO$_2$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_p$NR$^8$R$^9$, —NR$^8$S(O)$_2$R$^c$, —S(O)R$^c$, —S(O)$_2$R$^c$, C$_{1-6}$ alkyl substituted with 0-2 R$^{5a}$, C$_{2-6}$ alkenyl substituted with 0-2 R$^{5a}$, C$_{2-6}$ alkynyl substituted with 0-2 R$^{5a}$, —(CH$_2$)$_r$—C$_{3-10}$ carbocycle substituted with 0-3 R$^{5b}$, or —(CH$_2$)$_r$-5-10 membered heterocycle comprising carbon atoms and 1-4 heteroatoms selected from N, O, and $S(O)_p$, wherein said heterocycle is substituted with 0-3 $R^{5b}$;

$R^{5a}$ is, independently at each occurrence, H, =O, $OR^a$, $SR^a$, F, Cl, Br, I, $CF_3$, $OCF_3$, CN, $NO_2$, —$NR^7R^8$, —$NR^7R^8$, —$C(O)NR^7R^8$, —$NR^7C(O)R^b$, —$S(O)_2NR^8R^9$, —$NR^8S(O)_2R^c$, —$S(O)R^c$, or —$S(O)_2R^c$;

$R^{5b}$ is, independently at each occurrence, H, =O, =$NR^8$, F, Cl, Br, I, $OR^a$, $SR^a$, CN, $NO_2$, $CF_3$, —$SO_2R^c$, —$NR^7R^8$, —$C(O)R^a$, —$C(O)OR^a$, —$OC(O)R^a$, —$NR^7R^8$, —$C(O)NR^8R^9$, —$NR^7C(O)R^b$, —$S(O)_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkoxy-;

$R^6$ is, independently at each occurrence, H, $C_{1-6}$ alkyl, $C_{1-4}$ haloalkyl, —$CH_2OR^a$, —$C(O)R^c$, —$C(O)_2R^c$, —$S(O)_2R^c$, or —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)OC(O)—$(C_{1-4}$ alkyl), or —$C(O)O$—$(C_{1-4}$ alkyl)OC(O)—$(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, or —$(CH_2)_r$-phenyl, or —$(CH_2)_n$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{8a}$ is, independently at each occurrence, H, OH, $C_{1-6}$ alkyl, $C_{1-4}$ alkoxy, $(C_{6-10}$ aryl)-$C_{1-4}$ alkoxy, —$(CH_2)_n$-phenyl, —$(CH_2)_n$-(5-10 membered heteroaryl), —$C(O)R^c$, —$C(O)_2R^c$, —$C(O)O$—$(C_{1-4}$ alkyl)OC(O)—$(C_{1-4}$ alkyl), or —$C(O)O$—$(C_{1-4}$ alkyl)OC(O)—$(C_{6-10}$ aryl); wherein said phenyl, aryl, and heteroaryl is optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

$R^{9a}$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-3 $R^{10a}$, $C_{2-6}$ alkenyl substituted with 0-3 $R^{10a}$, $C_{2-6}$ alkynyl substituted with 0-3 $R^{10a}$, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)OR^a$, —$NR^7R^8$, —$C(O)NR^7R^8$, —$NR^7C(O)R^b$, —$S(O)_pNR^8R^9$, —$NR^8SO_2R^c$—, —$S(O)R^c$, or —$S(O)_2R^c$;

$R^{11}$ is $C_{1-4}$ haloalkyl, —$(CH_2)_rC(O)NR^8R^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CR^{14}R^{15})_r$—$C_{3-10}$ carbocycle substituted with 0-3 $R^{11b}$, or —$(CR^{14}R^{15})_r$-5- to 10-membered heterocycle comprising carbon atoms and 1-4 heteroatoms selected from N, O, and $S(O)_p$, wherein said heterocycle is substituted with 0-3 $R^{11b}$;

$R^{11a}$ is, independently at each occurrence, H, =O, $C_{1-4}$ alkyl, $OR^a$, $CF_3$, $SR^a$, F, CN, $NO_2$, $NR^7R^8$, —$C(O)NR^7R^8$, —$NR^7C(O)R^b$, —$S(O)_pNR^8R^9$, —$NR^8S(O)_pR^c$, —$C(O)R^a$, —$C(O)OR^a$, —$S(O)_pR^c$, $C_{3-6}$ cycloalkyl, $C_{1-4}$ haloalkyl, $C_{1-4}$ haloalkoxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$C(O)R^a$, —$C(O)OR^a$, —$SOR^c$, —$SO_2R^c$, —$NR^7R^8$, —$C(O)NR^7R^8$, —$NR^7C(O)R^b$, —$NR^8C(O)_2R^c$, —$S(O)_pNR^8R^9$, —$NR^8S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkoxy-, —$(CH_2)_r$—$C_{3-10}$ carbocycle substituted with 0-3 $R^d$, or —$(CH_2)_r$-5-10 membered heterocycle comprising: carbon atoms and 1-4 heteroatoms selected from N, O, and $S(O)_p$, wherein said heterocycle is substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{12}$ is, independently at each occurrence, H, F, or $C_{1-4}$ alkyl;

$R^{13}$ is, independently at each occurrence, H, $C_{1-6}$ alkyl, —$(CH_2)_n$-phenyl, —$(CH_2)_n$-(5-10 membered heteroaryl), —$C(O)R^c$, —$C(O)OR^c$, —$CONR^8R^c$, —$OCONR^8R^c$, —$S(O)_2R^c$, —$C(O)O$—$(C_{1-4}$ alkyl)-OC(O)—$(C_{1-4}$ alkyl), or —$C(O)O$—$(C_{1-4}$ alkyl)-OC(O)—$(C_{6-10}$ aryl); wherein the said alkyl, phenyl, heteroaryl, aryl are optionally substituted with 0-2 $R^f$;

$R^{14}$ and $R^{15}$ are, independently at each occurrence, H, F, or $C_{1-4}$ alkyl;

alternatively, $R^{14}$ combines with $R^{15}$ to form =O;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10 membered heterocycle comprising: carbon atoms and 1-4 heteroatoms selected from N, O, and $S(O)_p$; wherein said cycloalkyl, aryl and heteroaryl groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^d$, or —$(CH_2)_r$-5-10 membered heterocycle comprising: carbon atoms and 1-4 heteroatoms selected from N, O, and $S(O)_p$, wherein said heterocycle is substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, $(C_{6-10}$ aryl)-$C_{1-4}$ alkyl, or (5- to 10-membered heteroaryl)-$C_{1-4}$ alkyl, wherein said aryl and heteroaryl groups are optionally substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^8R^9$, —$C(O)R^a$, —$C(O)OR^a$, —$OC(O)R^a$, —$NR^8C(O)R^a$, —$C(O)NR^7R^8$, —$SO_2NR^8R^9$, $NR^8SO_2NR^8R^9$, —$NR^8SO_2$—$C_{1-4}$ alkyl, —$NR^8SO_2CF_3$, —NR⁸SO₂-phenyl, —S(O)₂CF₃, —S(O)$_p$—C$_{1-4}$ alkyl, —S(O)$_p$-phenyl, or —(CF₂)$_r$CF₃;

R$^f$ is, independently at each occurrence, H, =O, —(CH₂)$_r$—OR$^g$, F, Cl, Br, I, CN, NO₂, —NR$^{9a}$R$^{9a}$, —C(O)R$^g$, —C(O)OR$^g$, —NR$^{9a}$C(O)R$^g$, —C(O)NR$^{9a}$R$^{9a}$, —SO₂NR$^{9a}$R$^{9a}$, —NR$^{9a}$SO₂NR$^{9a}$R$^{9a}$, —NR$^{9a}$SO₂—C$_{1-4}$ alkyl, —NR$^{9a}$SO₂CF₃, —NR$^{9a}$SO₂-phenyl, —S(O)₂CF₃, —S(O)$_p$—C$_{1-4}$ alkyl, —S(O)$_p$-phenyl, —(CF₂)$_r$CF₃, C$_{1-6}$ alkyl, C$_{2-6}$ alkenyl, C$_{2-6}$ alkynyl, or —(CH₂)$_n$-phenyl;

R$^g$ is, independently at each occurrence, H, C$_{1-6}$ alkyl, or —(CH₂)$_n$-phenyl;

n, at each occurrence, is selected from 0, 1, 2, 3, and 4;
p, at each occurrence, is selected from 0, 1, and 2;
r, at each occurrence, is selected from 0, 1, 2, 3, and 4; and
s, at each occurrence, is selected from 1, 2, 3, and 4;
provided that:
(a). when group

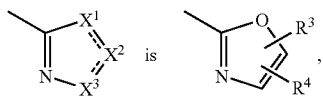

i. and when L is —NHC(O)—, R$^{14}$ does not combine with R$^{15}$ to form =O;
ii. and when L is —C(O)NH— and A is phenyl, R$^1$ is not —NHC(O)H;

(b). when group

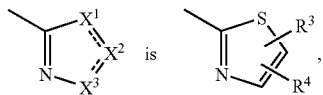

i. and when L is —NHC(O)— and R$^3$ combines with R$^4$ to form a phenyl ring fused with the thiazole, the phenyl ring is substituted with at least one R$^{3a}$;
ii. and when L is —C(O)NH— and A is phenyl, R$^1$ is not —NHC(O)H; and
(c). A is not a substituted or unsubstituted oxazolinone, thiophene, oxadiazole, or furan.

In a nineteenth aspect, the present invention includes compounds of Formula (V), within the scope of the eighteenth aspect wherein:

A is C$_{3-8}$ cycloalkyl substituted with 0-1 R$^1$ and 0-3 R$^2$, C$_{4-8}$ cycloalkenyl substituted with 0-1 R$^1$ and 0-3 R$^2$, phenyl substituted with 0-1 R$^1$ and 0-3 R$^2$, naphthyl substituted with 0-1 R$^1$ and 0-3 R$^2$, or a 5- to 10-membered heterocycle comprising: carbon atoms and 1-4 heteroatoms selected from N, O, and S(O)$_p$, wherein said heterocycle is substituted with 0-1 R$^1$ and 0-3 R$^2$; provided when A is a heterocycle containing one or more nitrogen atoms, A is not attached to L via any of the nitrogen atoms on the A ring;

Z is —C(R$^{11}$)(R$^{12}$)—;
L is —C(O)NR$^{10}$—, —NR$^{10}$C(O)—, —CH₂C(O)NR$^{10}$—, —CH₂NR$^{10}$C(O)—, —C(O)NR$^{10}$CH₂—, or —NR$^{10}$C(O)CH₂—;

R$^3$ is, independently at each occurrence, —(CH₂)$_r$C(O)NR$^8$R$^9$, —(CH₂)$_r$C(O)NR$^8$(CH₂)$_s$CO₂R$^{3b}$, —(CH₂)$_r$CO₂R$^{3b}$, —(CH₂)$_r$—C$_{3-8}$ cycloalkyl substituted with 0-2 R$^{3a}$ and 0-1 R$^{3d}$, —(CH₂)$_r$-phenyl substituted with 0-3 R$^{3a}$ and 0-1 R$^{3d}$, —(CH₂)$_r$-naphthyl substituted with 0-3 R$^{3a}$ and 0-1 R$^{3d}$, —(CH₂)$_r$-indanyl substituted with 0-3 R$^{3a}$ and 0-1 R$^{3d}$, or —(CH₂)$_r$-5-10 membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^4$ is H, F, Cl, Br, I, OCF₃, CF₃, OR$^a$, SR$^a$, CN, NO₂, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, —S(O)₂R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

R$^6$ is, independently at each occurrence, H, C$_{1-6}$ alkyl, —CH₂OR$^a$, —C(O)R$^c$, —C(O)₂R$^c$, or —(CH₂)$_r$-phenyl substituted with 0-3 R$^d$;

R$^{10}$ is, independently at each occurrence, H, C$_{1-6}$ alkyl substituted with 0-3 R$^{10a}$, —(CH₂)$_r$-phenyl substituted with 0-3 R$^d$, or —(CH₂)$_r$-5-10 membered heterocycle comprising carbon atoms and 1-4 heteroatoms selected from N, O, and S(O)$_p$, wherein said heterocycle is substituted with 0-3 R$^d$; and R$^{11}$ is C$_{1-4}$ haloalkyl, —(CH₂)$_r$C(O)NR$^8$R$^9$, C$_{1-6}$ alkyl substituted with 0-3 R$^{11a}$, C$_{2-6}$ alkenyl substituted with 0-3 R$^{11a}$, C$_{2-6}$ alkynyl substituted with 0-3 R$^{11a}$, —(CH₂)$_r$—C$_{3-10}$ carbocycle substituted with 0-3 R$^{11b}$, or —(CH₂)$_r$-5-10 membered heterocycle comprising carbon atoms and 1-4 heteroatoms selected from N, O, and S(O)$_p$, wherein said heterocycle is substituted with 0-3 R$^{11b}$.

In a twentieth aspect, the present invention includes compounds of Formula (V), within the scope of the eighteenth aspect wherein:

A is C$_{5-6}$ cycloalkyl substituted with 0-1 R$^1$ and 0-2 R$^2$, C$_{5-6}$ cycloalkenyl substituted with 0-1 R$^1$ and 0-2 R$^2$, phenyl substituted with 0-1 R$^1$ and 0-3 R$^2$, naphthyl substituted with 0-1 R$^1$ and 0-3 R$^2$, or a 5- to 10-membered heterocycle comprising: carbon atoms and 1-4 heteroatoms selected from N, O, and S(O)$_p$, wherein said heterocycle is substituted with 0-1 R$^1$ and 0-3 R$^2$; provided when A is a heterocycle containing one or more nitrogen atoms, A is not attached to L via any of the nitrogen atoms on the A ring;

R$^3$ is, independently at each occurrence, —(CH₂)$_r$C(O)NR$^8$R$^9$, —(CH₂)$_r$C(O)NR$^8$(CH₂)$_s$CO₂R$^{3b}$, —(CH₂)$_r$CO₂R$^{3b}$, —(CH₂)$_r$-phenyl substituted with 0-3 R$^{3a}$ and 0-1 R$^{3d}$, —(CH₂)$_r$-naphthyl substituted with 0-3 R$^{3a}$ and 0-1 R$^{3d}$, —(CH₂)$_r$-indanyl substituted with 0-3 R$^{3a}$ and 0-1 R$^{3d}$, or —(CH₂)$_r$-5-10 membered heterocycle comprising: carbon atoms and 1-4 heteroatoms selected from N, O, and S(O)$_p$, wherein said heterocycle is substituted with 0-3 R$^{3a}$ and 0-1 R$^{3d}$; and R$^6$ is, independently at each occurrence, H or C$_{1-6}$ alkyl.

In a twenty first aspect, the present invention includes compounds of Formula (V), within the scope of the eighteenth aspect wherein:

the group

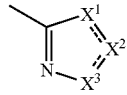

is selected from:

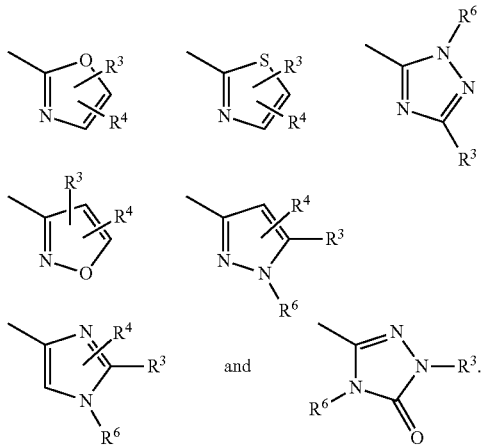

In a twenty second aspect, the present invention includes compounds of Formula (V), within the scope of the eighteenth aspect wherein:
the group

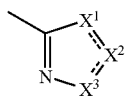

is selected from:

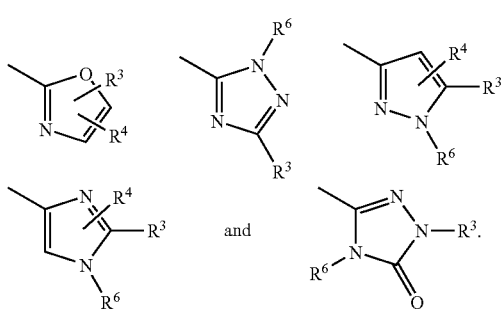

In a twenty third aspect, the present invention includes compounds of Formula (V), within the scope of the eighteenth aspect wherein.

A is substituted with 0-1 $R^1$ and 0-2 $R^2$ and selected from: $C_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;
the group

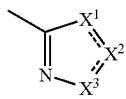

is selected from:

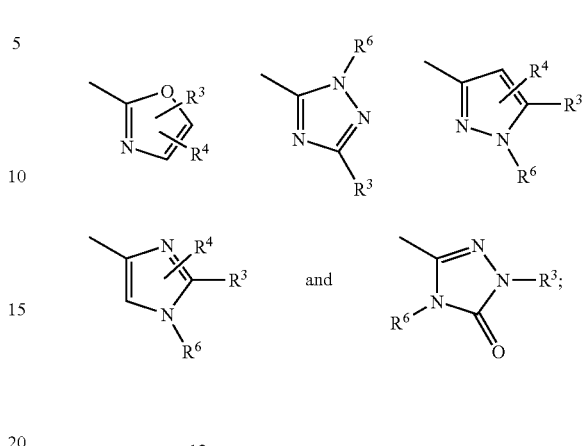

Z is —CH($R^{12}$)—;

L is —C(O)N$R^{10}$—, —N$R^{10}$C(O)—, —CH$_2$C(O)N$R^{10}$—, —CH$_2$N$R^{10}$C(O)—, —C(O)N$R^{10}$CH$_2$—, or —N$R^{10}$C(O)CH$_2$—;

$R^3$ is, independently at each occurrence, —(CH$_2$)$_r$C(O)N$R^8R^9$, —(CH$_2$)$_r$C(O)N$R^8$(CH$_2$)$_s$CO$_2R^{3b}$, —(CH$_2$)$_r$CO$_2R^{3b}$, —(CH$_2$)$_r$-phenyl substituted with 0-3 $R^{3a}$ and 0-1 $R^{3d}$, —(CH$_2$)$_r$-naphthyl substituted with 0-3 $R^{3a}$ and 0-1 $R^{3d}$, —(CH$_2$)$_r$-indanyl substituted with 0-3 $R^{3a}$ and 0-1 $R^{3d}$ or —(CH$_2$)$_r$-5-10 membered heterocycle comprising: carbon atoms and 1-4 heteroatoms selected from N, O, and S(O)$_p$, and substituted with 0-3 $R^{3a}$ and 0-1 $R^{3d}$;

$R^4$ is, independently at each occurrence, H, =O, F, Cl, Br, I, OCF$_3$, CF$_3$, CN, NO$_2$, —C(O)$R^a$, —C(O)O$R^a$, —N$R^7R^8$, —C(O)N$R^8R^9$, —N$R^7$C(O)$R^b$, —S(O)$_p$N$R^8R^9$, —N$R^8$S(O)$_pR^c$, —S(O)$R^c$, —S(O)$_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, phenyl substituted with 0-2 $R^{4b}$, or a 5-10 membered heterocycle comprising: carbon atoms and 1-4 heteroatoms selected from N, O, and S(O)$_p$, and substituted with 0-3 $R^{4b}$;

$R^6$ is H, $C_{1-6}$ alkyl, or —(CH$_2$)$_r$-phenyl substituted with 0-3 $R^d$;

$R^{10}$ is, independently at each occurrence, H, $C_{1-6}$ alkyl substituted with 0-2 $R^{10a}$, —(CH$_2$)$_r$-phenyl substituted with 0-2 $R^d$, or —(CH$_2$)$_r$-5-10 membered heterocycle comprising carbon atoms and 1-4 heteroatoms selected from N, O, and S(O)$_p$, wherein said heterocycle is substituted with 0-2 $R^d$; and $R^{12}$ is, independently at each occurrence, H, F, or Me.

In another aspect, the present invention includes compounds of Formula (V), within the scope of the twenty second aspect wherein.
the group

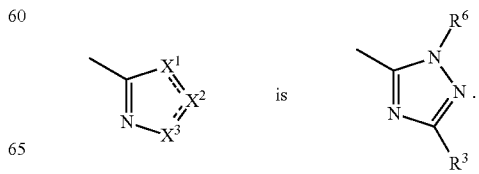

In a twenty fourth aspect, the present invention includes a compound of Formula (VI):

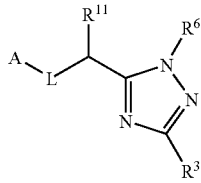

(VI)

or its stereoisomers, tautomers, pharmaceutically acceptable salts, solvates, or prodrugs thereof, within the scope of the eighteenth aspect wherein:

$R^3$ is —$(CH_2)_rC(O)NR^8R^9$, —$(CH_2)_sC(O)NR^8(CH_2)_r$ $CO_2R^{3b}$, —$(CH_2)_rCO_2R^{3b}$, —$(CH_2)_r$-phenyl substituted with 0-3 $R^{3a}$ and 0-1 $R^{3d}$, —$(CH_2)_r$-naphthyl substituted with 0-2 $R^{3a}$, —$(CH_2)_r$-indanyl substituted with 0-2 $R^{3a}$, or —$(CH_2)_r$-5-10 membered heterocycle comprising: carbon atoms and 1-4 heteroatoms selected from N, O, and S(O)$_p$, wherein said heterocycle is substituted with 0-3 $R^{3a}$ and 0-1 $R^{3d}$;

$R^6$ is, independently at each occurrence, H, $C_{1-6}$ alkyl, —$CH_2OR^a$, —$C(O)R^c$, —$C(O)_2R^c$, or —$(CH_2)_r$-phenyl substituted with 0-3 $R^d$;

$R^{10}$ is, independently at each occurrence, H, $C_{1-6}$ alkyl substituted with 0-3 $R^{10a}$, —$(CH_2)_r$—$C_{3-10}$ carbocycle substituted with 0-3 $R^d$, or —$(CH_2)_r$-5-10 membered heterocycle comprising carbon atoms and 1-4 heteroatoms selected from N, O, and S(O)$_p$, wherein said heterocycle is substituted with 0-3 $R^d$; and $R^{11}$ is $C_{1-4}$ haloalkyl, —$(CH_2)_rC(O)NR^8R^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CH_2)_r$—$C_{3-10}$ carbocycle substituted with 0-3 $R^{11b}$, or —$(CH_2)_r$-5-10 membered heterocycle comprising carbon atoms and 1-4 heteroatoms selected from N, O, and S(O)$_p$, wherein said heterocycle is substituted with 0-3 $R^{11b}$.

In a twenty fifth aspect, the present invention includes compounds of Formula (VI), within the scope of the twenty fourth aspect wherein:

$R^1$ is, independently at each occurrence, F, Cl, Me, Et, —$NH_2$, —$C(=NH)NH_2$, —$C(O)NH_2$, —$CH_2NH_2$, —$CH_2CH_2NH_2$, —$CH_2NHCO_2Bn$, —$CH_2NHCO_2(t\text{-}Bu)$, —$CH(Me)NH_2$, —$CMe_2NH_2$, —$NHEt$, —$NHCO_2(t\text{-}Bu)$, —$NHCO_2Bn$, —$SO_2NH_2$, $OR^a$, or —$CH_2R^{1a}$;

$R^3$ is —$CO_2H$, —$CO_2Me$, —$C(O)NHCH_2CO_2H$, —$C(O)NHCH_2CO_2Et$, —$C(O)NH_2$, —$C(O)NHMe$, —$C(O)NHBn$, —$(CH_2)_r$-phenyl substituted with 0-2 $R^{3a}$ and 0-1 $R^{3d}$, naphthyl substituted with 0-2 $R^{3a}$ and 0-1 $R^{3d}$, indanyl substituted with 0-2 $R^{3a}$ and 0-1 $R^{3d}$, or a —$(CH_2)_r$-5- to 10-membered heterocycle comprising: carbon atoms and 1-2 heteroatoms selected from N, O, and S(O)$_p$, wherein said heterocycle is substituted with 0-2 $R^{3a}$ and 0-1 $R^{3d}$;

$R^6$ is H;

$R^{10}$ is, independently at each occurrence, H, Me, benzyl, phenethyl, —$CH_2CH_2CO_2H$, —$CH_2CH_2CO_2Me$, —$CH_2CH_2CO_2Et$, —$CH_2CH_2CONH_2$, or —$CH_2CH_2CONHCH_2CH_2Ph$; and $R^{11}$ is $C_{1-6}$ alkyl, —$CH_2CONR^8R^9$, —$CH_2CH_2CONR^8R^9$, —$CH_2OBn$, —$CH_2SBn$, —$(CH_2)_r$—$C_{3-7}$ cycloalkyl substituted with 0-2 $R^{11b}$, —$(CH_2)_r$-phenyl substituted with 0-2 $R^{11b}$, —$(CH_2)_r$-naphthyl substituted with 0-2 $R^{11b}$, or —$(CH_2)_r$-5-10 membered heterocycle comprising carbon atoms and 1-4 heteroatoms selected from N, O, and S(O)$_p$, wherein said heterocycle is substituted with 0-2 $R^{11b}$.

In a twenty sixth aspect, the present invention includes a compound of Formula (VII):

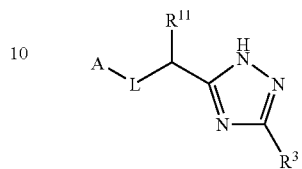

(VII)

or its stereoisomers, tautomers, pharmaceutically acceptable salts, solvates, or prodrugs thereof, within the scope of the eighteenth aspect wherein:

A is substituted with 0-2 $R^1$ and 0-1 $R^2$ and selected from: $C_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

L is —$C(O)NH$— or —$NHC(O)$—;

$R^1$ is, independently at each occurrence, F, Cl, Me, Et, —$NH_2$, —$C(=NH)NH_2$, —$C(O)NH_2$, —$CH_2NH_2$, —$CH_2NHCO_2Bn$, —$CH_2NHCO_2(t\text{-}Bu)$, —$CH(Me)NH_2$, —$CMe_2NH_2$, —$NHEt$, —$NHCO_2(t\text{-}Bu)$, —$NHCO_2Bn$, —$SO_2NH_2$, $OR^a$, or —$CH_2R^{1a}$;

$R^3$ is —$CO_2H$, —$CO_2Me$, —$C(O)NHCH_2CO_2H$, —$C(O)NHCH_2CO_2Et$, —$C(O)NH_2$, —$C(O)NHMe$, —$C(O)NHBn$, phenyl substituted with 0-2 $R^{3a}$, naphthyl substituted with 0-2 $R^{3a}$, indanyl substituted with 0-2 $R^{3a}$, or a 5- to 10-membered heterocycle comprising: carbon atoms and 1-2 heteroatoms selected from N, O, and S(O)$_p$, wherein said heterocycle is substituted with 0-2 $R^{3a}$;

$R^4$ is H, F, Cl, Br, $CF_3$, $CO_2H$, $CO_2Me$, $CO_2Et$, $C_{1-6}$ alkyl substituted with 0-2 $R^{4a}$, phenyl substituted with 0-2 $R^{4b}$, or 5-10 membered heterocycle comprising: carbon atoms and 1-4 heteroatoms selected from N, O, and S(O)$_p$, wherein said heterocycle is substituted with 0-2 $R^{4b}$;

$R^{11}$ is $C_{1-6}$ alkyl, —$CH_2CONR^8R^9$, —$CH_2CH_2CONR^8R^9$, —$CH_2OBn$, —$CH_2SBn$, —$(CH_2)_r$—$C_{3-7}$ cycloalkyl substituted with 0-2 $R^{11b}$, —$(CH_2)_r$-phenyl substituted with 0-2 $R^{11b}$, —$(CH_2)_r$-naphthyl substituted with 0-2 $R^{11b}$, or —$(CH_2)_r$-5- to 10-membered heteroaryl substituted with 0-2 $R^{11b}$ and selected from thiazolyl, oxazolyl, triazolyl, tetrazolyl, imidazolyl, pyridyl, pyrimidinyl, pyrazinyl, pyridazinyl, indolyl, isoindolyl, indolinyl, isoindolinyl, benzimidazolyl, benzothiazolyl, quinolinyl, isoquinolinyl, tetrahydroquinolinyl, and tetrahydroisoquinolinyl; and $R^{11b}$ is, independently at each occurrence, H, F, Cl, Br, $CF_3$, OMe, OEt, O(i-Pr), $OCF_3$, $OCHF_2$, CN, OPh, OBn, $NO_2$, —$NH_2$, —$C(O)R^a$, —$C(O)OR^a$, —$C(O)NR^7R^8$, —$NR^7C(O)R^b$, —$NR^8C(O)_2R^c$, —$S(O)_pNR^8R^9$, —$NR^8S(O)_pR^c$, —$SO_2R^c$, $C_1$-$C_4$-alkyl, Ph, or Bn;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 $R^g$.

In a twenty seventh aspect, the present invention includes compounds of Formula (V), within the scope of the twenty sixth aspect wherein:

A is 4-CH$_2$NH$_2$-cyclohexyl or 4-amidino-phenyl; and

R$^3$ is phenyl, 3-CN-phenyl, 4-CN-phenyl, 3-Br-phenyl, 4-Br-phenyl, 3-OMe-phenyl, 4-OMe-phenyl, 3-CF$_3$-phenyl, 4-CF$_3$-phenyl, 3-CO$_2$H-phenyl, 4-CO$_2$H-phenyl, 4-CO$_2$Me-phenyl, 4-CH$_2$CO$_2$H-phenyl, 4-CH$_2$CO$_2$Me-phenyl, 3-CONH$_2$-phenyl, 4-CONH$_2$-phenyl, 4-CONHMe-phenyl, 4-CON(Me)$_2$-phenyl, 4-CH$_2$CONH$_2$-phenyl, 4-amidino-phenyl, or 2,4-diF-phenyl.

In a twenty eighth aspect, the present invention includes, inter alia, a method for treating a thromboembolic or an inflammatory disorder, comprising: administering to a patient in need thereof a therapeutically effective amount of at least one compound of Formula (I):

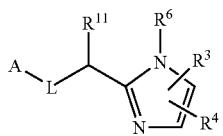

(I)

or its stereoisomers, tautomers, pharmaceutically acceptable salts, solvates, or prodrugs thereof, wherein:

A is C$_{3-10}$ carbocycle substituted with 0-3 R$^1$ and 0-1 R$^2$, or a 5- to 12-membered heterocycle comprising: carbon atoms and 1-4 heteroatoms selected from N, O, and S(O)$_p$, wherein said heterocycle is substituted with 0-3 R$^1$ and 0-1 R$^2$;

L is —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, —NR$^{10}$C(O)CH$_2$—, —S(O)$_2$NR$^{10}$—, —NR$^{10}$S(O)$_2$—, —CH$_2$S(O)$_2$NR$^{10}$—, —CH$_2$NR$^{10}$S(O)$_2$—, —S(O)$_2$NR$^{10}$CH$_2$—, —NR$^{10}$S(O)$_2$CH$_2$—, —CH$_2$CH$_2$—, —CH$_2$CH$_2$CH$_2$—, —CH$_2$NR$^7$—, —NR$^7$CH$_2$—, —CH$_2$CH$_2$NR$^7$—, —NR$^7$CH$_2$CH$_2$—, —CH$_2$NR$^7$CH$_2$—, —CH$_2$O—, —OCH$_2$—, —CH$_2$S(O)$_p$—, —S(O)$_p$CH$_2$—, —CH$_2$CH$_2$O—, —OCH$_2$CH$_2$—, —CH$_2$OCH$_2$—, —CH$_2$CH$_2$S(O)$_p$—, —S(O)$_p$CH$_2$CH$_2$—, —CH$_2$S(O)$_p$CH$_2$—, —CH$_2$C(O), —CH$_2$C(O)CH$_2$—, —CH$_2$CH$_2$C(O)—, —C(O)CH$_2$CH$_2$—, or —C(O)CH$_2$—;

R$^1$ is, independently at each occurrence, —NH$_2$, —NH(C$_1$-C$_3$ alkyl), —N(C$_1$-C$_3$ alkyl)$_2$, —C(=NH)NH$_2$, —C(O)NR$^8$R$^9$, —S(O)$_p$NR$^8$R$^9$, —(CH$_2$)$_r$NR$^7$R$^8$, —(CH$_2$)$_r$NR$^7$CO$_2$R$^a$, —CH$_2$NH$_2$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_1$-C$_3$ alkyl), —CH$_2$CH$_2$N(C$_{1-3}$ alkyl)$_2$, —CH(C$_{1-4}$ alkyl)NH$_2$, —C(C$_{1-4}$ alkyl)$_2$NH$_2$, —C(=NR$^{8a}$)NR$^7$R$^8$, —NHC(=NR$^{8a}$)NR$^7$R$^8$, =NR$^8$, —NR$^8$CR$^8$(=NR$^{8a}$), F, Cl, Br, I, OCF$_3$, CF$_3$, —(CH$_2$)$_r$OR$^a$, —(CH$_2$)$_r$SR$^a$, CN, 1-NH$_2$-1-cyclopropyl, or C$_{1-6}$ alkyl substituted with 0-1 R$^{1a}$;

R$^{1a}$ is H, —C(=NR$^{8a}$)NR$^7$R$^8$, —NHC(=NR$^{8a}$)NR$^7$R$^8$, —NR$^8$CH(=NR$^{8a}$), —NR$^7$R$^8$, —C(O)NR$^8$R$^9$, F, OCF$_3$, CF$_3$, OR$^a$, SR$^a$, CN, —NR$^9$SO$_2$NR$^8$R$^9$, —NR$^8$SO$_2$R$^c$, —S(O)$_p$—C$_{1-4}$ alkyl, —S(O)$_p$-phenyl, or —(CF$_2$)$_r$CF$_3$;

R$^2$ is, independently at each occurrence, H, =O, F, Cl, Br, I, OCF$_3$, CF$_3$, CHF$_2$, CN, NO$_2$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_2$NR$^8$R$^9$, —NR$^8$S(O)$_2$R$^c$, —S(O)R$^c$, —S(O)$_2$R$^c$, C$_{1-6}$ alkyl substituted with 0-2 R$^{2a}$, C$_{2-6}$ alkynyl substituted with 0-2 R$^{2a}$, —(CH$_2$)$_r$—C$_{3-10}$ carbocycle substituted with 0-3 R$^{2b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{2b}$;

R$^{2a}$ is, independently at each occurrence, H, F, Cl, Br, I, =O, =NR$^8$, CN, OCF$_3$, CF$_3$, OR$^a$, SR$^a$, —NR$^7$R$^8$, —C(O)NR$^8$R$^9$, —NR$^7$C(O)R$^b$, —S(O)$_p$NR$^8$R$^9$, —NR$^8$SO$_2$R$^c$, —S(O)R$^c$, or —S(O)$_2$R$^c$;

R$^{2b}$ is, independently at each occurrence, H, F, Cl, Br, I, =O, =NR$^8$, CN, NO$_2$, CF$_3$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_2$NR$^8$R$^9$, —S(O)$_2$R$^c$, —NR$^8$SO$_2$NR$^8$R$^9$, —NR$^8$SO$_2$R$^c$, —(CF$_2$)$_r$CF$_3$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkoxy-;

alternately, when R$^1$ and R$^2$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and S(O)$_p$, wherein said carbocycle or heterocycle is substituted with 0-2 R$^{2b}$;

R$^3$ is F, Cl, Br, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$—C$_{3-10}$ carbocycle substituted with 0-3 R$^{3a}$ and 0-1 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^{3a}$ is, independently at each occurrence, =O, F, Cl, Br, I, OCF$_3$, CF$_3$, NO$_2$, CN, —(CH$_2$)$_r$OR$^{3b}$, SR$^{3b}$, —(CH$_2$)$_r$NR$^7$R$^8$, C(=NR$^{8a}$)NR$^8$R$^9$, —NHC(=NR$^{8a}$)NR$^7$R$^8$, —NR$^8$CR$^8$(=NR$^{8a}$), —(CH$_2$)$_r$NR$^8$C(O)R$^{3b}$, =NR$^8$, —(CH$_2$)$_r$NR$^8$C(O)R$^{3b}$, —(CH$_2$)$_r$NR$^8$C(O)$_2$R$^{3b}$, —(CH$_2$)$_r$S(O)$_p$NR$^8$R$^9$, —(CH$_2$)$_r$NR$^8$S(O)$_p$R$^{3c}$, —S(O)$_p$R$^{3c}$, —S(O)$_p$R$^{3c}$, C$_{1-4}$ alkyl-C(O)—, —(CH$_2$)$_r$CO$_2$R$^{3b}$, —(CH$_2$)$_r$C(O)NR$^8$R$^9$, —(CH$_2$)$_r$OC(O)NR$^8$R$^9$, —NHCOCF$_3$, —NHSO$_2$CF$_3$, —SO$_2$NHR$^{3b}$, —SO$_2$NHCOR$^{3c}$, —SO$_2$NHCO$_2$R$^{3c}$, —CONHSO$_2$R$^{3c}$, —NHSO$_2$R$^{3c}$, —CONHOR$^{3b}$, C$_{1-4}$ haloalkyl, C$_{1-4}$ haloalkoxy-, C$_{1-6}$ alkyl substituted by R$^{3d}$, C$_{2-6}$ alkenyl substituted by R$^{3d}$, C$_{2-6}$ alkynyl substituted by R$^{3d}$, C$_{3-6}$ cycloalkyl substituted by 0-1 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

alternately, when two R$^{3a}$ groups are located on adjacent atoms, they can be taken together with the atoms to which they are attached to form a C$_{3-10}$ carbocycle substituted with 0-2 R$^{3d}$ or a 5- to 10-membered heterocycle comprising: carbon atoms and 1-4 heteroatoms selected from N, O, and S(O)$_p$, wherein said heterocycle is substituted with 0-2 R$^{3d}$;

R$^{3b}$ is, independently at each occurrence, H, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3c}$ is, independently at each occurrence, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3d}$ is, independently at each occurrence, H, =O, —(CH$_2$)$_r$OR$^a$, F, Cl, Br, CN, NO$_2$, —(CH$_2$)$_r$NR$^7$R$^8$, —C(O)R$^a$, —C(O)OR$^a$, —OC(O)R$^a$, —NR$^7$C(O)R$^b$, —C(O)NR$^8$R$^9$, —SO$_2$NR$^8$R$^9$, —NR$^8$SO$_2$NR$^8$R$^9$, —NR$^8$SO$_2$R$^c$, —S(O)$_p$R$^c$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^4$ is H, =O, F, Cl, Br, I, $OCF_3$, $CF_3$, $OR^a$, $SR^a$, CN, $NO_2$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, —$NR^8S(O)_pR^c$, —$S(O)R^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-6}$ alkyl, $OR^a$, $SR^a$, $CF_3$, CN, $NO_2$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, —$NR^8S(O)_2R^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, $CF_3$, —$SO_2R^c$, —$NR^7R^8$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkoxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl, $C_{1-4}$ haloalkyl, —$CH_2OR^a$, —$C(O)R^c$, —$C(O)_2R^c$, —$S(O)_2R^c$, or —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, or —$(CH_2)_n$-phenyl, or —$(CH_2)_n$-5-10 membered heterocycle comprising carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{8a}$ is, independently at each occurrence, H, OH, $C_{1-6}$ alkyl, $C_{1-4}$ alkoxy, $(C_{6-10}$ aryl)-$C_{1-4}$ alkoxy, —$(CH_2)_n$-phenyl, —$(CH_2)_n$-(5-10 membered heteroaryl), —$C(O)R^c$, —$C(O)_2R^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said phenyl, aryl, and heteroaryl is optionally substituted with 0-2 $R^f$;

$R^9$ is, independently at each occurrence, H, $C_{1-6}$ alkyl, or —$(CH_2)_r$-phenyl; wherein said alkyl and phenyl are optionally substituted with 0-2 $R^f$;

$R^{9a}$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-3 $R^{10a}$, $C_{2-6}$ alkenyl substituted with 0-3 $R^{10a}$, $C_{2-6}$ alkynyl substituted with 0-3 $R^{10a}$, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)OR^a$, —$NR^7R^8$, —$C(O)NR^7R^8$, —$NR^7C(O)R^b$, —$S(O)_pNR^8R^9$, —$NR^8SO_2R^c$—, —$S(O)R^c$, or —$S(O)_2R^c$;

$R^{11}$ is $C_{1-4}$ haloalkyl, —$(CH_2)_rC(O)NR^8R^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CR^{14}R^{15})_r$—$C_{3-10}$ carbocycle substituted with 0-3 $R^{11b}$, or —$(CR^{14}R^{15})_r$-5- to 10-membered heterocycle comprising carbon atoms and 1-4 heteroatoms selected from N, O, and $S(O)_p$, wherein said heterocycle is substituted with 0-3 $R^{11b}$;

$R^{11a}$ is, independently at each occurrence, H, =O, $C_{1-4}$ alkyl, $OR^a$, $CF_3$, $SR^a$, F, CN, $NO_2$, —$NR^7R^8$, —$C(O)NR^7R^8$, —$NR^7C(O)R^b$, —$S(O)_pNR^8R^9$, —$NR^8S(O)_pR^c$, —$C(O)R^a$, —$C(O)OR^a$, —$S(O)_pR^c$, $C_{3-6}$ cycloalkyl, $C_{1-4}$ haloalkyl, $C_{1-4}$ haloalkoxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$C(O)R^a$, —$C(O)OR^a$, —$SOR^c$, —$SO_2R^c$, —$NR^7R^8$, —$C(O)NR^7R^8$, —$NR^7C(O)R^b$, —$NR^8C(O)_2R^c$, —$S(O)_pNR^8R^9$, —$NR^8S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkoxy-, —$(CH_2)_r$—$C_{3-10}$ carbocycle substituted with 0-3 $R^d$, or —$(CH_2)_r$-5-10 membered heterocycle comprising: carbon atoms and 1-4 heteroatoms selected from N, O, and $S(O)_p$, wherein said heterocycle is substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{14}$ and $R^{15}$ are, independently at each occurrence, H, F, or $C_{1-4}$ alkyl;

alternately, $R^{14}$ combines with $R^{15}$ to form =O;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10 membered heterocycle comprising: carbon atoms and 1-4 heteroatoms selected from N, O, and $S(O)_p$; wherein said cycloalkyl, aryl and heterocycle groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^d$, or —$(CH_2)_r$-5-10 membered heterocycle comprising: carbon atoms and 1-4 heteroatoms selected from N, O, and $S(O)_p$, wherein said heterocycle is substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, $(C_{6-10}$ aryl)-$C_{1-4}$ alkyl, or (5- to 10-membered heteroaryl)-$C_{1-4}$ alkyl, wherein said aryl and heteroaryl groups are optionally substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$ —C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^8$R$^9$, —C(O)R$^a$, —C(O)OR$^a$, —OC(O) R$^a$, —NR$^8$C(O)R$^a$, —C(O)NR$^7$R$^8$, —SO$_2$NR$^8$R$^9$, NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$—OR$^g$, F, Cl, Br, I, CN, NO$_2$, —NR$^{9a}$R$^{9a}$, —C(O)R$^g$, —C(O)OR$^g$, —NR$^{9a}$C(O)R$^g$, —C(O)NR$^{9a}$R$^{9a}$, —SO$_2$NR$^{9a}$R$^{9a}$, —NR$^{9a}$SO$_2$NR$^{9a}$R$^{9a}$, —NR$^{9a}$SO$_2$—C$_{1-4}$ alkyl, —NR$^{9a}$SO$_2$CF$_3$, —NR$^{9a}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2;
r, at each occurrence, is selected from 0, 1, 2, 3, and 4; and
s, at each occurrence, is selected from 1, 2, 3, and 4.

In a twenty ninth aspect, the present invention provides a method for treating a thromboembolic or an inflammatory disorder, comprising: administering to a patient in need thereof a therapeutically effective amount of at least one compound of Formula (I), within the scope of the twenty eighth aspect wherein:

L is —C(O)NR$^{10}$—, —NR$^{10}$C(O)—, —CH$_2$CONR$^{10}$—, or —NR$^{10}$COCH$_2$—;

R$^3$ is —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$-phenyl substituted with 0-3 R$^{3a}$ and 0-1 R$^{3d}$, —(CH$_2$)$_r$-naphthyl substituted with 0-3 R$^{3a}$ and 0-1 R$^{3d}$, —(CH$_2$)$_r$-indanyl substituted with 0-3 R$^{3a}$ and 0-1 R$^{3d}$, or —(CH$_2$)$_r$-5-10 membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^4$ is H, F, Cl, Br, I, OCF$_3$, CF$_3$, OR$^a$, SR$^a$, CN, NO$_2$, —C(O)R$^a$, —C(O)OR$^a$, —NR$^7$R$^8$, —C(O)NR$^8$R$^9$, —NR$^7$C (O)R$^b$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

R$^6$ is H, C$_{1-6}$ alkyl, —CH$_2$OR$^a$, or —(CH$_2$)$_r$-phenyl substituted with 0-3 R$^d$;

R$^{10}$ is, independently at each occurrence, H, C$_{1-6}$ alkyl substituted with 0-2 R$^{10a}$, —(CH$_2$)$_r$-phenyl substituted with 0-2 R$^d$, or —(CH$_2$)$_r$-5-10 membered heterocycle comprising carbon atoms and 1-4 heteroatoms selected from N, O, and S(O)$_p$, wherein said heterocycle is substituted with 0-2 R$^d$; and R$^{11}$ is C$_{1-4}$ haloalkyl, —(CH$_2$)$_r$—CONR$^8$R$^9$, C$_{1-6}$ alkyl substituted with 0-2 R$^{11a}$, C$_{2-6}$ alkenyl substituted with 0-2 R$^{11a}$, C$_{2-6}$ alkynyl substituted with 0-2 R$^{11a}$, —(CH$_2$)$_r$—C$_{3-10}$ carbocycle substituted with 0-3 R$^{11b}$, or —(CH$_2$)$_r$-5-10 membered heterocycle comprising carbon atoms and 1-4 heteroatoms selected from N, O, and S(O)$_p$, wherein said heterocycle is substituted with 0-3 R$^{11b}$.

In a thirtieth aspect, the present invention provides a method for treating a thromboembolic or an inflammatory disorder, comprising: administering to a patient in need thereof a therapeutically effective amount of at least one compound of Formula (I), within the scope of the twenty eighth aspect wherein:

R$^1$ is, independently at each occurrence, F, Cl, Me, Et, —NH$_2$, —C(=NH)NH$_2$, —C(O)NH$_2$, —CH$_2$NH$_2$, —CH$_2$CH$_2$NH$_2$, —CH$_2$NHCO$_2$Bn, —CH$_2$NHCO$_2$(t-Bu), —CH(Me)NH$_2$, —C(Me)$_2$NH$_2$, —NHEt, —NHCO$_2$(t-Bu), —NHCO$_2$Bn, —SO$_2$NH$_2$, OR$^a$, or —CH$_2$OR$^{1a}$;

R$^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, —(CH$_2$)$_r$-phenyl substituted with 0-2 R$^{3a}$ and 0-1 R$^{3d}$, naphthyl substituted with 0-2 R$^{3a}$ and 0-1 R$^{3d}$, indanyl substituted with 0-2 R$^{3a}$ and 0-1 R$^{3d}$, or —(CH$_2$)$_r$-5-10 membered heterocycle comprising: carbon atoms and 1-4 heteroatoms selected from N, O, and S(O)$_p$, wherein said heterocycle is substituted with 0-2 R$^{3a}$ and 0-1 R$^{3d}$;

R$^4$ is H, F, Cl, Br, OMe, NH$_2$, CF$_3$, CO$_2$H, CO$_2$Me, CO$_2$Et, —CONR$^8$R$^9$, C$_{1-6}$ alkyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

R$^6$ is H, Me, benzyl, or phenethyl;

R$^{10}$ is, independently at each occurrence, H, Me, benzyl, phenethyl, —CH$_2$CH$_2$CO$_2$H, —CH$_2$CH$_2$CO$_2$Me, —CH$_2$CH$_2$CO$_2$Et, —CH$_2$CH$_2$CONH$_2$, or —CH$_2$CH$_2$CONHCH$_2$CH$_2$Ph; and R$^{11}$ is C$_{1-6}$ alkyl, —CH$_2$CONR$^8$R$^9$, —CH$_2$CH$_2$CONR$^8$R$^9$, —CH$_2$OBn, —CH$_2$SBn, —(CH$_2$)$_r$—C$_{3-7}$ cycloalkyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5-10 membered heterocycle comprising carbon atoms and 1-4 heteroatoms selected from N, O, and S(O)$_p$, wherein said heterocycle is substituted with 0-2 R$^{11b}$.

In a thirty first aspect, the present invention provides a method for treating a thromboembolic or an inflammatory disorder, comprising: administering to a patient in need thereof a therapeutically effective amount of at least one compound of Formula (II):

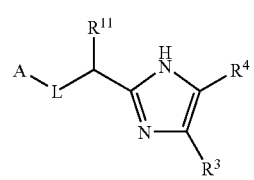

or its stereoisomers, tautomers, pharmaceutically acceptable salts, solvates, or prodrugs thereof, within the scope of the twenty eighth aspect wherein:

A is substituted with 0-1 R$^1$ and 0-2 R$^2$ and selected from: C$_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

L is —C(O)NH—, —C(O)NMe-, —C(O)N(benzyl)-, —C(O)N(phenethyl)-, —NHC(O)—, —S(O)$_2$NH—, —CH$_2$C(O)NH—, —C(O)NHCH$_2$—, —CH$_2$NHC(O)— or —NHC(O)CH$_2$—;

$R^1$ is, independently at each occurrence, F, Cl, Me, Et, —NH$_2$, —C(=NH)NH$_2$, —C(O)NH$_2$, —CH$_2$NH$_2$, —CH$_2$NHCO$_2$Bn, —CH$_2$NHCO$_2$(t-Bu), —CH(Me)NH$_2$, —CMe$_2$NH$_2$, —NHEt, —NHCO$_2$(t-Bu), —NHCO$_2$Bn, —SO$_2$NH$_2$, OR$^a$, or —CH$_2$R$^{1a}$;

$R^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, phenyl substituted with 0-2 R$^{3a}$, naphthyl substituted with 0-2 R$^{3a}$, indanyl substituted with 0-2 R$^{3a}$, or a 5- to 10-membered heterocycle comprising: carbon atoms and 1-2 heteroatoms selected from N, O, and S(O)$_p$, wherein said heterocycle is substituted with 0-2 R$^{3a}$;

$R^4$ is H, F, Cl, Br, OMe, NH$_2$, CF$_3$, CO$_2$H, CO$_2$Me, CO$_2$Et, C$_{1-6}$ alkyl substituted with 0-2 R$^{4a}$, phenyl substituted with 0-2 R$^{4b}$, or 5-10 membered heterocycle comprising: carbon atoms and 1-4 heteroatoms selected from N, O, and S(O)$_p$, wherein said heterocycle is substituted with 0-2 R$^{4b}$;

$R^{11}$ is C$_{1-6}$ alkyl, —CH$_2$CONR$^8$R$^9$, —CH$_2$CH$_2$CONR$^8$R$^9$, —CH$_2$OBn, —CH$_2$SBn, —(CH$_2$)$_r$—C$_{3-7}$ cycloalkyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5- to 10-membered heteroaryl substituted with 0-2 R$^{11b}$ and selected from thiazolyl, oxazolyl, triazolyl, tetrazolyl, imidazolyl, pyridyl, pyrimidinyl, pyrazinyl, pyridazinyl, indolyl, isoindolyl, indolinyl, isoindolinyl, benzimidazolyl, benzothiazolyl, quinolinyl, isoquinolinyl, tetrahydroquinolinyl, and tetrahydroisoquinolinyl; and $R^{11b}$ is, independently at each occurrence, H, F, Cl, Br, CF$_3$, OMe, OEt, O(i-Pr), OCF$_3$, OCHF$_2$, CN, OPh, OBn, NO$_2$, —NH$_2$, —C(O)R$^a$, —C(O)OR$^a$, —C(O)NR$^7$R$^8$, —NR$^7$C(O)R$^b$, —NR$^8$C(O)$_2$R$^c$, —S(O)$_p$NR$^8$R$^9$, —NR$^8$S(O)$_p$R$^c$, —SO$_2$R$^c$, C$_1$-C$_4$-alkyl, Ph, or Bn;

alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 R$^g$.

In a thirty second aspect, the present invention provides, inter alia, a method for treating a thromboembolic or an inflammatory disorder, comprising: administering to a patient in need thereof a therapeutically effective amount of at least one compound of Formula (V):

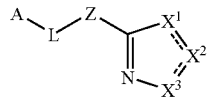
(V)

or its stereoisomers, tautomers, pharmaceutically acceptable salts, solvates, or prodrugs thereof, wherein:

A is C$_{3-10}$ carbocycle substituted with 0-3 R$^1$ and 0-1 R$^2$, or a 5- to 12-membered heterocycle comprising: carbon atoms and 1-4 heteroatoms selected from N, O, and S(O)$_p$, wherein said heterocycle is substituted with 0-3 R$^1$ and 0-1 R$^2$;

$X^1$, $X^2$, and $X^3$ are independently CR$^3$, CR$^4$, CR$^4$R$^5$, O, S(O)$_p$, N, NR$^3$, NR$^6$, or C(O); provided that no S—S, S—O, or O—O bond is present in the ring;

provided that

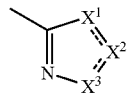

is other than

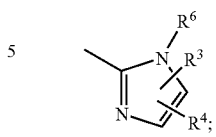

Z is —C(R$^{11}$)(R$^{12}$)—, —C(R$^{11}$)(R$^{12}$)—(CH$_2$)—, —NR$^{13}$—, or —NR$^{13}$CH$_2$—;

L is —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, —NR$^{10}$C(O)CH$_2$—, —S(O)$_2$NR$^{10}$—, —NR$^{10}$S(O)$_2$—, —CH$_2$S(O)$_2$NR$^{10}$—, —CH$_2$NR$^{10}$S(O)$_2$—, —S(O)$_2$NR$^{10}$CH$_2$—, —NR$^{10}$S(O)$_2$CH$_2$—, —CH$_2$CH$_2$—, —CH$_2$CH$_2$CH$_2$—, —CH$_2$NR$^7$—, —NR$^7$CH$_2$—, —CH$_2$CH$_2$NR$^7$—, —NR$^7$CH$_2$CH$_2$, —CH$_2$NR$^7$CH$_2$—, —CH$_2$O—, —OCH$_2$—, —CH$_2$S(O)$_p$—, —S(O)$_p$CH$_2$—, —CH$_2$CH$_2$O—, —OCH$_2$CH$_2$—, —CH$_2$OCH$_2$—, —CH$_2$CH$_2$S(O)$_p$—, —S(O)$_p$CH$_2$CH$_2$—, —CH$_2$S(O)$_p$CH$_2$—, —CH$_2$C(O), —CH$_2$C(O)CH$_2$—, —CH$_2$CH$_2$C(O)—, —C(O)CH$_2$CH$_2$—, or —C(O)CH$_2$—;

$R^1$ is, independently at each occurrence, —NH$_2$, —NH(C$_{1-3}$ alkyl), —N(C$_{1-3}$ alkyl)$_2$, —C(=NH)NH$_2$, —C(O)NR$^8$R$^9$, —S(O)$_p$NR$^8$R$^9$, —(CH$_2$)$_r$NR$^7$R$^8$, —(CH$_2$)$_r$NR$^7$C(O)OR$^a$, —CH$_2$NH$_2$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —CH(C$_{1-4}$ alkyl)NH$_2$, —C(C$_{1-4}$ alkyl)$_2$NH$_2$, —C(=NR$^{8a}$)NR$^7$R$^8$, —NHC(=NR$^{8a}$)NR$^7$R$^8$, =NR$^8$, —NR$^8$CR$^8$(=NR$^{8a}$), F, Cl, Br, I, OCF$_3$, CF$_3$, —(CH$_2$)$_r$OR$^a$, —(CH$_2$)$_r$SR$^a$, CN, 1-NH$_2$-1-cyclopropyl, or C$_{1-6}$ alkyl substituted with 0-1 R$^{1a}$;

$R^{1a}$ is H, —C(=NR$^{8a}$)NR$^7$R$^8$, —NHC(=NR$^{8a}$)NR$^7$R$^8$, —NR$^8$CH(=NR$^{8a}$), —NR$^7$R$^8$, —C(O)NR$^8$R$^9$, F, OCF$_3$, CF$_3$, OR$^a$, SR$^a$, CN, —NR$^9$SO$_2$NR$^8$R$^9$, —NR$^8$SO$_2$R$^c$, —S(O)$_p$—C$_{1-4}$ alkyl, —S(O)$_p$-phenyl, or —(CF$_2$)$_r$CF$_3$;

$R^2$ is, independently at each occurrence, H, =O, F, Cl, Br, I, OCF$_3$, CF$_3$, CHF$_2$, CN, NO$_2$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_2$NR$^8$R$^9$, —NR$^8$S(O)$_2$R$^c$, —S(O)R$^c$, —S(O)$_2$R$^c$, C$_{1-6}$ alkyl substituted with 0-2 R$^{2a}$, C$_{2-6}$ alkenyl substituted with 0-2 R$^{2a}$, C$_{2-6}$ alkynyl substituted with 0-2 R$^{2a}$, —(CH$_2$)$_r$—C$_{3-10}$ carbocycle substituted with 0-3 R$^{2b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{2b}$;

$R^{2a}$ is, independently at each occurrence, H, F, Cl, Br, I, =O, =NR$^8$, CN, OCF$_3$, CF$_3$, OR$^a$, SR$^a$, —NR$^7$R$^8$, —C(O)NR$^8$R$^9$, —NR$^7$C(O)R$^b$, —S(O)$_p$NR$^8$R$^9$, —NR$^8$SO$_2$R$^c$, —S(O)R$^c$, or —S(O)$_2$R$^c$;

$R^{2b}$ is, independently at each occurrence, H, F, Cl, Br, I, =O, =NR$^8$, CN, NO$_2$, CF$_3$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_2$NR$^8$R$^9$, —S(O)$_2$R$^c$, —NR$^8$SO$_2$NR$^8$R$^9$, —NR$^8$SO$_2$R$^c$, —(CF$_2$)$_r$CF$_3$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkoxy;

alternately, when R$^1$ and R$^2$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and S(O)$_p$, wherein said carbocycle or heterocycle is substituted with 0-2 R$^{2b}$;

$R^3$ is, independently at each occurrence, F, Cl, Br, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$—C$_{3-10}$ carbocycle substituted with 0-3 R$^{3a}$ and 0-1 R$^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, $NO_2$, CN, $-(CH_2)_rOR^{3b}$, $SR^{3b}$, $-(CH_2)_rNR^7R^8$, $C(=NR^{8a})NR^8R^9$, $-NHC(=NR^{8a})NR^7R^8$, $-NR^8CR^8(=NR^{8a})$, $-(CH_2)_rNR^8C(O)R^{3b}$, $=NR^8$, $-(CH_2)_rNR^8C(O)R^{3b}$, $-(CH_2)_rNR^8C(O)_2R^{3b}$, $-(CH_2)_rS(O)_pNR^8R^9$, $-(CH_2)_rNR^8S(O)_pR^{3c}$, $-S(O)_pR^{3c}$, $-S(O)_pR^{3c}$, $C_{1-4}$ alkyl-C(O)—, $-(CH_2)_rCO_2R^{3b}$, $-(CH_2)_rC(O)NR^8R^9$, $-(CH_2)_rOC(O)NR^8R^9$, $-NHCOCF_3$, $-NHSO_2CF_3$, $-SO_2NHR^{3b}$, $-SO_2NHCOR^{3c}$, $-SO_2NHCO_2R^{3c}$, $-CONHSO_2R^{3c}$, $-NHSO_2R^{3c}$, $-CONHOR^{3b}$, $C_{1-4}$ haloalkyl, $C_{1-4}$ haloalkoxy-, $C_{1-6}$ alkyl substituted by $R^{3d}$, $C_{2-6}$ alkenyl substituted by $R^{3d}$, $C_{2-6}$ alkynyl substituted by $R^{3d}$, $C_{3-6}$ cycloalkyl substituted by 0-1 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are located on adjacent atoms, they can be taken together with the atoms to which they are attached to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, $-(CH_2)_rOR^a$, F, Cl, Br, CN, $NO_2$, $-(CH_2)_rNR^7R^8$, $-C(O)R^a$, $-C(O)OR^a$, $-OC(O)R^a$, $-NR^7C(O)R^b$, $-C(O)NR^8R^9$, $-SO_2NR^8R^9$, $-NR^8SO_2NR^8R^9$, $-NR^8SO_2R^c$, $-S(O)_pR^c$, $-(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $-(CH_2)_r-C_{3-10}$ carbocycle substituted with 0-3 $R^d$, or $-(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, $OCF_3$, $CF_3$, $OR^a$, $SR^a$, CN, $NO_2$, $-C(O)R^a$, $-C(O)OR^a$, $-OC(O)R^a$, $-NR^7R^8$, $-C(O)NR^8R^9$, $-NR^7C(O)R^b$, $-S(O)_pNR^8R^9$, $-NR^8S(O)_pR^c$, $-S(O)R^c$, $-S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, $-(CH_2)_r-C_{3-10}$ carbocycle substituted with 0-3 $R^{4b}$, or $-(CH_2)_r$-5- to 10-membered heterocycle comprising carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-6}$ alkyl, $OR^a$, $SR^a$, $CF_3$, CN, $NO_2$, $-C(O)R^a$, $-C(O)OR^a$, $-OC(O)R^a$, $-NR^7R^8$, $-C(O)NR^8R^9$, $-NR^7C(O)R^b$, $-S(O)_pNR^8R^9$, $-NR^8S(O)_2R^c$, $-S(O)R^c$, or $-S(O)_2R^c$;

$R^{4b}$ is, independently at each occurrence, H, =O, =$NR^8$, F, Cl, Br, I, $OR^a$, $SR^a$, CN, $NO_2$, $CF_3$, $-SO_2R^c$, $-NR^7R^8$, $-C(O)R^a$, $-C(O)OR^a$, $-OC(O)R^a$, $-NR^7R^8$, $-C(O)$ $NR^8R^9$, $-NR^7C(O)R^b$, $-S(O)_pNR^8R^9$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkoxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^5$ is, independently at each occurrence, H, F, $OCF_3$, $CF_3$, $OR^a$, $SR^a$, CN, $NO_2$, $-C(O)R^a$, $-C(O)OR^a$, $-OC(O)R^a$, $-NR^7R^8$, $-C(O)NR^7R^8$, $-NR^7C(O)R^b$, $-S(O)_pNR^8R^9$, $-NR^8S(O)_2R^c$, $-S(O)R^c$, $-S(O)_2R^c$, $C_{1-6}$ alkyl substituted with 0-2 $R^{5a}$, $C_{2-6}$ alkenyl substituted with 0-2 $R^{5a}$, $C_{2-6}$ alkynyl substituted with 0-2 $R^{5a}$, $-(CH_2)_r-C_{3-10}$ carbocycle substituted with 0-3 $R^{5b}$, or $-(CH_2)_r$-5-10 membered heterocycle comprising carbon atoms and 1-4 heteroatoms selected from N, O, and $S(O)_p$, wherein said heterocycle is substituted with 0-3 $R^{5b}$;

$R^{5a}$ is, independently at each occurrence, H, =O, $OR^a$, $SR^a$, F, Cl, Br, I, $CF_3$, $OCF_3$, CN, $NO_2$, $-NR^7R^8$, $-NR^7R^8$, $-C(O)NR^7R^8$, $-NR^7C(O)R^b$, $-S(O)_2NR^8R^9$, $-NR^8S(O)_2R^c$, $-S(O)R^c$, or $-S(O)_2R^c$;

$R^{5b}$ is, independently at each occurrence, H, =O, =$NR^8$, F, Cl, Br, I, $OR^a$, $SR^a$, CN, $NO_2$, $CF_3$, $-SO_2R^c$, $-NR^7R^8$, $-C(O)R^a$, $-C(O)OR^a$, $-OC(O)R^a$, $-NR^7R^8$, $-C(O)NR^8R^9$, $-NR^7C(O)R^b$, $-S(O)_2NR^8R^9$, $-S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkoxy-;

$R^6$ is, independently at each occurrence, H, $C_{1-6}$ alkyl, $C_{1-4}$ haloalkyl, $-CH_2OR^a$, $-C(O)R^c$, $-C(O)_2R^c$, $-S(O)_2R^c$, or $-(CH_2)_r$-phenyl substituted with 0-3 $R^{3d}$;

$R^7$ is, independently at each occurrence, H, $C_{1-6}$ alkyl, $-(CH_2)_n-C_{3-10}$ carbocycle, $-(CH_2)_n$-(5-10 membered heteroaryl), $-C(O)R^c$, $-CHO$, $-C(O)_2R^c$, $-S(O)_2R^c$, $-CONR^8R^c$, $-OCONHR^c$, $-C(O)O-(C_{1-4}$ alkyl)OC(O)$-(C_{1-4}$ alkyl), or $-C(O)O-(C_{1-4}$ alkyl)OC(O)$-(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, or $-(CH_2)_r$-phenyl, or $-(CH_2)_n$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{8a}$ is, independently at each occurrence, H, OH, $C_{1-6}$ alkyl, $C_{1-4}$ alkoxy, $(C_{6-10}$ aryl)-$C_{1-4}$ alkoxy, $-(CH_2)_n$-phenyl, $-(CH_2)_n$-(5-10 membered heteroaryl), $-C(O)R^c$, $-C(O)_2R^c$, $-C(O)O-(C_{1-4}$ alkyl)OC(O)$-(C_{1-4}$ alkyl), or $-C(O)O-(C_{1-4}$ alkyl)OC(O)$-(C_{6-10}$ aryl); wherein said phenyl, aryl, and heteroaryl is optionally substituted with 0-2 $R^f$;

$R^9$ is, independently at each occurrence, H, $C_{1-6}$ alkyl, or $-(CH_2)_n$-phenyl; wherein said alkyl and phenyl are optionally substituted with 0-2 $R^f$;

$R^{9a}$ is, independently at each occurrence, H, $C_{1-6}$ alkyl, or $-(CH_2)_n$-phenyl;

alternatively, $R^8$ and $R^9$, when attached to the same nitrogen, combine to form a 5- to 10-membered heterocyclic ring comprising carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-3 $R^{10a}$, $C_{2-6}$ alkenyl substituted with 0-3 $R^{10a}$, $C_{2-6}$ alkynyl substituted with 0-3 $R^{10a}$, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, wherein said heterocycle is substituted with 0-3 $R^d$;

$R^{10a}$ is, independently at each occurrence, H, =O, $C_{1-4}$ alkyl, OR$^a$, SR$^a$, F, CF$_3$, CN, NO$_2$, —C(O)OR$^a$, —NR$^7$R$^8$, —C(O)NR$^7$R$^8$, —NR$^7$C(O)R$^b$, —S(O)$_p$NR$^8$R$^9$, —NR$^8$SO$_2$R$^c$—, —S(O)R$^c$, or —S(O)$_2$R$^c$;

$R^{11}$ is $C_{1-4}$ haloalkyl, —(CH$_2$)$_r$C(O)NR$^8$R$^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —(CR$^{14}$R$^{15}$)$_r$—$C_{3-10}$ carbocycle substituted with 0-3 $R^{11b}$, or —(CR$^{14}$R$^{15}$)$_r$-5- to 10-membered heterocycle comprising carbon atoms and 1-4 heteroatoms selected from N, O, and S(O)$_p$, wherein said heterocycle is substituted with 0-3 $R^{11b}$;

$R^{11a}$ is, independently at each occurrence, H, =O, $C_{1-4}$ alkyl, OR$^a$, CF$_3$, SR$^a$, F, CN, NO$_2$, —NR$^7$R$^8$, —C(O)NR$^7$R$^8$, —NR$^7$C(O)R$^b$, —S(O)$_p$NR$^8$R$^9$, —NR$^8$S(O)$_p$R$^c$, —C(O)R$^a$, —C(O)OR$^a$, —S(O)$_p$R$^c$, $C_{3-6}$ cycloalkyl, $C_{1-4}$ haloalkyl, $C_{1-4}$ haloalkoxy-, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

$R^{11b}$ is, independently at each occurrence, H, =O, =NR$^8$, OR$^a$, F, Cl, Br, CN, NO$_2$, CF$_3$, OCF$_3$, OCHF$_2$, —C(O)R$^a$, —C(O)OR$^a$, —SOR$^c$, —SO$_2$R$^c$, —NR$^7$R$^8$, —C(O)NR$^7$R$^8$, —NR$^7$C(O)R$^b$, —NR$^8$C(O)$_2$R$^c$, —S(O)$_p$NR$^8$R$^9$, —NR$^8$S(O)$_p$R$^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkoxy-, —(CH$_2$)$_r$—$C_{3-10}$ carbocycle substituted with 0-3 $R^d$, or —(CH$_2$)$_r$-5-10 membered heterocycle comprising: carbon atoms and 1-4 heteroatoms selected from N, O, and S(O)$_p$, wherein said heterocycle is substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 $R^g$;

$R^{12}$ is, independently at each occurrence, H, F, or $C_{1-4}$ alkyl;

$R^{13}$ is, independently at each occurrence, H, $C_{1-6}$ alkyl, —(CH$_2$)$_n$-phenyl, —(CH$_2$)$_n$-(5-10 membered heteroaryl), —C(O)R$^c$, —C(O)OR$^c$, —CONR$^8$R$^c$, —OCONR$^8$R$^c$, —S(O)$_2$R$^c$, —C(O)O—(C$_{1-4}$ alkyl)-OC(O)—(C$_{1-4}$ alkyl), or —C(O)O—(C$_{1-4}$ alkyl)-OC(O)—(C$_{6-10}$ aryl); wherein the said alkyl, phenyl, heteroaryl, aryl are optionally substituted with 0-2 R$^f$;

$R^{14}$ and $R^{15}$ are, independently at each occurrence, H, F, or $C_{1-4}$ alkyl;

alternately, $R^{14}$ combines with $R^{15}$ to form =O;

$R^a$ is, independently at each occurrence, H, CF$_3$, $C_{1-6}$ alkyl, —(CH$_2$)$_r$—$C_{3-7}$ cycloalkyl, —(CH$_2$)$_r$—$C_{6-10}$ aryl, or —(CH$_2$)$_r$-5- to 10 membered heterocycle comprising: carbon atoms and 1-4 heteroatoms selected from N, O, and S(O)$_p$; wherein said cycloalkyl, aryl and heteroaryl groups are optionally substituted with 0-2 R$^f$;

$R^b$ is, independently at each occurrence, CF$_3$, OH, $C_{1-4}$ alkoxy, $C_{1-6}$ alkyl, —(CH$_2$)$_r$—$C_{3-10}$ carbocycle substituted with 0-3 $R^d$, or —(CH$_2$)$_r$-5-10 membered heterocycle comprising: carbon atoms and 1-4 heteroatoms selected from N, O, and S(O)$_p$, wherein said heterocycle is substituted with 0-3 $R^d$;

$R^c$ is, independently at each occurrence, CF$_3$, $C_{1-6}$ alkyl substituted with 0-2 R$^f$, $C_{3-6}$ cycloalkyl substituted with 0-2 R$^f$, $C_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl and heteroaryl groups are optionally substituted with 0-3 R$^f$;

$R^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^a$, —C(O)NR$^7$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl substituted with 0-2 R$^e$, $C_{2-6}$ alkenyl substituted with 0-2 R$^e$, or $C_{2-6}$ alkynyl substituted with 0-2 R$^e$;

$R^e$ is, independently at each occurrence, =O, OR$^a$, F, Cl, Br, I, CN, NO$_2$, —NR$^8$R$^9$, —C(O)R$^a$, —C(O)OR$^a$, —OC(O)R$^a$, —NR$^8$C(O)R$^a$, —C(O)NR$^7$R$^8$, —SO$_2$NR$^8$R$^9$, NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

$R^f$ is, independently at each occurrence, H, =O, —(CH$_2$)$_r$—OR$^g$, F, Cl, Br, I, CN, NO$_2$, —NR$^{9a}$R$^{9a}$, —C(O)R$^g$, —C(O)OR$^g$, —NR$^{9a}$C(O)R$^g$, —C(O)NR$^{9a}$R$^{9a}$, —SO$_2$NR$^{9a}$R$^{9a}$, —NR$^{9a}$SO$_2$NR$^{9a}$R$^{9a}$, —NR$^{9a}$SO$_2$—C$_{1-4}$ alkyl, —NR$^{9a}$SO$_2$CF$_3$, —NR$^{9a}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl, $C_{2-6}$ alkenyl, $C_{2-6}$ alkynyl, or —(CH$_2$)$_n$-phenyl;

$R^g$ is, independently at each occurrence, H, $C_{1-6}$ alkyl, or —(CH$_2$)$_n$-phenyl;

n, at each occurrence, is selected from 0, 1, 2, 3, and 4;

p, at each occurrence, is selected from 0, 1, and 2;

r, at each occurrence, is selected from 0, 1, 2, 3, and 4; and s, at each occurrence, is selected from 1, 2, 3, and 4.

In a thirty third aspect, the present invention provides a method for treating a thromboembolic or an inflammatory disorder, comprising: administering to a patient in need thereof a therapeutically effective amount of at least one compound of Formula (V), within the scope of the thirty second aspect wherein:

A is $C_{3-8}$ cycloalkyl substituted with 0-1 $R^1$ and 0-3 $R^2$, $C_{4-8}$ cycloalkenyl substituted with 0-1 $R^1$ and 0-3 $R^2$, phenyl substituted with 0-1 $R^1$ and 0-3 $R^2$, naphthyl substituted with 0-1 $R^1$ and 0-3 $R^2$, or a 5- to 10-membered heterocycle comprising: carbon atoms and 1-4 heteroatoms selected from N, O, and S(O)$_p$, wherein said heterocycle is substituted with 0-1 $R^1$ and 0-3 $R^2$;

Z is —C(R$^{11}$)(R$^{12}$)—;

L is —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, or —NR$^{10}$C(O)CH$_2$—;

$R^3$ is, independently at each occurrence, F, Cl, Br, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$—$C_{3-8}$ cycloalkyl substituted with 0-2 $R^{3a}$ and 0-1 $R^{3d}$, —(CH$_2$)$_r$-phenyl substituted with 0-3 $R^{3a}$ and 0-1 $R^{3d}$, —(CH$_2$)$_r$-naphthyl substituted with 0-3 $R^{3a}$ and 0-1 $R^{3d}$, —(CH$_2$)$_r$-indanyl substituted with 0-3 $R^{3a}$ and 0-1 $R^{3d}$, or —(CH$_2$)$_r$-5-10 membered heterocycle comprising: carbon atoms and 1-4 heteroatoms selected from N, O, and S(O)$_p$, wherein said heterocycle is substituted with 0-3 $R^{3a}$ and 0-1 $R^{3d}$;

$R^4$ is H, F, Cl, Br, I, OCF$_3$, CF$_3$, OR$^a$, SR$^a$, CN, NO$_2$, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, —S(O)$_2$R$^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, phenyl substituted with 0-2 $R^{4b}$, or a 5-10 membered heterocycle comprising: carbon atoms and 1-4 heteroatoms selected from N, O, and S(O)$_p$, wherein said heterocycle is substituted with 0-3 $R^{4b}$;

$R^6$ is, independently at each occurrence, H, $C_{1-6}$ alkyl —$CH_2OR^a$, —$C(O)R^c$, —$C(O)_2R^c$, or —$(CH_2)_r$-phenyl substituted with 0-3 $R^d$;

$R^{10}$ is, independently at each occurrence, H, $C_{1-6}$ alkyl substituted with 0-3 $R^{10a}$, —$(CH_2)_r$—$C_{3-10}$ carbocycle substituted with 0-3 $R^d$, or —$(CH_2)_r$-5-10 membered heterocycle comprising carbon atoms and 1-4 heteroatoms selected from N, O, and $S(O)_p$, wherein said heterocycle is substituted with 0-3 $R^d$; and $R^{11}$ is $C_{1-4}$ haloalkyl, —$(CH_2)_rC(O)NR^8R^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CH_2)_r$—$C_{3-10}$ carbocycle substituted with 0-3 $R^{11b}$, or —$(CH_2)_r$-5-10 membered heterocycle comprising carbon atoms and 1-4 heteroatoms selected from N, O, and $S(O)_p$, wherein said heterocycle is substituted with 0-3 $R^{11b}$.

In a thirty fourth aspect, the present invention provides a method for treating a thromboembolic or an inflammatory disorder, comprising: administering to a patient in need thereof a therapeutically effective amount of at least one compound of Formula (V), within the scope of the thirty second aspect wherein:

A is $C_{5-6}$ cycloalkyl substituted with 0-1 $R^1$ and 0-2 $R^2$, $C_{5-6}$ cycloalkenyl substituted with 0-1 $R^1$ and 0-2 $R^2$, phenyl substituted with 0-1 $R^1$ and 0-3 $R^2$, naphthyl substituted with 0-1 $R^1$ and 0-3 $R^2$, or a 5- to 10-membered heterocycle comprising: carbon atoms and 1-4 heteroatoms selected from N, O, and $S(O)_p$, wherein said heterocycle is substituted with 0-1 $R^1$ and 0-3 $R^2$;

$R^3$ is, independently at each occurrence, F, Cl, Br, —$(CH_2)_rC(O)NR^8R^9$, —$(CH_2)_rC(O)NR^8(CH_2)_sCO_2R^{3b}$, —$(CH_2)_rCO_2R^{3b}$, —$(CH_2)_r$-phenyl substituted with 0-3 $R^{3a}$ and 0-1 $R^{3d}$, —$(CH_2)_r$-naphthyl substituted with 0-3 $R^{3a}$ and 0-1 $R^{3d}$, —$(CH_2)_r$-indanyl substituted with 0-3 $R^{3a}$ and 0-1 $R^{3d}$, or —$(CH_2)_r$-5-10 membered heterocycle comprising: carbon atoms and 1-4 heteroatoms selected from N, O, and $S(O)_p$, wherein said heterocycle is substituted with 0-3 $R^{3a}$ and 0-1 $R^{3d}$; and $R^6$ is, independently at each occurrence, H or $C_{1-6}$ alkyl.

In a thirty fifth aspect, the present invention provides a method for treating a thromboembolic or an inflammatory disorder, comprising: administering to a patient in need thereof a therapeutically effective amount of at least one compound of Formula (V), within the scope of the thirty second aspect wherein:

the group

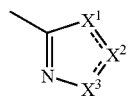

is selected from:

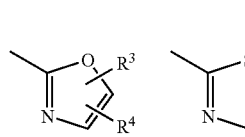 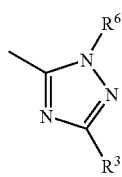

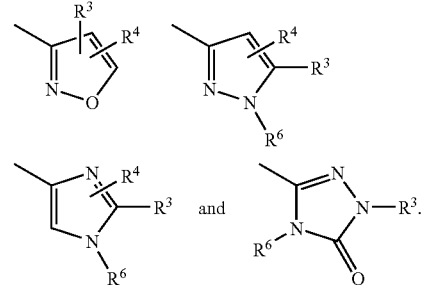

In a thirty sixth aspect, the present invention provides a method for treating a thromboembolic or an inflammatory disorder, comprising: administering to a patient in need thereof a therapeutically effective amount of at least one compound of Formula (V), within the scope of the thirty second aspect wherein:

the group

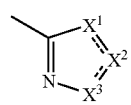

is selected from:

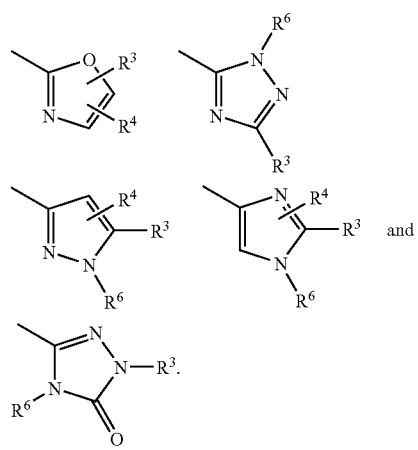

In a thirty seventh aspect, the present invention provides a method for treating a thromboembolic or an inflammatory disorder, comprising: administering to a patient in need thereof a therapeutically effective amount of at least one compound of Formula (III), within the scope of the thirty second aspect wherein.

A is substituted with 0-1 $R^1$ and 0-2 $R^2$ and selected from: $C_{3-7}$ cycloalkyl, phenyl, naphthyl, 1,2,3,4-tetrahydronaphthyl, pyridyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

the group

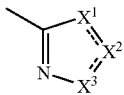

is selected from:

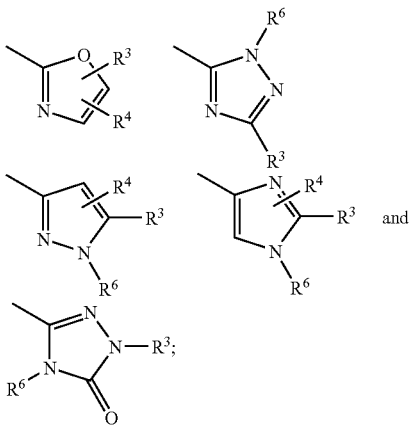

Z is —CH(R$^{12}$)—;

L is —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, or —NR$^{10}$C(O)CH$_2$—;

R$^3$ is, independently at each occurrence, F, Cl, Br, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$-phenyl substituted with 0-3 R$^{3a}$ and 0-1 R$^{3d}$, —(CH$_2$)$_r$-naphthyl substituted with 0-3 R$^{3a}$ and 0-1 R$^{3d}$, —(CH$_2$)$_r$-indanyl substituted with 0-3 R$^{3a}$ and 0-1 R$^{3d}$ or —(CH$_2$)$_r$-5-10 membered heterocycle comprising: carbon atoms and 1-4 heteroatoms selected from N, O, and S(O)$_p$, and substituted with 0-3 R$^{3a}$ and 0-1 R$^{3d}$;

R$^4$ is, independently at each occurrence, H, =O, F, Cl, Br, I, OCF$_3$, CF$_3$, CN, NO$_2$, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, and substituted with 0-3 R$^{4b}$;

R$^6$ is H, C$_{1-6}$ alkyl, or —(CH$_2$)$_r$-phenyl substituted with 0-3 R$^d$;

R$^{10}$ is, independently at each occurrence, H, C$_{1-6}$ alkyl substituted with 0-2 R$^{10a}$, —(CH$_2$)$_r$-phenyl substituted with 0-2 R$^d$, or —(CH$_2$)$_r$-5-10 membered heterocycle comprising carbon atoms and 1-4 heteroatoms selected from N, O, and S(O)$_p$, wherein said heterocycle is substituted with 0-2 R$^d$; and R$^{12}$ is, independently at each occurrence, H, F, or Me.

In another aspect, the present invention provides a method for treating a thromboembolic or an inflammatory disorder, comprising: administering to a patient in need thereof a therapeutically effective amount of at least one compound of Formula (III), within the scope of the twenty eighth aspect wherein.

the group

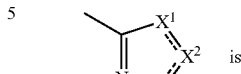 is 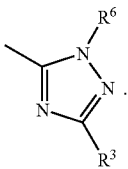.

In another aspect, L is —C(O)NR$^{10}$— or —NR$^{10}$C(O)—.
In another aspect, L is —C(O)NR$^{10}$—.
In another aspect, L is —NR$^{10}$C(O)—.
In another aspect, L is —C(O)NH— or —NHC(O)—.
In another aspect, L is —C(O)NH—.
In another aspect, L is —NHC(O)—.

In another aspect, the present invention provides a compound selected from the exemplified examples or stereoisomers, tautomers, pharmaceutically acceptable salts, solvates, or prodrugs thereof.

In another embodiment, the present invention provides a novel pharmaceutical composition, comprising: a pharmaceutically acceptable carrier and a therapeutically effective amount of a compound of the present invention or a stereoisomer, tautomer, a pharmaceutically acceptable salt, solvate or prodrug form thereof.

In another embodiment, the present invention provides a novel process for making a compound of the present invention or a stereoisomer, tautomer, pharmaceutically acceptable salt, solvate or prodrug form thereof.

In another embodiment, the present invention provides a novel intermediate for making a compound of the present invention or a stereoisomer, tautomer, pharmaceutically acceptable salt, solvate or prodrug form thereof.

In another embodiment, the present invention provides a pharmaceutical composition further comprising additional therapeutic agent(s) selected from potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other kallikrein inhibitors, factor VIa inhibitors and factor Xa inhibitors, and antiplatelet agents selected from GPIIb/IIIa blockers, $P2Y_1$ and $P2Y_{12}$ antagonists, thromboxane receptor antagonists, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment the present invention provides a method for modulation of the coagulation cascade and/or contact activation system comprising administering to a patient in need of such treatment a therapeutically effective amount of at least one of the compounds of the present invention or a stereoisomer, tautomer, a pharmaceutically acceptable salt, solvate or prodrug form thereof.

In another embodiment, the present invention provides a novel method for treating thromboembolic disorders comprising: administering to a patient in need of such treatment a therapeutically effective amount of at least one of the compounds of the present invention or a stereoisomer, tautomer, a pharmaceutically acceptable salt, solvate or prodrug form thereof.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer, tautomer, a pharmaceutically acceptable salt, solvate or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a stereoisomer, tautomer, a pharmaceutically acceptable salt, solvate or prodrug form thereof in an amount effective to treat a thromboembolic disorder.

In another embodiment, the present invention provides a method of treating a patient in need of inflammatory disorder treatment, comprising: administering a compound of the present invention or a stereoisomer, tautomer, a pharmaceutically acceptable salt, solvate or prodrug form thereof in an amount effective to treat an inflammatory disorder.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer, tautomer, a pharmaceutically acceptable salt, solvate or prodrug form thereof; and (c) a package insert stating that the pharmaceutical composition can be used for the treatment of a thromboembolic and/or inflammatory disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer, tautomer, a pharmaceutically acceptable salt, solvate or prodrug form thereof; and (c) a package insert stating that the pharmaceutical composition can be used in combination with a second therapeutic agent to treat a thromboembolic and/or inflammatory disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel method, comprising: administering a compound of the present invention or a stereoisomer, tautomer, a pharmaceutically acceptable salt, solvate or prodrug form thereof in an amount effective to treat a thromboembolic and/or inflammatory disorder.

In another embodiment, the present invention provides a compound of the present invention or a stereoisomer, tautomer, a pharmaceutically acceptable salt, solvate or prodrug form thereof, for use in therapy.

In another embodiment, the present invention also provides the use of a compound of the present invention or a stereoisomer, tautomer, a pharmaceutically acceptable salt, solvate or prodrug form thereof, for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_1$-$C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2Cl_5$, and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

When a dotted ring is used within a 5- to 8-membered ring structure, this indicates that the ring structure may be saturated, partially saturated or unsaturated.

As used herein, the term "protecting group" for amines means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: (Fmoc); (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Design of Prodrugs, edited by H. Bundgaard, (Elsevier, 1985), and *Methods in Enzymology*, Vol. 42, at pp. 309-396, edited by K. Widder, et. al. (Academic Press, 1985);

b) A Textbook of Drug Design and Development, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

It should further be understood that solvates (e.g., hydrates) of the compounds of the present invention are also with the scope of the present invention. Methods of salvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein. "Therapeutically effective amount" is also intended to include an amount of the combination of compounds claimed that is effective to inhibit factor XIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor XIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier. A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g. stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group(s) (PG) used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

All references cited herein are hereby incorporated in their entirety herein by reference.

Imidazole compounds useful for the synthesis of the compounds of this invention may be synthesized according to the general method outlined in Scheme 1 (Con tour-Galcera et al. *Bioorg. Med. Chem. Lett.* 2001, 11(5), 741-745). An appropriately protected or derivatized alpha amino acid [1; Y=R$^{10}$(PG)N— or Y=AC(O)N(R$^{10}$)—] or malonic acid derivative [1; Y=alkyl-OC(O)—] is dissolved in an suitable solvent, such as ethanol/water (1:1), and treated with a base, such as cesium carbonate, to form the cesium salt. The salt is isolated and re-suspended in a suitable solvent, such as dimethyl formamide, and combined with an alpha-bromoketone 2 to form the keto ester 3. Alternatively, formation of keto ester 3 (X=aryl or heteroaryl) may be carried out in a single reaction vessel by forming the cesium salt of 1 in the same solvent (e.g., dimethyl formamide) used for the alkylation step.

The imidazole having structure 4 is formed by heating the keto ester 3 to reflux in a suitable solvent, such as xylenes, in the presence of excess ammonium acetate using a Dean-Stark trap to remove water. Formation of the imidazole can also be carried out by combining the keto ester 3 and ammonium acetate in a suitable solvent, such as xylene or ethanol or a combination of solvents such as dimethylforamide and ethanol (1:1), using microwave heating. When Y=R$^{10}$(PG)N—, the protecting group on the amine is removed in preparation for acylation of the amine, which is outlined in Scheme 18. For example, when the protecting group is a BOC moiety, the amine is de-protected with strong acid, such as trifluoroacetic acid in suitable solvent, such as dichloromethane, to give compound 5, where Y'=R$^{10}$HN—. When Y=Alk-OCO—, the ester may be hydrolyzed by dissolving it in a suitable solvent such as methanol and treating the ester with a base such as aqueous sodium hydroxide to give 5 where Y=—CO$_2$H.

Further functional group incorporation on to the imidazole ring may be achieved by bromination of the C-5 carbon of the imidazole ring using, for example, bromine or N-bromosuccinimide, in a suitable solvent such as methylene chloride or chloroform to give compounds 6 and 9. Alternatively, the C-5 carbon may be chlorinated with, for example, N-chlorosuccinimide, using a suitable solvent such as methylene chloride, acetonitrile or chloroform to give compounds 7 and 10.

The brominated imidazoles 6 and 9 provide suitable functionality for further elaboration using a wide variety of palladium catalyzed cross coupling procedures known to those skilled in the art such as described by Tsuji (*Palladium Reagents and Catalysts: New Perspectives for the 21$^{st}$ Century*, John Wiley & Sons, Ltd., 2004). By way of example, application of a Suzuki coupling protocol using a modified method of Zhong et al. (*Org. Lett.* 2004, 6, 929-931) and Bellina et al. (*Synthesis* 2004, 15, 2419-2440), where the bromides 6 or 9 are combined with a boronic acid in the presence of a base, typically tribasic potassium phosphate or sodium carbonate, and a palladium catalyst, typically bis-(tri-t-butylphosphine) palladium (0), tris-(dibenzylidene-acetone) palladium (0), or tetrakis-(triphenylphosphine) palladium (0), in a suitable solvent, such as toluene or 1,4-dioxane heated to between 80-110° C. using conventional or microwave heating, provides structures 8 and 11, where X=aryl or heteroaryl.

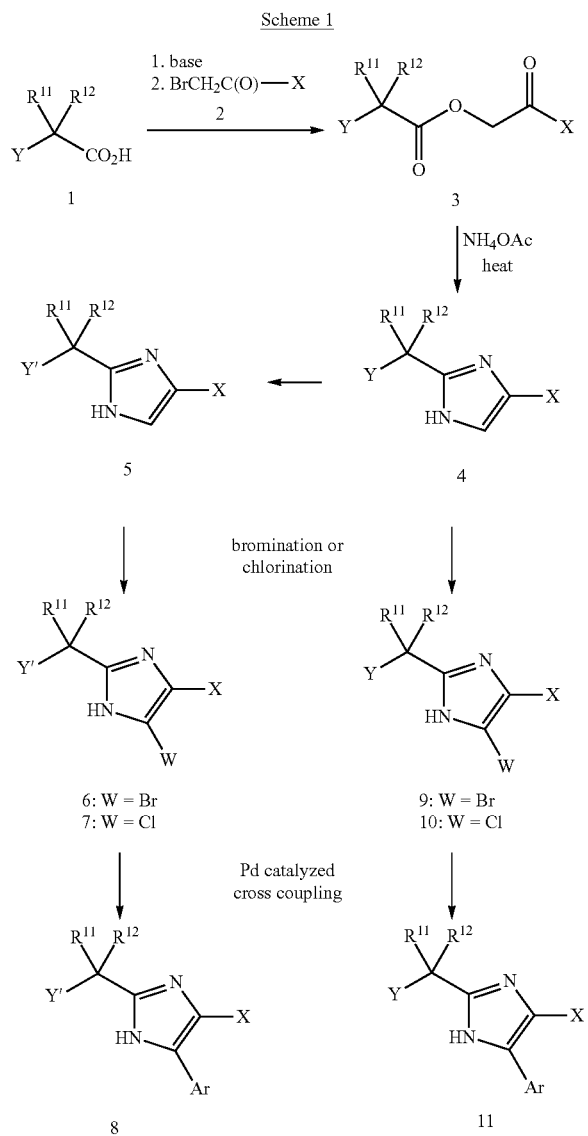

An alternate synthesis of the imidazole core is shown in Scheme 2. A suitably protected beta amino aldehyde 12, glyoxal trimeric dihydrate 13 and ammonia are combined in a suitable solvent such as methanol and stirred together at room temperature. The resulting imidazole 14 is dissolved in a suitable solvent such as chloroform and brominated using, for example, N-bromosuccinimide. Other brominating reagents may be employed, such as bromine, and other solvents suitable for bromination conditions, such as methylene chloride or carbon tetrachloride, may be used. The 4,5-dibromo imidazole 15 is treated with a reducing agent such as sodium hydrogen sulfite utilizing a biphasic solvent system consisting of, for example, 1,4-dioxane and water, and a phase transfer catalyst such as tetrabutylammonium hydrogen sulfate. The mono-bromide 16 thus produced may be combined with a suitably functionalized aryl boronic acid or heteroaryl boronic acid in a suitable solvent such as 1,4-dioxane or toluene, and treated at elevated temperature with a reagent combination consisting of, for example, palladium (I) tri-tert-butylphosphine bromide dimer and tribasic potassium phosphate according to a modified procedure of Zhong et al. and Bellini et al. referenced previously. Other reagent combinations that may be utilized for the Suzuki coupling procedure are palladium tris-(dibenzylidene-acetone) palladium (0), tri-(tert-butyl)-phosphonium tetra-fluoroborate, and tribasic potassium phosphate. The protecting group on the amine is removed in preparation for acylation of the amine, which is outlined in Scheme 17. For example, when the protecting group is a BOC moiety, the amine is de-protected with strong acid, such as trifluoroacetic acid, in suitable solvent, such as dichloromethane, to give amine 18 as the bis-TFA salt.

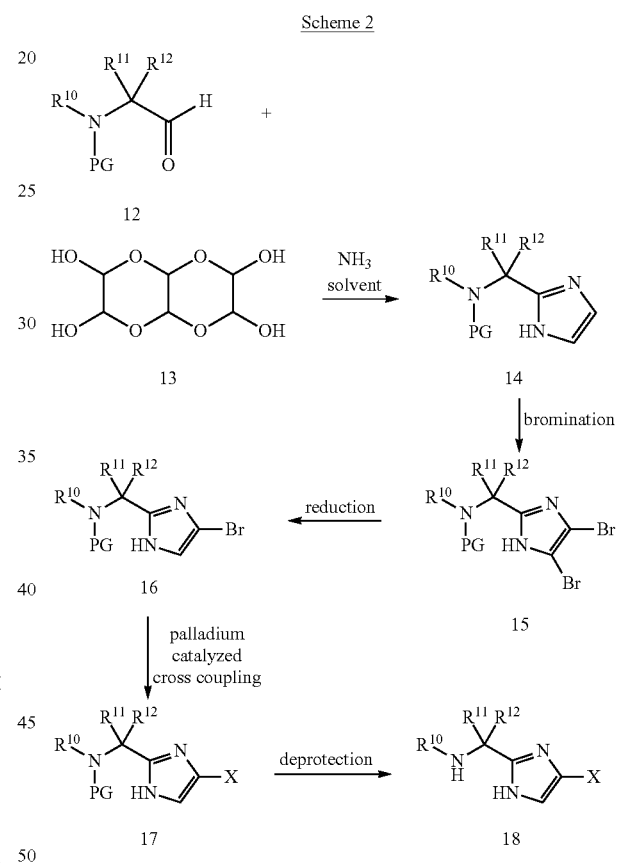

Another alternative method for the synthesis of the imidazole ring is shown in Scheme 3. 3,3-Dibromo-1,1,1-trifluoropropan-2-one (19) is combined with ammonium acetate in a suitable solvent such as water and heated to 90°, followed by the addition of a suitably protected aldehyde 12. The trifluoromethyl imidazole thus produced provides an intermediate for the synthesis of C-5 trifluoro methyl analogs illustrated by compound 24, where $X=CF_3$. Such compounds may be accessed by methods previously illustrated in Schemes 1 and 2. Alternatively, the trifluoromethyl moiety may be hydrolyzed under strongly basic conditions using, for example sodium methoxide, to provide the ortho ester which is hydrolyzed to the methyl ester 21, where $X=\!=\!\!-CO_2CH_3$. This intermediate may be utilized using procedures already illustrated in Schemes 1 and 2 to access compounds such as 24, where $X=\!=\!\!-CO_2CH_3$.

Scheme 3

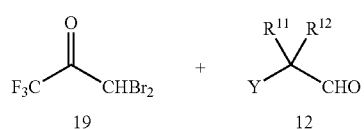

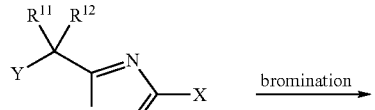

- 20: X = CF₃
- 21: X = CO₂CH₃

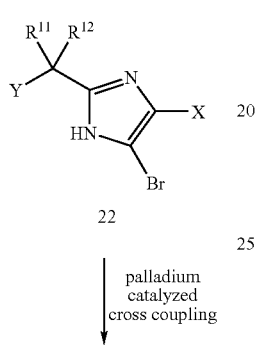

22

↓ palladium catalyzed cross coupling

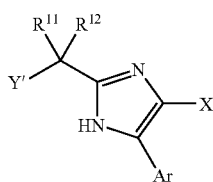 ← 

24    23

Scheme 4

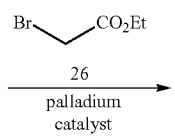

25

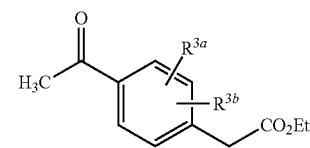

27

↓ bromination

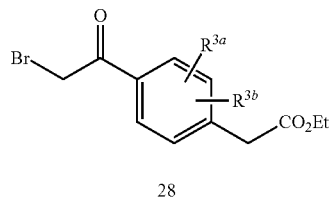

28

Phenylalanine analogs bearing substituents on the phenyl ring not commercially available are readily accessed using methods known to those skilled in the art. For an authoritative review of methods for the synthesis of such analogs starting from glycine see Maruoka and Ooi (*Chem. Rev.* 2003, 103, 3013-3028).

Certain 2-bromoacetophenone analogs that are not commercially available may be synthesized from commercially available starting materials. For example, ethyl 2-(4-(2-bromoacetyl)phenyl)acetate (27: $R^{3a}$=$R^{3b}$=H) can be prepared as shown in Scheme 4. 2,4'-dibromoacetophenone (25: $R^{3a}$=$R^{3b}$=H), and ethyl bromoacetate (26) are dissolved in a suitable solvent, such as tetrahydrofuran, and treated at elevated temperature with a combination of reagents, such as palladium (II) acetate, tris-(1-naphthyl) phosphine and tribasic potassium phosphate according to the method of Gossen et al. (*Chem. Commun.* 2001, 669-670). The intermediate, ethyl 2-(4-acetylphenyl)acetate (27) is brominated by dissolving in a suitable solvent such as chloroform and treating with a brominating reagent such as bromine to give ethyl 2-(4-(2-bromoacetyl)phenyl)acetate (28). This reaction sequence may also be employed to prepare the other regioisomers and analogs of 28 containing functional groups compatible with the reaction sequence described.

Certain functional groups present in the final structures must, by virtue of incompatibility with the formation of the imidazole shown in Schemes 1-3, be incorporated into the structure after the imidazole ring has been formed. Examples of such functional groups include, but are not limited to, carbamoyl, aminoindazolyl, aminobenzisoxazolyl, and aminoquinazolinoyl (see Schemes 5 and 6).

The carbamoyl group, illustrated in structure 29 in Scheme 5, may be incorporated into the final structure by hydrolysis of a nitrile using, for example, potassium carbonate, hydrogen peroxide, and DMSO as solvent, according to the method of Katritzky et al. (*Synthesis* 1989, 12, 949-50). When the nitrile is located para to the imidazole ring, magnesium oxide must be added to the reaction mixture. The amidine group, illustrated in structure 31, may be incorporated into the final structure via Pinner reaction followed by ammonolysis. Alternatively, the nitrile 28 may be combined with hydroxylamine hydrochloride in the presence of a base, such as triethylamine, to give the amidoxime 32, which after acetylation with acetic anhydride is reduced by a variety of methods including, but not limited by, catalytic hydrogenation using, for example, palladium on carbon and hydrogen (Judkins et al. *Syn. Comm.* 1996, 26, 4351-4367), or by using an active metal such as zinc. By way of illustration, the precursor nitrile group shown in structure 28 in Scheme 5 may be incorporated on to the intermediate structure(s) by using, in separate reactions, 4-(2-bromo-acetyl)-benzonitrile, 3-(2-bromo-acetyl)-benzonitrile, or 2-(2-bromo-acetyl)-benzonitrile for the reagent described as $BrCH_2C(O)X$ in Scheme 1.

Scheme 5

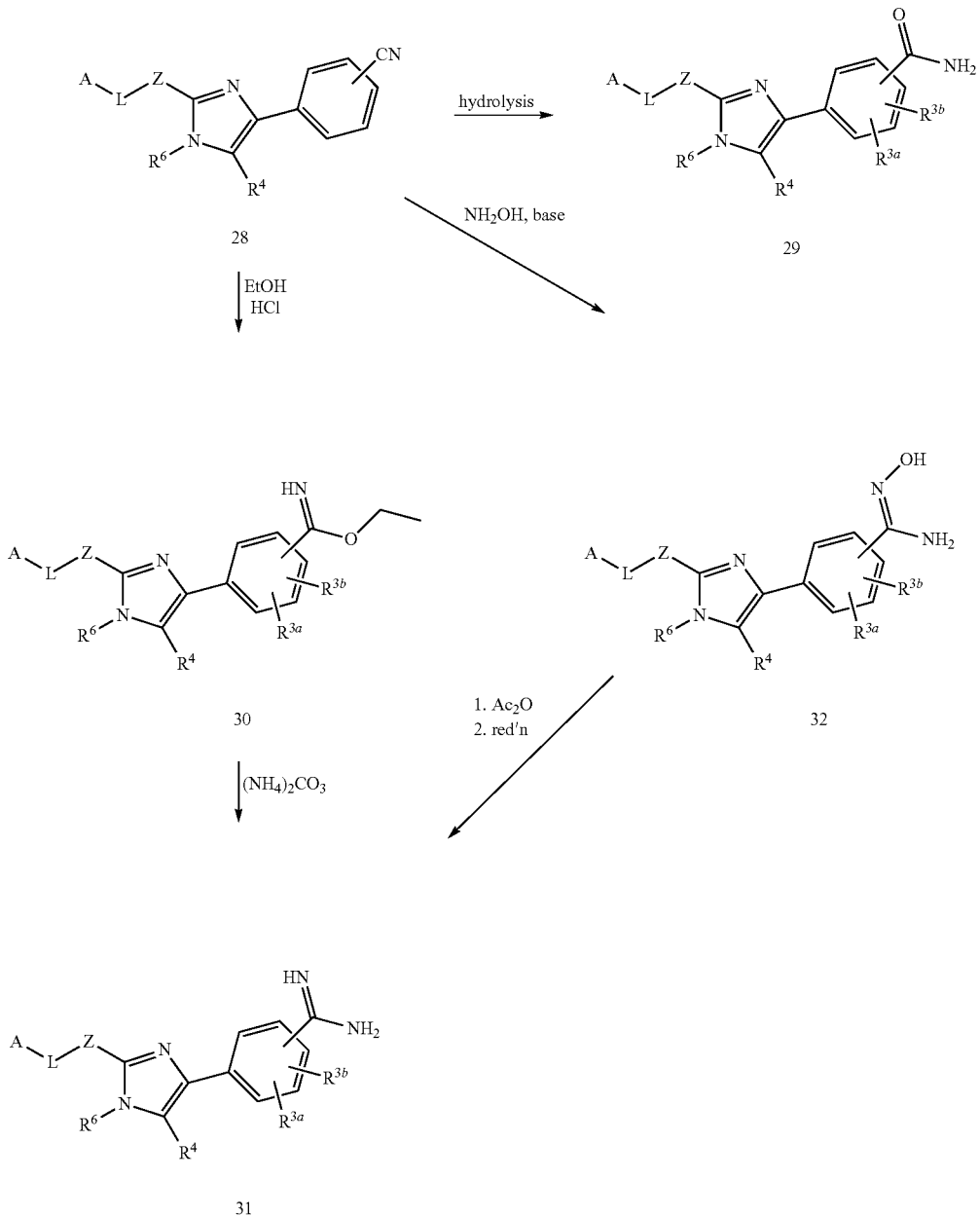

The aminoindazole, aminobenzisoxazole and aminoquinazoline functional groups may be incorporated into the final structure using a common intermediate containing a phenyl ring bearing an ortho fluoro nitrile as illustrated in structure 33 (Scheme 6). The amino-indazole functional group (34) is produced, for example, by heating 33 with hydrazine monohydrate in a suitable solvent, such as n-butanol. Heating may be done conventially or via microwave irradiation, and the temperature required for conversion of the ortho fluoro nitrile to the aminoindazole depends upon the regioisomeric relationship between the ortho fluoro nitrile and the imidazole ring. Typically, temperatures of 160° C. are required for formation of the amino-indazole when the nitrile is located para to the imidazole ring. The aminoquinazoline (35) is produced by combining the ortho-fluoronitrile (33) with formamidine acetate, or other suitable salt forms, in a suitable solvent such as dimethyl acetamide or dimethyl formamide, and heating to approximately 140° C. Conversion of the ortho-fluoronitrile to the aminobenzisoxazole (36) may be accomplished by combining the fluoro nitrile 33 with acetoxyhydroxamic acid in the presence of a base such as potassium carbonate.

Scheme 6

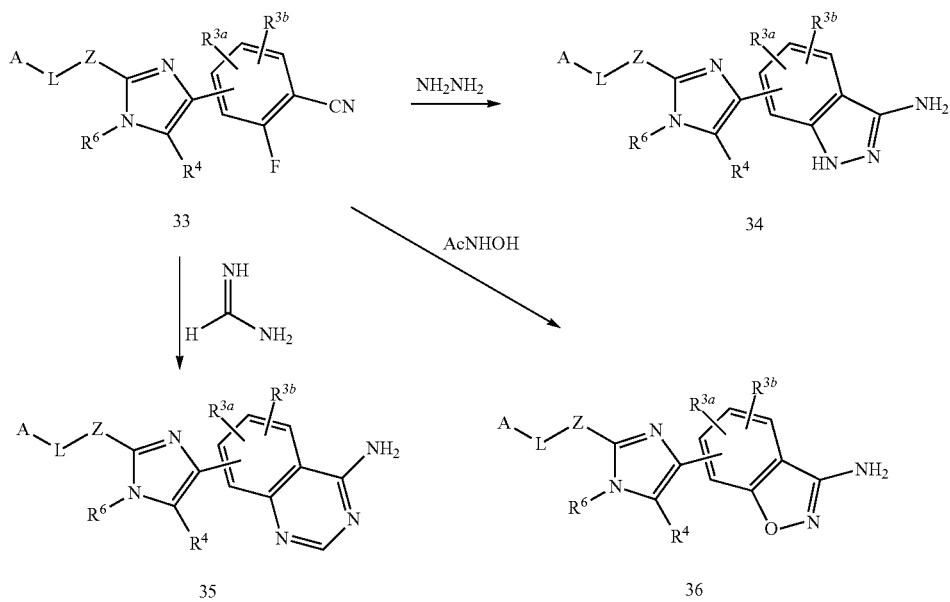

A general synthesis of alpha bromoketones containing an ortho fluoro nitrile is illustrated in Scheme 7. A suitably substituted bromo-fluoro-benzoic acid (37) is converted to the corresponding nitrile 38 using, for example, zinc cyanide and palladium (0) tetrakis-(triphenylphosphine) in a suitable solvent, such as dimethyl formamide, and heating to 90° C. The nitrile 38 thus produced is treated sequentially with oxalyl chloride in a suitable solvent, such as dichloromethane, containing a few drops of DMF, then treated with trimethylsilyldiazomethane in a suitable solvent or solvent combination, such as acetonitrile and hexane. The intermediate diazoketone is isolated and treated with hydrobromic acid and acetic acid to provide the alpha bromoketone 39.

Scheme 7

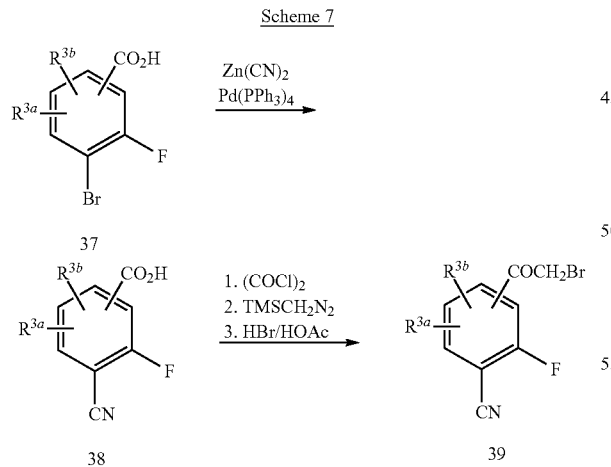

Alternatively, the bromoketone 39 may be synthesized from a suitably substituted ortho fluoro nitrile containing a bromide (40 Scheme 8) by treatment sequentially with tributyl-(1-methoxyvinyl) stannane and a palladium catalyst, such as bis-(triphenylphosphine)-dichloro-palladium (II), in a suitable solvent, such as toluene, and heated to reflux, followed by aqueous hydrochloric acid, typically at 5% (w/v) concentration. The resulting methyl ketone 41 is combined with bromine in a suitable solvent, such as chloroform or methylene chloride, to produce the bromoketone 39. Alternate synthetic routes to 39 other than those illustrated in Schemes 7 and 8 may be envisioned by one skilled in the art depending on the regioisomers commercially available for possible combinations of $R^{3a}$ and $R^{3b}$ contained on the carbocylic ring.

Scheme 8

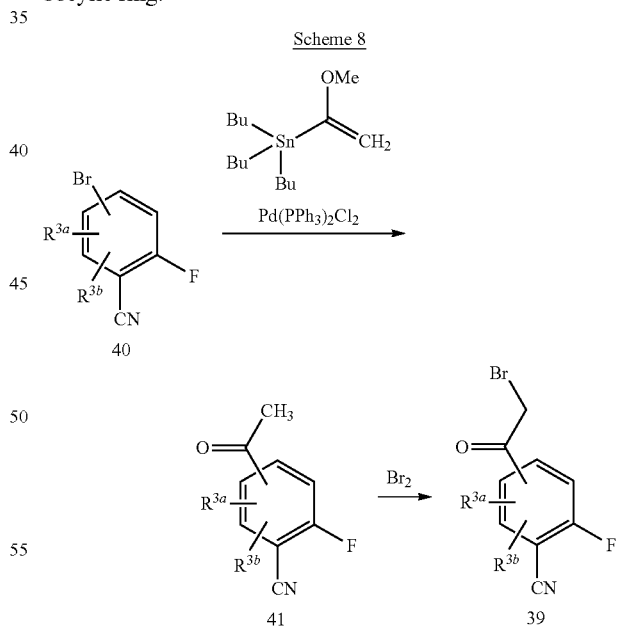

A different sequence of chemical transformations provides for the synthesis of a second regioisomer of the imidazoles useful in the preparation of compounds of this invention as shown in Scheme 9. An alpha-bromoketone 42 containing suitable substitution is combined with sodium formate in a suitable solvent, such as ethanol, and heated to reflux. The keto ester 43 thus formed is dissolved in a solvent, for example ethanol, and combined with a suitably substituted amidine 44 (X=aryl or heteroaryl) in the presence of a base, for example sodium bicarbonate. The imidazole 45 thus formed has the opposite regio-configuration compared to the imidazoles illustrated in Schemes 1-3. Removal of the amine protecting group, PG, in preparation for acylation of the amino group is carried out as described previously to give the amino imidazole 46.

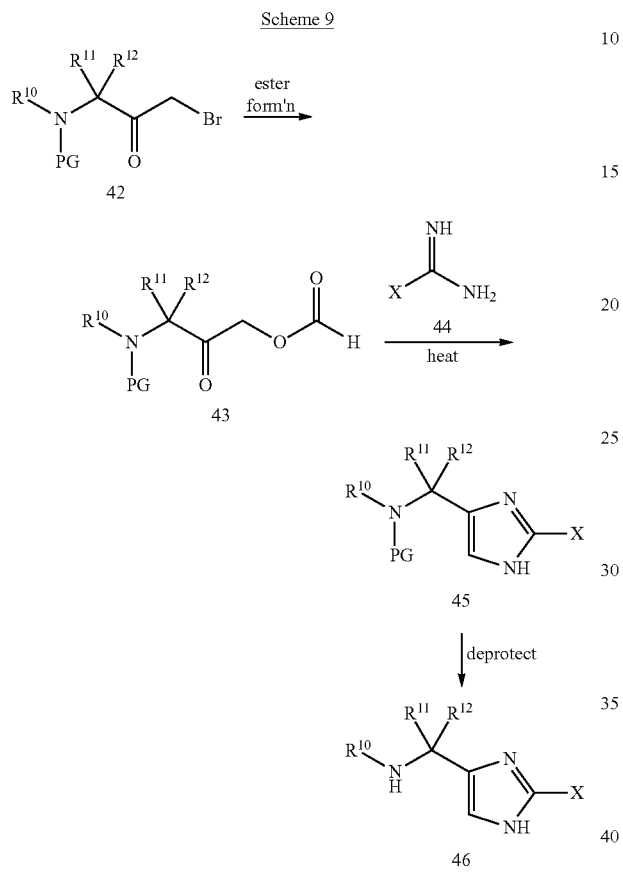

Benzimidazole compounds useful for preparing compounds of this invention can be synthesized according to the general procedure shown in Scheme 10. A suitably protected amino acid and a suitably substituted phenyl diamine 22 are dissolved in a solvent, for example pyridine, and treated with an amide bond forming reagent, such as BOP-reagent. The reaction mixture is heated to 80° C. to effect ring closure to the benzimidazole 23. The protecting group on the amine is removed as before in preparation for acylation of the amine, as outlined below in Scheme 17.

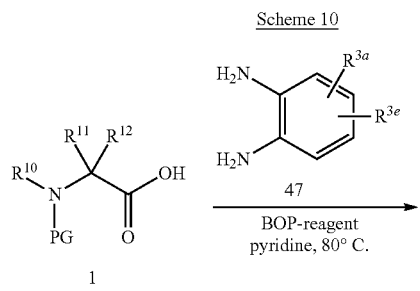

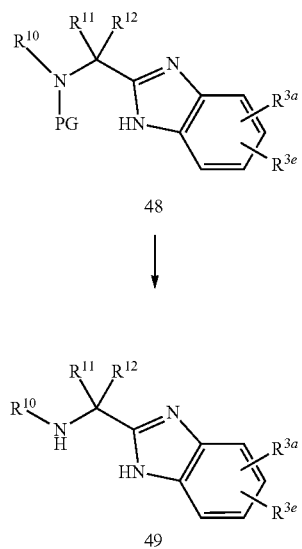

A general procedure for the synthesis of oxazoles having substituents in the 2- and 4-positions useful for the synthesis of compounds of this invention is shown in Scheme 6. A suitably protected amino acid 1 and beta-keto amine 50 (X=aryl or heteroaryl) are dissolved in a suitable solvent, for example pyridine, and treated with amide coupling reagent, for example BOP reagent, at room temperature. The keto amide 51 thus formed is dehydrated by dissolving in a suitable solvent such as DMF and treating the solution with phosphorous oxychloride at elevated temperature (Sow et al. *J. Org. Chem.* 1990, 55, 386). The oxazole 52 is deprotected in preparation for acylation of the amine 53, which is outlined in Scheme 17.

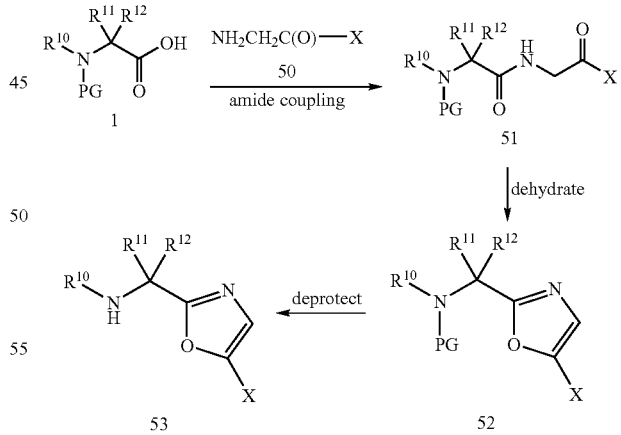

Suitably functionalized triazoles useful for the synthesis of compounds of this invention can be synthesized according to the procedure outlined in Scheme 12. A suitably protected amino acid 1 and hydrazine are dissolved in a suitable solvent, such as pyridine, and treated with an amide bond forming reagent. The resulting hydrazoic acid 54 is condensed with a suitably substituted imidate 55 (X=aryl or heteroaryl). When the imidate is in the form of a hydrochloride salt, addition of a base such as triethylamine is required. Solvents such as acetonitrile may be employed. The triazole 56 thus formed is deprotected to provide amine 57, which is used in Scheme 17 below. For example, when the protecting group is a BOC moiety, the amine is de-protected with trifluoroacetic acid in dichloromethane to give amine 53 as the bis-TFA salt.

Suitably substituted pyrazoles useful for the synthesis of compounds of this invention may be synthesized using the procedures shown in Scheme 13 (Shunsaku Ohta et al. *Chem. Pharm. Bull* 1981, 29 (10), 2762). A suitably substituted β-keto ester 58 (X=aryl or heteroaryl) is dissolved in a suitable solvent and the ester hydrolyzed with, for example, sodium hydroxide. The magnesium salt (60) of the beta keto acid 59 is formed by dissolving the acid in a suitable solvent such as methanol and THF followed by addition of magnesium ethoxide. In a separate reaction sequence, the carboxylic acid of a suitably protected amino acid 1 (Y=$R^{10}$N(PG)-) is activated with, for example, carbonyl diimidazole to give the activated amino acid 61 (LG=imidazol-1-yl in this illustration). Compound 60 and 61 are combined in a suitable solvent, for example DMF, to give the beta diketone 62. Treatment of 62 with hydrazine at elevated temperatures affords the pyrazole 63. When the amino group of 64 is protected with a CBz moiety, the protecting group may be removed by catalytic hydrogenation using, for example, palladium on carbon and elemental hydrogen to give amine 64.

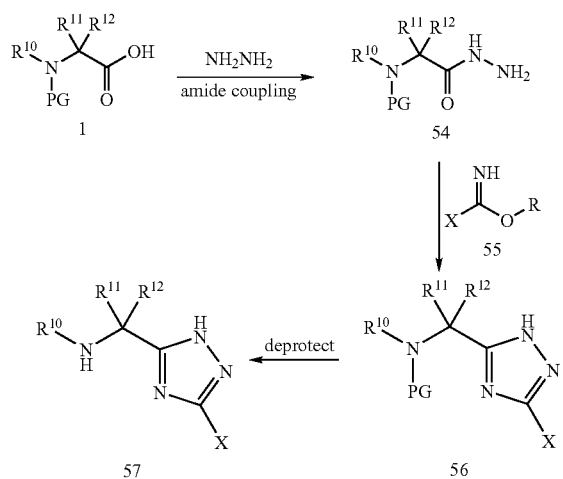

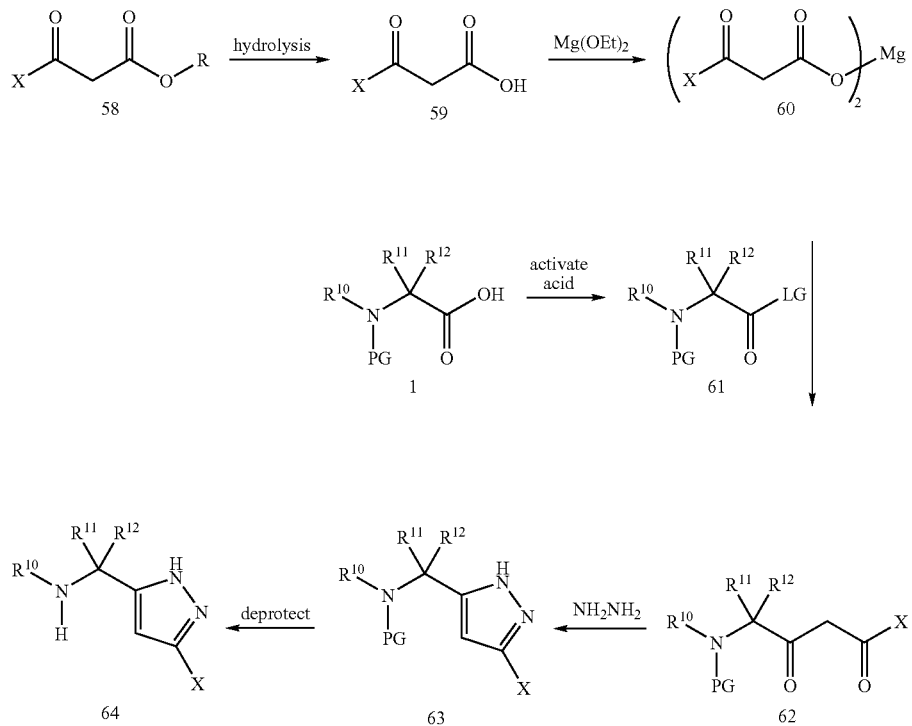

A general procedure for the formation of substituted triazolones useful for the synthesis of compounds of this invention is shown in Scheme 14. A suitably substituted protected beta-amino nitrile 65 is treated with the sodium salt of an alcohol, for example sodium methoxide, to form the imidate 66. The imidate 66 is reacted with a suitably substituted hydrazine 67 (X=aryl or heteroaryl) to form the amino amidine 68 (Yanagisawa et al. *J. Med. Chem.* 1984, 27(7), 849). Treatment of 68 with a bis-activated carbonyl such as carbonyl diimidazole (LG=imidazol-1-yl) provides the triazolone 69. Deprotection of the amino group of 69 is carried out in preparation for acylation of the nitrogen, which is outlined in Scheme 17. For example, when the amine is protected with a CBz moiety, the protecting group may be removed using catalytic hydrogenation using, for example, palladium on carbon and hydrogen or, alternatively, by treatment with HBr in HOAC or neat TFA to give amine 70.

dazole 71 is available according to the chemistry outlined in Scheme 3. The imidazole 71 is dissolved in a suitable solvent such as methanol and heated in the presence of a base such as sodium methoxide. The methyl ester 72 thus formed is dissolved in a suitable solvent, for example, tetrahydrofuran, and combined with an aniline 47 substituted in the ortho position with either hydroxy, amino, mono alkyl amino or thiol. The aniline employed may have additional substituents, $R^{3a}$ and $R^{3e}$, known to those skilled in the art to be compatible with the reaction conditions. The two reactants are treated with a protic acid, for example, para-toluene sulfonic acid, to effect addition of the aniline and subsequent cyclization and dehydration to form the fused heterocycle 74. The amine protecting group is removed in preparation for acylation of the amine, which is outlined in Scheme 17. When the protecting group is a BOC moiety, the amine is de-protected with strong

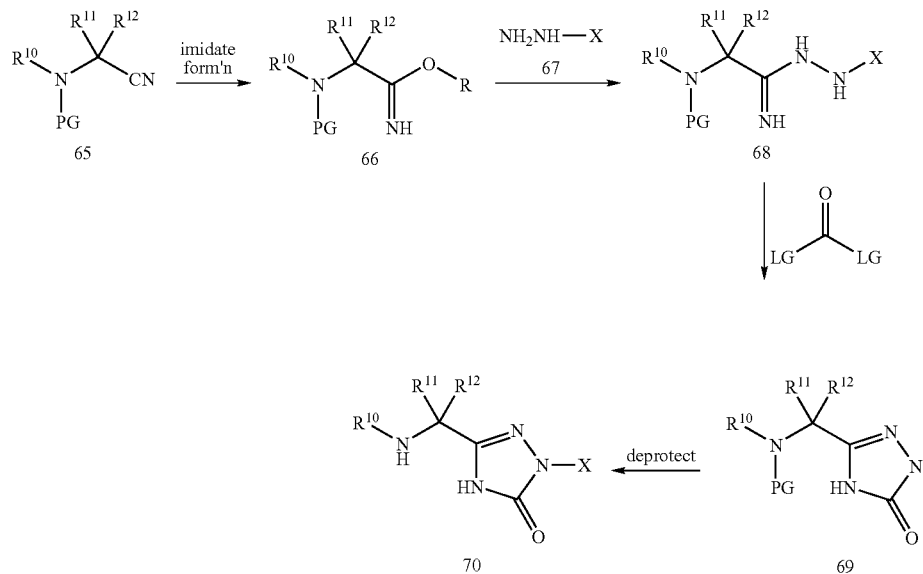

The synthesis of imidazoles substituted with fused ring heterocycles in the 4-position is shown in Scheme 15. A suitably protected and functionalized 4-trifluoromethyl imidazole 71 is available according to the chemistry outlined in acid such as trifluoroacetic acid or HCl in suitable solvent such as dichloromethane or dioxane to give amine 75 as the bis-TFA salt.

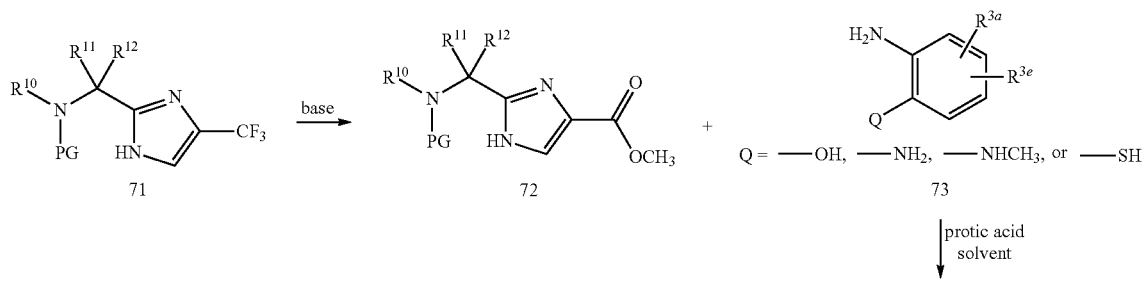

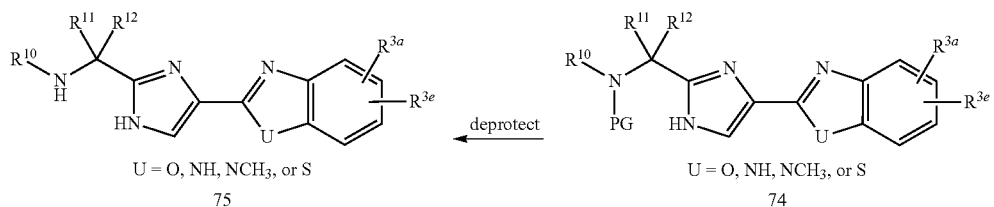

Thiazol-2-yl imidazole derivatives useful for the synthesis of compounds of this invention can be prepared as shown in Scheme 16. A suitably substituted ester 76 and a beta amino thiol such as cysteine methyl ester 77 are combined in a suitable solvent such as tetrahydrofuran and treated with a protic acid such as camphor sulfonic acid. Other beta amino thiols having functional groups compatible with these conditions may be employed in this reaction. The resulting thiazolidine 78 is oxidized to the thiazole 79 using, for example, manganese dioxide. Other suitable oxidants may be employed in this step such as 2,3-dichloro-5,6-dicyano-1,4-benzoquinone. The amino group of 79 is deprotected in preparation for acylation. For example, when the protecting group is a BOC moiety, the amine is de-protected with strong acid such as trifluoroacetic acid in suitable solvent such as dichloromethane to give amine 80 as the bis-TFA salt.

9-16 can be reacted with suitable substituted alkylating agents or sulfonyl halides, using methods known to one skilled in the art. It should be recognized that additional deprotection steps and further functional group manipulations of compounds obtained via Scheme 17 using methods known in the art will then provide additional compounds of this invention.

Alternatively, when the heterocycle contains a aliphatic carboxylic acid containing side chain, amide bond formation may be effected by reaction with a suitably substituted amine or aniline with the reagent combinations described herein (Scheme 17B).

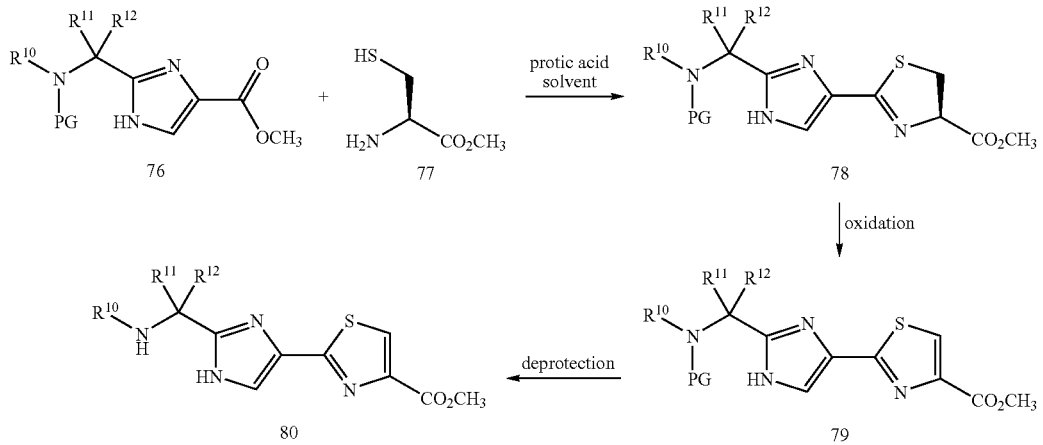

Each of the aforementioned reaction Schemes 1-3 and 9-16 produce a heterocycle containing an aminoalkyl side chain suitable for reacting with suitably substituted carboxylic acids, for example, N-Boc tranexamic acid or 4-cyanobenzoic acid, under standard amide bond coupling conditions (Scheme 17A). Reagent combinations commonly employed for this transformation may be used and include, but are not limited to: BOP-reagent and pyridine; EDCI, HOAt, N-methyl morpholine; or EDCI, HOBt, N-methyl morpholine. Solvents suitable for this transformation include, but are not limited to, pyridine, THF and dimethylformamide. Solvent combinations may also be used such as dichloromethane and DMF in ratios suitable to achieve solubility of the reagents employed. Alternately, the amines from Schemes 1-3 and

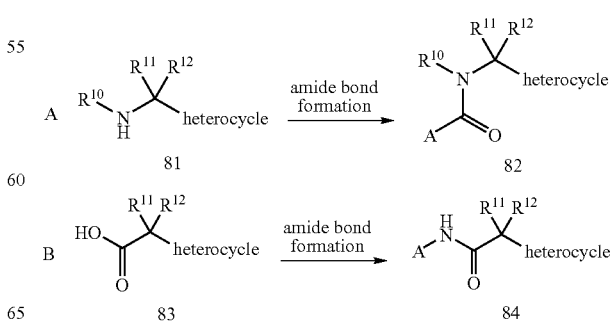

A suitably substituted carboxylic acid (A-CO₂H) is used in the amide coupling shown in Scheme 17A. Many of these carboxylic acids are commercially available. In case where the carboxylic acids are not commercially available, they can be prepared from the corresponding bromide 87, alcohol 85, aldehyde 88, or ester 89 as shown in Scheme 18 using methods known in the art. The $R^1$ and $R^2$ groups can be further manipulated using methods known in the art to provide additional compounds of this invention. For example, the cyano group can be used as $R^1$, which can be reduced to give $CH_2NH_2$ with a suitable reducing agent or converted to the amidine by reaction with hydroxylamine, and followed by palladium catalyzed hydrogenation using methods described previously.

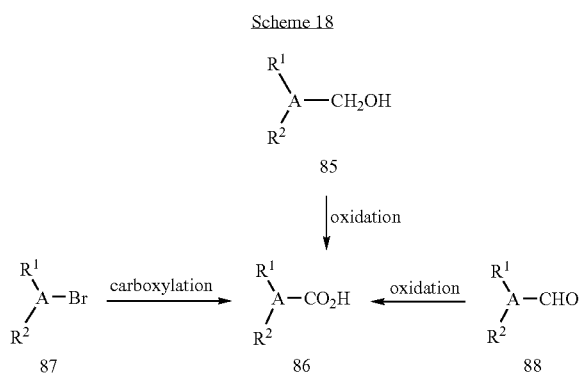

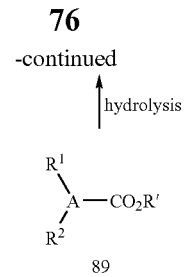

When A is an isoquinoline moiety a modified procedure from US2004/0077865 is followed. Heating the 2-methyl benzonitrile derivative 90 with 1-(t-butoxy)-N,N,N',N'-tetramethylmethanediamine in a suitable solvent such as DMF gives the enamine 91. Condensation of enamine 91 and 2,4-dimethoxybenzylamine in DMPU at elevated temperatures gives the 1-imino-1,2-dihydroisoquinoline skeleton and subsequent hydrolysis provides 92. Debenzylation of 92 with anisole in TFA at elevated temperatures provides 1-aminoisoquinoline 93. When A is a 5,6,7,8-tetrahydroisoquinoline moiety a modified procedure of McEachern et al. is followed (*J. Org. Chem.* 2002, 67, 7890). Acid 92 is converted to the ester 94. Debenzylation of 94 with anisole in TFA at elevated temperatures and acetylation with acetyl chloride and triethylamine yields 95. Hydrogenation over platinum oxide in the presence of TFA provides the 1-amino-5,6,7,8-tetrahydroisoquinoline. Saponification of the ester with NaOH and hydrolysis of the amide under acidic conditions gives 96.

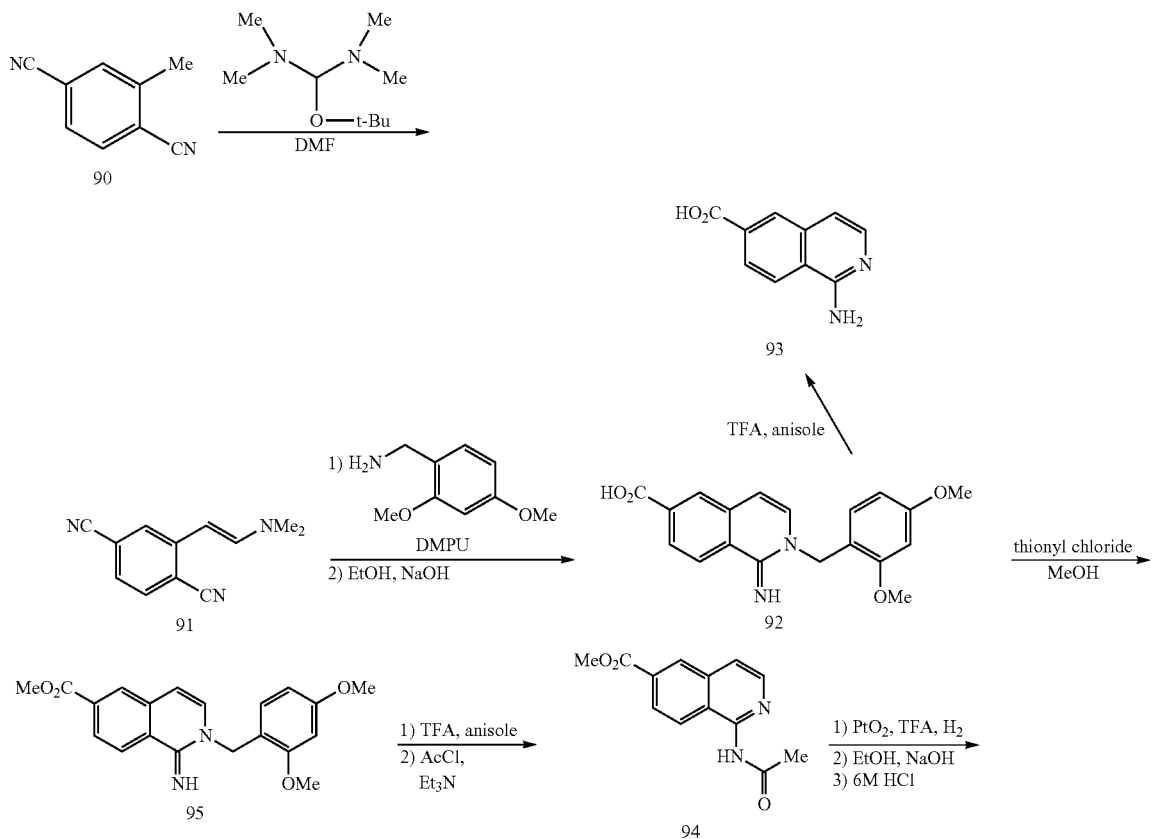

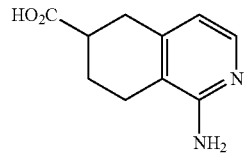

96

When A is a 4-aminoquinazoline moiety, heating an appropriately substituted ortho-fluoro benzonitrile 97 with formamidine acetate or acetamidine acetate in DMA, according to a modified procedure of Lam (Lam, P. Y. S. et al. *J. Med. Chem.* 2003, 46, 4405.), gives 4-aminoquinazoline 98 and 99. Saponification of the ester under basic conditions provides 100 and 101.

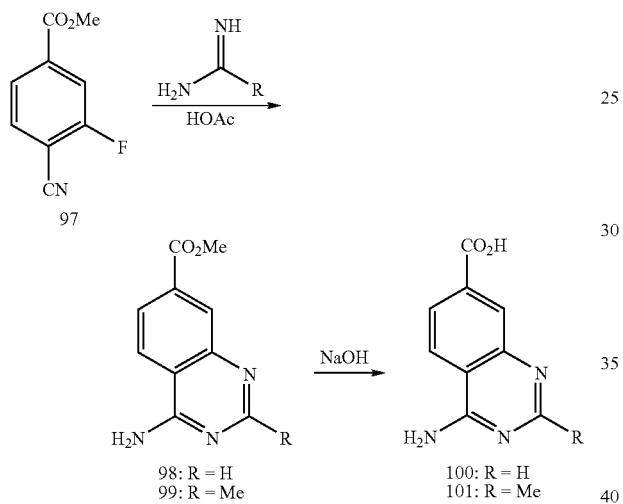

Scheme 20

98: R = H
99: R = Me

100: R = H
101: R = Me

Other features of the invention will become apparent in the course of the following descriptions of exemplary embodiments that are given for illustration of the invention and are not intended to be limiting thereof.

EXAMPLES

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

As used throughout the specification, the following abbreviations for chemical reagents apply:
HOAc or AcOH=acetic acid
Bn=benzyl
Bu=butyl
t-Bu=tertiary butyl
Boc=tert-butyl oxycarbonyl
BOP reagent=benzotriazol-1-yloxy-tris(dimethylamino) phosphonium hexafluorophosphate
Brine=saturated aqueous sodium chloride
CSA=camphor sulfonic acid
DMF=dimethylformamide
DMSO=dimethyl sulfoxide
EDCI=1-(3-(dimethylamino)propyl)-3-ethylcarbodiimide hydrochloride
Et=ethyl
EtOH=ethanol
EtOAc=ethyl acetate
Me=methyl
MeOH=methanol
NaOAc=sodium actetate
OAc=acetate
Ph=phenyl
Pr=propyl
i-Pr=isopropyl
i-PrOH=isopropanol
TFA=trifluoroacetic acid
THF=tetrahydrofuran
° C.=degrees Celsius
atm=atmosphere
conc.=concentrated
eq=equivalent(s)
h or hr=hour(s)
g=gram(s)
mg=milligram(s)
L=liter(s)
mL=milliliter(s)
μL=microliter(s)
mmol=millimolar
M=molar
meq=milliequivalent(s)
Min=minute(s)
MW=molecular weight
mp=melting point
rt or RT=room temperature
sat or sat'd=saturated
ESI=electrospray ionization mass spectroscopy
HPLC=high performance liquid chromatography
MS=mass spectrometry
LC/MS=liquid chromatography mass spectrometry
HRMS=high resolution mass spectrometry
NMR=nuclear magnetic resonance spectroscopy
TLC=thin layer chromatography "α", "β", "R", "S", "E", and "Z" are stereochemical designations familiar to one skilled in the art. One stereoisomer of a compound of Formula I may display superior activity compared with the others. Thus, each stereoisomer of a compound of Formula I is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

The following Examples have been prepared, isolated and characterized using the methods disclosed herein. The following Examples demonstrate a partial scope of the invention and are not meant to be limiting of the scope of the invention.

Example 1

(S)-4-carbamimidoyl-N-(2-phenyl-1-(4-phenyl-1H-imidazol-2-yl)ethyl)benzamide, bistrifluoroacetic acid salt Part A: (S)-tert-butyl 2-phenyl-1-(4-phenyl-1H-imidazol-2-yl)ethylcarbamate: To a solution of L-N-(Boc)-phenylalanine (750 mg, 3.77 mmol) in EtOH/H$_2$O (1:1; 7.4 mL) was added with Cs$_2$CO$_3$ (650 mg, 1.89 mmol). The reaction was stirred at rt for 1 h. The solvent was removed under vacuum and the resulting salt suspended in DMF (4.7 mL). 2-Bromoacetophenone (1.0 g, 3.77 mmol) was added in a single portion and the reaction stirred at rt for 1.5 h. The reaction was filtered to remove CsBr. The solids were washed with DMF. The combined washings and filtrate were concentrated in vacuo to yield a yellow solid (650 mg). The crude intermediate was placed in a flask fitted with a Dean-Stark trap and dissolved in xylenes (10 mL). NH$_4$OAc (2.64 g, 30 mmol) was added to the flask and the reaction was heated to reflux for 3 h. The reaction was cooled to rt and the solvent removed in vacuo. The residue was redissolved in EtOAc and washed with saturated aqueous NaHCO$_3$ and brine, dried over Na$_2$SO$_4$, filtered and evaporated to dryness to yield 780 mg of the desired product (57% yield). MS 364.2 (M+H)$^+$.

Alternatively, the keto ester intermedite and 10 equivalents of NH$_4$OAc were dissolved in ethanol and heated to 160° C. in a sealed tube for 30 min using microwave irradiation. The reaction was cooled to rt, the ethanol was evaporated in vacuo and the residue was redissolved in EtOAc. The organic layer was washed with ½ saturated brine (2 times), dried over MgSO$_4$ and evaporated to dryness. The crude product thus formed was sufficiently pure to carry on to the next step.

Part B: (S)-2-Phenyl-1-(4-phenyl-1H-imidazol-2-yl)ethanamine bis-trifluoroacetic acid salt: The product from Example 1 Part A (100 mg, 0.28 mmol) was dissolved in CH$_2$Cl$_2$ (2.8 mL) and treated with neat TFA (0.2 mL, 10% v/v). The reaction was stirred at rt for 16 h. The solvent and TFA were removed in vacuo. The residue was redissolved in methanol. The solvent was removed in vacuo, the residue was re-dissolved in MeOH and the solvent wad evaporated in vacuo to yield 124 mg (92% yield) of crude amine as the bis-TFA salt. MS 262.2 (M−H)$^−$.

Part C: (S)-4-carbamimidoyl-N-(2-phenyl-1-(4-phenyl-1H-imidazol-2-yl)ethyl)benzamide, bistrifluoroacetic acid salt: The product from Example 1 Part B (124 mg, 0.25 mmol) and 4-amidinobenzoic acid hydrochloride (94 mg, 0.47 mmol) were dissolved in anhydrous pyridine (2 mL). BOP reagent (249 mg, 0.56 mmol) was added and the reaction was stirred at rt for 16 h. The solvent was removed in vacuo and the residue redissolved in MeOH/H$_2$O (9:1) containing 0.1% TFA. The solution was filtered and the title compound was isolated by prep HPLC to yield 9.2 mg of the desired product (3% yield). $^1$H-NMR (500 MHz, d$_4$-MeOH) δ 3.37 (dd, J=8.5 and 13 Hz, 1H), 3.46 (dd, J=8.5 and 13 Hz, 1H), 5.48 (app t, J=8.2 Hz, 1H), 7.14-7.21 (m, 5H), 7.34-7.41 (m, 3H), 7.56 (m, 2H), 7.68 (s, 1H), 7.80 (d, J=8.2 Hz), 7.96 (d, J=8.2 Hz, 2H): HRMS (M+H)$^+$ for C$_{25}$H$_{23}$N$_5$O, calcd m/z: 410.1981, obs: 410.1974.

Example 2

(S)-4-(aminomethyl)-N-(2-phenyl-1-(4-phenyl-1H-imidazol-2-yl)ethyl)cyclohexanecarboxamide, bistrifluoroacetic acid salt Part A: (S)-tert-Butyl (4-((2-phenyl-1-(4-phenyl-1H-imidazol-2-yl)ethyl)carbamoyl)cyclohexyl)methylcarbamate: The product from Example 1 Part B (75 mg, 0.15 mmol) and N-(Boc)-tranexamic acid (75 mg, 0.29 mmol) were dissolved in pyridine (1.7 mL). BOP reagent (152 mg, 0.344 mmol) was added and the reaction was stirred at rt for 12 h. The reaction was diluted with water and extracted with EtOAc. The combined organic layers were washed with brine, dried over Na$_2$SO$_4$, filtered and evaporated in vacuo. The crude product was carried on to the next step without further purification. MS 503.2 (M+H)$^+$.

Alternately, the product from Example 1 Part B was coupled with 1.0 equivalents of N-Boc-tranexamic acid, 1.2 equivalents HOAt, 5.0 equivalents of N-methylmorpholine, and 1.2 equivalents of EDCI. The amine, N-Boc-tranexamic acid and HOAt are dissolved in DMF. N-Methylmorpholine is added followed by EDCI. The reaction is stirred at rt for 2 and 16 h. The reaction is diluted with EtOAc, washed with ½ saturated brine (4-6 times), dried over MgSO$_4$, filtered and evaporated to dryness to give the crude product.

Part B: (S)-4-(aminomethyl)-N-(2-phenyl-1-(4-phenyl-1H-imidazol-2-yl)ethyl)cyclohexanecarboxamide, bistrifluoroacetic acid salt: The product from Example 2 Part A (100 mg) was dissolved in 30% TFA in CH$_2$Cl$_2$ (2.0 mL). The reaction was stirred at rt for 3 h. The reaction was diluted with toluene and dried in vacuo. The residue was re-dissolved in toluene and solution evaporated to dryness. The crude product was re-dissolved in MeOH/H$_2$O (9:1) containing 0.1% TFA and the title compound was isolated by prep HPLC (46 mg as the bis-TFa salt, 49% yield). $^1$H-NMR (500 MHz, d$_4$-MeOH) δ 1.02-1.11 (m, 2H), 1.32-1.45 (m, 2H), 1.54-1.61 (m, 1H), 1.80 (br d, J=12.1 Hz, 1H), 1.86 (br d, J=11.5 Hz, 3H), 2.28 (dt, J=12.1, 3.30 Hz, 1H), 2.77 (d, J=7.15 Hz, 2H), 3.28-3.33 (dd, 1H, obscured by CH$_3$OH peak), 3.38 (dd, J=13.5, 8.0 Hz), 5.31 (t, J=8.25 Hz, 1H), 7.18 (d, J=7.15 Hz, 2H), 7.22-7.30 (m, 3H), 7.43-7.50 (m, 3H), 7.62 (app d, J=6.6 Hz, 2H), 7.75 (s, 1H): MS 403.2 (M+H)$^+$.

Example 25

(S)-Ethyl 2-(4-(2-(1-(4-(aminomethyl)cyclohexanecarboxamido)-2-phenylethyl)-1H-imidazol-4-yl)phenyl)acetate, bistrifluoroacetic acid salt Part A: Ethyl 4-acetyl-phenylacetate: Ethyl bromoacetate (1.70 g, 10.2 mmol), tris-(1-naphthylene)phosphine (379 mg, 0.93 mmol) and tribasic potassium phosphate (10.8 g, 51 mmol) were placed in a flask. The flask was evacuated and back-filled with argon. A solution of 4-acetylphenylboronic acid (2.0 g, 12.2 mmol) in anhyd THF (40 mL) was added to the flask. The reaction was stirred at rt for 16 h. The reaction was diluted with EtOAc, washed with water and brine, dried over MgSO$_4$, filtered and evaporated to dryness. The residue was pre-adsorbed on to SiO$_2$ and the product isolated via SiO$_2$ chromatography to yield 616 mg (29%) of ethyl 4-acetyl-phenylacetate. MS 207.1 (M+H)$^+$.

Part B: Ethyl 2-(4-(2-bromoacetyl)phenyl)acetate: Ethyl 4-acetyl-phenylacetate from Example 25 Part A (489 mg, 2.4 mmol) was dissolved in CH$_2$Cl$_2$. Bromine (379 mg, 2.4 mmol) was added dropwise. The reaction was stirred at rt for 16 h. The reaction had decolorized from rust red to light yellow. The solvent was evaporated in vacuo to yield 680 mg (99%) of ethyl 2-(4-(2-bromoacetyl)phenyl)acetate as a light yellow oil. The product was used in the next step without further purification. MS 287.0 and 289.0 of equal intensities $(M+H)^+$.

Part C: (S)-Ethyl 2-(4-(2-(1-(tert-butoxycarbonyl)-2-phenylethyl)-1H-imidazol-4-yl)phenyl)acetate: N-(Boc)-phenylalanine (633 mg, 2.38 mmol) was dissolved in DMF (2.0 mL). $Cs_2CO_3$ (775 mg, 1.19 mmol) was added to the flask in a single portion, and the reaction was stirred for 1 h. A solution of ethyl 2-(4-(2-bromoacetyl)phenyl)acetate from Example 25 Part B (680 mg, 2.38 mmol) in DMF (2.0 mL) was added to the reaction vessel, and the reaction was stirred at rt for 16 h. The solids were filtered off and rinsed with DMF. The organic layers were combined and evaporated to dryness. The residue was re-dissolved in EtOAc and washed with a solution of 1:1 water and brine, dried over $MgSO_4$, filtered and evaporated to yield 1.03 g of a light tan solid. The solid was re-dissolved in xylenes (14 mL). $NH_4OAc$ (3.42 g, 44 mmol) was added, and the flask fitted with a Dean-Stark trap. The reaction was heated to reflux for 5 h with removal of water. The reaction was cooled to rt, and the solvent removed in vacuo. The residue was re-dissolved in EtOAc, washed with water and brine, dried over $MgSO_4$, filtered and evaporated to yield 951 mg (96%) of a light tan solid. MS 450.1 $(M+H)^+$.

Part D: (S)-Ethyl 2-(4-(2-(1-amino-2-phenylethyl)-1H-imidazol-4-yl)phenyl)acetate: The product from Example 25 Part C (951 mg, 2.12 mmol) was treated according to the procedure described for Example 1 Part B to yield 1.14 g (100%) of a dark brown glass, which was used without further purification in the next step. MS 333.1 $(M-NH_2)^+$.

Part E: (S)-Ethyl 2-(4-(2-(1-(4-((tert-butoxycarbonyl)methyl)cyclohexanecarboxamido)-2-phenylethyl)-1H-imidazol-4-yl)phenyl)acetate: The product from Example 25 Part D (729 mg, 1.26 mmol), N-(Boc)-tranexamic acid (325 mg, 1.26 mmol) and HOAt (206 mg, 1.51 mmol) were dissolved in DMF (6.3 mL). N-methylmorpholine (637 mg, 6.3 mmol) was added followed by EDCI (289 mmol, 1.51 mmol). The reaction was stirred at rt for 16 h, diluted with EtOAc, washed with a 1:1 mixture of water and brine, dried over $MgSO_4$, filtered and evaporated to yield 732 mg (99%) of product, which was used in the next step without further purification. MS 589.1 $(M+H)^+$.

Part F: (S)-Ethyl 2-(4-(2-(1-(4-(aminomethyl)cyclohexanecarboxamido)-2-phenylethyl)-1H-imidazol-4-yl)phenyl)acetate, bistrifluoroacetic acid salt: The product from Example 25 Part E (99 mg, 0.17 mmol) was treated with TFA according to the procedure described for Example 1 Part B. The product was isolated by prep HLPC to yield 61 mg (50%) of the title compound as the bis-TFA salt. $^1$H-NMR (500 MHz, $d_4$-MeOH) δ 1.02-1.11 (m, 2H), 1.24 (t, J=7.15 Hz, 3H), 1.32-1.45 (m, 2H), 1.53-1.61 (m, 1H), 1.80 (br d, J=12.6 Hz, 1H), 1.86 (br d, J=11.0 Hz, 3H), 2.28 (tt, J=12.4, 3.0 Hz, 1H), 2.775 (d, J=7.15 Hz, 2H), 3.28-3.32 (dd, obscured by MeOH peak), 3.38 (dd, J=13.5, 8.0 Hz, 1H), 3.70 (s, 2H), 4.145 (q, J=7.15 Hz, 2H), 5.31 (t, J=8.5 Hz, 1H), 7.175 (d, J=7.15 Hz, 2H), 7.22-7.30 (m, 3H), 7.41 (d, J=8.25 Hz, 2H), 7.59 (d, J=8.25 Hz, 2H), 7.74 (s, 1H). HRMS $(M+H)^+$ for $C_{29}H_{36}N_4O_3$, calcd m/z: 489.2866, obs: 489.2861.

Example 26

(S)-2-(4-(2-(1-(4-(aminomethyl)cyclohexanecarboxamido)-2-phenylethyl)-1H-imidazol-4-yl)phenyl)acetic acid, bistrifluoroacetic acid salt (S)-Ethyl 2-(4-(2-(1-(4-(aminomethyl)cyclohexanecarboxamido)-2-phenylethyl)-1H-imidazol-4-yl)phenyl)acetate bis trifluoroacetic acid salt from Example 25 (30 mg, 0.042 mmol) was dissolved in MeOH (2 mL) and treated with 1 N NaOH (0.2 mL). The reaction was stirred at rt for 16 h. The solvent was removed in vacuo and the residue re-dissolved in $MeOH/H_2O$ (9:1) containing 0.1% TFA and then purified by prep HPLC to yield 22 mg of the title compound as its bis-TFA salt (76% yield). $^1$H-NMR (500 MHz, $d_4$-MeOH) δ 1.02-1.11 (m, 1H), 1.31-1.45 (m, 2H), 1.53-1.61 (m, 1H), 1.79 (br d, J=12.1 Hz, 1H), 1.865 (br d, J=12.1 Hz, 3H), 2.28 (tt, J=3.2 and 12.1 Hz, 1H), 2.77 (d, J=7.15 Hz, 2H), 3.28-3.32 (dd, obscured by MeOH peak), 3.375 (dd, J=8.0 and 13.4 Hz, 1H), 3.67 (s, 2H), 5.31 (t, J=8.25 Hz, 1H), 7.175 (d, J=6.6 Hz, 2H), 7.22-7.30 (m, 3H), 7.42 (d, J=8.25 Hz, 2H), 7.59 (d, J=8.25 Hz, 2H), 7.74 (s, 1H). HRMS $(M+H)^+$ for $C_{27}H_{32}N_4O_3$, calcd m/z: 461.2553, obs: 461.2572.

Example 27

(S)-4-(aminomethyl)-N-{1-[(4-carbamoylmethyl-phenyl)-1H-imidazol-2-yl]-2-phenyl-ethyl}-cyclohexanecarboxamide, bistrifluoroacetic acid salt Part A: (S)-2-(4-(2-(1-(4-((tert-Butoxycarbonyl)methyl)cyclohexanecarboxamido)-2-phenylethyl)-1H-imidazol-4-yl)phenyl)acetic acid: The product from Example 25 Part E (200 mg, 0.34 mmol) was dissolved in MeOH (3 mL) and treated with 1 N NaOH (0.34 mL). The reaction was stirred at rt for 16 h. The solvent was removed in vacuo. The residue was re-dissolved in $MeOH/H_2O$ (9:1) containing 0.1% TFA. The product was isolated by prep HPLC (90 mg, 47%). MS 561.1 $(M+H)^+$.

Part B: (S)-tert-Butyl (4-((1-(4-(4-(2-amino-2-oxoethyl)phenyl)-1H-imidazol-2-yl)-2-phenylethyl)carbamoyl)cyclohexyl)methylcarbamate: The product from Example 27 Part A (33 mg, 0.060 mmol) and HOAt (9.7 mg, 0.071 mmol) were dissolved in DMF (1 mL). N-Methylmorpholine (18.2 mg, 0.18 mmol) and EDCI (13.6 mg, 0.071 mmol) were added sequentially. The reaction as stirred for 30 min at rt. Conc. aqueous ammonia (5 drops from a Pasteur pipet) was added and the reaction stirred at rt for 16 h. The reaction was diluted with EtOAc and washed with a 1:1 mixture of water and brine (5×), 1 N aqueous HCl and brine, dried over $MgSO_4$, filtered and dried in vacuo. The residue was re-dissolved in $MeOH/H_2O$ (9:1) containing 0.1% TFA, and the product isolated by prep HPLC to yield 9 mg (22%). MS 560.1 $(M+H)^+$.

Part C: (S)-N-(1-(4-(4-(2-amino-2-oxoethyl)phenyl)-1H-imidazol-2-yl)-2-phenylethyl)-4-(aminomethyl)-cyclohexanecarboxamide, bistrifluoroacetic acid salt: The product from Example 27 Part B (9 mg, 0.016 mmol) was treated with TFA according to the procedure described for Example 1 Part B to provide the title compound (11 mg, 99%). $^1$H-NMR (500 MHz, $d_4$-MeOH) δ 1.02-1.11 (m, 2H), 1.28-1.44 (m, 2H), 1.57 (m, 1H), 1.79 (br d, J=12.6 Hz, 1H), 1.85 (br d, J=11 Hz, 3H), 2.28 (tt, J=3.0, 12.1 Hz, 1H), 2.77 (d, J=7.15 Hz, 2H), 3.28-3.32 (dd, obscured by MeOH), 3.375 (dd, J=8.0, 13.0 Hz, 1H), 3.57 (s, 2H), 5.31 (t, J=8.2 Hz, 1H), 7.175 (d, J=7.2 Hz, 2H), 7.22-7.30 (m, 3H), 7.43 (d, J=8.2 Hz, 2H), 7.59 (d, J=8.2 Hz, 2H), 7.74 (s, 1H); HRMS $(M+H)^+$ for $C_{27}H_{33}N_5O_2$, calcd m/z: 460.2713, obs: 460.2714.

Example 28

4-(2-((S)-1-(trans-4-(aminomethyl)cyclohexanecarboxamido)-2-phenylethyl)-1H-imidazol-4-yl)benzamide, bistrifluoroacetic acid salt Part A: tert-Butyl)trans-4-(((S)-1-(4-(4-carbamoylphenyl)-1H-imidazol-2-yl)-2-phenylethyl)carbamoyl)cyclohexyl)methylcarbamate: tert-Butyl (trans-4-(((S)-1-(4-(4-cyanophenyl)-1H-imidazol-2-yl)-2-phenylethyl)carbamoyl)cyclohexyl)methylcarbamate formed from 2-bromo-4'-cyanoacetophenone using the procedures from Example 1 Part A-B and Example 2 Part A (117 mg, 0.22 mmol) was dissolved in DMSO (2 mL) and treated with $K_2CO_3$ (90.0 mg, 0.65 mmol) under argon. 30% $H_2O_2$ in water (0.8 mL, 2.4 mmol) and magnesium oxide (44 mg, 1.11 mmol) were added sequentially to the reaction. The reaction was stirred at rt for 4 h. The reaction was diluted with EtOAc, washed with 1 N HCl and brine, dried over $MgSO_4$, filtered and evaporated to dryness. The product (109 mg, 90% yield) was isolated as a yellow solid. MS 546.3 $(M+H)^+$.

Part B: 4-(2-((S)-1-(trans-4-(aminomethyl)cyclohexanecarboxamido)-2-phenylethyl)-1H-imidazol-4-yl)benzamide, bistrifluoroacetic acid salt: The product from Example 28 Part A (109 mg, 0.20 mmol) was treated with TFA according to the procedure described for Example 2 Part B. The product was isolated by prep HLPC to yield 17.3 mg of the title compound (20%). $^1$H NMR (500 MHz, $d_4$-MeOH) δ 0.36 (m, 2H), 0.68 (m, 2H), 0.87 (m, 1H), 1.14 (m, 3H), 2.07 (d, J=7.15 Hz, 2H), 2.63 (m, 2H), 4.61 (t, J=8.25 Hz, 1H), 6.47 (d, J=7.15 Hz, 2H), 6.53 (t, J=7.42 Hz, 1H), 6.58 (t, J=7.15 Hz, 2H), 7.04 (d, J=8.25 Hz, 2H), 7.14 (s, 1H), 7.28 (d, J=8.25 Hz, 2H); HRMS (M+H) for $C_{26}H_{31}N_5O_2$, calcd m/z: 446.2556, obs: 446.2570.

Example 29

3-(2-((S)-1-(4-(aminomethyl)cyclohexanecarboxamido)-2-phenylethyl)-1H-imidazol-4-yl)benzamide, bistrifluoroacetic acid salt The title compound was synthesized by appropriate application of the procedures described for Example 28. $^1$H NMR (500 MHz, $d_4$-MeOH) δ 1.06 (m, 2H), 1.39 (m, 2H), 1.57 (m, 1H), 1.80 (d, J=12.10 Hz, 1H), 1.86 (d, J=11.55 Hz, 3H), 2.28 (tt, J=12.10, 3.30 Hz, 2H), 2.77 (d, J=7.15 Hz, 2H), 3.34 (d, J=8.25 Hz, 1H), 3.39 (dd, J=13.40, 8.25 Hz, 1H), 3.98 (s, 1H), 5.34 (t, J=8.25 Hz, 1H), 7.19 (d, J=6.60 Hz, 2H), 7.24 (t, J=7.15 Hz, 1H), 7.29 (t, J=7.15 Hz, 2H), 7.60 (t, J=7.70 Hz, 1H), 7.82 (m, J=5.50 Hz, 2H), 7.93 (d, J=8.25 Hz, 1H) 8.18 (s, 1H); MS 446.2 $(M+H)^+$.

Example 30

4-(2-((S)-1-(trans-4-(aminomethyl)cyclohexanecarboxamido)-2-phenylethyl)-1H-imidazol-4-yl)-N-methylbenzamide, bistrifluoroacetic acid salt Part A: 4-(2-((S)-1-(trans-4-((tert-Butoxycarbonyl)methyl)cyclohexanecarboxamido)-2-phenylethyl)-1H-imidazol-4-yl)benzoic acid: Methyl 4-(2-((S)-1-(trans-4-((tert-butoxycarbonyl)methyl)cyclohexanecarboxamido)-2-phenylethyl)-1H-imidazol-4-yl)benzoate formed from 2-bromo-4'-carboxymethylacetophenone using the procedures from Example 1 Part A-B and Example 2 Part A (162 mg, 0.28 mmol) was dissolved in MeOH (5 ml) and EtOAc (1 mL). 1 N NaOH (2 mL) and magnesium oxide (112 mg, 2.8 mmol) were added sequentially and the mixture was stirred for 5 hrs at rt. The solvent was evaporated to dryness in vacuo. The residue was diluted with water and treated with 1 N HCl. The resulting solution was diluted with EtOAc, washed with brine and dried over $MgSO_4$, filtered and evaporated to yield 75 mg (60% yield) of a clear glass. MS 548.0 $(M+H)^+$.

Part B: tert-Butyl (trans-4-(((S)-1-(4-(4-(methylcarbamoyl)phenyl)-1H-imidazol-2-yl)-2-phenylethyl)carbamoyl)cyclohexyl)methylcarbamate: The product from Example 30 Part A (45 mg, 0.08 mmol) and methylamine (0.2 mL, 0.09 mmol) were treated under the conditions described in Example 2 Part B with the substitution of HOBt for HOAt. The resulting yellow oil (44.0. mg, 93% yield) was carried to the next step without further purification. MS 560.1 $(M+H)^+$ Part C: 4-(2-((S)-1-(trans)-4-(aminomethyl)cyclohexanecarboxamido)-2-phenylethyl)-1H-imidazol-4-yl)-N-methylbenzamide, bistrifluoroacetic acid salt: The product from Example 30 Part B (44.0 mg, 0.079 mmol) was treated with TFA according the procedure described for Example 2 Part B. The resulting residue was re-dissolved in $MeOH/H_2O$ (9:1) containing 0.1% TFA and isolated by prep HPLC to yield 1.0 mg of the title compound (3%). $^1$H NMR (500 MHz, $d_4$-MeOH) δ 1.05 (m, 1H), 1.39 (ddd, J=30.24, 12.92, 3.02 Hz, 1H), 1.55 (m, J=12.10 Hz, 1H), 1.79 (m, 1H), 1.86 (d, J=11.00 Hz, 1H), 2.26 (m, 1H), 2.77 (d, J=7.15 Hz, 1H), 2.92 (s, 1H), 3.15 (m, 1H), 3.3 (m, 2H), 5.29 (t, J=8.25 Hz, 1H), 7.16 (d, J=7.15 Hz, 1H), 7.23 (t, J=7.15 Hz, 1H), 7.28 (t, J=7.15 Hz, 1H), 7.72 (d, J=8.25 Hz, 1H), 7.86 (s, 1H), 7.92 (d, J=8.80 Hz, 1H); HRMS $(M+H)^+$ for $C_{27}H_{33}N_5O_2$, calcd m/z: 460.2713, obs: 460.2735.

Example 31

(S)-4-(2-(1-trans-(4-(aminomethyl)cyclohexanecarboxamido)-2-phenylethyl)-1H-imidazol-4-yl)-N,N-dimethylbenzamide, bistrifluoroacetic acid salt The title compound was synthesized by appropriate application of the procedures described for the synthesis of Example 30. $^1$H NMR (500 MHz, $d_4$-MeOH) δ 1.06 (m, 2H), 1.39 (m, 2H), 1.57 (m, 1H), 1.81 (d, J=14.85 Hz, 1H), 1.86 (d, J=10.45 Hz, 3H), 2.28 (tt, J=12.30, 3.30 Hz, 1H), 2.77 (d, J=7.15 Hz, 2H), 3.01 (s, 3H), 3.12 (s, 3H), 3.39 (dd, J=13.30, 8.24 Hz, 1H), 5.31 (t, J=8.25 Hz, 1H), 7.18 (d, J=7.15 Hz, 2H), 7.24 (t, J=7.15 Hz, 1H), 7.29 (t, J=7.42 Hz, 2H), 7.55 (d, J=8.25 Hz, 2H), 7.72 (d, J=8.25 Hz, 2H), 7.85 (s, 1H); HRMS $(M+H)^+$ for $C_{28}H_{35}N_5O_2$, calcd m/z: 474.2870, obs: 474.2875.

Example 32 trans-N-((S)-1-(4-(1H-benzo[d]imidazol-2-yl)-1H-imidazol-2-yl)-2-phenylethyl)-4-(aminomethyl)cyclohexanecarboxamide, tristrifluoroacetic acid salt Part A: (S)-tert-Butyl 2-phenyl-1-(4-(trifluoromethyl)-1H-imidazol-2-yl)ethylcarbamate: To a solution of sodium acetate (0.88 g, 6.44 mmol) in 3 mL of water was added 1,1-dibromotrifluoroacetone (0.87 g, 3.22 mmol). The mixture was heated at 90° C. under $N_2$ for 30 min. It was cooled to 0° C. and a solution of (S)-(−)-2-(t-butoxycarbonylamino)-3-phenylpropanal (1.73 g, 2.93 mmol) in 15 mL of methanol was added, followed by concentrated ammonium hydroxide (4 mL of concentrated solution). The resulting mixture was stirred at RT under $N_2$ for 12 h. The solvent was removed and water was added. The precipitate was filtered and then re-dissolved in EtOAc. The EtOAc solution was washed with brine, dried over $Na_2SO_4$, and filtered. The filtrate was concentrated to give 0.80 g of the desired product as an off-white solid (76.9% yield). MS, 356.30 $(M+H)^+$.

Part B: (S)-tert-Butyl 2-phenyl-1-(4-(trimethoxymethyl)-1H-imidazol-2-yl)ethylcarbamate: The product from Example 32 Part A (0.1 g, 0.4 mmol) was dissolved in MeOH (2 mL) and treated with NaOMe (25% wt in MeOH, 1.7 mL, 7.4 mmol). The reaction mixture was heated using microwave irradiation in a sealed tube for 5 min at 100° C. Upon cooling to rt, the solvent was removed under vacuum, and the residue dissolved in EtOAc (15 mL). The solution was washed with H$_2$O, brine, dried over Na$_2$SO$_4$, filtered, and evaporated to dryness to yield a brown gum (0.15 g). MS 392.1 (M+H)$^+$.

Part C: tert-Butyl (trans-4-(((S)-1-(4-(1H-benzo[d]imidazol-2-yl)-1H-imidazol-2-yl)-2-phenylethyl)carbamoyl)cyclohexyl)methylcarbamate: The crude intermediate from Example 32 Part B was dissolved in THF (2 mL). 1,2-Phenylenediamine (41 mg, 0.38 mmol) and p-toluenesulfonic acid monohydrate (7.3 mg, 0.038 mmol) were added to the reaction. The reaction was stirred at rt for 6 h and the solvent removed in vacuo. The residue was dissolved in EtOAc and washed with saturated aqueous NaHCO$_3$ and brine, dried over Na$_2$SO$_4$, filtered and evaporated to dryness. The residue was purified by flash chromatography (silica gel, 0-100% EtOAc in hexane gradient) to yield 59 mg (37%), as a yellow solid. HRMS m/z Calc'd for C$_{23}$H$_{26}$N$_5$O$_2$ [M+H]$^+$: 404.2087. Found 404.2079.

Part D: trans-N-((S)-1-(4-(1H-benzo[d]imidazol-2-yl)-1H-imidazol-2-yl)-2-phenylethyl)-4-(aminomethyl)cyclohexanecarboxamide, bistrifluoroacetic acid salt: The product from Example 32 Part C (59 mg, 0.15 mmol) was dissolved in CH$_2$Cl$_2$ (0.7 mL) and treated with neat TFA (0.3 mL, 30% v/v). The reaction was stirred at rt for 1 h. The solvent and TFA were removed in vacuo. The residue was redissolved in DMF (1 mL). Et$_3$N (0.073 mL, 0.53 mmol), N-Boc-tranexamic acid (42 mg, 0.16 mmol), HOBt (0.03 g, 0.23 mmol), and EDCI (43 mg, 0.23 mmol) were added and the reaction was stirred at rt for 4 h. EtOAc (15 mL) was added, followed by H$_2$O (10 mL). The separated organic phase was washed with water, brine, dried over Na$_2$SO$_4$, filtered and evaporated to dryness. The residue was dissolved in CH$_2$Cl$_2$ (0.7 mL) and treated with neat TFA (0.3 mL, 30% v/v). After 40 min. at rt, the reaction was concentrated. Purification by Prep HPLC gave 66 mg (56%) of the title compound. $^1$H-NMR (400 MHz, CD$_3$OD) δ 0.99-1.09 (m, 2H), 1.27-1.49 (m, 2H), 1.54-1.60 (m, 1H), 1.69-1.72 (m, 1H), 1.82-1.85 (m, 3H), 2.16-2.23 (m, 1H), 2.76 (d, J=7.0 Hz, 2H), 3.20 (dd, J=8.8, 13.6 Hz, 1H), 3.46 (dd, J=6.6, 13.6 Hz, 1H), 5.35 (dd, J=7.0, 8.8 Hz, 1H), 7.16-7.26 (m, 5H), 7.54-7.58 (m, 2H), 7.72-7.76 (m, 2H), 8.04 (s, 1H); HRMS m/z Calc'd for C$_{26}$H$_{31}$N$_6$O [M+H]$^+$: 443.2559. Found 443.2545.

Examples 33-35 listed in Table 2 were similarly synthesized by appropriate application of the procedures described for Example 32.

Example 36

Methyl 2-(2-((S)-1-(trans-4-(aminomethyl)cyclohexanecarboxamido)-2-phenylethyl)-1H-imidazol-4-yl)thiazole-4-carboxylate, bistrifluoroacetic acid salt Part A: Methyl 2-(2-((S)-1-(tert-butoxycarbonyl)-2-phenylethyl)-1H-imidazol-4-yl)-4,5-dihydrothiazole-4-carboxylate: (S)-tert-Butyl 2-phenyl-1-(4-(trifluoromethyl)-1H-imidazol-2-yl)ethylcarbamate produced in Example 32 Part A (0.43 g, 1.21 mmol) was dissolved in MeOH (5 mL). NaOMe (25% wt in MeOH, 5.5 mL, 24.2 mmol) was added. The reaction mixture was heated for 42 h at 60° C., then cooled to rt. The solvent was removed under vacuum, and the residue dissolved in EtOAc (50 mL). The solution was washed with H$_2$O, brine, dried over Na$_2$SO$_4$, filtered and evaporated to dryness to yield a brown gum (0.54 g). A portion of the crude intermediate (0.19 g) was dissolved in THF (5 mL). L-cysteine methyl ester hydrochloride (0.073 g, 0.43 mmol) and CSA (0.01 g, 0.043 mmol) were added to the reaction. The reaction was stirred at rt for 22 h and the solvent was removed in vacuo. The residue was purified by flash chromatography to yield 0.022 g of the desired product (12%) as a yellow solid. MS 431.08 (M+1)$^+$.

Part B: Methyl 2-(2-((S)-1-(tert-butoxycarbonyl)-2-phenylethyl)-1H-imidazol-4-yl)thiazole-4-carboxylate: The product from Example 36 Part A (0.022 g, 0.051 mmol) was dissolved in toluene (1 mL) and treated with MnO$_2$ (0.067 g, 0.77 mmol). The reaction was stirred at rt for 5 h. The reaction mixture was filtered, and the filter cake washed with EtOAc. The combined filtrates were concentrated to dryness. The residue was purified by flash chromatography to yield 0.017 g of the triazole (78%) as a white solid. HRMS m/z Calc'd for C$_{21}$H$_{25}$N$_4$O$_5$S [M+H]$^+$: 429.1597. Found 429.1586.

Part C: Methyl 2-(2-((S)-1-(trans-4-(aminomethyl)cyclohexanecarboxamido)-2-phenylethyl)-1H-imidazol-4-yl)thiazole-4-carboxylate, bistrifluoroacetic acid salt: The product from Example 36 Part B was deprotected with TFA, coupled with N-(Boc)-tranexamic acid, and then deprotected following by the same procedures described in Example 32 Part D to give the title compound, after purification by Prep HPLC (0.014 g, 50%). $^1$HNMR (400 MHz, CD$_3$OD) δ 0.96-1.10 (m, 2H), 1.27-1.47 (m, 2H), 1.51-1.61 (m, 1H), 1.72-1.89 (m, 4H), 2.18-2.28 (m, 1H), 2.76 (d, J=7.0 Hz, 2H), 3.25-3.35 (m, 2H), 3.94 (s, 3H), 5.31 (t, J=7.9 Hz, 1H), 7.17-7.28 (m, 5H), 7.98 (s, 1H), 8.43 (s, 1H); HRMS m/z Calc'd for C$_{24}$H$_{30}$Cl$_2$N$_5$O$_3$S (M+H)$^+$: 468.2069. Found 468.2063.

Example 37

Methyl 2-((S)-1-(trans-4-(aminomethyl)cyclohexanecarboxamido)-2-phenylethyl)-1H-imidazole-4-carboxylate, bistrifluoroacetic acid salt Part A: (S)-Methyl 2-(1-amino-2-phenylethyl)-1H-imidazole-4-carboxylate: The product formed in Example 32 Part B (492 mg, 1.43 mmol) was treated according to the procedure described for Example 1 Part B to yield 350 mg of the product (99%). MS 244.22 (M−1)$^−$.

Part B: Methyl 2-((S)-1-trans)-4-((tert-butoxycarbonyl)methyl)cyclohexanecarboxamido)-2-phenylethyl)-1H-imidazole-4-carboxylate: The product formed in Example 37 Part A (350 mg, 1.4 mmol) was coupled with N-(Boc)-tranexamic acid according to the procedure described for Example 2 Part A to yield 290 mg of the product (43%). MS 485.22 (M+H)$^+$.

Part C: Methyl 2-((S)-1-(trans-4-(aminomethyl)cyclohexanecarboxamido)-2-phenylethyl)-1H-imidazole-4-carboxylate, bistrifluoroacetic acid salt: The product formed in Example 37 Part B (290 mg, 0.60 mmol) was treated according to the procedure described for Example 2 Part B to yield the title compound (138 mg, 49%). $^1$H NMR (500 MHz, d$_4$-MeOH) δ 1.05 (ddd, J=12.51, 8.66, 4.12 Hz, 3H) 1.36 (ddd, J=29.14, 12.65, 3.30 Hz, 3H) 1.56 (dd, J=7.15, 3.85 Hz, 1H) 1.75 (d, J=12.10 Hz, 1H) 1.84 (dd, J=10.17, 2.47 Hz, 4H) 2.21 (m, 1H) 2.63 (d, J=9.35 Hz, 1H) 2.76 (d, J=7.15 Hz, 3H) 3.24 (dd, J=7.97, 2.47 Hz, 3H) 3.88 (s, 4H) 5.24 (t, J=7.97 Hz, 1H) 7.12 (d, J=7.15 Hz, 3H) 7.20 (t, J=7.15 Hz, 1H) 7.25 (m, 3H) 7.86 (s, 1H); MS 385.33 (M+H)$^+$.

Example 38

2-((S)-1-(trans-4-(Aminomethyl)cyclohexanecarboxamido)-2-phenylethyl)-1H-imidazole-4-carboxylic acid, bistrifluoroacetic acid salt Part A: 2-((S)-1-(trans)-4-((tert-Butoxycarbonyl)methyl)cyclohexanecarboxamido)-2-phenylethyl)-1H-imidazole-4- carboxylic acid: The product from Example 37 Part B (290 mg, 0.62 mmol) was dissolved in a solution of MeOH (2 mL) and 1 N NaOH (4 mL) and stirred for 72 hrs at rt. The solvent was evaporated to dryness. The residue was diluted with water and treated with 1 N HCl. The resulting solution was diluted with EtOAc, washed with brine, dried over $MgSO_4$, filtered and evaporated to yield 138 mg of the acid (49%). MS 471.05 $(M+1)^+$.

Part B: 2-((S)-1-(trans-4-(aminomethyl)cyclohexanecarboxamido)-2-phenylethyl)-1H-imidazole-4-carboxylic acid, bistrifluoroacetic acid salt: The product from Example 38 Part A (50 mg, 0.11 mmol) was treated with the TFA according the procedure described for Example 2 Part B. The resulting residue was re-dissolved in $MeOH/H_2O$ (9:1) containing 0.1% TFA and isolated by prep HPLC to yield 17.1 mg of the title compound (44%). $^1H$ NMR (500 MHz, $d_4$-MeOH) δ 0.93 (m, 3H), 1.24 (m, 3H), 2.12 (m, 1H), 2.64 (d, J=6.87 Hz, 3H), 2.73 (s, 1H), 2.86 (s, 1H), 3.13 (dd, J=13.75, 8.25 Hz, 1H), 3.2 (m, 2H), 7.01 (d, J=6.87 Hz, 3H), 7.11 (d, J=7.33 Hz, 1H), 7.15 (t, J=7.33 Hz, 3H), 7.81 (s, 1H); HRMS $(M+H)^+$ for $C_{20}H_{26}N_4O_3$, calcd m/z: 371.2083, obs: 371.2072.

Example 39

Ethyl 2-(2-((S)-1-(trans-4-(aminomethyl)cyclohexanecarboxamido)-2-phenylethyl)-1H-imidazole-4-carboxamido)acetate, bistrifluoroacetic acid salt Part A: Ethyl 2-(2-((S)-1-(trans-4-((tert-butoxycarbonyl)methyl)cyclohexanecarboxamido)-2-phenylethyl)-1H-imidazole-4-carboxamido)acetate: The product from Example 38 Part A (30.0 mg, 0.06 mmol) and ethyl 2-aminoacetate (10 mg, 0.09 mmol) were treated under the conditions described in Example 2 Part A with the substitution of HOBt (10 mg, 0.09 mmol) for the HOAt. The resulting yellow oil (33.0. mg, 97% yield) was carried to the next step without further purification. MS 556.45 $(M+H)^+$.

Part B: Ethyl 2-(2-((S)-1-(trans-4-(aminomethyl)cyclohexanecarboxamido)-2-phenylethyl)-1H-imidazole-4-carboxamido)acetate, bistrifluoroacetic acid salt: The product from Example 39 Part A (33.0 mg, 0.06 mmol) was treated with TFA according the procedure described for Example 1 Part B. The resulting residue was re-dissolved in $MeOH/H_2O$ (9:1) containing 0.1% TFA and isolated by prep HPLC to yield 2.0 mg of the title compound(7%). $^1H$ NMR (500 MHz, $d_4$-MeOH) δ 1.03 (m, 3H), 1.27 (t, J=7.15 Hz, 4H), 1.37 (m, 3H), 1.56 (m, 2H), 1.72 (d, J=13.20 Hz, 1H), 1.83 (dd, J=8.80, 3.85 Hz, 4H), 2.20 (m, 1H), 2.76 (d, J=7.15 Hz, 3H), 3.19 (dd, J=13.75, 8.25 Hz, 1H), 3.25 (m, 2H), 4.10 (s, 3H), 4.20 (q, J=7.15 Hz, 3H), 5.25 (t, J=7.70 Hz, 1H), 7.16 (t, J=7.15 Hz, 3H), 7.19 (d, J=7.15 Hz, 1H), 7.24 (t, J=7.15 Hz, 3H), 7.67 (s, 1H): HRMS $(M+Na)^+$ for $C_{24}H_{33}N_5O_4$, calcd m/z: 478.2403, obs: 478.2453.

Example 42

Methyl 2-((S)-1-(trans-4-(aminomethyl)cyclohexanecarboxamido)-2-phenylethyl)-1H-benzo[d]imidazole-5-carboxylate, bistrifluoroacetic acid salt Part A: (S)-Methyl 2-(1-(tert-butoxycarbonyl)-2-phenylethyl)-1H-benzo[d]imidazole-5-carboxylate: To a solution of L-N-(Boc)-phenylalanine (265 mg, 1.0 mmole) and BOP reagent (464 mg, 1.0 mmole) in pyridine (10 mL) was added methyl 3,4-diaminobenzoate (166 mg, 1.0 mmole). The reaction mixture was stirred at 80° C. for 3 d. The solvent was removed under vacuum. The residue was re-dissolved in EtOAc. The solution was washed with water and brine, dried over $Na_2SO_4$, filtered and evaporated to dryness. The crude product was purified by prep HPLC to yield 178 mg of the amide (45%). MS 340.2 $(M+H)^+$.

Part B: (S)-Methyl 2-(1-amino-2-phenylethyl)-1H-benzo[d]imidazole-5-carboxylate: The product formed in Example 42 Part A (178 mg, 0.45 mmol) was treated with TFA according to the procedure described for Example 1 Part B to yield 180 mg of the amine (76%). MS 296.2 $(M+H)^+$.

Part C: Methyl 2-((S)-1-(trans-4-((tert-butoxycarbonyl)methyl)cyclohexanecarboxamido)-2-phenylethyl)-1H-benzo[d]imidazole-5-carboxylate: The product formed in Example 42 Part B (178 mg, 0.34 mmol) was coupled with N-(Boc)-tranexamic acid according to the procedure described for Example 2 Part A to yield 75 mg of the desired product (41%). MS 535.5 $(M+H)^+$.

Part D: Methyl 2-((S)-1-(trans-4-(aminomethyl)cyclohexanecarboxamido)-2-phenylethyl)-1H-benzo[d]imidazole-5-carboxylate, bistrifluoroacetic acid salt: The product formed in Example 42 Part C (15 mg, 0.028 mmol) was treated with TFA according to the procedure described for Example 2 Part B to yield 12 mg of the title compound (65%). $^1H$-NMR (500 MHz, $d_4$-MeOH) δ 1.04-1.10 (m, 2H), 1.29-1.42 (m, 2H). 1.52-1.60 (m, 1H), 1.75 (m, 1H), 1.83-1.86 (m, 3H), 2.27-2.29 (m, 1H), 2.77, (d, J=7.15 Hz, 2H), 3.45 (m, 2H), 3.96 (s, 3H), 5.48 (t, J=8.25 Hz, 1H), 7.22-7.26 (m, 5H), 7.80 (d, J=7.0 Hz, 1H), 8.19 (dd, J=7.0 Hz, 1.2 Hz, 1H), 8.36 (s, 1H); MS 435.3 $(M+H)^+$.

Example 43

2-((S)-1-(trans-4-(Aminomethyl)cyclohexanecarboxamido)-2-phenylethyl)-1H-benzo[d]imidazole-5-carboxylic acid, bistrifluoroacetic acid salt Part A: 2-((S)-1-(trans-4-((tert-Butoxycarbonyl)methyl)cyclohexanecarboxamido)-2-phenylethyl)-1H-benzo[d]imidazole-5-carboxylic acid: The compound from Example 42 Part C (50 mg, 0.093 mmol) was hydrolyzed using conditions described for Example 38 Part A with the exception that ethanol was used in place of methanol yielding 38 mg of the acid (78%). MS 521.3 $(M+H)^+$.

Part B: 2-((S)-1-(trans-4-(Aminomethyl)cyclohexanecarboxamido)-2-phenylethyl)-1H-benzo[d]imidazole-5-carboxylic acid, bistrifluoroacetic acid salt: The compound from Example 43 Part A (15 mg, 0.029 mmol) was converted to the title product using the procedure described for Example 2 Part B (12 mg, 64%). $^1H$-NMR (400 MHz, $d_4$-MeOH) δ 1.04-1.10 (m, 2H), 1.29-1.42 (m, 2H), 1.56 (m, 1H), 1.75 (m, 1H), 1.83-1.86 (m, 3H), 2.27-2.28 (m, 1H), 2.77 (d, J=7.03 Hz, 2H), 3.43 (d, J=8.34 Hz, 2H), 5.48 (t, J=8.12 Hz, 1H), 7.22-7.26 (m, 5H), 7.80 (d, J=8.78 Hz, 1H), 8.19 (dd, J=8.35 Hz and 1.3 Hz, 1H), 8.36 (s, 1H); MS 421.2 $(M+H)^+$.

Example 44

2-((S)-1-(trans-4-(Aminomethyl)cyclohexanecarboxamido)-2-phenylethyl)-1H-benzo[d]imidazole-5-carboxamide, bistrifluoroacetic acid salt Part A: tert-Butyl (trans-4-(((S)-1-(5-carbamoyl-1H-benzo[d]imidazol-2-yl)-2-phenylethyl)carbamoyl)cyclohexyl)methylcarbamate: The compound from Example 43 Part A (23 mg, 0.044 mmol) was subjected to the conditions described for Example 1 Part C with the exception that ammonium hydroxide was used in place of 4-amidinobenzoic acid hydrochloride to provide 18 mg of the desired product (79%). MS 520.0 (M+H)+.

Part B: 2-((S)-1-(trans-4-(Aminomethyl)cyclohexanecarboxamido)-2-phenylethyl)-1H-benzo[d]imidazole-5-carboxamide, bistrifluoroacetic acid salt: The compound from Example 44 Part A (18 mg, 0.034 mmol) was reacted with TFA following the conditions described for Example 2 Part B to yield 8 mg of the title compound (36%). $^1$H-NMR (500 MHz, d$_4$-MeOH) δ 1.04-1.10 (m, 2H), 1.29-1.42 (m, 2H), 1.56 (m, 1H), 1.75 (m, 1H), 1.83-1.86 (m, 3H), 2.27-2.28 (m, 1H), 2.77 (d, J=7.14 Hz, 2H), 3.43 (d, J=7.70 Hz, 2H), 5.48 (t, J=8.24 Hz, 1H), 7.22-7.27 (m, 5H), 7.80 (d, J=8.78 Hz, 1H), 8.05 (dd, J=8.79 Hz, 1.64 Hz, 1H), 8.25 (s, 1H); MS 420.2 (M+H)+.

Example 45

Ethyl 2-(2-((S)-1-(trans-4-(aminomethyl)cyclohexanecarboxamido)-2-phenylethyl)-1H-benzo[d]imidazol-5-yl)acetate, bistrifluoroacetic acid salt Part A: Ethyl 2-(4-amino-3-nitrophenyl)acetate: To a solution of 4-(aminophenyl)acetic acid ethyl ester (538 mg, 3.0 mmole) in acetic acid (20 mL) was added nitric acid (90%, 420 mg, 6 mmole). The reaction mixture was stirred at 100° C. for 4 h. The reaction was cooled to rt. Acetic acid was partially removed under vacuum. The residue was diluted with EtOAc. The pH of the solution was adjusted to 8-9 with 10% NaOH. It was washed with water and brine, dried over Na$_2$SO$_4$, filtered and evaporated. The crude product was isolated by silica gel chromatography to give 128 mg (20% yield) of a bright yellow solid. It was taken into the next step without further purification.

Part B: Ethyl 2-(3,4-diaminophenyl)acetate: To a suspension of 10% palladium on carbon (15 mg) in 2 mL of MeOH was added a solution of the product from Example 45 Part A (128 mg) in MeOH (8 mL). The reaction mixture was stirred under one atmosphere of hydrogen at rt for 4 h. The catalyst was filtered. To the filtrate was added 1 N HCl (0.1 mL) and the solvent was evaporated to dryness to yield 130 mg the crude product as the HCl salt (86% yield). MS 195.2 (M+H)+.

Part C: (S)-Ethyl 2-(2-(1-(tert-butoxycarbonyl)-2-phenylethyl)-1H-benzo[d]imidazol-5-yl)acetate: The product from Example 45 Part B (130 mg, 0.49 mmol) and L-N-(Boc)-phenylalanine (130 mg, 0.49 mmol) were subjected to the conditions described for Example 42 Part A to yield 210 mg (100% yield) of the desired product. MS 424.3 (M+H)+.

Part D: Ethyl 2-(2-((S)-1-(trans-4-(aminomethyl)cyclohexanecarboxamido)-2-phenylethyl)-1H-benzo[d]imidazol-5-yl)acetate, bistrifluoroacetic acid salt: The product from Example 45 Part C was treated with TFA and then coupled with N-(Boc)-tranexamic acid according to the procedures described for Example 2 Part A to yield the desired product which was reacted with TFA following the conditions described for Example 2 Part B to yield the title compound. MS 463.43 (M+H)+. $^1$H-NMR (500 MHz, d$_4$-MeOH) δ 1.05 (m, 2H), 1.24 (t, J=3.30 Hz, 3H), 1.35 (m, 2H), 1.56 (m, 1H), 1.78 (br d, J=12.65 Hz, 1H), 1.86 (m, 3H), 2.28 (m, 1H), 2.77 (d, J=7.15 Hz, 2H), 3.31 (s, 2H), 3.42 (d, J=7.70 Hz, 2H), 3.84 (s, 2H), 4.16 (q, J=7.15 Hz, 2H), 5.46 (t, J=8.25 Hz, 1H), 7.23 (m, 5H), 7.51 (d, J=8.80 Hz, 1H), 7.68 (d, J=8.80 Hz, 2H); MS 463.4 (M+H)+.

Example 46

2-(2-((S)-1-(trans-4-(Aminomethyl)cyclohexanecarboxamido)-2-phenylethyl)-1H-benzo[d]imidazol-5-yl)acetic acid, bistrifluoroacetic acid salt The product from Example 45 Part D was hydrolyzed with LiOH and then treated with TFA following the conditions described for Example 2 Part B to yield the title compound. MS 435.4 (M+H)+. $^1$H-NMR (500 MHz, d$_4$-MeOH) δ 1.05 (m, 2H), 1.35 (m, 2H), 1.55 (m, 1H), 1.78 (br d, J=12.10 Hz, 1H), 1.86 (m, 3H), 2.28 (m, 1H), 2.77 (d, J=6.60 Hz, 2H), 3.31 (s, 2H), 3.42 (d, J=8.25 Hz, 2H), 3.82 (s, 2H), 5.46 (t, J=8.25 Hz, 1H), 7.23 (m, 5H), 7.52 (d, J=8.24 Hz, 1H), 7.67 (d, J=8.25 Hz, 2H); MS 435.4 (M+H)+.

Example 47 trans-N-((S)-1-(5-(2-amino-2-oxoethyl)-1H-benzo[d]imidazol-2-yl)-2-phenylethyl)-4-(aminomethyl)cyclohexanecarboxamide, bistrifluoroacetic acid salt This compound was prepared from the product from Example 45 Part D using the same procedures described for the synthesis of Example 44. $^1$H-NMR (500 MHz, d$_4$-MeOH) δ 1.06 (m, 2H), 1.35 (m, 2H), 1.55 (m, 1H), 1.78 (br d, J=11.86 Hz, 1H), 1.86 (m, 3H), 2.28 (m, 1H), 2.77 (d, J=7.03 Hz, 2H), 3.31 (s, 2H), 3.42 (d, J=8.35 Hz, 2H), 3.70 (s, 2H), 5.46 (t, J=8.35 Hz, 1H), 7.23 (m, 5H), 7.52 (d, J=8.35 Hz, 1H), 7.67 (d, J=8.325 Hz, 2H); MS 434.3 (M+H)+.

Example 48 trans-4-(Aminomethyl)-N-((S)-2-phenyl-1-(5-phenyloxazol-2-yl)ethyl)cyclohexanecarboxamide, bistrifluoroacetic acid salt Part A: (S)-2-(1,3-Dioxo-1,3-dihydro-isoindol-2-yl)-N-(2-oxo-2-phenyl-ethyl)-3-phenyl-propionamide: N-Phthaloyl-L-phenylalanine (290 mg, 1 mmol) and 2-aminoacetophenone (171 mg, 1 mmol) were dissolved in 10 mL of pyridine. Bop reagent (470 mg, 1.1 mmol) was added The mixture was stirred at rt under N$_2$ for 12 h. The solvent was removed. The residue was dissolved in EtOAc and washed with water and sat. NaHCO$_3$. The organic layer was dried over Na$_2$SO$_4$, filtered, and concentrated to yield 412 mg of the product (100% yield). MS 413.2 (M+H)+.

Part B: (S)-2-(2-Phenyl-1-(5-phenyloxazol-2-yl)ethyl)isoindoline-1,3-dione: The product from Example 48 Part A (412 mg, 1 mmol) was dissolved in DMF and treated with phosphorous oxychloride (460 mg, 3 mmol) at 90° C. according to the procedure described by Robert Dow et al. (J. Org. Chem., 1990, 55, 386) to yield 160 mg (41% yield) of the product. MS 395.2 (M+H)+.

Part C: (S)-2-Phenyl-1-(5-phenyloxazol-2-yl)ethanamine: A solution of the product from Example 48 Part B (160 mg, 0.4 mmol) in EtOH (10 mL) was added to hydrazine (39 mg, 1.2 mmol). The reaction mixture was refluxed for 2 h. It was cooled to rt. EtOH was removed under vacuum. The residue was re-dissolved in dichloromethane. The undissolved solid was removed by filtration. The filtrate was concentrated to yield 95 mg of the product as a yellow solid (90% yield). MS 265.1 (M+H)+.

Part D: trans-4-(Aminomethyl)-N-((S)-2-phenyl-1-(5-phenyloxazol-2-yl)ethyl)cyclohexanecarboxamide, bistrifluoroacetic acid salt: The product from Example 48 Part C (95 mg, 0.35 mmol) was converted to the title compound by sequential application of the procedures described for Example 2 Part A and Part B (26%). $^1$H-NMR (500 MHz, d$_4$-MeOH) δ 1.04-1.10 (m, 2H), 1.29-1.42 (m, 2H), 1.56 (m, 1H), 1.75 (m, 1H), 1.83-1.86 (m, 3H), 2.22 (m, 1H), 2.77 (d, J=7.14 Hz, 2H), 3.20 (m, 1H), 3.33 (m, 1H), 5.41 (m, 1H), 7.22-7.27 (m, 5H), 7.34 (t, J=7.15 Hz, 1H), 7.42 (m, 3H), 7.63-7.65 (d, J=8.25 Hz, 2H); MS 404.3 (M+H)$^+$.

Example 49 trans-4-(Aminomethyl)-N-((S)-2-phenyl-1-(5-phenyl-2H-1,2,4-triazol-3-yl)ethyl)cyclohexane-carboxamide, bistrifluoroacetic acid salt Part A: (S)-tert-Butyl 2-phenyl-1-(5-phenyl-2H-1,2,4-triazol-3-yl)ethylcarbamate: L-N-(Boc)-phenylalanine (265 mg, 1 mmole) and hydrazine (64 mg, 2 mmol) were combined using the conditions described for Example 1 Part C to form 279 mg of hydrazoic acid (100% yield). MS 280.1 (M+H)$^+$. To a solution of hydrazoic acid (279 mg, 1.0 mmole) and Et$_3$N (161 mg, 1.6 mmole) in 10 mL of acetonitrile was added ethylbenzimidate hydrochloride (278 mg, 1.5 mmole). The reaction was heated to reflux for 24 h. The reaction was cooled to rt and diluted with EtOAc. The mixture was washed with water and brine, dried over Na$_2$SO$_4$, filtered and evaporated to dryness in vacuo. The crude product was purified by prep HPLC to yield 154 mg of an oil (42% yield). MS 365.2 (M+H)$^+$.

Part B: trans-4-(Aminomethyl)-N-((S)-2-phenyl-1-(5-phenyl-2H-1,2,4-triazol-3-yl)ethyl)cyclohexane-carboxamide, bistrifluoroacetic acid salt: The product from Example 49 Part A (154 mg, 0.42 mmol) was converted to the title compound by sequential application of the procedures described for Example 1 Part B, Example 2 Part A and Part B (28%). $^1$H-NMR (400 MHz, d$_4$-MeOH) δ 1.02-1.06 (m, 2H), 1.29-1.42 (m, 2H), 1.56 (m, 1H), 1.75 (m, 1H), 1.83-1.86 (m, 3H), 2.21 (m, 1H), 2.77 (d, J=7.03 Hz, 2H), 3.18-3.21 (m, 1H), 3.31 (m, 1H), 5.42 (t, J=8.12 Hz, 1H), 7.22-7.26 (m, 5H), 7.51-7.52 (m, 3H), 7.96-7.98 (m, 2H); MS 404.2 (M+H)$^+$.

Example 50 trans-4-(Aminomethyl)-N-((S)-2-phenyl-1-(3-phenyl-1H-pyrazol-5-yl)ethyl)cyclohexanecarboxamide, bistrifluoroacetic acid salt Part A: 3-Oxo-3-phenylpropanoic acid: To a solution of ethyl benzoyl acetate (2.88 g, 15 mmol) in EtOH (30 mL) was added 1N NaOH (30 mL). The reaction mixture was stirred at rt for 72 h. It was cooled to 0° C. and acidified with 1N HCl. EtOH was removed under reduced pressure. The aqueous layer was extracted twice with dichloromethane. The combined dichloromethane solution was washed with brine, dried over Na$_2$SO$_4$, filtered and concentrated in vacuo to give a light yellow solid. (600 mg, 24%). MS 165.1 (M+H)$^+$.

Part B: (S)-Benzyl 3,5-dioxo-1,5-diphenylpentan-2-yl carbamate: To a solution of the product from Example 50 Part A (600 mg, 3.65 mmol) in THF (20 mL) and MeOH (20 mL) was added magnesium ethoxide (417 mg, 3.65 mmol). The mixture was stirred at r.t. for 4 h. The solvents were removed under reduced pressure. The crude product was dissolved in DMF (2 mL) and added to a mixture of N-CBZ-L-phenylalanine (800 mg, 2.68 mmol), 1,1'-carbonyldiimidazole (520 mg, 3.21 mmol) in DMF (4 mL) which had been stirred for 2 h at rt. The resulting mixture was stirred at rt overnight. It was diluted with EtOAc, washed with diluted HCl, water and brine, dried over Na$_2$SO$_4$, filtered and concentrated in vacuo. The crude product was purified by prep HPLC to give the product (140 mg, 13%). MS 402.1 (M+H)$^+$.

Part C: ((S)-Benzyl 2-phenyl-1-(3-phenyl-1H-pyrazol-5-yl)ethylcarbamate: To a solution of Example 50 part B (32 mg, 0.08 mmol) in EtOH (3 mL) was added hydrazine hydrate (3 mg, 0.09 mmol). The reaction mixture was heated at 60° C. for 3 h. EtOH was removed in vacuo to give the desired product (0.32 mg, 100%). MS 398.1 (M+H)$^+$.

Part D: (S)-2-Phenyl-1-(3-phenyl-1H-pyrazol-5-yl)ethanamine: To a solution from Example 50 Part C in MeOH (3 mL) was added 10% Pd/C (5 mg). The reaction mixture was stirred under H$_2$ at rt for 4 h. The catalyst was removed by filtration. The crude mixture was purified by prep HPLC to give the desired product (12 mg, 57%). MS 262.2 (M–H)$^-$.

Part E: trans-4-(Aminomethyl)-N-((S)-2-phenyl-1-(3-phenyl-1H-pyrazol-5-yl)ethyl)cyclohexanecarboxamide, bistrifluoroacetic acid salt: The product from Example 50 Part D (12 mg, 0.046 mmol) was converted to the title compound by sequential application of the procedures described for Example 2 Part A and Part B (11 mg, 46%). $^1$H-NMR (500 MHz, d$_4$-MeOH) δ 1.02-1.06 (m, 2H), 1.30-1.33 (m, 1H), 1.43-1.46 (m, 1H), 1.56 (m, 1H), 1.64 (m, 1H), 1.83 (m, 3H), 2.16-2.18 (m, 1H), 2.75 (d, J=7.03 Hz, 2H), 3.08-3.10 (m, 1H), 3.27 (m, 1H), 5.35 (t, J=8.12 Hz, 1H), 6.61 (s, 1H), 7.22 (m, 1H), 7.23 (m, 4H), 7.35-7.36 (t, J=7.15 Hz, 1H), 7.41-7.44 (t, J=7.70 Hz, 2H), 7.69-7.71 (d, J=7.15 Hz, 2H); MS 403.1 (M+H)$^+$.

Example 51 trans-4-(aminomethyl)-N-((S)-1-(5-oxo-1-phenyl-4,5-dihydro-1H-1,2,4-triazol-3-yl)-2-phenylethyl)-cyclohexanecarboxamide, bistrifluoroacetic acid salt Part A: (S)-Benzyl 1-(5-oxo-1-phenyl-4,5-dihydro-1H-1,2,4-triazol-3-yl)-2-phenylethylcarbamate: A solution of (S)-N-CBZ-phenylalanine nitrile (140 mg, 0.5 mmol) and sodium methoxide (13 mg, 0.24 mmol) in MeOH (4 mL) was stirred at 30° C. for 3 h. Acetic acid (1 mg, 0.2 mmol) was added, followed by phenyl hydrazine (108 mg, 1 mmol). The reaction mixture was stirred at rt for 18 h. The mixture was cooled to 0° C., and the solid was removed by filtration. The MeOH solution was purified by silica gel chromatography to give a yellow oil, which was dissolved in THF (6 mL) and 1,1'-carbonyldiimidazole (68 mg, 0.42 mmole) was added. The mixture was heated to reflux for 48 h. The reaction was cooled to rt, diluted with CH$_2$Cl$_2$, washed with water and brine, dried over Na$_2$SO$_4$, filtered and concentrated in vacuo to give 38 mg (66%) of the product as a red solid. MS 413.2 (M–H)$^-$.

Part B: Trans-4-(aminomethyl)-N-((S)-1-(5-oxo-1-phenyl-4,5-dihydro-1H-1,2,4-triazol-3-yl)-2-phenylethyl)-cyclohexanecarboxamide, bistrifluoroacetic acid salt: The product of Example 51 Part A (38 mg, 0.09 mmol) was converted to the title compound by sequential application of the procedures described for Example 50 Part D, and Example 2 Part A and Part B (8 mg, 17%). $^1$H-NMR (500 MHz, d$_4$-MeOH) δ 1.02-1.06 (m, 2H), 1.30-1.33 (m, 1H), 1.43-1.46 (m, 1H), 1.56 (m, 1H), 1.67 (m, 1H), 1.81-1.86 (m, 3H), 2.16-2.18 (m, 1H), 2.75 (d, J=7.15 Hz, 2H), 3.08-3.10 (m, 1H), 3.31 (m, 1H), 5.15-5.17 (m, 1H), 7.19-7.21 (m, 2H), 7.27-7.28 (m, 4H), 7.40-7.43 (t, J=7.97 Hz, 2H), 7.85-7.87 (d, J=7.69 Hz, 2H); MS 420.1 (M+H)$^+$.

Example 52 trans-4-(aminomethyl)-N-((S)-2-phenyl-1-(2-phenyl-1H-imidazol-4-yl)ethyl)cyclohexane-carboxamide, bistrifluoroacetic acid salt Part A: (S)-Benzyl 2-phenyl-1-(2-phenyl-1H-imidazol-4-yl)ethylcarbamate: A solution of (S)-benzyl-4-bromo-3-oxo-1-phenylbutan-2-yl carbamate (376 mg, 1.0 mmole) and sodium formate (68 mg, 1.0 mmole) in EtOH (15 mL) was heated to reflux for 14 h. Benzamidine (240 mg, 1.5 mmole) and sodium bicarbonate (400 mg, 4.7 mmole) were added to the reaction. The reaction mixture was heated to refluxed for an additional 24 h. The reaction was cooled to rt and the dried in vacuo. The residue was re-dissolved in EtOAc, washed with water and brine, dried over $Na_2SO_4$, filtered and concentrated in vacuo. The crude product was purified by silica gel chromatography to yield 33 mg (8% yield). MS 398.1 $(M+H)^+$.

Part B: Trans-4-(aminomethyl)-N-((S)-2-phenyl-1-(2-phenyl-1H-imidazol-4-yl)ethyl)cyclohexane-carboxamide, bistrifluoroacetic acid salt: The product from Example 52 Part A (33 mg, 0.083 mmol) was converted to the title compound by sequential application of the procedures described for Example 50 Part D, and Example 2 Part A and Part B (5 mg, 12% yield). $^1$H-NMR (400 MHz, $d_4$-MeOH) δ 1.02-1.06 (m, 2H), 1.30-1.33 (m, 1H), 1.43-1.46 (m, 1H), 1.56 (m, 1H), 1.67 (m, 1H), 1.83 (m, 3H), 2.16-2.18 (m, 1H), 2.75 (d, J=7.03 Hz, 2H), 3.08-3.10 (m, 1H), 3.31 (m, 1H), 5.34-5.36 (m, 1H), 7.22-7.29 (m, 5H), 7.51 (s, 1H), 7.62-7.68 (m, 3H), 7.87-7.89 (m, 2H); MS 403.3 $(M+H)^+$.

Example 53

N-(4-Carbamimidoylphenyl)-3-phenyl-2-(4-phenyl-1H-imidazol-2-yl)propanamide, Bis-trifluoroacetic acid salt Part A: 2-Benzyl-3-methoxy-3-oxopropanoic acid: Benzyl malonic acid (19.4 g, 0.10 mol) was dissolved in 180 mL of MeOH. The mixture was cooled in an ice-bath and to it was added thionyl chloride dropwise over 30 min (7.3 mL, 0.10 mol). The mixture was stirred in the ice-bath for 30 min and then at RT for 30 min under $N_2$. The solvent was removed, and the residue was dissolved in aqueous $NaHCO_3$. The basic solution was extracted with EtOAc to remove the bis-ester which was discarded. The aqueous solution was then acidified with aqueous HCl to pH 5 and extracted with EtOAc. The EtOAc extract was washed with brine, dried over $Na_2SO_4$, and concentrated to give 7.2 g of 2-benzyl-3-methoxy-3-oxopropanoic acid (35%). MS 209.24 $(M+H)^+$.

Part B: Methyl 3-phenyl-2-(4-phenyl-1H-imidazol-2-yl)propanoate: The product from Example 53 Part A (1.04 g, 5.0 mmol) was dissolved in EtOH (13 mL) and a solution of $Cs_2CO_3$ (0.81 g, 2.5 mmol) in $H_2O$ (13 mL) was added. The reaction mixture was stirred at RT for 1 h under $N_2$. The solvent was removed under vacuum, and the resulting salt was suspended in DMF (20 mL). 2-Bromoacetophenone (1.3 g, 6.6 mmol) was added in a single portion, and the reaction stirred at RT under $N_2$ for 2 h. The reaction was filtered to remove CsBr. The solids were washed with DMF. The combined washings and filtrate were concentrated in vacuo to yield a yellow solid. The crude intermediate was placed in a flask fitted with a Dean-Stark trap and dissolved in xylene (40 mL). $NH_4OAc$ (7.78 g, 100 mmol) was added to the flask and the reaction was heated to reflux for 3 h. The reaction was cooled to RT and the solvent removed in vacuo. The residue was redissolved in EtOAc and washed with saturated aqueous $NaHCO_3$ and brine, dried over $Na_2SO_4$, filtered, concentrated, and purified by flash chromatography (silica gel, EtOAc/hexane) to yield 600 mg of the desired product (39%). MS 307.29 $(M+H)^+$.

Part C: 3-Phenyl-2-(4-phenyl-1H-imidazol-2-yl)propanoic acid: The product from Example 53 Part B (350 mg, 1.14 mmol) was dissolved in 9 mL of EtOH and 1N NaOH (3 mL) was added. The mixture was stirred at RT under $N_2$ for 30 min. Aqueous HCl was added to the reaction mixture until pH 5. The precipitate formed was filtered and dried to afford 284 mg of the desired product (85%). MS 293.33 $(M+H)^+$.

Part D: N-(4-Carbamimidoylphenyl)-3-phenyl-2-(4-phenyl-1H-imidazol-2-yl)propanamide bis-TFA salt: The product from Example 53 from Part C (40 mg, 0.14 mmol) and 4-amidinobenzamidine hydrochloride (48 mg, 0.16 mmol) were dissolved in anhydrous pyridine (2 mL). BOP reagent (90 mg, 0.16 mmol) was added and the reaction was stirred at RT under $N_2$ for 48 h. The solvent was removed in vacuo. The residue was redissolved in $CH_3OH/H_2O$ (9:1) containing 0.1% TFA, and purified by reverse phase HPLC (C18, 28×100 mm, $MeOH/H_2O$/0.1% TFA gradient) to yield 15 mg of the title compound (17% yield). $^1$H-NMR (400 MHz, $d_4$-MeOH) δ 3.33 (dd, J=13.40, 9.45 Hz, 1H), 3.52 (dd, J=13.62, 7.03 Hz, 1H), 4.54 (dd, J=9.23, 7.03 Hz, 1H), 7.12 (m, 5H), 7.39 (m, 3H), 7.57 (d, J=6.59 Hz, 2H), 7.70 (m, 3H), 7.76 (m, 2H). HRMS $(M+H)^+$ for $C_{25}H_{24}N_5O$, calcd m/z: 410.1981, obs: 410.2001.

Example 54

N-(3-Carbamimidoylphenyl)-3-phenyl-2-(4-phenyl-1H-imidazol-2-yl)propanamide, Bis-trifluoroacetic acid salt The title compound was prepared using the same procedures described for Example 53. NMR (400 MHz, $d_4$-MeOH) δ 3.42 (dd, J=13.62, 9.23 Hz, 1H), 3.61 (dd, J=13.62, 7.03 Hz, 1H), 4.61 (dd, J=9.01, 7.25 Hz, 1H), 7.24 (m, 5H), 7.51 (m, 5H), 7.66 (d, J=7.91 Hz, 2H), 7.77 (m, 2H), 8.19 (s, 1H); MS 410.20, $(M+H)^+$.

Example 55 trans-N-(4-(Aminomethyl)cyclohexyl)-3-phenyl-2-(4-phenyl-1H-imidazol-2-yl)propanamide, bistrifluoroacetic acid salt Part A: Benzyl (trans-4-aminocyclohexyl)methylcarbamate: t-Butyl trans-4-aminomethylcyclohexylcarbamate (344 mg, 1.5 mmol) was dissolved in $CH_2Cl_2$ (7 mL) and cooled in an ice-bath. Triethylamine (0.21 mL, 1.5 mmol) was added, followed by benzyl chloroformate (0.22 mL, 1.5 mmol) dropwise. The mixture was stirred at rt under $N_2$ for 2 h. The reaction mixture was diluted with $CH_2Cl_2$ and washed with water and brine, dried over $Na_2SO_4$, filtered, and concentrated to a white solid. This solid was dissolved in 10 mL of 4 N HCl-dioxane and stirred at rt for 10 min. The solvent was removed. The residue was dried under vacuum to give 350 mg of the desired product as a white solid (78%). MS 263.36 $(M+H)^+$.

Part B: Benzyl (trans-4-(3-phenyl-2-(4-phenyl-1H-imidazol-2-yl)propanamido)cyclohexyl)methylcarbamate: The product from Example 55 Part A (75 mg, 0.25 mmol) and the product from Example 53 Part C (60 mg, 0.21 mmol) were dissolved in anhydrous pyridine (5 mL). BOP reagent (115 mg, 0.26 mmol) was added and the reaction was stirred at RT under N₂ for 4 h. The solvent was removed in vacuo. The residue was re-dissolved in EtOAc, washed with water and brine, dried over Na₂SO₄, concentrated and purified by flash chromatography (EtOAc/hexane) to yield 50 mg of the desired product (44%). MS 537.32 (M+H)⁺.

Part C: N-(trans-4-(aminomethyl)cyclohexyl)-3-phenyl-2-(4-phenyl-1H-imidazol-2-yl)propanamide, Bis-trifluoroacetic acid salt: The product from Example 55 Part B (50 mg, 0.093 mmol) was dissolved in MeOH (8 mL) and a catalytic amount of 10% Pd/C was added. The mixture was placed under 1 atm of H₂ for 4 h. It was filtered through celite and washed with MeOH. The filtrate was concentrated and purified by reverse phase HPLC to give 33 mg of the title compound (56%). ¹H-NMR (400 MHz, d₄-MeOH) δ 0.92-1.22 (m, 4H), 1.59 (m, 1H), 1.70-1.88 (m, 4H), 2.69 (m, 2H), 3.21 (m, 1H), 3.35 (m, 1H), 3.50 (m, 1H), 4.32 (t, J=8.35 Hz, 1H), 7.12-7.32 (m, 5H), 7.38-7.54 (m, 3H), 7.66 (d, J=7.03 Hz, 2H), 7.75 (s, 1H). MS 403.39 (M+H)⁺.

Example 56

4-(2-(1-(4-Carbamimidoylphenylamino)-1-oxo-3-phenylpropan-2-yl)-1H-imidazol-4-yl)benzamide, bis-trifluoroacetic acid salt Part A: Methyl 2-(4-(4-cyanophenyl)-1H-imidazol-2-yl)-3-phenylpropanoate: 2-Benzyl-3-methoxy-3-oxopropanoic acid from Example 53 Part A (5.0 g, 24.0 mmol) was dissolved in EtOH (40 mL) and a solution of Cs₂CO₃ (4.0 g, 12.0 mmol) in H₂O (40 mL) was added. The reaction mixture was stirred at rt for 1 h under N₂. The solvent was removed under vacuum and the resulting salt was suspended in DMF (85 mL). 4-(2-bromoacetyl)benzonitrile (5.4 g, 24.0 mmol) was added in a single portion and the reaction stirred at rt under N₂ for 4 h. The reaction was filtered to remove CsBr. The solids were washed with DMF. The combined washings and filtrate were concentrated in vacuos to yield a yellow solid. The crude intermediate was placed in a flask fitted with a Dean-Stark trap and dissolved in xylene (200 mL). NH₄OAc (38.9 g, 500 mmol) was added to the flask and the reaction was heated to reflux for 3 h. The reaction was cooled to rt and the solvent removed in vacuo. The residue was redissolved in EtOAc and washed with saturated aqueous NaHCO₃ and brine, dried over Na₂SO₄, filtered, concentrated, and purified by flash chromatography (silica gel, EtOAc/hexane) to yield 2.4 g of desired product (30%). MS 332.27 (M+H)⁺.

Part B: 2-(4-(4-carbamoylphenyl)-1H-imidazol-2-yl)-3-phenylpropanoic acid: The product from Example 56 Part A (0.99 g, 3.0 mmol) was dissolved in 10 mL of DMSO. Potassium carbonate (1.24 g, 9.0 mmol) was added. The mixture was cooled to 0-5° C. and 30% H₂O₂ (3.18 mL of 30% aqueous solution) was added, followed by magnesium oxide (0.24 g, 15 mmol). The cooling bath was removed and the mixture was stirred at RT under N₂ for 4 h. The mixture was filtered to remove inorganic material. Water (30 mL) was added to the filtrate and the resulting mixture was stirred at rt for 40 min. The mixture was acidified with 1N HCl to pH 5. The precipitate formed was filtered and dried to afford 0.67 g of the acid (67%). MS 336.30 (M+H)⁺.

Part C: 4-(2-(1-(4-Carbamimidoylphenylamino)-1-oxo-3-phenylpropan-2-yl)-1H-imidazol-4-yl)benzamide, bis-trifluoroacetic acid salt: The acid from Example 56 Part B (55 mg, 0.16 mmol) and 4-amidinobenzamidine hydrochloride (58 mg, 0.34 mmol) were dissolved in anhydrous pyridine (3 mL). BOP reagent (108 mg, 0.24 mmol) was added and the reaction was stirred at RT under N₂ for 48 h. The solvent was removed in vacuo. The residue was redissolved in CH₃OH/H₂O (9:1) containing 0.1% TFA, and purified by reverse phase HPLC (MeOH/H₂O/0.1% TFA gradient) to yield 11 mg of the title compound (10%). ¹H-NMR (400 MHz, d₄-MeOH) δ 3.34 (m, 1H), 3.49 (m, 1H), 4.29 (t, J=7.91 Hz, 1H), 7.17 (m, 1H), 7.22 (m, 4H), 7.56 (s, 1H), 7.78 (m, 6H), 7.89 (m, 2H). HRMS (M+H)⁺ for C₂₆H₂₅N₆O₂, calcd m/z: 453.2039, obs: 453.2025.

Example 57

4-(2-(1-(1-Aminoisoquinolin-6-ylamino)-1-oxo-3-phenylpropan-2-yl)-1H-imidazol-4-yl)benzamide, bis-trifluoroacetic acid salt 2-(4-(4-Carbamoylphenyl)-1H-imidazol-2-yl)-3-phenylpropanoic acid from Example 56 Part B (36 mg, 0.11 mmol) and tert-butyl 6-aminoisoquinolin-1-ylcarbamate (18 mg, 0.050 mmol) were dissolved in anhydrous pyridine (3 mL). BOP reagent (50 mg, 0.11 mmol) was added and the reaction was stirred at 60° C. under N₂ for 3 h and then at rt for 48 h. The solvent was removed in vacuo. The residue was redissolved in EtOAc (1 mL) and 4N HCl-dioxane (1 mL) and stirred at rt for 1.5 h. The mixture was concentrated and then re-dissolved in CH₃OH/H₂O (9:1) containing 0.1% TFA, and purified by reverse phase HPLC (MeOH/H₂O/0.1% TFA gradient) to yield 6.0 mg of the title compound (17%). ¹H-NMR (400 MHz, MeOH-d₄) δ 3.45 (m, 1H), 3.63 (m, 1H), 4.62 (dd, J=7.03 Hz, 1H), 7.14 (d, J=7.03 Hz, 1H), 7.26 (m, 5H), 7.53 (d, J=7.03 Hz, 1H), 7.79 (d, J=8.35 Hz, 2H), 7.85 (dd, J=9.23, 2.20 Hz, 1H), 7.90 (s, 1H), 7.99 (d, J=8.35 Hz, 2H), 8.33 (d, J=1.76 Hz, 1H), 8.38 (d, J=8.79 Hz, 1H). MS 477.3 (M+H)⁺.

Example 58

4-(2-(1-(Isoquinolin-6-ylamino)-1-oxo-3-phenylpropan-2-yl)-1H-imidazol-4-yl)benzamide, bis-trifluoroacetic acid salt The title compound was prepared using the same methods described in Example 57. MS 462.19 (M+H)⁺. ¹H-NMR (400 MHz, MeOH-d₄) δ 3.36 (d, J=7.47 Hz, 1H), 3.51 (d, J=8.35 Hz, 1H), 4.31 (t, J=7.91 Hz, 1H), 7.15 (m, 1H), 7.23 (d, J=6.59 Hz, 4H), 7.54 (s, 1H), 7.65 (dd, J=8.79, 2.20 Hz, 2H), 7.74 (d, J=6.15 Hz, 1H), 7.80 (d, J=8.79 Hz, 2H), 7.89 (m, 2H), 8.03 (d, J=9.23 Hz, 1H), 8.35 (m, 1H), 9.10 (s, 1H).

Example 59

4-(2-(4-(4-carbamimidoylphenyl)-1H-imidazol-2-yl)-3-phenylpropanamido)benzamide, bis-trifluoroacetic acid salt Part A: 2-(4-(4-Cyanophenyl)-1H-imidazol-2-yl)-3-phenylpropanoic acid: Methyl 2-(4-(4-cyanophenyl)-1H-imidazol-2-yl)-3-phenylpropanoate from Example 56 Part A (60 mg, 0.20 mmol) was dissolved in 4 mL of EtOH. NaOH (1.5 mL of 1N aqueous solution) was added and the mixture was stirred RT for 1.5 h. The mixture was acidified with 1N HCl to pH 5. The precipitate formed was filtered and dried to give 40 mg of the acid (63%). MS 318.3 (M+H)⁺.

Part B: 4-(2-(4-(4-Cyanophenyl)-1H-imidazol-2-yl)-3-phenylpropanamido)benzamide: The acid from Example 59 Part A (100 mg, 0.32 mmol), triethylamine (150 μL, 1.2 mmol), and BOP reagent (210 mg, 0.48 mmol) were dissolved in THF (9 mL). The mixture was stirred for 15 min and 4-aminobenzamide (47 mg, 0.35 mmol) was added. The resulting mixture was heated at 70° C. under N₂ for 1 h. The mixture was concentrated and then re-dissolved in EtOAc. It was washed with water and brine, dried over Na$_2$SO$_4$, concentrated, and purified by flash chromatography (silica gel, EtOAc/hexane) to give 45 mg of the desired product (32%). MS 436.3 (M+H)$^+$.

Part C: 4-(2-(4-(4-Carbamimidoylphenyl)-1H-imidazol-2-yl)-3-phenylpropanamido)benzamide, bis-trifluoroacetic acid salt: Hydroxylamine hydrochloride (72 mg, 1.0 mmol) was dissolved in DMSO (1 mL) and triethylamine (0.14 mL, 10 eq) was added. The mixture was stirred for 5 min and the precipitate was filtered off. The filtrate was added to the product from Example 59 Part B (28 mg, 0.064 mmol) and the mixture was stirred at rt for 15 min, then 4-aminobenzamide (47 mg, 0.35 mmol) was added. The resulting mixture was heated at 65° C. under N$_2$ for 1.5 h. It was cooled and water was added. The precipitate formed was filtered and dried. The solid was then dissolved in CH$_2$Cl$_2$ (3 mL) and acetic anhydride (13 µL) was added. The mixture was stirred at rt under N$_2$ for 1.5 h. The CH$_2$Cl$_2$ was removed and the residue was dissolved in MeOH—HOAc (3 mL of 10:1 solution). Pd/C (10%, 18 mg) was added and the mixture was placed under a balloon of hydrogen for 3 h. It was filtered through Celite, concentrated, then re-dissolved in CH$_3$OH/H$_2$O (9:1) containing 0.1% TFA, and purified by reverse HPLC (MeOH/H$_2$O/0.1% TFA gradient) to yield 8.0 mg of the title compound (18%). $^1$H-NMR (400 MHz, MeOH-d$_4$) δ 3.37 (m, 1H), 3.45 (m, 1H), 4.24 (t, J=7.91 Hz, 1H), 7.16 (m, 1H), 7.22 (m, 4H), 7.62 (d, J=8.79 Hz, 3H), 7.80 (m, 4H), 7.94 (d, J=8.79, 2H). MS 453.4 (M+H)$^+$.

Example 60

4-(2-(1-(4-Carbamimidoylbenzylamino)-1-oxo-3-phenylpropan-2-yl)-1H-imidazol-4-yl)benzamide, bis-trifluoroacetic acid salt The acid from Example 56 Part B was coupled with 4-cyanobenzylamine following the procedure of Example 59 Part B. The cyano group was then converted to the corresponding benzamidine using the procedures of Example 59 Part C. MS 467.22 (M+H)$^+$. $^1$H-NMR (400 MHz, MeOH-d$_4$) δ 3.37 (dd, J=13.62, 8.35 Hz, 1H), 3.53 (m, 1H), 4.37 (d, J=15.82 Hz, 1H), 4.55 (m, 2H), 7.22 (m, 2H), 7.29 (m, 5H), 7.71 (d, J=8.35 Hz, 2H), 7.79 (d, J=8.79 Hz, 2H), 7.91 (s, 1H), 7.99 (d, J=8.35 Hz, 2H).

Example 61

N-(4-Carbamimidoylphenyl)-4-phenyl-3-(4-phenyl-1H-imidazol-2-yl)butanamide, Bis-trifluoroacetic acid salt This compound was prepared following the same procedures described in Example 53 using 2-benzylsuccinic acid as the starting material. MS 424.21 (M+H)$^+$. $^1$H-NMR (400 MHz, MeOH-d$_4$) δ 3.107 (d, J=3.95 Hz, 1H), 3.15 (m, 1H), 3.25 (dd, J=13.40, 6.37 Hz, 1H), 3.95 (m, 1H), 7.12 (d, J=6.95 Hz, 2H), 7.25 (m, 3H), 7.46 (m, 3H), 7.61 (d, J=7.03 Hz, 2H), 7.69 (s, 1H), 7.75 (m, 4H).

Example 62

4-(Aminomethyl)-N-((S)-1-(4-(3-methoxyphenyl)-1H-imidazol-2-yl)-2-phenylethyl)cyclohexane-carboxamide, bistrifluoroacetic acid salt Part A: (S)-tert-Butyl 1-(1H-imidazol-2-yl)-2-phenylethylcarbamate: (S)-Tert-butyl 1-oxo-3-phenylpropan-2-yl carbamate (5.08 g, 20.4 mmol) and glyoxal trimeric dihydrate (2.2 g, 10.1 mmol) were dissolved in anhydrous MeOH (30 mL). Ammonia in methanol (2.0 M, 45.6 mL, 92.4 mmol) was added and the reaction was stirred for 48 h at rt. The solvent was removed under vacuum. The resulting oil was diluted with EtOAc, washed with brine, dried over MgSO$_4$, filtered and evaporated in vacuo to yield 1.4 g (47%) of white solid. MS 288.15 (M+H)$^+$.

Part B: (S)-tert-Butyl 1-(4,5-dibromo-1H-imidazol-2-yl)-2-phenylethylcarbamate: The product from Example 62 Part A (510 mg, 1.8 mmol) was dissolved in chloroform (10 mL) and treated with NBS (600 mg, 3.38 mmol) at rt. The reaction was stirred for 1 h. The solvent was removed under vacuum and the crude product purified using silica gel chromatography to yield 510 mg (64%) of a white solid. MS 445.91 (M+H)$^+$.

Part C: (S)-tert-Butyl 1-(4-bromo-1H-imidazol-2-yl)-2-phenylethylcarbamate: The product from Example 62 Part B (821 mg, 2.38 mmol) was dissolved in mixture of 1,4 dioxanes (8 ml) and water (2 mL). Sodium sulfite (3.00 g, 23.8 mmol) and tetrabutylammonium hydrogensulfate (2.01 g, 5.95 mmol) were added. The reaction was heated at 100° C. for 48 h. The reaction was diluted with EtOAc and the solids were filtered off. The filtrate was washed with brine, dried over MgSO$_4$, filtered and evaporated to dryness. The crude was purified by silica gel chromatography to provide 200 mg (24%) of a white solid. MS 366.3 (M+H)$^+$.

Part D: (S)-1-(4-bromo-1H-imidazol-2-yl)-2-phenylethanamine: The product from Example 62 Part C (560 mg, 1.53 mmol) was treated with TFA according to the procedure described for Example 1 Part B to provide 490 mg of the crude product as a yellow oil that contained excess TFA. The crude product was used in the next reaction without further purification. MS 268.3 (M+H)$^+$.

Part E: tert-Butyl ((1S,4r)-4-(((S)-1-(4-bromo-1H-imidazol-2-yl)-2-phenylethyl)carbamoyl)cyclohexyl)methylcarbamate: The product from Example 62 Part D (494 mg, 1.86 mmol) and N-Boc-tranexamic acid (480 mg, 1.8 mmol) were treated using the conditions described in Example 2 Part A. The resulting white solid (780 mg, 83%) was carried to the next step without further purification. MS 503.28 (M+H)$^-$.

Part F: tert-Butyl ((1S,4r)-4-(((S)-1-(4-(3-methoxyphenyl)-1H-imidazol-2-yl)-2-phenylethyl)carbamoyl)cyclohexyl)methylcarbamate: The product from Example 62 Part E (30.0 mg, 0.059 mmol) was weighed into a vial containing 3-methoxyphenyl boronic acid (11 mg, 0.07 mmol) and K$_3$PO$_4$ (38 mg, 0.177 mmol). The solids were dissolved in 1,4 dioxanes (0.5 mL). Palladium (I) tri tert-butyl phosphine bromide dimer (19 mg, 0.024 mmol) was added, and the vial was sealed under argon. The reaction was heated using microwave irradiation at 110° C. for 1 hr. The reaction was cooled to rt, and the solids filtered off. The filtrate was collected and dried under vacuum. The crude product, contaminated with starting material, was carried forward to next step. MS 433.22 (M+H)$^+$.

Part G: 4-(Aminomethyl)-N-((S)-1-(4-(3-methoxyphenyl)-1H-imidazol-2-yl)-2-phenylethyl)cyclohexane-carboxamide, bistrifluoroacetic acid salt: The product from Example 62 Part F (30 mg, 0.059 mmol) was treated with TFA according to the procedure described for Example 1 Part B. The product was isolated by prep HLPC to yield 6.00 mg (24%) of as the title compound. $^1$H NMR (500 MHz, d$_4$-MeOH) δ 1.07 (m, 2H) 1.16 (dd, J=12.37, 3.57 Hz, 1H) 1.27 (d, J=15.40 Hz, 1H) 1.39 (m, 2H) 1.57 (m, 2H) 1.80 (d, J=12.10 Hz, 1H) 1.86 (d, J=11.00 Hz, 3H) 1.94 (d, J=11.00 Hz, 1H) 2.26 (m, 2H) 2.77 (d, J=7.15 Hz, 2H) 2.83 (d, J=7.15 Hz, 1H) 3.37 (m, 1H) 3.78 (s, 1H) 3.85 (s, 3H) 5.30 (t, J=8.25

Hz, 1H) 6.63 (m, 1H) 6.81 (m, 1H) 6.81 (m, 1H) 7.19 (m, 4H) 7.24 (t, J=7.42 Hz, 1H) 7.28 (m, 3H) 7.39 (m, 1H) 7.76 (s, 1H): MS 433.22 (M+H)+.

Examples 63-65 and 89 listed in Table 2 were similarly synthesized by appropriate application of the procedures described for Example 62 or by straightforward extension of those procedures by one skilled in the art.

Example 66 trans-3-(2-((S)-1-(4-(Aminomethyl)cyclohexanecarboxamido)-2-phenylethyl)-1H-imidazol-4-yl)-benzoic acid, bistrifluoroacetic acid salt The product from Example 7 (85 mg, 0.18 mmol) was hydrolyzed according to the procedure described for Example 26. The crude product was re-dissolved in MeOH/H$_2$O (9:1) containing 0.1% TFA and evaporated to dryness to yield 86 mg (71%) of the title compound. $^1$H NMR (500 MHz, CDCl$_3$) δ 0.92 (m, 2H), 1.18 (m, 2H), 1.48 (m, 1H), 1.64 (d, J=12.60 Hz, 1H), 1.77 (d, J=11.00 Hz, 3H), 2.15 (t, J=12.10 Hz, 1H), 2.61 (m, 2H), 3.23 (m, 1H), 3.42 (m, J=5.50 Hz, 1H), 5.37 (bs, 1H), 7.21 (t, J=6.32 Hz, 1H), 7.27 (m, 3H), 7.63 (t, J=7.42 Hz, 1H), 8.00 (m, 3H), 8.15 (d, J=6.60 Hz, 1H), 8.39 (s, 1H); HRMS (M+H)+ for C$_{26}$H$_{30}$N$_4$O$_3$, calcd m/z: 447.2396, obs: 447.2407.

Examples 67 and 68

Methyl 4-(2-((S)-1-(trans-4-(aminomethyl)cyclohexanecarboxamido)-2-phenylethyl)-1H-imidazol-4-yl) benzoate, bis-trifluoroacetic acid salt (67) and 4-(2-((S)-1-(trans-4-(aminomethyl)cyclohexanecarboxamido)-2-phenylethyl)-1H-imidazol-4-yl) benzoic acid, bis-trifluoroacetic acid salt (68)

Part A: (S)-ethyl 4-(2-(1-(tert-butoxycarbonyl)-2-phenylethyl)-1H-imidazol-4-yl)benzoate: The product (8.5 g, 97% over two steps) was synthesized from L-N-(Boc)-phenylalanine (3.99 g, 20 mmol), Cs$_2$CO$_3$ (3.25 g, 10 mg), ethyl 4-(2-bromoacetyl)benzoate (5.4 g, 20 mmol) and ammonium acetate (31 g, 400 mmol) by appropriate application of the conditions described for Example 1 Part A. MS 436.1 (M+1)+.

Part B: Ethyl 4-(2-((S)-1-(trans-4-(aminomethyl)cyclohexanecarboxamido)-2-phenylethyl)-1H-imidazol-4-yl) benzoate, bistrifluoroacetic acid salt: The product from Part A (220 mg, 0.48 mmol) was treated sequentially according to the procedures for Example 1 Part B, and Example 2 Part A and Part B to provide 200 mg of product (56% over three steps). MS 334.2 (M-H)−.

Part C: Example 67 and 68: The product from Part B (200 mg, 0.28 mmol) was dissolved in MeOH/H$_2$O (9:1) containing 0.1% TFA (2 mL). The pH of the solution was adjusted to 12-14 using 1 N aqueous NaOH. The reaction was stirred at rt for 16 h. TFA was added to the solution until it reached pH=1 and the products were isolated by prep HPLC to yield 66 mg of Example 67 (34%) and 34 mg of Example 68 (18%).

Data for Example 67: $^1$H-NMR (500 MHz, d$_4$-MeOH) δ 1.06 (m, 2H), 1.38 (m, 2H), 1.57 (m, 1H), 1.80 (d, J=11.55 Hz, 1H), 1.86 (d, J=11.55 Hz, 3H), 2.28 (tt, J=12.10, 3.30 Hz, 1H), 2.77 (d, J=6.60 Hz, 2H), 3.33 (d, J=8.25 Hz, 1H), 3.38 (dd, J=13.20, 8.00 Hz, 1H), 3.93 (s, 3H), 5.33 (t, J=8.25 Hz, 1H), 7.18 (d, J=7.15 Hz, 2H), 7.23 (t, J=7.15 Hz, H), 7.29 (t, J=7.15 Hz, 2H), 7.77 (d, J=8.80 Hz, 2H), 7.89 (s, 1H), 8.11 (d, J=8.80 Hz, 2H); HRMS (M+H)+ for C$_{27}$H$_{32}$N$_4$O$_3$, calcd m/z: 461.2523, obs: 461.2570.

Data for Example 68: $^1$H-NMR (500 MHz, d$_4$-MeOH) δ 1.06 (m, 2H), 1.39 (m, 2H), 1.57 (m, 1H), 1.80 (d, J=12.10 Hz, 1H), 1.86 (d, J=11.55 Hz, 3H), 2.28 (tt, J=12.10, 3.30 Hz, 1H), 2.77 (d, J=7.15 Hz, 2H), 3.33 (d, J=8.25 Hz, 1H), 3.39 (dd, J=13.50, 8.25 Hz, 1H), 5.33 (t, J=8.25 Hz, 1H), 7.19 (d, J=7.15 Hz, 2H), 7.24 (t, J=7.15 Hz, 1H), 7.29 (t, J=7.15 Hz, 2H), 7.76 (d, J=8.25 Hz, 2H), 7.89 (s, 1H), 8.12 (d, J=8.80 Hz, 2H); HRMS (M+H)+ for C$_{26}$H$_{30}$N$_4$O$_3$, calcd m/z: 447.2396, obs: 447.2397.

Example 69 trans-N-((S)-1-(4-(3-Amino-1H-indazol-6-yl)-1H-imidazol-2-yl)-2-phenylethyl)-4-(aminomethyl)-cyclohexanecarboxamide, bistrifluoroacetic acid salt The product from Example 65 (10 mg, 0.022 mmol) was dissolved in 1-butanol. Hydrazine (66 mg, 1.32 mmol) was added and the reaction mixture was heated to 118° C. using microwave irradiation in a sealed tube for 4.5 h. The reaction was cooled to rt and stirred for an additional 8 h. The solvent and excess hydrazine were removed in vacuo. The product was re-dissolved in MeOH/H$_2$O (9:1) containing 0.1% TFA. The solvent was removed under vacuum to provide the title compound (8.8 mg, 59%). HRMS (M+H)+ for C$_{26}$H$_{31}$N$_7$O, calcd m/z: 458.2668, obs: 458.2650.

Example 70 trans-4-(Aminomethyl)-N-benzyl-N-((S)-2-phenyl-1-(4-phenyl-1H-imidazol-2-yl)ethyl)cyclohexanecarboxamide, bistrifluoroacetic acid salt Part A: (S)-N-Benzyl-2-phenyl-1-(4-phenyl-1H-imidazol-2-yl)ethanamine: The product from Example 1 Part B (33 mg, 0.1 mmol) and benzaldehyde (16 mg, 0.15 mmol) were dissolved in CH$_2$Cl$_2$ (4 mL). NaBH(OAc)$_3$ (32 mg, 0.15 mmol) was added, followed by a few drops of HOAc. The reaction was stirred at rt for 48 h. The reaction was diluted with CH$_2$Cl$_2$ and washed with water and brine. It was dried over Na$_2$SO$_4$, filtered and evaporated in vacuo to give 42 mg, of the crude product. MS 354.5 (M+H)+.

Part B: trans-4-(Aminomethyl)-N-benzyl-N-((S)-2-phenyl-1-(4-phenyl-1H-imidazol-2-yl)ethyl)cyclohexanecarboxamide, bistrifluoroacetic acid sal: The product from Example 70 Part A was converted to the title compound following the same procedures described in Example 2 Part A-B. $^1$H-NMR (500 MHz, d$_4$-MeOH) δ 0.95 (m, 2H), 1.25 (m, 1H), 1.60 (m, 3H), 1.80 (m, 3H), 2.49 (t, J=8.52 Hz, 1H), 2.72 (d, J=7.15 Hz, 2H), 3.53 (d, J=3.30 Hz, 2H), 4.80 (m, 2H), 6.14 (t, J=8.25 Hz, 1H), 7.00-7.53 (m, 16H). MS 493.20 (M+H)+.

Examples 71-74 and Example 85 listed in Table 5 were synthesized by appropriate application of the procedures described for Example 70 or by straightforward extension of the procedures described for Example 70 by one skilled in the art.

Example 77 trans-4-Aminomethyl-cyclohexanecarboxylic acid [2-phenyl-1-(4-phenyl-1H-imidazol-2-yl)-ethyl]-amide, bistrifluoroacetic acid salt Part A: {4-[2-Phenyl-1-(4-phenyl-1H-imidazol-2-yl)-ethylcarbamoyl]-cyclohexyl-methyl-carbamic acid phenyl ester The product from Example 55 Part A (36 mg, 0.1 mmol) was dissolved in THF/DMF (2:1, 6 mL) and cooled to 0° C. Dicyclohexyl-carbodiimide (162 mg, 0.1 mmol) was added to the solution. The resulting mixture was stirred at 0° C. for 1 h. The product from Example 1 Part B (33 mg, 0.1 mmol) was added, and the reaction was warmed to 50° C. for 5 h. The reaction was cooled to rt, diluted with EtOAc, washed with water and brine (3×), dried over $Na_2SO_4$, filtered, and dried in vacuo. The title compound was isolated by preparative HPLC to yield 27 mg (40%) as a colorless solid. MS 552.1 $(M+H)^+$.

Part B: 4-Aminomethyl-cyclohexanecarboxylic acid [2-phenyl-1-(4-phenyl-1H-imidazol-2-yl)-ethyl]-amide: The product from Example 77 Part A (27 mg mg, 0.04 mmol) was converted to the final product (16 mg, 75%) using the procedure described for Example 50 Part C. $^1$H-NMR (500 MHz, $d_4$-MeOH) δ 1.09 (m, 2H), 1.19 (m, 2H), 1.57 (m, 1H), 1.81 (m, 2H) 1.92 (m, 2H), 2.76 (d, J=6.60 Hz, 2H), 3.25 (m, 1H), 3.35 (m, 2H), 5.21 (t, J=7.42 Hz, 1H), 7.16 (d, J=7.15 Hz, 2H), 7.24-7.29 (m, 3H), 7.44-7.49 (m, 3H), 7.65 (d, J=8.24 Hz, 2H), 7.72 (s, 1H). MS 418.1 $(M+1)^+$.

Example 82

(S)-4-[2-[1-[4-(aminomethyl)cyclohexanecarboxamido]amino]-2-phenylethyl]-4-(bromo-1H-imidazol-5-yl)-benzamide Part A: (4-{1-[5-Bromo-4-(4-carbamoyl-phenyl)-1H-imidazol-2-yl]-2-phenyl-ethylcarbamoyl}-cyclohexylmethyl)-carbamic acid tert-butyl ester: The product from Example 28 Part A (70 mg, 0.13 mmol) was dissolved in $CHCl_3$ (10 mL) and treated with bromine (21 mg, 0.13 mmol). After stirring for 16 h, the reaction was evaporated to dryness in vacuo to yield 93 mg (>99%) of product. MS 625.3/627.3 (1:1; $M+H)^+$.

Part B: 4-(2-{1-[(4-Aminomethyl-cyclohexanecarbonyl)-amino]-2-phenyl-ethyl}-5-bromo-1H-imidazol-4-yl)-benzamide: The crude product from Example 82 Part A (93 mg, 0.13 mmol) was converted to the title compound (35.8 mg, 36%) using the procedure described for Example 2 Part B. $^1$H-NMR (500 MHz, $d_4$-MeOH) δ 1.38 (m, 1H) 1.57 (m, 1H) 1.76 (d, J=12.65 Hz, 1H) 1.85 (d, J=9.90 Hz, 3H) 2.23 (dt, J=12.10, 3.30 Hz, 1H) 2.77 (d, J=7.15 Hz, 2H) 3.20 (dd, J=13.20, 8.25 Hz, 1H) 3.26 (dd, J=13.30, 7.70 Hz, 1H) 5.23 (t, J=7.97 Hz, 1H) 7.17 (d, J=7.15 Hz, 2H) 7.21 (d, J=7.15 Hz, 1H) 7.26 (t, J=7.15 Hz, 2H) 7.75 (d, J=8.80 Hz, 2H) 7.95 (d, J=8.80 Hz, 2H). MS 524.3/526.3 (1:1; $M+H)^+$.

Example 107

(S)-4-[2-[1-[4-(aminomethyl)cyclohexanecarboxamido]-2-phenylethyl]-4-(trifluoromethyl)-1H-imidazol-5-yl]-benzamide, bis-trifluoroacetic acid salt Part A: trans-{4-[(S)-1-(4-Bromo-5-trifluoromethyl-1H-imidazol-2-yl)-2-phenyl-ethylcarbamoyl]-cyclohexylmethyl}-carbamic acid tert-butyl ester: The product from Part A of Example 32 was converted to the title compound by sequential application of the procedures described for Example 1 Part B, Example 2 Part A and Example 82 Part A. MS: 573.3/575.3 $(M+1)^+$.

Part B: trans-(4-{(S)-1-[4-(4-Carbamoyl-phenyl)-5-trifluoromethyl-1H-imidazol-2-yl]-2-phenyl-ethylcarbamoyl}-cyclohexylmethyl)-carbamic acid tert-butyl ester: The product from Example 107 Part A (47 mg, 0.069 mmol), 4-carbamoylphenyl-boronic acid (30 mg, 0.18 mmol), $K_3PO_4$ (75 mg, 0.35 mmol), and $Pd(PPh_3)_4$ (22 mg) were added together with 6 mL of 1,4-dioxane. The mixture was heated in a sealed tube in the microwave at 110° C. for 1.5 h. The solvent was removed. The residue was dissolved in EtOAc and washed with water and brine. It was dried over $MgSO_4$, concentrated, and purified by flash chromatography (silica, EtOAc/hexane) to give 25 mg of the desired product. MS: 614.4 $(M+1)^+$.

Part C: trans-4-(2-{(S)-1-[(4-Aminomethyl-cyclohexanecarbonyl)-amino]-2-phenyl-ethyl}-5-trifluoromethyl-1H-imidazol-4-yl)-benzamide, bis-trifluoroacetic acid salt: The product from Example 107 Part B was converted to Example 107 (15 mg) by the appropriate application of the procedure described for Example 2 Part B. MS: 514.3 $(M+1)^+$. $^1$HNMR (400 MHz, $d_4$-MeOH) δ 1.04 (m, 2H), 1.39 (m, 2H), 1.57 (m, 1H), 1.82 (m, 4H), 2.21 (m, 1H), 2.76 (d, J=7.03 Hz, 2H), 3.20 (m, 2H), 5.25 (m, 1H), 7.20 (m, 5H), 7.50 (d, J=8.35 Hz, 2H), 7.93 (d, J=8.79 Hz, 2H).

Example 108

N-{(S)-1-[4-(4-Carbamimidoyl-phenyl)-1H-imidazol-2-yl]-2-phenyl-ethyl}-benzamide Hydroxylamine hydrochloride (10 eq) was dissolved in DMSO (1 mL) and triethylamine (10 eq) added. The mixture was stirred for 5 min then filtered to remove triethylamine hydrochloride. The compound of Example 178 Part A (80 mg) was added to the filtrate and the mixture was heated at 65° C. for 1-1.5 h. Reaction was cooled to room temperature, diluted with ~10 mL water, and resulting precipitate collected, washed with water and dried to give the amidoxime intermediate (73 mg, 84%). m/z 426.4 $(M+H)^+$. This material was suspended in methylene chloride (10 mL) and acetic anhydride (0.040 mL) was added. The mixture was stirred for 20 min at room temperature under Argon then evaporated to dryness. The residue was dissolved in a mixture of methanol/HOAc (10:1), 10% Pd/C was added and the mixture was stirred under 1 atm $H_2$ for 2 h. Catalyst was removed by filtration, filtrate evaporated and residue purified by prep C18 HPLC to provide the bis TFA salt of the title compound (65 mg, 60%) $^1$H NMR (400 MHz, MeOH-D4) δ 3.41-3.59 (m, 2H) 5.53 (t, J=8.13 Hz, 1H) 7.20-7.31 (m, 5H) 7.46 (t, J=7.69 Hz, 2H) 7.56 (t, J=7.47 Hz, 1H) 7.84 (d, J=7.03 Hz, 2H) 7.87-7.95 (m, 5H) m/z 410.2 $(M+H)^+$.

Example 109 trans-5-(2-{(S)-1-[(4-Aminomethyl-cyclohexanecarbonyl)-amino]-2-phenyl-ethyl}-1H-imidazol-4-yl)-2-cyano-benzoic acid, bistrifluoroacetic acid salt Part A: 5-Acetyl-2-cyano-benzoic acid methyl ester: Triflic anhydride (10 g, 35.4 mmol) was added dropwise to a cold (−40° C.) solution of 5-acetyl-2-hydroxy-benzoic acid methyl ester (6.9 g, 35.4 mmol) and DIPEA (5.3 g, 42.5 mmol) in $CH_2Cl_2$ (100 mL). The reaction was warmed to −10° C. and stirred for 16 h. The reaction was warmed to rt, evaporated to dryness in vacuo, and re-dissolved in EtOAc. The organic layer was washed with ½ sat. brine, dried over $MgSO_4$, filtered and evaporated in vacuo. A portion of the crude triflate (5.01 g, 15.3 mmol) was dissolved in DMF (40 mL). Palladium (0) tetrakis(triphenylphosphine) (1.3 g, 1.1 mmol) and zinc cyanide (2.16 g, 18.4 mmol) were added to the flask, and the mixture was heated to 90° C. for 2.5 h. The reaction was cooled to rt and stirred with a 1:1 solution of conc. $NH_4OH$ and water (160 mL). The resulting suspension was extracted with ETOAc. The combined organic extracts were washed with ½ sat. brine, dried over MgSO$_4$, filtered and evaporated in vacuo. The title compound was isolated by SiO$_2$ chromatography to yield 439 mg (14%) of a white solid. MS 221.1 (M+NH$_4$)$^+$.

Part B: 5-(2-Bromo-acetyl)-2-cyano-benzoic acid methyl ester: The product from Example 109 Part A (107 mg, 0.53 mmol) was dissolved in CH$_2$Cl$_2$ (5 mL) and treated with bromine (84 mg, 0.53 mmol). The solution changed color from rust red to yellow after 3 h indicating the reaction was complete. The reaction was diluted with CH$_2$Cl$_2$, washed with sat'd NaHCO$_3$, dried over Na$_2$SO$_4$, filtered and evaporated in vacuo to yield 160 mg (>99%) of a colorless solid. $^1$H NMR (500 MHz, CDCl$_3$) δ 4.05 (s, 3H) 4.47 (s, 2H) 7.97 (d, J=7.70 Hz, 1H) 8.26 (m, 1H) 8.69 (s, 1H).

Part C: (S)-2-{[4-(tert-Butoxycarbonylamino-methyl)-cyclohexanecarbonyl]-amino}-3-phenyl-propionic acid: 4-(tert-Butoxycarbonylamino-methyl)-cyclohexanecarboxylic acid (1.7 g, 6.6 mmol) and ethyl phenylalanine hydrochloride (2.0 g, 6.6 mmol) were dissolved in DMF (30 mL) and combined with HOAt (0.5 M in DMF, 16 mL, 8 mmol) and 4-methylmorpholine (2.33 g, 23 mmol). To this mixture was added EDCI (1.76 g, 9.2 mmol). The reaction was stirred at rt for 12 h, diluted with EtOAc, washed several times with ½ sat'd brine, dried over MgSO$_4$, filtered and evaporated in vacuo to yield 2.8 g (99%) of a colorless solid which was dissolved in MeOH (30 mL) and treated with 1 N NaOH (19 mL) at rt for 3 h. The MeOH was removed in vacuo and the residue redissolved in water. The aqueous solution was acidified with 1 N HCl to pH 1 and extracted with EtOAc. The combined organic extracts were dried over MgSO$_4$, filtered and concentrated in vacuo to yield 2.5 g (95%) of the title compound as the free acid. MS 403.0 (M+H+).

Part D: 5-[2-((S)-1-{[4-(tert-Butoxycarbonylamino-methyl)-cyclohexanecarbonyl]-amino}-2-phenyl-ethyl)-1H-imidazol-4-yl]-2-cyano-benzoic acid ethyl ester: The product from Example 109 Part B (149 mg, 0.53 mmol) and the product from Example 109 Part D (214 mg, 0.53 mmol) were combined according to the procedure described for Example 1 Part A to yield 73.6 mg (24%) of the title compound. MS 584.4 (M−H$^+$)$^−$.

Part E: 5-(2-{(S)-1-[(4-Aminomethyl-cyclohexanecarbonyl)-amino]-2-phenyl-ethyl}-1H-imidazol-4-yl)-2-cyano-benzoic acid: The product from Example 109 Part B (149 mg, 0.53 mmol) and the product from Example 109 Part D (214 mg, 0.53 mmol) were combined according to the procedure described for Example 1 Part A to yield 73.6 mg (24%) of the title compound. MS 584.4 (M−H$^+$)$^−$.

Part F: 5-(2-{(S)-1-[(4-Aminomethyl-cyclohexanecarbonyl)-amino]-2-phenyl-ethyl}-1H-imidazol-4-yl)-2-cyano-benzoic acid: The product from Example 109 Part E (13 mg, 0.022 mmol) was dissolved in anhyd. MeOH and cooled to 0° C. Anhyd. ammonia gas was bubbled into the solution for ca. 15 min, then the reaction vessel was tightly capped and the reaction stirred for 24 h at rt. The reaction was sparged with nitrogen and evaporated to dryness. The crude product was dissolved in 10% TFA in CH$_2$Cl$_2$ (v/v) and stirred for 16 h at rt. The solvent and TFA were evaporated in vacuo. The crude product was re-dissolved in MeOH/H$_2$O (9:1) containing 0.1% TFA. The title compound was isolated as a colorless glass via preparative HPLC to yield 2.0 mg (19%). $^1$H NMR (500 MHz, d$_4$-MeOH) □ 1.06 (m, 2H) 1.39 (m, 2H) 1.57 (m, 1H) 1.79 (d, J=12.10 Hz, 1H) 1.86 (d, J=12.10 Hz, 3H) 2.26 (m, 1H) 2.77 (d, J=6.60 Hz, 2H) 3.33 (d, J=8.25 Hz, 2H) 5.32 (t, J=7.97 Hz, 1H) 7.19 (d, J=6.60 Hz, 2H) 7.22 (m, 1H) 7.28 (t, J=7.15 Hz, 3H) 7.92 (s, 2H) 8.09 (d, J=7.70 Hz, 1H) 8.13 (s, 1H). MS 472.3 (M+H$^+$)$^+$.

Example 113

(S)-N-[1-[4-(3-amino-1H-indazol-6-yl)-5-bromo-1H-imidazol-2-yl]-2-phenylethyl]-4-(aminomethyl)-trans-cyclohexanecarboxamide, bis-trifluoroacetic acid salt Example 113 was synthesized by appropriate application of the procedures described in Example 120, except that the procedure for Example 82 Part A was used in place of the procedure for Example 120 Part D. $^1$H NMR (500 MHz, d$_4$-MeOH) δ 1.05 (m, 2H) 1.39 (m, 2H) 1.57 (m, 1H) 1.75 (bd, J=12.10 Hz, 1H) 1.85 (bd, J=13.20 Hz, 3H) 2.22 (m, 1H) 2.77 (d, J=7.15 Hz, 2H) 3.16 (dd, J=13.20, 8.25 Hz, 1H) 3.24 (dd, J=13.20, 7.40 Hz, 1H) 5.21 (t, J=7.97 Hz, 1H) 7.18 (m, 3H) 7.25 (t, J=7.42 Hz, 2H) 7.47 (d, J=9.90 Hz, 1H) 7.70 (s, 1H) 7.92 (d, J=8.25 Hz, 1H). MS: 536 (M+H+)+.

Example 114

(S)-5-[4-(carbamoylphenyl)-2-[1-[4-(aminomethyl) cyclohexanecarboxamido]-2-phenylethyl]-1H-imidazole-4-carboxylic acid, methyl ester, bis-trifluoroacetic acid salt Part A: 2-((S)-1-tert-Butoxycarbonylamino-2-phenylethyl)-3H-imidazole-4-carboxylic acid methyl ester: The compound from Part B of Example 32 (0.42 g, 1.07 mmol) was dissolved in MeOH (8 mL) and TFA (0.8 mL) was added. The mixture was stirred at RT under N$_2$ for 30 minutes. Aqueous NaHCO$_3$ was added and the MeOH was removed. The aqueous was extracted with CH$_2$Cl$_2$. The CH$_2$Cl$_2$ solution was washed with brine, dried over MgSO$_4$, and concentrated to a yellow foam (0.40 g). LC/MS: 346.4 (M+1)$^+$.

Part B: 5-Bromo-2-((S)-1-tert-butoxycarbonylamino-2-phenyl-ethyl)-3H-imidazole-4-carboxylic acid methyl ester: The product from Example 114 Part A (1.2 g of 83% pure, 0.28 mmol) was dissolved in CHCl$_3$ (20 mL) and NBS (0.93 g, 0.41 mmol) was added. The mixture was stirred at RT under N$_2$ for 1.5 h. It was diluted with CHCl$_3$ and washed with water and brine. It was then dried over MgSO$_4$ and concentrated to a white solid (0.79 g). MS: 424.4/426.2 (M+1)$^+$.

Part C: trans-5-Bromo-2-((S)-1-{[4-(tert-butoxycarbonylamino-methyl)-cyclohexanecarbonyl]-amino}-2-phenylethyl)-3H-imidazole-4-carboxylic acid methyl ester: The product from Example 114 Part B was converted to the title compound by sequential application of the procedures described for Example 1 Part B and Example 2 Part A. LC/MS: 563.3 (M+1)$^+$.

Part D: trans-2-{(S)-1-[(4-Aminomethyl-cyclohexanecarbonyl)-amino]-2-phenyl-ethyl}-5-(4-carbamoyl-phenyl)-3H-imidazole-4-carboxylic acid methyl ester, bis-trifluoroacetic acid salt: The product from Example 114 Part C was converted to Example 114 by sequential application of the procedures described for Example 107 Part B and Example 2 Part B. MS: 504.4 (M+1)$^+$. $^1$HNMR (400 MHz, d$_4$-MeOH) δ 1.05 (m, 2H), 1.39 (m, 2H), 1.57 (m, 1H), 1.81 (m, 4H), 2.23 (m, 1H), 2.77 (d, J=7.03 Hz, 2H), 3.24 (m, 2H), 3.82 (s, 3H), 5.28 (t, J=7.91 Hz, 1H), 7.21 (m, 5H), 7.76 (d, J=8.35 Hz, 2H), 7.94 (d, J=8.35 Hz, 2H).

Example 117

(S)-N-[1-[4-[4-(carbamoyl)phenyl]-1H-imidazol-2-yl]-2-phenylethyl]-4-(aminomethyl)-benzamide This compound was prepared by appropriate application of the methods described in Example 28. MS: 440.2 (M+1)$^+$.

¹HNMR (400 MHz, d₄-MeOH) δ 3.53 (m, 2H), 4.19 (s, 2H), 5.55 (m, 1H), 7.27 (m, 5H), 7.57 (m, 2H), 7.77 (m, 2H), 7.80-8.02 (m, 5H).

Example 118

4-Aminomethyl-N-{(S)-1-[4-(4-carbamoyl-phenyl)-1H-imidazol-2-yl]-2-phenyl-ethyl}-2-fluoro-benzamide Example 118 was prepared by appropriate application of the methods described in Example 28. MS: 458.2 (M+1)⁺. ¹HNMR (400 MHz, d₄-MeOH) δ 3.47 (dd, J=13.84 and 8.13 Hz, 2H), 4.18 (s, 2H), 5.59 (t, J=7.91 Hz, 1H), 7.29 (m, 7H), 7.77 (m, 3H), 7.89 (s, 1H), 7.98 (d, J=8.79 Hz, 2H).

Example 119 trans-2-{(S)-1-[(4-Aminomethyl-cyclohexanecarbonyl)-amino]-2-phenyl-ethyl}-5-(4-carboxy-phenyl)-3H-imidazole-4-carboxylic acid, bis-trifluoroacetic acid salt The product from Example 114 was hydrolyzed with LiOH/THF to give the Example 119. MS: 491.4 (M+1)⁺. ¹HNMR (400 MHz, d₄-MeOH) δ 1.05 (dd, J=12.52 and 4.17 Hz, 2H), 1.39 (m, 2H), 1.57 (m, 1H), 1.85 (m, 4H), 2.23 (m, 1H), 2.77 (d, J=7.03 Hz, 2H), 3.23 (m, 2H), 5.29 (t, J=7.91 Hz, 1H), 7.21 (m, 5H), 7.81 (d, J=8.35 Hz, 2H), 8.06 (d, J=8.79 Hz, 2H).

Example 120

(S)-N-[1-[4-(3-amino-1H-indazol-6-yl)-5-chloro-1H-imidazol-2-yl]-2-phenylethyl]-4-(aminomethyl)-trans-cyclohexanecarboxamide, bis-trifluoroacetic acid salt Part A: 4-Cyano-3-fluorobenzoic acid: 4-Bromo-3-fluorobenzoic acid (7.5 g, 0.034 mol), Zn(CN)₂ (4.0 g, 0.034 mol) and Pd(PPh₃)₄ (3.95 g, 0.0034 mol) were added together with 60 mL of DMF (degassed). The mixture was heated at 90° C. under N₂ for 3 h. It was cooled to room temperature and filtered to remove insoluble inorganic salts (discarded). The filtrate was diluted with water and extracted with EtOAc. The EtOAc mixture was washed with water, brine, dried over MgSO₄, and concentrated to yield 4.5 g of the desired product with 90% purity. This material was taken into the next step without further purification. ¹H-NMR (500 MHz, d₄-MeOH) δ 7.82 (m, 1H), 7.90 (m, 3H), 7.56 (d, J=10.0 Hz, 1H), 7.68 (s, 1H), 7.96 (d, J=8.4 Hz, 1H).

Part B: 4-(2-Bromoacetyl)-2-fluorobenzonitrile: 4-Cyano-3-fluorobenzoic acid (4.0 g of 90% pure material, 0.02 mol) was dissolved in CH₂Cl₂ (50 mL). To it was added dropwise oxalyl chloride over 15 minutes (2.3 mL, 0.026 mol). The mixture was stirred at rt for 1 h and then heated at reflux for 1 h under N₂. The solvent was removed, and the residue was redissolved in CH₃CN (50 mL). This solution was cooled to −15° C., and to it was added (trimethylsilyl)diazomethane (11.5 mL of 2.0M in hexane) dropwise over 20 minutes. The resulting mixture was stirred at −15° C. for 1 h under N₂. To it was added dropwise a solution of HBr in HOAc (4.25 mL of 33% wt) over 20 minutes, and the reaction mixture was stirred at −15° C. for 20 minutes. The solvent was removed, and the residue was dissolved in EtOAc, washed with water, brine, dried over MgSO₄, and concentrated to 3.2 g of the desired product. MS: 240.1, 242.1, (M+H)⁺. ¹H-NMR (400 MHz, d₄-MeOH) δ 2.42 (s, 2H), 7.76-7.85 (m, 3H).

Part C: tert-butyl (S)-1-(4-(4-cyano-3-fluorophenyl)-1H-imidazol-2-yl)-2-phenylethylcarbamate: 4-(2-Bromoacetyl)-2-fluorobenzonitrile (3.2 g 0.013 mol), L-Boc-phenylalanine (3.5 g, 0.013 mol), and Cs₂CO₃ (2.6 g, 0.008 mol) were added together with DMF (20 mL). The mixture was stirred at 15° C. for 1 h under N₂. It was diluted with 100 mL of EtOAc, washed with water, brine, dried over MgSO₄, concentrated, and purified by flash chromatography (120 g×2 silica, 10-55% EtOAc in hexane) to give 3.5 g of the desired ester. LC/MS: 425.3. This material was then combined with ammonium acetate (12 g) and suspended in xylenes (100 mL). The mixture was heated under N₂ at 150° C. for 2.5 h in a flask equipped with a Dean-Stark trap. The xylenes were removed. The residue was dissolved in EtOAc, and washed with water and brine. It was dried over MgSO₄, concentrated, and purified by flash chromatography (120 g×2 silica, 15-70% EtOAc in hexane) to give 2.2 g of the desired imidazole. MS: 407 (M+H)⁺. ¹H-NMR (400 MHz, CDCl₃) δ 1.39 (s, 9H), 3.30 (m, 2H), 4.86 (d, J=6.59 Hz, 1H), 5.32 (d, J=7.47 Hz, 1H), 7.14-7.24 (m, 6H), 7.53-7.61 (m, 3H).

Part D: tert-butyl (S)-1-(5-chloro-4-(4-cyano-3-fluorophenyl)-1H-imidazol-2-yl)-2-phenylethylcarbamate: The product from Example 120 Part C (2.2 g, 5.4 mmol) and N-chlorosuccinimide (0.80 g, 6.7 mmol) were added together with CH₃CN (100 mL). The mixture was heated at reflux for 7 h under N₂. The solvent was removed, and the residue was dissolved in EtOAc. It was washed with water, aqueous NaHCO₃, and brine, dried over MgSO₄, and concentrated to give 2.4 g of foam. MS: 441.3, (M+H)⁺. ¹H-NMR (400 MHz, CDCl₃) δ 1.27 (s, 9H), 3.23 (m, 2H), 4.89 (m, 1H), 5.46 (d, J=7.03 Hz, 1H), 7.07 (d, J=6.15 Hz, 2H), 7.25-7.26 (m, 5H), 7.54 (m, 1H).

Part E: 4-(2-((S)-1-amino-2-phenylethyl)-5-chloro-1H-imidazol-4-yl)-2-fluorobenzonitrile: The product from Example 120 Part D (0.20 g, 0.45 mmol) was stirred with CH₂Cl₂ (6 mL) and TFA (1.5 mL) under N₂ for 0.5 h. The solvents were removed. The residue was dried under vacuum to give 0.26 g of the bis-TFA salt. MS: 340.94, (M+H)⁺. ¹H-NMR (400 MHz, d₄-MeOH) δ 3.33 (m, 2H), 4.56 (dd, J=8.57, 6.37 Hz, 1H), 7.12 (d, J=6.59 Hz, 2H), 7.25-7.30 (m, 3H), 7.67 (m, 2H), 7.81 (m, 1H).

Part F: trans-(4-{(S)-1-[5-Chloro-4-(4-cyano-3-fluoro-phenyl)-1H-imidazol-2-yl]-2-phenyl-ethylcarbamoyl}-cyclohexylmethyl)-carbamic acid tert-butyl ester: Boc-tranexamic acid (0.14 g, 0.54 mmol), Bop reagent (0.24 g, 0.54 mmol) and TEA (0.38 mL, 2.7 mmol) were added together with 10 mL of THF. The mixture was stirred at rt for 15 minutes under N₂, and the product from Example 120 Part E (0.26 g, 0.45 mmol) was added. The resulting mixture was heated at 75° C. for 15 minutes under N₂. The reaction mixture was cooled to rt and the solvent was removed. The residue was dissolved in EtOAc and washed with water and brine. It was dried over MgSO₄, concentrated, and purified by flash chromatography (40 g silica, 10-100% EtOAc in hexane) to give 0.21 g of the desired product. MS: 580.3, (M+H)⁺. ¹H-NMR (400 MHz, d₄-MeOH) δ 0.94 (m, 2H), 1.25-1.37 (m, 4H), 1.42 (s, 9H), 1.76-1.79 (m, 3H), 2.15 (m, 1H), 2.85 (m, 2H), 3.20-3.30 (m, 2H), 5.17 (m, 1H), 7.16-7.23 (m, 5H), 7.67-7.80 (m, 3H).

Part G: trans-4-Aminomethyl-cyclohexanecarboxylic acid {(S)-1-[5-chloro-4-(4-cyano-3-fluoro-phenyl)-1H-imidazol-2-yl]-2-phenyl-ethyl}-amide: The product from Example 120 Part F (0.21 g, 0.36 mmol) was stirred with CH₂Cl₂ (8 mL) and TFA (2 mL) under N₂ for 0.5 h. The solvents were removed. The residue was dried under vacuum to give 0.25 g of the bis-TFA salt. MS: 480.3, (M+H)+.

Part H: trans-4-Aminomethyl-cyclohexanecarboxylic acid {(S)-1-[4-(3-amino-1H-indazol-6-yl)-5-chloro-1H-imidazol-2-yl]-2-phenyl-ethyl}-amide, bis-trifluoroacetic acid salt: The product from Example 120 Part G (0.21 g, 0.36 mmol) and hydrazine monohydrate (0.69 mL) were added together with 8 mL of n-butanol. The mixture was heated at 120° C. under $N_2$ for 1 h. The solvent was removed. The residue was purified by reverse phase HPLC to give 0.14 g of the title compound as the bis-TFA salt. MS: 492.3, (M+H)+. $^1$H-NMR (400 MHz, DMSO-$d_6$) δ 0.82-0.84 (m, 2H), 1.11-1.22 (m, 2H), 1.36 (m, 1H), 1.52 (m, 1H), 1.61-1.70 (m, 3H), 2.02 (m, 1H), 2.52-2.61 (m, 2H), 2.94-3.09 (m, 2H), 5.15 (m, 1H), 7.13-7.20 (m, 5H), 7.77-8.27 (m, 3H).

Example 121

N-((S)-1-(4-(3-amino-1H-indazol-6-yl)-5-chloro-1H-imidazol-2-yl)-2-phenylethyl)-4-(aminomethyl)benzamide, bis-trifluoroacetic acid salt Example 121 was prepared by the appropriate application of the procedures described for Example 120, where 4-((tert-butoxycarbamoyl)methyl)benzoic acid instead of Boc-tranexamic acid was used in Example 120 Part F. MS: 486.3, (M+H)+. $^1$HNMR (500 MHz, $d_4$-MeOH) δ 3.33-3.35 (m, 2H), 4.18 (s, 2H), 5.44 (t, J=7.42 Hz, 1H), 7.22-7.25 (m, 5H), 7.52-7.55 (m, 3H), 7.72 (s, 1H) 7.88 (d, J=8.25 Hz, 2H), 7.97 (d, J=8.80 Hz, 1H).

Example 122

3-amino-N-((S)-1-(4-(3-amino-1H-indazol-6-yl)-5-chloro-1H-imidazol-2-yl)-2-phenylethyl)-1H-indazole-6-carboxamide, bis-trifluoroacetic acid salt Part A: tert-Butyl (S)-1-(4-(3-amino-1H-indazol-6-yl)-5-chloro-1H-imidazol-2-yl)-2-phenylethylcarbamate: The product from part D of Example 120 (0.52 g, 1.2 mmol) was converted to the aminoindazole by appropriate application of the method described in Part H of Example 120. MS: 453.3 (M+H)+.

Part B: 6-(2-((S)-1-amino-2-phenylethyl)-5-chloro-1H-imidazol-4-yl)-1H-indazol-3-amine: The Boc protecting group in the product from Example 122 Part A was removed with TFA as described in Part G of Example 120. LC/MS: 353.1 (M−H)+.

Part C: N-((S)-1-(4-(3-Amino-1H-indazol-6-yl)-5-chloro-1H-imidazol-2-yl)-2-phenylethyl)-4-cyano-3-fluorobenzamide: The product from Example 122 Part B was coupled with 4-cyano-3-fluorobenzoic acid using the methods described in Part F of Example 120. MS: 500.3 (M+H)+.

Part D: 3-amino-N-((S)-1-(4-(3-amino-1H-indazol-6-yl)-5-chloro-1H-imidazol-2-yl)-2-phenylethyl)-1H-indazole-6-carboxamide, bis-trifluoroacetic acid salt: The product from Example 122 Part C was converted to Example 122 using the method described in Part H of Example 120. MS: 510.3 (M−H)−. $^1$HNMR (400 MHz, $d_4$-MeOH) δ 3.37 (m, 2H), 5.45 (t, J=7.42 Hz, 1H), 7.23-7.27 (m, 5H), 7.54-7.58 (m, 2H), 7.72 (s, 1H), 7.86 (s, 1H), 7.91-7.97 (m, 2H).

Example 123

3-amino-N-((S)-1-(4-(3-amino-1H-indazol-6-yl)-5-chloro-1H-imidazol-2-yl)-2-phenylethyl)benzo[d]isoxazole-6-carboxamide, bis-trifluoroacetic acid salt The product from Part C of Example 122 was converted to the aminobenzisoxazole with acetohydroxamic acid and potassium carbonate in DMF. MS: 513.1 (M+1)+. $^1$HNMR (400 MHz, $d_4$-MeOH) δ 3.37 (m, 2H), 5.44 (t, J=7.42 Hz, 1H), 7.23-7.27 (m, 5H), 7.54 (d, J=8.79 Hz, 1H), 7.68 (d, J=8.24 Hz, 1H), 7.72 (s, 1H), 7.82 (d, J=8.24 Hz, 1H), 7.83 (s, 1H), 7.97 (d, J=8.79 Hz, 1H).

Example 124

N-((S)-1-(4-(3-amino-1H-indazol-6-yl)-5-chloro-1H-imidazol-2-yl)-2-phenylethyl)-4-(aminomethyl)-2-fluorobenzamide, bis-trifluoroacetic acid salt Example 124 was prepared by appropriate application of the procedures described for Example 120, where 4-cyano-2-fluorobenzoic acid instead of Boc-tranexamic acid was used in Example 120 Part F. The cyano group was reduced with $(Boc)_2O/NiCl_2/NaBH_4$ in MeOH at 0° C. The title compound was isolated as the bis-TFA salt after TFA deprotection by appropriate application of the procedure described for Example 2 Part B. MS: 504.1, (M+H)+. $^1$H-NMR (400 MHz, $d_4$-MeOH) δ 3.34 (m, 2H), 4.18 (s, 2H), 5.44 (t, J=7.42 Hz, 1H), 7.20-7.27 (m, 5H), 7.33-7.35 (m, 2H), 7.54 (dd, J=8.34 Hz and 1.31 Hz, 1H), 7.75 (m, 2H), 7.97 (d, J=9.22 Hz, 1H).

Example 128

N-((S)-1-(4-(3-amino-1H-indazol-6-yl)-5-chloro-1H-imidazol-2-yl)-2-phenylethyl)-4-chloro-2-fluorobenzamide, bis-trifluoroacetic acid salt Example 128 was prepared similarly by appropriate application of the procedures for Example 120, where 4-chloro-2-fluorobenzoic acid instead of Boc-tranexamic acid used in Example 120 Part F. MS: 509.3, (M+H)+. $^1$H-NMR (500 MHz, $d_4$-MeOH) δ 3.34 (m, 2H), 5.44 (t, J=7.42 Hz, 1H), 7.21-7.34 (m, 7H), 7.53 (dd, J=8.79 Hz and 1.1 Hz, 1H), 7.66 (t, J=8.24 Hz, 1H), 7.72 (s, 1H), 7.99 (d, J=8.79 Hz, 1H).

Example 129

N-((S)-1-(4-(3-amino-1H-indazol-6-yl)-5-chloro-1H-imidazol-2-yl)-2-phenylethyl)-2-fluoro-5-methoxybenzamide, bis-trifluoroacetic acid salt Example 121 was prepared similarly by appropriate application of the procedures described for Example 120, where 2-fluoro-5-methoxybenzoic acid instead of Boc-tranexamic acid used in Example 120 Part F. MS: 505.3, (M+H)+. $^1$H-NMR (500 MHz, $d_4$-MeOH) δ 3.34 (m, 2H), 3.78 (s, 3H), 5.44 (t, J=7.42 Hz, 1H), 7.06 (m, 1H), 7.12 (m, 1H), 7.19 (m, 1H), 7.23-7.27 (m, 5H), 7.55 (dd, J=8.79 Hz and 1.1 Hz, 1H), 7.73 (s, 1H), 7.98 (d, J=8.79 Hz, 1H).

Example 130

(S)-4-[2-[(1-[4-(aminomethyl)cyclohexanecarboxamido]-2-phenylethyl]-4-chloro-1H-imidazol-5-yl]-benzamide, bis-trifluoroacetic acid salt The product from Part A of Example 28 was chlorinated with $NCS/CHCl_3$ at RT using the procedure described in Example 120 Part D. The Boc group was then removed using the procedure for Example 2 Part B to give the final product as the bis-TFA salt. MS: 506.2 (M+1)+. $^1$HNMR (400 MHz, $d_4$-MeOH) δ 1.05 (m, 2H), 1.38 (m, 2H), 1.56 (m, 1H), 1.75 (m, 1H), 1.85 (d, J=10.55 Hz, 3H), 2.20 (m, 1H), 2.76 (d, J=7.03 Hz, 2H), 3.17 (m, 2H), 5.20 (t, J=7.91 Hz, 1H), 7.21 (m, 5H), 7.73 (d, J=8.79 Hz, 2H), 7.92 (d, J=8.79 Hz, 2H).

Example 131 trans-Cyclohexane-1,4-dicarboxylic acid 1-amide 4-({(S)-1-[4-(3-amino-1H-indazol-6-yl)-5-chloro-1H-imidazol-2-yl]-2-phenyl-ethyl}-amide), bis-trifluoroacetic acid salt Example 131 was prepared similarly by appropriate application of the procedures for Example 120, where 4-trans-(methoxycarbonyl)cyclohexanecarboxylic acid instead of Boc-tranexamic acid was used in Example 120 Part F. The intermediate methyl ester was then converted to the amide by sequential application of the procedures used for Example 26 Part A and Example 44 Part A. MS: 506.2, (M+H)+. $^1$HNMR (500 MHz, d$_4$-MeOH) δ 1.33-1.38 (m, 1H), 1.45-1.48 (m, 3H), 1.72 (m, 1H) 1.88 (m, 3H), 2.18-2.23 (m, 2H), 3.17 (m, 1H), 3.26 (m, 1H), 5.21 (t, J=7.42 Hz, 1H), 7.19 (m, 3H), 7.25 (m, 2H), 7.52 (dd, J=8.24 Hz and 1.1 Hz, 1H), 7.70 (s, 1H), 7.99 (d, J=8.24 Hz, 1H).

Example 132

(S)-N-[1-[4-(3-amino-1H-indazol-6-yl)-5-chloro-1H-imidazol-2-yl]-2-phenylethyl]-1,4-benzenedicarboxamide, bis-trifluoroacetic acid salt Example 132 was prepared by appropriate application of the procedures described for Example 120 wherein 4-carbamoylbenzoic acid was used instead of Boc-tranexamic acid in Example 120 Part F. MS: 500.1, (M+H)+. $^1$H-NMR (500 MHz, d$_4$-MeOH) δ 3.34 (m, 2H), 5.44 (t, J=7.42 Hz, 1H), 7.24-7.26 (m, 5H), 7.54 (dd, J=8.79 and 1.1 Hz, 1H), 7.72 (s, 1H), 7.89 (d, J=8.3 Hz, 2H), 7.95 (d, J=8.3 Hz, 2H), 7.97 (d, J=8.79 Hz, 1H).

Example 135

(S)-4-[2-[1-[4-(aminomethyl)cyclohexanecarboxamido]-2-phenylethyl]-4-phenyl-1H-imidazol-5-yl]-benzamide, bis-trifluoroacetic acid salt The product from Part A of Example 28 was converted to (4-{(S)-1-[5-Bromo-4-(4-carbamoyl-phenyl)-1H-imidazol-2-yl]-2-phenyl-ethylcarbamoyl}-cyclohexylmethyl)-carbamic acid tert-butyl ester by appropriate application of the procedure for Example 82 Part A. This compound was then coupled with phenyl boronic acid by appropriate application of the conditions described for Example 107 Part B. Deprotection of the Boc group with TFA using the procedure from Example 2 Part B afforded the Example 135 as the bis-TFA salt. MS: 522.4 (M+1)+. $^1$HNMR (400 MHz, d$_4$-MeOH) δ δ 1.07 (m, 2H), 1.42 (m, 2H), 1.59 (m, 1H), 1.85 (m, 4H), 2.30 (m, 1H), 2.78 (d, J=6.59 Hz, 2H), 3.41 (m, 2H), 5.32 (t, J=8.13 Hz, 1H), 7.29 (m, 7H), 7.44 (m, 2H), 7.90 (d, J=8.35 Hz, 2H).

Example 136

1-amino-N-((S)-1-(4-(3-amino-1H-indazol-6-yl)-5-chloro-1H-imidazol-2-yl)-2-phenylethyl)-isoquinoline-6-carboxamide, bis-trifluoroacetic acid salt This product was prepared using 1-aminoisoquinoline-6-carboxylic acid from Part D of Example 147 and the product from Part E of Example 120 by sequential application of the procedures described for Example 147 Part F and Example 120 Part F. MS: 523.2 (M+1)+. $^1$HNMR (400 MHz, d$_4$-MeOH) δ 3.39 (dd, J=15.82, 7.91 Hz, 2H), 5.48 (t, J=7.91 Hz, 1H), 7.25-7.27 (m, 6H), 7.52 (d, J=10.11 Hz, 1H), 7.61 (d, J=7.03 Hz, 1H), 7.72 (s, 1H), 7.96 (d, J=8.35 Hz, 1H), 8.08 (dd, J=8.79, 1.76 Hz, 1H), 8.30 (s, 1H), 8.49 (d, J=8.79 Hz, 1H).

Example 137

1-amino-N-((S)-1-(4-(3-amino-1H-indazol-6-yl)-5-chloro-1H-imidazol-2-yl)-2-phenylethyl)-5,6,7,8-tetrahydroisoquinoline-6-carboxamide, bis-trifluoroacetic acid salt Example 137 was prepared from the product of Part F of Example 147 by appropriate application of the procedures for Example 120 Part H. MS: 527.3 (M+1)+. $^1$HNMR (400 MHz, d$_4$-MeOH) δ 2.44 (m, 2H), 2.76 (m, 2H), 2.88 (m, 1H), 3.21 (m, 2H), 3.34 (m, 2H) 5.29 (m, 1H), 6.66 (t, J=7.9 Hz, 1H), 7.24 (m, 5H), 7.56 (m, 2H), 7.73 (s, 1H), 7.97 (d, J=7.9 Hz, 1H).

Example 138

2-(3-amino-1H-indazol-6-yl)-N-((S)-1-(4-(3-amino-1H-indazol-6-yl)-5-chloro-1H-imidazol-2-yl)-2-phenylethyl)acetamide, bis-trifluoroacetic acid salt This compound was prepared by appropriate application of the methods described for Example 122, wherein 2-(4-cyano-3-fluorophenyl)acetic acid was replaced by 4-cyano-3-fluorobenzoic acid. MS: 526.3 (M+1)+. $^1$HNMR (400 MHz, d$_4$-MeOH) δ 3.17 (m, 1H), 3.26 (m, 1H), 3.69 (d, J=5.71 Hz, 2H), 5.26 (t, J=7.03 Hz, 1H), 7.02 (d, J=8.34 Hz, 1H), 7.16 (m, 5H), 7.26 (s, 1H), 7.52 (d, J=8.79 Hz, 1H), 7.71 (s, 1H), 7.81 (d, J=8.34 Hz, 1H), 7.97 (d, J=8.79 Hz, 1H).

Example 139 trans-4-(2-{(S)-1-[(4-Aminomethyl-cyclohexanecarbonyl)-amino]-2-phenyl-ethyl}-5-bromo-1-methyl-1H-imidazol-4-yl)-benzamide, bis-trifluoroacetic acid salt The product from Example 82 Part A was methylated with MeI/K$_2$CO$_3$/DMF. The major isomer isolated was deprotected using the procedure described for Example 2 Part B to give Example 139. MS: 538.2/540.2 (M+1)+. $^1$HNMR (400 MHz, d$_4$-MeOH) δ 1.04 (m, 2H), 1.39 (m, 2H), 1.56 (m, 1H), 1.80 (m, 4H), 2.20 (m, 1H), 2.76 (d, J=7.03 Hz, 2H), 3.27 (m, 2H), 3.41 (s, 3H), 5.35 (t, J=7.91 Hz, 1H), 7.22 (m, 5H), 7.96 (m, 4H).

Example 140

4-Aminomethyl-N-{(S)-1-[4-(4-carbamoyl-phenyl)-1H-imidazol-2-yl]-2-phenyl-ethyl}-2-ethylamino-benzamide, bis-trifluoroacetic acid salt Part A: tert-Butyl 4-cyano-2-fluorobenzoate: 4-Cyano-2-fluorobenzoic acid (1.0 g, 6.1 mmol) was dissolved in t-BuOH (9 mL) and THF (3 mL). Boc anhydride (2.64 g, 12.1 mmol) was added followed by DMAP (0.24 g, 1.97 mmol). The mixture was stirred at RT under N$_2$ for 12 h. The solvents were removed. The residue was dissolved in EtOAc and washed with saturated aqueous NaHCO$_3$ and brine. It was dried over MgSO$_4$ and concentrated to an oil which became solid under vacuum (1.3 g). $^1$HNMR (400 MHz, d$_4$-MeOH) δ 1.59 (s, 9H), 7.44 (dd, J=25.71 and 9.01 Hz, 2H), 7.95 (m, 1H).

Part B: tert-Butyl 4-cyano-2-(ethylamino)benzoate: The product from Example 140 Part A (0.30 g, 1.36 mmol) and ethylamine hydrochloride (0.22 g, 2.72 mmol) were added together with 5 mL of DMF. The mixture was heated at 50° C. under N$_2$ for 2 h. Water was added, and the mixture was extracted with EtOAc. The EtOAc extract was washed with brine, dried over MgSO$_4$ and concentrated, and the residue was purified by flash chromatography (silica, EtOAc/hexane) to give 50 mg of the desired product. MS: 247.3 (M+1)$^+$.

Part C: 4-Cyano-2-(ethylamino)benzoic acid: The product from Example 140 Part B (50 mg, 0.20 mmol) was stirred with 5 mL of TFA and 5 mL of CH$_2$Cl$_2$ at RT for 1 h, and then heated at reflux for 1 h under N$_2$. The solvent was removed. The residue was dried to give 45 mg of the acid. $^1$HNMR (400 MHz, d$_4$-MeOH) δ 1.28 (m, 3H), 3.18 (m, 2H), 76.75 (m, 1H), 6.86 (s, 1H), 7.95 (d, J=7.91 Hz, 1H).

Part D: (S)-4-(2-(1-(1-(4-Cyano-2-(ethylamino)phenyl)vinylamino)-2-phenylethyl)-1H-imidazol-4-yl)benzamide: Cyano-2-(ethylamino)benzoic acid from Example 140 Part C (40 mg, 0.2 mmol), Bop reagent (108 mg, 0.24 mmol), and Et$_3$N (0.28 mL) were added together with 5 mL of THF. The mixture was stirred at RT for 15 minutes and (S)-4-(2-(1-Amino-2-phenylethyl)-1H-imidazol-4-yl)benzamide (107 mg, 0.2 mmol), obtained from N-boc-(L)-phenylalanine and 4-(2-Bromo-acetyl)-benzonitrile by the sequential application of the procedures described for Example 1 Part A, Example 28 Part A and Example 1 Part B, was added. The resulting mixture was heated to reflux under N$_2$ for 2 h. The solvent were removed. The residue was dissolved in EtOAc and washed with water and brine. It was dried over MgSO$_4$, concentrated, and purified by ISCO flash chromatography (silica, EtOAc/hexane) to give 50 mg of the desired product. LC/MS: 479.3 (M+1)$^+$.

Part E: 4-Aminomethyl-N-{(S)-1-[4-(4-carbamoyl-phenyl)-1H-imidazol-2-yl]-2-phenyl-ethyl}-2-ethylamino-benzamide, bis-trifluoroacetic acid salt: The product from Example 140 Part D was dissolved in 10 mL of MeOH and 1 mL of 4N HCl in dioxane. Catalytic amount of Pd/C (10%) was added. The mixture was placed under a balloon of H$_2$ for 12 h. It was filtered through Celite, concentrated, and purified by reverse phase HPLC to give 24 mg of bis-TFA salt. LC/MS: 483.4 (M+1)$^+$. $^1$HNMR (400 MHz, d$_4$-MeOH) δ 1.22 (t, J=7.25 Hz, 3H), 3.18 (q, J=7.03 Hz, 2H), 3.47 (dd, J=32.52 and 8.35 Hz, 2H), 4.05 (s, 2H), 5.50 (t, J=8.35 Hz, 1H), 6.66 (d, J=7.91 Hz, 1H), 6.77 (s, 1H), 7.26 (m, 5H), 7.70 (d, J=7.91 Hz, 1H), 7.76 (d, J=8.35 Hz, 2H), 7.88 (s, 1H), 7.98 (d, J=8.35 Hz, 2H).

Example 142

(S)-N-(1-(4-(4-Carbamoylphenyl)-1H-imidazol-2-yl)-2-phenylethyl)-1,2,3,4-tetrahydroisoquinoline-6-carboxamide Example 142 was prepared by appropriate application of the methods described in Example 28. MS: 466.2 (M+1)$^+$. $^1$HNMR (400 MHz, d$_4$-MeOH) δ 3.15 (t, J=6.37 Hz, 2H), 3.49 (m, 4H), 4.41 (s, 2H), 5.53 (t, J=8.35 Hz, 1H), 7.27 (m, 6H), 7.75 (m, 4H), 7.88 (s, 1H), 7.97 (d, J=8.79 Hz, 2H).

Example 143

4-Aminomethyl-N-{(S)-1-[4-(4-carbamoyl-phenyl)-1H-imidazol-2-yl]-2-phenyl-ethyl}-2-ethyl-benzamide Part A: Methyl 4-bromo-2-chlorobenzoate: 2-Bromo-4-chlorobenzoic acid (1.0 g, 4.25 mmol) was dissolved in 10 mL of MeOH. The mixture was cooled in an ice-bath and to it was added thionyl chloride (3.1 mL, 42.5 mmol) dropwise. The cooling bath was removed and the mixture was stirred at rt under N$_2$ for 12 h. The solvent was removed and dried under vacuum to give 1.0 g of colorless oil. LC/MS: 251.1 (M+1)$^+$.

Part B: Methyl 2-chloro-4-cyanobenzoate: The product from Example 143 Part A (1.0 g, 4.0 mmol), Zn(CN)$_2$ (0.52 g, 4.8 mmol), Pd(PPh$_3$)$_4$ (0.23 g, 0.2 mmol) were added together with 9 mL of DMF. The mixture was degassed and then heated at 90° C. for 6 h. Water and EtOAc were added to the reaction mixture. It was filtered to remove inorganic solids. The layers were separated and the EtOAc layer was washed with water and brine. It was dried over MgSO$_4$, concentrated, and purified by flash chromatography (silica, EtOAc/hexane) to give 0.28 g of the desired product. MS: 196.1 (M+1)$^+$.

Part C: Methyl 4-cyano-2-ethylbenzoate: The product from Example 143 Part B (160 mg, 0.82 mmol), ethyl boronic acid (120 mg, 1.64 mmol), K$_3$PO$_4$ (344 mg (1.64 mmol), and Pd(PPh$_3$)$_4$ (114 mg, 0.1 mmol) were added together with 9 mL of DME. The mixture was heated at 150° C. in a microwave for 15 minutes. The DME was removed and EtOAc was added. It was washed with water and brine, dried over MgSO$_4$, concentrated, and purified by flash chromatography (silica, EtOAc/hexane) to give 100 mg of the desired product. MS: 190.21 (M+H$^+$)$^+$ and 222.3 (M+Na$^+$)$^+$.

Part D: 4-Cyano-2-ethylbenzoic acid: The product from Example 143 Part C (100 mg, 0.53 mmol) was dissolved in 5 mL of EtOH and 1 mL of 1N aqueous NaOH was added. The mixture was stirred at RT under N$_2$ for 2 h. Aqueous 1N HCl was added to adjust the pH to 4. The EtOH was removed, and the mixture was diluted with EtOAC and water. The two layers were separated. The water layer was extracted with EtOAc. The combined EtOAc solution was washed with water and brine, dried over MgSO$_4$, and concentrated to give 90 mg of the desired acid. $^1$HNMR (400 MHz, d$_4$-MeOH) δ 1.22 (m, 3H), 3.00 (m, 2H), 7.71 (m, 1H), 7.67 (s, 1H), 7.92 (d, J=8.35 Hz, 1H).

Part E: N-{(S)-1-[4-(4-Carbamoyl-phenyl)-1H-imidazol-2-yl]-2-phenyl-ethyl}-4-cyano-2-ethyl-benzamide: The product from Example 143 Part D (90 mg, 0.51 mmol), Bop reagent (265 mg, 0.61 mmol), and triethylamine (0.42 mL, 1.5 mmol) were added together with 5 mL of THF. The mixture was stirred at RT under N$_2$ for 15 minutes and (S)-4-(2-(1-amino-2-phenylethyl)-1H-imidazol-4-yl)benzamide prepared using the methods described in Examples 2 and 28 (365 mg, 0.51 mg) was added. The resulting mixture was heated at 75° C. for 70 minutes. The THF was removed, and the residue was dissolved in EtOAc. It was washed with waster and brine, dried over MgSO$_4$, concentrated, and purified by flash chromatography (silica, EtOAc/hexane) to give 80 mg of the desired product. MS: 464.4 (M+1)$^+$.

Part F: 4-Aminomethyl-N-{(S)-1-[4-(4-carbamoyl-phenyl)-1H-imidazol-2-yl]-2-phenyl-ethyl}-2-ethyl-benzamide: The product from Example 143 Part E (70 mg, 0.15 mmol) was dissolved in 10 mL of MeOH and 1 mL of 4 N HCl in dioxane. Catalytic amount of Pd/C (10%) was added and the mixture was placed under a balloon of H$_2$ for 6 h. It was filtered through Celite and washed with MeOH. The filtrate was concentrated and purified by reverse phase HPLC to give 75 mg of the bis-TFA salt. LC/MS: 468.4 (M+1)$^+$. $^1$HNMR (400 MHz, d$_4$-MeOH) δ 1.08 (t, J=7.47 Hz, 3H), 2.61 (t, J=7.47 Hz, 2H), 3.44 (dd, J=13.62, 8.35 Hz, 2H), 4.12 (s, 2H), 5.59 (t, J=8.35 Hz, 1H), 7.34 (m, 7H), 7.80 (d, J=8.35 Hz, 2H), 7.89 (s, 1H), 7.99 (d, J=8.35 Hz, 2H).

Example 144

3-amino-N-((S)-1-(4-(3-amino-1H-indazol-6-yl)-5-chloro-1H-imidazol-2-yl)-2-phenylethyl)-1-methyl-1H-indazole-6-carboxamide, bis-trifluoroacetic acid salt The product from Part C of Example 122 was converted to the desired product by appropriate application of the method described in Part H of Example 120, where methyl hydrazine was used instead of hydrazine. MS: 526.3 (M+H)$^+$. $^1$HNMR (400 MHz, d$_4$-MeOH) δ 3.35 (m, 2H), 3.84 (s, 3H), 5.46 (m, 1H), 7.23 (m, 5H), 7.39 (d, J=8.35 Hz, 2H), 7.64 (s, 1H), 7.72 (d, J=8.35 Hz, 1H), 7.79 (s, 1H), 7.84 (d, J=7.91 Hz, 1H).

Example 147

1-amino-N-((S)-1-(4-(3-amino-1H-indazol-6-yl)-5-chloro-1H-imidazol-2-yl)-2-phenylethyl)-5,6,7,8-tetrahydroisoquinoline-6-carboxamide, bis-trifluoroacetic acid salt Part A: (E)-2-(2-(Dimethylamino)vinyl)terephthalonitrile: Methylterephthalonitrile (1.42 g, 1.0 mmol) and t-butoxybis(dimethylamine)methane (3.5 g, 2.0 mmol) were heated with 15 mL of DML at 75° C. for 12 h under N$_2$. The DMF was removed and hexane was added. The precipitate formed was filtered and dried to give 1.85 g of the desired product. MS: 504.4, (M+H)$^+$. $^1$H-NMR (400 MHz, d$_4$-MeOH) δ 2.95 (s, 6H), 5.27 (d, J=13.62 Hz, 1H), 7.14 (m, 1H), 7.42 (d, J=13.18 Hz, 1H), 7.54 (d, J=7.91 Hz, 1H), 7.86 (s, 1H).

Part B: 2-(2,4-Dimethoxybenzyl)-1-imino-1,2-dihydroisoquinoline-6-carbonitrile: The product from Example 147 Part A (1.85 g, 9.38 mmol) and 2,4-dimethoxybenzylamine (2.6 mL, 15.03 mmol) were heated with 5 mL of DMPU at 140° C. for 3 h under N$_2$. The reaction mixture was cooled, and EtOAc/hexane(1:2) was added. The precipitate formed was filtered and dried in vacuo to give 2.5 g of the desired product. $^1$H-NMR (400 MHz, DMSO-d$_6$) δ 3.72 (s, 3H, 3.81 (s, 3H), 4.95 (s, 2H), 6.10 (d, J=7.03 Hz, 1H, 6.44 (d, J=7.91 Hz, 1H), 6.57 (s, 1H), 7.02 (d, J=8.35 Hz, 1H), 7.22 (d, J=6.15 Hz, 1H) 7.68 (d, J=7.91 Hz, 1H), 7.94 (s, 1H), 8.34 (d, J=7.91 Hz, 1H).

Part C: 2-(2,4-Dimethoxybenzyl)-1-imino-1,2-dihydroisoquinoline-6-carboxylic acid: The product from Example 147 Part B (2.5 g, 7.84 mmol) was heated with 40 mL of MeOH-15% NaOH(1:1) at 90° C. for 1.5 h under N$_2$. The reaction mixture was cooled and aq. HCl was added dropwise to adjust the pH to about 5. The methanol was removed and EtOAc/hexane (1:2) were added. The precipitate formed was filtered and dried to give 2.42 g of the desired product. LC/MS: 339.2, (M+H)$^+$. $^1$HNMR (400 MHz, d$_4$-MeOH) δ 2.00 (s, 2H), 3.82 (d, J=9.67 Hz, 6H), 6.62 (m, 2H), 7.23 (d, J=7.91 Hz, 2H), 7.50 (d, J=7.03 Hz, 1H), 8.23 (s, 1H), 8.31 (s, 1H), 8.42 (d, J=8.79 Hz, 1H).

Part D: 1-Aminoisoquinoline-6-carboxylic acid: The product from Example 147 Part C (2.12 g, 6.28 mmol) was heated with 17 mL of anisole and 20 mL of TFA at 105° C. for 12 h under N$_2$. The solvents were removed, and EtOAc/hexane(1:2) were added. The precipitate formed was filtered and dried to give 1.77 g of the TFA salt. LC/MS: 189.04, (M+H)$^+$. $^1$HNMR (400 MHz, d$_4$-MeOH) δ 7.34 (d, J=7.03 Hz, 1H), 7.62 (d, J=7.03 Hz, 1H), 8.30 (d, J=8.79 Hz, 1H), 8.51 (d, J=8.79 Hz, 1H), 8.56 (s, 1H).

Part E: 1-Amino-5,6,7,8-tetrahydroisoquinoline-6-carboxylic acid: The product from Example 147 Part D (1.0 g, 3.31 mmol) and platinum oxide (87 mg, 0.38 mmol) were added together with 21 mL of TFA. The reaction mixture was placed under a balloon of hydrogen gas and then warmed to 60° C. for 16 h. The mixture was cooled to RT and filtered through Celite to remove platinum oxide. The solvent was removed, and the residue was purified by reverse phase HPLC to give 0.21 g of the desired product as the TFA salt. LC/MS: 193.1, (M+H)$^+$. $^1$HNMR (400 MHz, d$_4$-MeOH) δ 2.00 (m, 1H), 2.28 (m, 1H), 2.57 (m, 2H) 2.85 (m, 1H), 3.02 (d, J=7.03 Hz, 2H), 6.75 (d, J=6.59 Hz, 1H), 7.61 (d, J=6.59 Hz, 1H).

Part F: 1-Amino-N-((S)-1-(4-chloro-5-(4-cyano-3-fluorophenyl)-1H-imidazol-2-yl)-2-phenylethyl)-5,6,7,8-tetrahydroisoquinoline-6-carboxamide: The product from Example 147 Part E (0.21 g, 0.67 mmol), Bop reagent (0.44 g, 1.0 mmol), and triethylamine (0.91 mL, 6.54 mmol) were added together with 15 mL of THF. The mixture was stirred at RT for 20 minutes under N$_2$ and the product from Part E of Example 120 (0.41 g, 0.90 mmol) was added. The resulting mixture was heated at 75° C. for 1 h under N$_2$. The reaction mixture was cooled and the solvent was removed. The residue was dissolved in EtOAc and washed with water and brine. It was dried over MgSO$_4$, concentrated, and purified by flash chromatography (40 g silica, 0-15% MeOH in dichloromethane) to give 0.31 g of the desired product. LC/MS: 515.4, (M+H)$^+$. $^1$HNMR (400 MHz, d$_4$-MeOH) δ 1.73 (dd, J=12.96, 5.93 Hz, 1H), 2.10 (m, 1H) 2.39 (m, 1H), 2.58 (m, 4H), 3.22 (m, 2H), 5.24 (t, J=7.69 Hz, 1H), 6.37 (d, J=5.27 Hz, 1H), 7.23 (m, 5H), 7.64 (m, 3H) 7.79 (m, 1H).

Part G: Chiral separation of the product from Part F: The product from Example 147 Part F was separated by chiral prep-HPLC (OD column, 30% EtOH/MeOH (1:1) and 70% heptane with 0.15% DEA) to give diastereomer A and diastereomer B.

Part H: (S)-1-Amino-5,6,7,8-tetrahydro-isoquinoline-6-carboxylic acid {(S)-1-[4-(3-amino-1H-indazol-6-yl)-5-chloro-1H-imidazol-2-yl]-2-phenyl-ethyl}-amide: Diastereomer A from Example 147 Part G (0.10 g, 0.19 mmol) and hydrazine (0.50 mL) were added together with 7 mL of n-butanol. The mixture was heated at 120° C. under N$_2$ for 1.5 h. The solvent was removed. The residue was purified by reverse phase HPLC to give 0.10 g of the desired product as the bis-TFA salt. LC/MS: 527.21, (M+H)$^+$. $^1$HNMR (400 MHz, d$_4$-MeOH) δ 1.84 (m, 1H), 2.14 (m, 1H), 2.51 (m, 2H), 2.72 (m, 3H), 3.19 (m, 2H), 5.24 (m, 1H), 6.66 (d, J=6.59 Hz, 1H), 7.24 (m, 5H), 7.49 (d, J=8.35 Hz, 1H), 7.59 (d, J=6.59 Hz, 1H) 7.69 (s, 1H), 7.93 (d, J=9.23 Hz, 1H).

Example 155

N-((S)-1-(4-(3-amino-1H-indazol-6-yl)-5-chloro-1H-imidazol-2-yl)-2-phenylethyl)-1,2,3,4-tetrahydroisoquinoline-6-carboxamide, bis-trifluoroacetic acid salt Example 155 was prepared by appropriate application of the procedures described for Example 120, where 2-(tert-butoxycarbonyl)-1,2,3,4-tetrahydroisoquinoline-6-carboxylic acid instead of Boc-tranexamic acid was used in Example 120 Part F. MS: 512.2, (M+H)$^+$. $^1$H-NMR (400 MHz, d$_4$-MeOH) δ 3.17 (t, J=6.37 Hz, 2H, 3.35 (m, 2H) 3.53 (t, J=6.37 Hz, 2H), 4.41 (s, 2H), 5.41 (t, J=7.91 Hz, 1H), 7.22 (m, 5H), 7.32 (d, J=8.35 Hz, 1H), 7.50 (d, J=10.11 Hz, 1H) 7.71 (m, 3H) 7.94 (d, J=8.35 Hz, 1H).

Example 157 trans-4-Aminomethyl-cyclohexanecarboxylic acid {(S)-1-[5-(3-amino-1H-indazol-6-yl)-1H-imidazol-2-yl]-3-[(pyridin-2-ylmethyl)-carbamoyl]-propyl}-amide, tris-trifluoroacetic acid salt Part A: (S)-2-Benzyloxycarbonylamino-pentanedioic acid 5-tert-butyl ester 1-[2-(4-cyano-3-fluoro-phenyl)-2-oxo-ethyl]ester: (S)-2-Benzyloxycarbonylamino-pentanedioic acid 5-tert-butyl ester (674 mg, 2 mmol), $Cs_2CO_3$ (326 mg, 1 mmol) and DMF 5 mL) were stirred room temperature for 0.5 h. A solution of 1'-bromo-3-fluoro-4-cyanoacetophenone (484 mg, 2 mmol) in DMF (5 mL) was added. Stirring was continued for 16 h. The reaction mixture was diluted with EtOAc (100 mL). Three washings with a 10% LiCl solution, drying over $MgSO_4$, filtration and removal of solvent in vacuo provided an orange oil (900 mg, 91% yield): $^1$H-NMR ($CDCl_3$, 400 MHz): δ 7.77 (m, 3H), 7.35 (m, 5H), 5.52 (m, 1H), 5.42 (d, 1H, J=16), 5.25 (d, 1H, J=16), 5.11 (s, 2H), 4.60 (m, 1H), 2.45 (m, 2H), 1.44 (s, 9H); MS: 497 (M–H+)–.

Part B: (S)-4-Benzyloxycarbonylamino-4-[5-(4-cyano-3-fluoro-phenyl)-1H-imidazol-2-yl]-butyric acid tert-butyl ester: The intermediate from Example 157 Part A (900 mg, 1.81 mmol), $NH_4OAc$ (1.54 g, 20 mmol) and xylenes (30 mL) were stirred at reflux temperature for 2.5 h. The reaction mixture was cooled to ambient temperature. Solvent was removed in vacuo. The residue was partitioned between EtOAc and a saturated $Na_2CO_3$ solution three times. The combined organic layers were dried over $MgSO_4$ and filtered. Solvent was removed in vacuo to give a red orange oil. HPLC (0% to 100% EtOAc-hexanes) gave an orange oil (400 mg, 46% yield): $^1$H-NMR ($CDCl_3$, 400 MHz): δ 10.3 (s, 1H), 7.59 (m, 4H), 7.35 (m, 5H), 5.83 (s, 1H), 5.13 (m, 2H), 4.79 (m, 1H), 2.53 (m, 1H), 2.34 (m, 3H), 1.45 (s, 9H); MS: 477 (M–H+)–.

Part C: (S)-4-Amino-4-[5-(4-cyano-3-fluoro-phenyl)-1H-imidazol-2-yl]-butyric acid tert-butyl ester: The intermediate from Example 157 Part B (400 mg, 0.84 mmol), 10% Pd on C (40 mg) and EtOH (4 mL) were stirred under a hydrogen atmosphere for 2 h. The reaction mixture was filtered through Celite. Solvent was removed in vacuo to give an oil. HPLC (0% to 10% MeOH—$CH_2Cl_2$) provided a pale yellow solid (189 mg, 65% yield): $^1$H-NMR ($CDCl_3$, 400 MHz): δ 10.3 (s, 1H), 7.59 (m, 2H), 7.34 (1, 2H), 4.81 (t, 1H, J=7), 2.59 (m, 2H), 2.28 (m, 2H), 1.42 (s, 9H); MS: 343 (M–H+)–.

Part D: trans-(S)-4-{[4-(Benzyloxycarbonylamino-methyl)-cyclohexanecarbonyl]-amino}-4-[5-(4-cyano-3-fluoro-phenyl)-1H-imidazol-2-yl]butyric acid tert-butyl ester: N-CBz-tranexamic acid (160 mg, 0.66 mmol), $HOBt.H_2O$ (82 mg, 0.61 mmol), EDCI (117 mg, 0.61 mmol), $(i-Pr)_2NEt$ (388 mg, 0.52 mL, 3 mmol) and DMF (1 mL) were stirred at room temperature for 15 min. A solution of the intermediate from Example 157 Part C (189 mg, 0.55 mmol) in DMF (1 mL) was added. Stirring was continued for 24 h. The reaction mixture was diluted with EtOAc (40 mL). The organic mix was washed with a 10% LiCl solution. Drying over $MgSO_4$, filtration and removal of solvent in vacuo afforded a tan solid (330 mg, 97% yield): $^1$H-NMR ($CDCl_3$, 400 MHz): δ 10.1 (s, 1H), 7.60 (m, 1H), 7.35 (m, 2H), 6.97 (d, 1H, J=8), 5.09 (s, 2H), 4.90 (d, 1H, J=8), 4.81 (m, 1H), 3.06 (t, 2H, J=7), 2.37 (m, 2H), 2.27 (m, 1H), 1.87 (m, 2H), 1.46 (s, 9H), 1.03 (m, 2H); HRMS (ES+): Calcd for $C_{34}H_{41}FN_5O_5$: 618.3092, Found: 618.3098 (M+H+)+.

Part E: trans-(S)-4-{[4-(Benzyloxycarbonylamino-methyl)-cyclohexanecarbonyl]-amino}-4-[5-(4-cyano-3-fluoro-phenyl)-1H-imidazol-2-yl]-butyric acid: The intermediate from Example 157 Part D (330 mg, 0.53 mmol), TFA (0.5 mL) and $CH_2Cl_2$ (0.5 mL) were stirred at ambient temperature for 2 h. Solvent was removed in vacuo to give a tan solid (300 mg, 100% yield): $^1$H-NMR (DMSO-$d_6$, 400 MHz): δ 8.24 (m, 1H), 8.04 (s, 1H), 7.97 (m, 1H), 7.88 (d, 1H, J=9), 7.81 (d, 1H, J=9), 7.35 (m, 6H), 7.25 (m, 1H), 5.01 (s, 2H), 5.0 (m, 1H), 3.63 (m, 1H), 3.13 (m, 1H), 2.86 (m, 2H), 2.31 (m, 2H), 2.15 (m, 2H), 2.04 (m 1H), 1.75 (m, 2H), 1.27 (m, 5H), 0.88 (m, 1H); HRMS (ES+): Calcd for $C_{30}H_{33}FN_5O_5$: 562.2466, Found: 562.2453 (M+H)+.

Part F: trans-(4-{(S)-1-[5-(4-Cyano-3-fluoro-phenyl)-1H-imidazol-2-yl]-3-[(pyridin-2-ylmethyl)-carbamoyl]-propylcarbamoyl}-cyclohexylmethyl)-carbamic acid benzyl ester: The intermediate from the Example 157 Part E (325 mg, 0.53 mmol), $HOBt.H_2O$ (81 mg, 0.6 mmol), EDC (115 mg, 0.6 mmol), $(i-Pr)_2NEt$ (388 mg, 0.52 mL, 3.0 mmol) and DMF (1 mL) were stirred at room temperature under a nitrogen atmosphere for 15 min. 2-Aminomethylpyridine (65 mg, 0.6 mmol) was added, and stirring was continued for 88 h. The reaction mixture was diluted with EtOAc (20 mL) and the organic mix was washed with a 10% LiCl solution (5 mL) three times. The organic layer was dried over $MgSO_4$ and filtered. Solvent was removed in vacuo. HPLC (0% to 10% MeOH—$CH_2Cl_2$) provided a pale yellow solid (40 mg, 12% yield): $^1$H-NMR (MeOH-$d_4$, 400 MHz): δ 8.49 (m, 1H), 7.81 (t, 1H, J=8), 7.73 (m, 2H), 7.35 (m, 11H), 5.08 (s, 1H), 4.50 (s, 2H), 3.37 (m, 4H), 2.98 (d, 2H, J=7), 2.40 (m, 2H), 2.25 (m, 2H), 1.86 (m, 6H), 1.47 (m, 2H), 1.05 (m, 2H); HRMS (ES+): Calcd for $C_{36}H_{39}FN_7O_4$: 652.3048, Found: 652.3063 (M+H).

Part G: trans-4-Aminomethyl-cyclohexanecarboxylic acid {(S)-1-[5-(4-cyano-3-fluoro-phenyl)-1H-imidazol-2-yl]-3-[(pyridin-2-ylmethyl)-carbamoyl]-propyl}-amide, tris-trifluoroacetic acid salt: The intermediate from Example 157 Part F (98 mg, 0.15 mmol) and a solution of HBr in acetic acid (33%, 3 mL) were stirred at ambient temperature for 21 h. Solvent was removed in vacuo to provide an oil. Reverse phase HPLC (0% to 100% $CH_3CN$—$H_2O$ with 0.1% TFA) provided a white solid (20 mg, 39% yield): $^1$H-NMR (MeOH-$d_4$, 400 MHz): δ 8.70 (d, 1H, J=5), 8.38 (t, 1H, J=8), 8.00 (s, 1H), 7.80 (m, 5H), 5.18 (t, 1H, J=6), 4.93 (m, 5H), 4.69 (d, 1H, J=16), 4.63 (d, 1H, J=16), 2.78 (d, 2H, J=7), 2.51 (m, 2H), 2.31 (m, 4H), 1.62 (m, 2H), 1.45 (m, 4H), 1.09 (m, 2H); HRMS (ES+): Calcd for $C_{28}H_{33}FN_7O_2$: 518.2680, Found: 518.2698 (M+H).

Part H: trans-4-Aminomethyl-cyclohexanecarboxylic acid {(S)-1-[5-(3-amino-1H-indazol-6-yl)-1H-imidazol-2-yl]-3-[(pyridin-2-ylmethyl)-carbamoyl]-propyl}-amide, tris-trifluoroacetic acid salt: The intermediate from Example 157 Part F (20 mg, 0.02 mmol), hydrazine hydrate (0.5 mL) and n-BuOH (0.5 mL) were heated in a microwave apparatus for 15 min at 120° C. Solvent was removed in vacuo to provide a white solid (10 mg, 49% yield): $^1$H-NMR (MeOH-$d_4$, 400 MHz): δ 8.48 (d, 1H, J=2), 7.80 (t, 1H, J=8), 7.67 (m, 2H), 7.35 (m, 4H), 5.11 (t, 1H, J=7), 4.86 (m, 8H), 4.50 (s, 2H), 3.57 (t, H, J=7), 2.81 (d, 2H, J=7), 2.39 (m, 2H), 2.24 (m, 4H), 1.95 (m, 4H), 1.53 (m, 2H), 0.96 (t, 2H, J=7); HRMS (ES+): Calcd for $C_{28}H_{36}N_9O_2$: 530.2992, Found: 530.2991 (M+H)

Example 158 trans-4-Aminomethyl-cyclohexanecarboxylic acid {(S)-1-[5-phenyl-1H-imidazol-2-yl]-3-[(pyridin-2-ylmethyl)-carbamoyl]-ethyl}-amide This compound was prepared following the procedures described in Example 157, Parts A through H: $^1$H-NMR (MeOH-d$_4$, 400 MHz): δ 8.30 (d, 1H, J=8), 7.58 (d, 2H, J=8), 7.43 (t, 1H, J=8), 7.25 (m, 3H), 7.13 (m, 2H), 7.05 (d, 1H, J=8), 5.40 (t, 1H, J=7), 4.76 (m, 5H), 4.38 (d, 1H, J=16), 4.30 (d, 1H, J=16), 2.94 (dd, 1H, J=15.7), 2.84 (dd, 1H, J=15.7), 2.43 (d, 2H, J=7), 2.10 (m, 1H), 1.77 (m, 4H), 1.34 (m, 4H), 0.89 (m, 1H); HRMS (ES$^+$): Calcd for C$_{26}$H$_{33}$N$_6$O$_2$: 461.2665. Found: 461.2657 (M+H).

Example 159

N-[2-(2S)-[2-[4-(3-amino-1H-indazol-6-yl)-1H-imidazol-2-yl]-2-[[trans-[4-(aminomethyl)cyclohexanecarboxamido]ethyl]phenyl]-phenylacetamide, bis-trifluoroacetic acid salt Part A: trans-{4-[(S)-1-[4-(4-Cyano-3-fluoro-phenyl)-1H-imidazol-2-yl]-2-(2-nitro-phenyl)-ethylcarbamoyl]-cyclohexylmethyl}-carbamic acid tert-butyl ester: T-2-Nitro-N-(Boc)-phenylalanine (2.24 g, 7.23 mmol) was treated sequentially according to the procedures described in Example 1 part A and Part B and Example 2 part A to yield 3.0 g (98% yield) of the desired product. MS 450 (M−H)$^−$.

Part B: trans-(4-{(S)-2-(2-Amino-phenyl)-1-[4-(4-cyano-3-fluoro-phenyl)-1H-imidazol-2-yl]-ethylcarbamoyl}-cyclohexylmethyl)-carbamic acid tert-butyl ester: The product from Example 159 Part A (284 mg, 0.48 mmol) was dissolved acetic acid (3.5 mL) and 5 drops of water. Iron powder (273 mg, 4.8 mmol) was added to the flask, and the reaction was heated to 50° C. for 5 h. The reactions was cooled to rt, diluted with 50 mL of MeOH, and filtered through Celite. The solvents were removed in vacuo to yield 265 mg (98% yield) of the crude aniline. MS 559 (M−H)−.

Part C: trans-{4-[(S)-1-[4-(4-Cyano-3-fluoro-phenyl)-1H-imidazol-2-yl]-2-(2-phenylacetylamino-phenyl)-ethylcarbamoyl]-cyclohexylmethyl}-carbamic acid tert-butyl ester: The product from Example 159 Part B (132 mg, 0.23 mmol) and phenyl acetic acid (40 mg, 0.28 mmol) were dissolved in pyridine (0.7 mL, 0.71 mmol) and 1.5 mL of DMF. HOBt (45 mg, 0.3 mmol) and EDCI (60 mg, 0.30 mmol) were added to the flask, and the reaction was stirred at rt for 12 h. The reaction was diluted with EtOAc, extracted with ½ sat. brine (4-6 times), dried over MgSO$_4$, filtered and evaporated to dryness to yield the desired product 150 mg (95% yield). MS 677 (M−H)−.

Part E: trans-4-Aminomethyl-cyclohexanecarboxylic acid [(S)-1-[4-(4-cyano-3-fluoro-phenyl)-1H-imidazol-2-yl]-2-(2-phenylacetylamino-phenyl)-ethyl]-amide: The product from Example 159 part C (150 mg, 0.22 mmol) was treated under the condition described in Example 2 part B and purified by prep HPLC (MeOH/H$_2$O/0.1% TFA gradient) to yield 18 mg (14% yield) of the desired product. MS 577 (M−H)−.

Part F: trans-4-Aminomethyl-cyclohexanecarboxylic acid [(S)-1-[4-(3-amino-1H-indazol-6-yl)-1H-imidazol-2-yl]-2-(2-phenylacetylamino-phenyl)-ethyl]-amide, bis trifluoroacetic acid salt: The product from Example 159 Part D (18 mg, 0.03 mol) was treated under the conditions described in Example 120 Part H to yield 2.3 mg (11% yield) of Example 159. $^1$H NMR (500 MHz, MeOH-d$_4$) δ 0.93-1.11 (m, 1H) 1.35 (ddd, J=58.97, 12.78, 3.57 Hz, 1H) 1.48-1.62 (m, 1H) 1.59-1.73 (m, 1H) 1.74-1.92 (m, 2H) 2.10-2.31 (m, 1H) 2.76 (d, J=7.15 Hz, 1H) 3.75 (q, J=13.75 Hz, 1H) 5.24 (t, J=8.25 Hz, 1H) 7.05-7.22 (m, 2H) 7.26-7.33 (m, 1H) 7.37 (t, J=6.60 Hz, 2H) 7.63 (s, 1H) 7.78 (s, 1H) 7.88 (d, J=8.80 Hz, 1H)HRMS m/z Calc'd for C$_{34}$H$_{39}$N$_8$O$_2$ (M+H)$^+$: 591.3196 Found 591.3221.

Example 162

(S)-4-(aminomethyl)-N-[1-[4-(4-amino-7-quinazolinyl)-5-chloro-1H-imidazol-2-yl]-2-phenylethyl]-trans-cyclohexanecarboxamide, bis-trifluoroacetic acid salt Part A: (4-{(S)-1-[4-(4-Amino-quinazolin-7-yl)-5-chloro-1H-imidazol-2-yl]-2-phenyl-ethylcarbamoyl}-cyclohexylmethyl)-carbamic acid tert-butyl ester: The product from Example 120 Part F (0.53 g, 0.9 mmol) and formamidine acetate (1.5 g, 14.4 mmol) were added together with 20 mL of DMAC. The mixture was heated at 140° C. under N$_2$ for 8 h. Additional formamidine (1.5 g, 14.4 mmol) was added, and the mixture was heated for additional 12 h. The mixture was cooled and water was added. The mixture was adjusted to pH 7 with aqueous NaHCO$_3$, and it was then extracted with EtOAc. The combined EtOAC extracts were washed with brine, dried over MgSO$_4$, concentrated, and purified by flash chromatography (120 g silica, 0-10% MeOH in CH$_2$Cl$_2$) to give 80 mg of the desired product. LC/MS: 604.1, 606.1, (M+H)$^+$.

Part B: 4-Aminomethyl-cyclohexanecarboxylic acid {(S)-1-[4-(4-amino-quinazolin-7-yl)-5-chloro-1H-imidazol-2-yl]-2-phenyl-ethyl}-amide, bis-trifluoroacetic acid salt: The product from Example 162 Part A (80 mg, 0.13 mmol) was stirred with CH$_2$Cl$_2$ (5 mL) and TFA (2 mL) under N$_2$ for 0.5 h. The solvents were removed. The residue was purified by reverse phase HPLC to give 75 mg of the desired product as the bis-TFA salt. MS: 504.4, (M+H)$^+$. $^1$H-NMR (400 MHz, d$_4$-MeOH) δ 1.02-1.06 (m, 2H), 1.34-1.47 (m, 2H), 1.55 (bs, 1H), 1.75-1.90 (m, 4H), 2.22 (m, 1H), 2.76 (d, J=7.03 Hz, 2H), 3.12-3.24 (m, 2H), 5.20 (m, 1H), 7.16-7.22 (m, 5H), 8.00 (m, 1H), 8.13 (s, 1H), 8.34 (m, 1H), 8.65 (s, 1H).

Example 175

N-[1-[4-(3-amino-1H-indazol-6-yl)-5-chloro-1H-imidazol-2-yl]-2-[3-(difluoromethoxy)phenyl]ethyl]-4-(aminomethyl)-trans-cyclohexanecarboxamide, bis-trifluoroacetic acid salt Part A: 2-(Benzhydrylidene-amino)-3-(3-difluoromethoxy-phenyl)-propionic acid ethyl ester: N-(Diphenylmethylene) Glycine ethyl ester (500 mg, 1.87 mmol), Tetrabuylammonium Bromide (63 mg, 0.187 mmol) and 3-(Difluoromethoxy)benzyl bromide (0.5 mL, 1.87 mmol) were placed in a flask. The flask was evacuated and backfilled with argon. Anhyd dichloromethane was added to the flask, and the reaction was cooled in dry-ice acetone bath to −78° C. 2-tert-butylimino-2-diethylamino-1,3-dimethylperhydro-1,3,2-diazaphosphorine (0.7 mL, 2.44 mmol) was added slowly under argon at −78° C. The reaction was allowed to stir at −78° C. for 30 minutes, and then warmed to room temperature over 16 h. The solvent was removed under vacuum. The residue was pre-adsorbed on to SiO$_2$ and the product was isolated via SiO$_2$ to yield 700 mg of light yellow oil. MS 424.0 (M+H)+.

Part B: 2-Amino-3-(3-difluoromethoxy-phenyl)-propionic acid ethyl ester: The product from Example 175 Part A (700 mg, 1.65 mmol) was placed in a flask and dissolved in THF (30 mL). 30% (w/v)Citric acid (aqueous solution, 30 mL) was added and the reaction was stirred at rt for 72 h. The solution was extracted with diethyl ether (50 mL), and the aqueous layer was adjusted to a pH 6 using a saturated NaHCO$_3$ solution. The aqueous solution was extracted with dichloromethane, washed with brine, dried over MgSO₄, filtered and evaporated to yield 420 mg (97% yield) of a clear glass. MS 260 (M+H)⁺.

Part C: trans-2-{[4-(tert-Butoxycarbonylamino-methyl)-cyclohexanecarbonyl]-amino}-3-(3-difluoromethoxy-phenyl)-propionic acid ethyl ester: The product from Example 175 part B (420 mg, 1.62 mmol) was treated using the procedure described in Example 2 part A to yield 800 mg (97% yields) of a white solid. MS 497(M−H)⁻.

Part D: trans-2-{[4-(tert-Butoxycarbonylamino-methyl)-cyclohexanecarbonyl]-amino}-3-(3-difluoromethoxy-phenyl)-propionic acid: The product from Example 175 part C (800 mg, 1.6 mmol) was treated accorded to the procedure described in Example 26 to yield 750 mg of a white tacky solid. MS 469 (M−H+)−.

Part E: trans-4-Aminomethyl-cyclohexanecarboxylic acid [1-[4-(3-amino-1H-indazol-6-yl)-1H-imidazol-2-yl]-2-(3-difluoromethoxy-phenyl)-ethyl]-amide, bis-trifluororacetic acid salt: The product from Example 175 part D (284 mg, 0.6 mmol) was treated sequentially according to the procedures described in Example 1 part A, Example 2 Part B and Example 120 Part H to yield 1.1 mg (9% yield) of the title compound as a clear glass after purification by prep HPLC. ¹H NMR (500 MHz, MeOH-d4) δ 0.98-1.20 (m, 1H) 1.33 (s, 1H) 1.49-1.65 (m, 1H) 1.74-1.91 (m, J=11.55 Hz, 1H) 2.25 (s, 1H) 2.77 (d, J=7.15 Hz, 1H) 3.16 (s, 1H) 3.55-3.69 (m, 1H) 5.34 (t, J=7.97 Hz, 1H) 6.77 (s, 1H) 7.00 (s, 1H) 7.06 (dd, J=24.74, 8.25 Hz, 1H) 7.33 (t, J=7.97 Hz, 1H) 7.77 (d, J=8.25 Hz, 1H) 7.84 (s, 1H) 7.98 (d, J=8.80 Hz, 1H); HRMS m/z Calc'd for C₂₇H₃₂N₅O₃F₂ (M+H)⁺: 512.2473. Found 512.2485

Example 176

(S)-3-amino-N-[1-[4-[4-(carbamimidoyl)phenyl]-1H-imidazol-2-yl]-2-phenylethyl]-1H-indazole-5-carboxamide Part A: 4-[2-((S)-1-Amino-2-phenyl-ethyl)-1H-imidazol-4-yl]-benzonitrile dihydrochloride salt: {(S)-1-[4-(4-Cyanophenyl)-1H-imidazol-2-yl]-2-phenylethyl}carbamic acid tert-butyl ester prepared as described in Ex. 28, Part A (1.0 g, 2.57 mmol) was dissolved in dioxane (10 mL) and 4 N HCl in dioxane (10 mL) and an additional 5 mL dioxane were added. The resulting mixture was stirred for 2-2.5 h at room temperature under N₂, then diluted with ether. The resulting solid was triturated with additional ether and collected by filtration, washed with ether and hexane and dried to provide the amine dihydrochloride salt as a light green solid (0.89 g, 96%). ¹H NMR (500 MHz, DMSO-D6) δ 3.25-3.32 (m, 1H) 3.33-3.40 (m, 1H) 4.60 (s, 1H) 7.11 (d, J=7.15 Hz, 2H) 7.16-7.29 (m, 3H) 7.78-7.89 (m, 3H) 7.95 (d, J=8.25 Hz, 2H) 8.65 (s, 2H). m/z 289.2 (M+H)⁺.

Part B: 3-Cyano-N-{(S)-1-[4-(4-cyano-phenyl)-1H-imidazol-2-yl]-2-phenyl-ethyl}-4-fluoro-benzamide: A mixture of the compound of Example 176 Part A (100 mg, 0.28 mmol), 3-cyano-4-fluorobenzoic acid (46 mg, 0.28 mmol), triethylamine (0.085 mL, 0.61 mmol) and BOP (0.18 g, 0.4 mmol) in THF (5 mL) was stirred at rt overnight under N₂. Reaction mixture was diluted with water and extracted 3× with EtOAc. The combined extracts were washed with sat'd. NaHCO₃ and brine and then dried over anhydrous Na₂SO₄, filtered and evaporated. Chromatography on silica gel (hexane/EtOAc) provided the amide product (88 mg, 72%). ¹H NMR (500 MHz, CDCl₃) δ 3.41 (dd, J=13.75, 7.15 Hz, 1H) 3.58 (dd, J=13.47, 7.97 Hz, 1H) 5.33 (q, J=7.70 Hz, 1H) 7.01-7.09 (m, 1H) 7.18-7.37 (m, 7H) 7.66 (d, J=8.25 Hz, 2H) 7.85 (d, J=8.25 Hz, 2H) 7.89-7.96 (m, 1H) 7.95-8.03 (m, 1H) 9.74 (s, 1H). m/z 436.1 (M+H)⁺.

Part C: 3-Amino-1H-indazole-6-carboxylic acid {(S)-1-[4-(4-cyano-phenyl)-1H-imidazol-2-yl]-2-phenyl-ethyl}-amide: The compound of Example 176 Part B (86 mg, 0.20 mmol) was dissolved in nBuOH (2 mL) and excess hydrazine (0.1 mL) was added. The mixture was heated in a sealed tube at 160° C. for 10 min using microwave irradiation. Reaction mixture was cooled to room temperature, diluted with water and extracted with EtOAc (2×). The combined extracts were washed with water and brine, dried over Na₂SO₄, filtered and evaporated. The crude aminoindazole [m/z 448.1 (M+H)⁺] was used without purification in the next step.

Part D: N-3-Amino-1H-indazole-5-carboxylic acid {(S)-1-[4-(4-carbamimidoyl-phenyl)-1H-imidazol-2-yl]-2-phenyl-ethyl}-amide: The compound of Example 176 Part C was dissolved in ethanol (8 mL) and the solution stirred in an ice bath while HCl(g) was bubbled through the solution for 10-15 min. The flask was then tightly capped and kept in the refrigerator overnight. Flask was warmed to room temperature, and contents stirred for 3-4 h, then ethanol was evaporated. The resulting residue was triturated with ether to give a solid which was collected by filtration and dried in vacuo. The imidate thus obtained was redissolved in ethanol (5 mL) and excess ammonium carbonate (0.2 g) added. The mixture was stirred in a tightly capped flask for 48 h at room temperature. The reaction mixture was diluted with methanol, decanted and evaporated to dryness. The residue was redissolved in methanol and purified by prep C18 HPLC to provide the bis TFA salt of the title amidine product as an off-white solid (85 mg, 61%) after evaporation of solvents. ¹H NMR (500 MHz, DMSO-D6) δ 3.35-3.47 (m, 2H) 5.51 (q, J=7.15 Hz, 1H) 7.18 (t, J=7.15 Hz, 1H) 7.21-7.34 (m, 6H) 7.80 (d, J=8.80 Hz, 1H) 7.89 (d, J=8.25 Hz, 2H) 7.99 (d, J=8.80 Hz, 2H) 8.03-8.15 (m, 1H) 8.32 (s, 1H) 8.94 (s, 1H) 9.03 (s, 2H) 9.31 (s, 2H) 11.86 (s, 1H). m/z 465.0 (M+H)⁺.

Example 182

N-{(S)-1-[4-(4-Carbamimidoyl-phenyl)-1-ethyl-1H-imidazol-2-yl]-2-phenyl-ethyl}-benzamide Part A: N-{(S)-1-[4-(4-Cyano-phenyl)-1H-imidazol-2-yl]-2-phenyl-ethyl}-benzamide: The compound of Example 176 Part A (0.15 g, 0.42 mmol) was coupled with benzoic acid using the procedure of Example 176 Part B to provide the title compound (0.12 g, 76%). ¹H NMR (400 MHz, CDCl₃) δ 3.45-3.65 (m, 2H) 5.34 (d, J=8.35 Hz, 1H) 6.82 (d, J=7.47 Hz, 1H) 7.19-7.35 (m, 7H) 7.40 (t, J=7.69 Hz, 2H) 7.45-7.56 (m, 1H) 7.64 (d, J=7.03 Hz, 4H) 7.86 (d, J=8.35 Hz, 2H). m/z 393.1 (M+H)⁺.

Part B: N-{(S)-1-[4-(4-Cyano-phenyl)-1-ethyl-1H-imidazol-2-yl]-2-phenyl-ethyl}-benzamide: The compound of Example 182 Part A (60 mg, 0.15 mmol) was dissolved in DMF (2.5 mL) and potassium carbonate (32 mg, 0.23 mmol) was added followed by ethyl iodide (0.015 mL, 0.19 mmol), and the resulting mixture was stirred overnight at room temperature. The reaction mixture was diluted with water and extracted with EtOAc (3×). The combined extracts were washed with water and brine, then dried over Na₂SO₄, filtered and evaporated. The residue was chromatographed on silica gel to provide the product (48 mg, 76%). ¹H NMR (400 MHz, DMSO-D6) δ 1.17 (t, J=7.25 Hz, 3H) 3.34-3.48 (m, 2H) 3.89-4.05 (m, 2H) 5.46 (d, J=7.03 Hz, 1H) 7.14 (d, J=7.03 Hz, 1H) 7.21 (t, J=7.47 Hz, 2H) 7.31 (d, J=7.47 Hz, 2H) 7.41 (t, J=7.25 Hz, 2H) 7.48 (d, J=7.03 Hz, 1H) 7.76-7.84 (m, 3H) 7.88 (s, 1H) 7.94 (d, J=8.79 Hz, 2H) 9.08 (d, J=8.35 Hz, 1H). m/z 421.2 (M+H)+.

Part C: N-{(S)-1-[4-(4-Carbamimidoyl-phenyl)-1-ethyl-1H-imidazol-2-yl]-2-phenyl-ethyl}-benzamide: The compound of Example 182 Part B (17 mg) was dissolved in ethanol (2 mL) and hydroxylamine hydrochloride (15 mg, 5 eq) and triethylamine (0.03 mL, 5 eq) were added. The mixture was heated in a sealed tube at 125° C. for 15 min using microwave irradiation. Additional aliquots of hydroxylamine hydrochloride and triethylamine were added and microwave irradiation repeated for an additional 10 min at 120° C. Solvent was evaporated, and the residue redissolved in acetic acid (2 mL) and treated with acetic anhydride (0.015 mL, 3 eq). The solution was stirred for 15 min at room temperature followed by addition of zinc dust (25 mg, 10 eq) and a little MeOH. Mixture was then stirred overnight at room temperature. The reaction was filtered through a pad of Celite and solids washed with MeOH. Filtrate was evaporated, and residue purified by prep C18 HPLC to provide the bis-TFA salt of the title compound as a white solid (16 mg, 60%). $^1$H NMR (400 MHz, DMSO-D6) δ 1.20 (t, J=7.03 Hz, 3H) 3.33-3.52 (m, 2H) 3.93-4.10 (m, 2H) 5.49 (d, J=7.47 Hz, 1H) 7.16 (t, J=7.47 Hz, 1H) 7.23 (t, J=7.25 Hz, 2H) 7.32 (d, J=7.03 Hz, 2H) 7.43 (t, J=7.47 Hz, 2H) 7.51 (t, J=7.47 Hz, 1H) 7.84 (dd, J=7.69, 5.49 Hz, 4H) 7.95 (s, 1H) 8.00 (d, J=8.35 Hz, 2H) 8.92 (s, 2H) 9.12 (d, J=7.91 Hz, 1H) 9.25 (s, 2H). m/z 450.2 (M+H)+.

Example 183

N1-{(S)-1-[4-(4-Carbamimidoyl-phenyl)-1H-imidazol-2-yl]-2-phenyl-ethyl}-2-fluoro-terephthalamide Part A: ((S)-1-{4-[4-(5-Methyl-[1,2,4]oxadiazol-3-yl)-phenyl]-1H-imidazol-2-yl}-2-phenyl-ethyl)-carbamic acid tert-butyl ester: {(S)-1-[4-(4-Cyanophenyl)-1H-imidazol-2-yl]-2-phenylethyl}carbamic acid tert-butyl ester prepared as described in Example 28 Part A (1.00 equiv; 2.57 mmoles; 1.00 g) was dissolved in 15 mL EtOH and Hydroxylamine Hydrochloride (12.87 mmoles; 894.42 mg) and Triethylamine (12.87 mmoles; 1.79 mL) were added. The resulting solution was heated at reflux in an 80° C. oil bath under N$_2$ overnight. Reaction was cooled to room temperature and evaporated to remove EtOH. Residue was suspended in a mixture of EtOAc/EtOH (~10:1) and filtered to remove inorganic solids. Filtrate was reconcentrated to a yellow foam. This residue was redissolved in 10 mL HOAc and treated with stirring under N$_2$ with Acetic Anhydride (4.23 mmoles; 400 µL). Solution was stirred for 20 min at room temperature, then heated in 80° C. oil bath for 2 h, cooled to room temperature and stirred overnight. Most of HOAc was removed on rotary evaporator, then residue was diluted with water and carefully neutralized by addition of sat'd NaHCO$_3$ to pH ~8. Extracted 3× with CH$_2$Cl$_2$. Combined extracts were washed with brine then dried over MgSO$_4$, filtered and evaporated to a 1t red foam. Residue was purified on silica gel to provide the product as a 1t pinkish tan foam. (590 mg; 51.4%). $^1$H NMR (500 MHz, CDCl$_3$) δ 1.41 (s, 9H) 2.65 (s, 3H) 3.28-3.44 (m, 2H) 4.88 (d, J=7.70 Hz, 1H) 5.23 (s, 1H) 7.13-7.36 (m, 5H) 7.42-7.55 (m, 1H) 7.88 (d, J=8.25 Hz, 2H) 8.06 (d, J=8.25 Hz, 2H) 9.67 (s, 1H). m/z 446.1 (M+H)+.

Part B: (S)-1-{4-[4-(5-Methyl-[1,2,4]oxadiazol-3-yl)-phenyl]-1H-imidazol-2-yl}-2-phenyl-ethylamine dihydrochloride: The BOC group was removed from the compound of Example 183 Part A using procedure of Ex. 176, Part A to provide the hydrochloride salt of the amine as a tan solid in 46% yield. $^1$H NMR (500 MHz, CDCl$_3$) δ 2.67 (s, 3H) 2.87 (dd, J=13.75, 9.35 Hz, 1H) 3.44 (dd, J=13.75, 4.40 Hz, 1H) 4.44 (dd, J=9.35, 4.40 Hz, 1H) 7.20-7.31 (m, 5H) 7.34 (t, J=7.42 Hz, 3H) 7.85 (s, 1H) 8.08 (d, J=8.80 Hz, 2H). m/z 346.0 (M+H)+, 330.0 (M+H–NH3)+.

Part C: 4-Cyano-2-fluoro-N-((S)-1-{4-[4-(5-methyl-[1,2,4]oxadiazol-3-yl)-phenyl]-1H-imidazol-2-yl}-2-phenyl-ethyl)-benzamide: The compound of Example 183 Part B was coupled to 4-cyano-2-fluorobenzoic acid using the procedure of Example 176 Part B to provide the amide in 90% yield. $^1$H NMR (500 MHz, CDCl$_3$) δ ppm 2.64 (s, 3H) 3.43 (dd, J=13.75, 7.15 Hz, 1H) 3.58 (dd, J=13.75, 7.70 Hz, 1H) 5.38 (q, J=7.15 Hz, 1H) 7.20-7.33 (m, 7H) 7.42 (d, J=9.90 Hz, 1H) 7.54 (d, J=8.25 Hz, 2H) 7.86 (s, 1H) 8.05 (d, J=8.25 Hz, 2H) 8.14 (t, J=7.70 Hz, 1H) 9.43 (s, 1H). m/z 493.1 (M+H)+.

Part D: 2-Fluoro-N1-((S)-1-{4-[4-(5-methyl-[1,2,4]oxadiazol-3-yl)-phenyl]-1H-imidazol-2-yl}-2-phenyl-ethyl)-terephthalamide: A mixture of the compound of Example 183 Part C (75 mg, 0.15 mmol), potassium carbonate (66 mg, 3 eq) and 30% hydrogen peroxide (0.055 mL, 11 eq) in DMSO (2.5 mL) was stirred at room temperature under N$_2$ overnight. Reaction mixture was diluted with water and EtOAc, and phases separated. Aqueous phase was reextracted with EtOAc (2×). Combined organic phases were washed with water and brine, dried over anhydrous Na$_2$SO$_4$, filtered and evaporated. The resulting crude amide was used without purification. m/z 511.0 (M+H)+.

Part E: N1-{(S)-1-[4-(4-Carbamimidoyl-phenyl)-1H-imidazol-2-yl]-2-phenyl-ethyl}-2-fluoro-terephthalamide: The compound of Example 183 Part D (68 mg) and 10% Pd/C (35 mg, wet, Degussa) were suspended in a mixture of methanol and triethylamine (4.5 ml, 8:1) and stirred under 1 atm H$_2$ overnight. Catalyst was removed by filtration through Celite and washed with MeOH. Filtrate was evaporated and residue purified by prep C18 HPLC to provide the bis TFA salt of the title compound as a white solid (48 mg, 53%). $^1$H NMR (500 MHz, DMSO-D6) δ ppm 3.23-3.31 (m, 1H) 3.41 (dd, J=13.75, 6.60 Hz, 1H) 5.43 (q, J=7.70 Hz, 1H) 7.13-7.23 (m, 1H) 7.23-7.31 (m, 5H) 7.59-7.66 (m, 2H) 7.67-7.77 (m, 2H) 7.87 (t, J=7.70 Hz, 2H) 7.99 (d, J=8.25 Hz, 3H) 8.13 (s, 1H) 8.95 (s, 2H) 8.98-9.06 (m, 1H) 9.27 (s, 2H). m/z 471.0 (M+H)+.

Example 188

N1-((S)-1-(4-(3-amino-1H-indazol-6-yl)-5-chloro-1H-imidazol-2-yl)-2-phenylethyl)-2-fluoroterephthalamide, bis-trifluoroacetic acid salt Example 188 was prepared similarly by appropriate application of the procedures described for Example 120, where 4-carbamoyl-2-fluorobenzoic acid instead of Boc-tranexamic acid was used in Example 120 Part F. $^1$H-NMR (500 MHz, DMSO-d6) δ 3.16 (dd, J=13.75, 8.80 Hz, 1H), 3.30 (dd, J=13.75, 6.05 Hz, 1H) 5.31-5.43 (m, 1H), 7.16-7.23 (m, 1H), 7.25-7.31 (m, 5H), 7.38 (d, J=8.80 Hz, 1H), 7.55 (t, J=7.42 Hz, 1H), 7.62 (d, J=5.50 Hz, 2H), 7.65-7.76 (m, 2H), 7.86 (d, J=8.80 Hz, 1H), 8.12 (s, 1H), 8.97 (d, J=8.25 Hz, 2H), 12.05 (s, 1H), 12.81 (s, 1H).

Example 189

N1-((S)-1-(4-(4-aminoquinazolin-7-yl)-5-chloro-1H-imidazol-2-yl)-2-phenylethyl)-2-fluoroterephthalamide, bis-trifluoroacetic acid salt Example 189 was prepared by appropriate application of the procedures for Example 162, excluding Example 162 Part G and using 4-carbamoyl-2-fluorobenzoic acid instead of Boc-tranexamic acid in the procedure from Example 120 Part F. MS: 530.01, (M+H)+. $^1$HNMR (500 MHz, DMSO-$d_6$) δ 3.14-3.24 (m, 1H), 3.25-3.35 (m, 1H) 5.31-5.44 (m, 1H), 7.15-7.24 (m, 1H), 7.24-7.33 (m, 5H), 7.54 (t, J=7.70 Hz, 1H), 7.64 (s, 1H), 7.66-7.76 (m, 3H), 7.99 (d, J=8.80 Hz, 1H), 8.13 (s, 2H), 8.46 (d, J=8.80 Hz, 1H), 8.80 (s, 1H), 9.07 (d, J=6.60 Hz, 1H), 13.20 (s, 1H).

Example 190

1-amino-N-((S)-1-(4-(3-amino-1H-indazol-6-yl)-5-chloro-1H-imidazol-2-yl)-2-phenylethyl)-5,6,7,8-tetrahydroisoquinoline-6-carboxamide, bis-trifluoroacetic acid salt Example 190 was similarly prepared by appropriate application of the procedures for Example 147 Part H using the diastereomer B from Part G of Example 147. $^1$H-NMR (400 MHz, $d_4$-MeOH) δ 1.75 (dd, J=13.40, 10.33 Hz, 1H), 2.01 (m, 1H), 2.45 (t, J=6.37 Hz, 2H), 2.73 (m, 1H), 2.90 (m, 2H), 3.20 (m, 2H), 5.28 (m, 1H), 6.69 (d, J=6.59 Hz, 1H), 7.25 (m, 5H), 7.51 (d, J=8.79 Hz, 1H), 7.59 (d, J=6.59 Hz, 1H), 7.71 (s, 1H), 7.95 (d, J=8.79 Hz, 1H).

Example 191

1-amino-N-((S)-1-(4-(4-aminoquinazolin-7-yl)-5-chloro-1H-imidazol-2-yl)-2-phenylethyl)-5,6,7,8-tetrahydroisoquinoline-6-carboxamide, bis-trifluoroacetic acid salt Example 191 was prepared using the product from Part F of Example 147 by appropriate application of the procedures described in Part A of Example 162. LC/MS: 539.2 (M+1)+. $^1$HNMR (400 MHz, $d_4$-MeOH) δ 1.77 (m, 1H), 2.00 (d, J=3.95 Hz, 1H) 2.45 (m, 2H), 2.74 (m, 2H) 2.91 (m, 1H), 3.21 (m, 2H), 5.26 (m, 1H), 6.67 (t, J=7.25 Hz, 1H), 7.23 (m, 5H), 7.59 (t, J=6.59 Hz, 1H), 8.02 (m, 1H), 8.16 (d, J=4.39 Hz, 1H), 8.36 (dd, J=8.79 and 1.76 Hz, 1H), 8.65 (s, 1H).

Example 192

1-amino-N-((S)-1-(4-(3-amino-1H-indazol-6-yl)-5-chloro-1H-imidazol-2-yl)-2-phenylethyl)-3-methylisoquinoline-6-carboxamide, bis-trifluoroacetic acid salt Part A: (Z)-3-(3-Bromophenyl)-2-methylacrylic acid: 3-Bromobenziladelhyde (2.6 g, 0.014 mol) and (carbethoxyethylidene)triphenylphosphorane (5.6 g, 0.015 mol) were added together with 30 mL of toluene. The mixture was stirred at RT under $N_2$ for 24 h. The solvent was removed. The residue was dissolved in EtOAc and washed with water and brine. It was dried over $MgSO_4$, concentrated, and purified by flash chromatography (silica, Hexane/EtOAc) to give 3.7 g of the desired ester. MS: 271.2/273.2 (M+1)+. The ester was then dissolved in 30 mL of THF and 10 mL of water. LiOH (1.32 g, 0.031 mol) was added. The mixture was stirred at RT under $N_2$ for 72 h. The THF was removed. The resulting mixture was diluted with water and extracted with EtOAc (discarded). The aqueous mixture was acidified with HCl and extracted with EtOAc. This EtOAc extract was washed with brine, dried over $MgSO_4$ and concentrated to a white solid (3.2 g). $^1$HNMR (400 MHz, $CDCl_3$) δ 2.12 (s, 3H), 7.29 (m, 2H), 7.47 (d, J=7.91 Hz, 1H), 7.56 (s, 1H), 7.73 (s, 1H).

Part B: 6-Bromo-3-methylisoquinolin-1(2H)-one: The product from Example 192 Part A (2.76 g, 11.45 mmol) and triethylamine (3.60 mL, 22.90 mmol) were added together with 18 mL of acetone. The mixture was cooled to 0° C., followed by the dropwise addition of ethyl chloroformate (1.85 mL, 17.17 mmol). The reaction mixture was stirred at 0-5° C. under $N_2$ for 1 h. To it was added the slurry of sodium azide (1.34 g, 20.60 mmol) in 2 mL of water. The reaction mixture was stirred at rt under $N_2$ overnight. The solvent was removed. The residue was dissolved in EtOAc and washed with water and brine. It was dried over $MgSO_4$, concentrated, and dried in vacuo to give 3.4 g of 80% pure desired acyl azide. A solution of tributylamine (4.40 mL, 18.49 mmol) and diphenylmethane (15 mL) was heated to 190 C. To it was added dropwise the solution of the acyl azide (3.4 g of 80% pure material, 10.3 mmol) in diphenylmethane (12 mL) over 12 minutes. The mixture was stirred at 220° C. for 2 h under $N_2$. It was cooled to RT. The crude product was precipitated and filtered. It was purified by flash chromatography (120 g silica, 0-10% MeOH in dichloromethane) to give 0.43 g of the desired product. MS: 238.2, 240.1 (M+1)+. $^1$HNMR (400 MHz, DMSO-$d_6$) δ 2.20 (s, 3H), 6.30 (s, 1H), 7.52 (d, J=8.79 Hz, 1H), 7.80 (s, 1H), 7.81 (d, J=8.35 Hz, 1H).

Part C: 6-Bromo-3-methylisoquinolin-1-amine: Phosphorus oxychloride (2.5 mL) was cooled in an ice-bath and was then added dropwise to the product from Example 192 Part B (120 mg, 0.5 mmol). The mixture was heated to 110° C. under $N_2$ for 1.5 h. The reaction was cooled, and quenched with water and MeOH. More water was then added. The solid was filtered and washed with 1N NaOH and water to give 115 mg of solid. The solid obtained (51 mg) was combined with 1 mL of 13-15% $NH_3$ in ethylene glycol. The mixture was heated in a sealed tube via microwave irradiation at 170° C. for 20 minutes. The reaction was cooled and water was added. The solid was filtered and purified by ISCO flash chromatography (silica, $CH_2Cl_2$/MeOH) to give 12 mg of the desired product. MS: 237.1/239.1 (M+1)+. $^1$HNMR (400 MHz, $d_4$-MeOH) δ 2.39 (s, 3H), 6.76 (s, 1H), 7.53 (m, 1H), 7.81 (d, J=1.76 Hz, 1H), 7.98 (d, J=8.79 Hz, 1H).

Part D: 1-Amino-3-methylisoquinoline-6-carbonitrile: The product from Example 192 Part C (22 mg, 0.093 mmol), $Zn(CN)_2$ (12 mg), and $Pd(PPh_3)_4$ (8 mg) were added with 2 mL of DMF. The mixture was heated in a sealed tube in a microwave at 180° C. for 10 minutes. The mixture was filtered and washed with EtOAc. The filtrate was concentrated, and purified by flash chromatography (silica, $CH_2Cl_2$/MeOH) to give 12 mg of the desired product. LC/MS: 184.18 (M+1)+.

Part E: 1-amino-3-methylisoquinoline-6-carboxylic acid: The product from Example 192 Part D (35 mg) was added with 4 mL of MeOH and 4 mL of 15% aqueous NaOH. The mixture was heated at 70-85° C. for 2 h. It was concentrated, acidified with HCl and TFA to pH=5. The solid was filtered and purified by reverse phase prep-HPLC to give 18 mg of the TFA salt. LC/MS: 203.03 (M+1)+.

Part F: 1-amino-N-((S)-1-(4-(3-amino-1H-indazol-6-yl)-5-chloro-1H-imidazol-2-yl)-2-phenylethyl)-3-methylisoquinoline-6-carboxamide, bis-trifluoroacetic acid salt: The product from Example 192 Part E and the product from Part E of Example 120 were coupled and then converted to the aminoindazole using the methods described in Example 120 Part F and Part H, respectively. MS: 537.0 (M+1)+. $^1$HNMR (400 MHz, $d_4$-MeOH) δ 2.52 (s, 3H), 3.41 (m, 2H), 5.46 (t, J=7.91 Hz, 1H), 7.05 (s, 1H), 7.23 (m, 5H), 7.50 (d, J=8.79 Hz, 1H) 7.71 (s, 1H), 7.98 (m, 2H), 8.19 (s, 1H), 8.43 (d, J=8.79 Hz, 1H).

Example 200

4-Aminomethyl-cyclohexanecarboxylic acid {(S)-2-[4-(3-amino-1H-indazol-6-yl)-1H-imidazol-2-yl]-1-benzyl-ethyl}-amide, bis-trifluoroacetic acid salt This compound was prepared following the procedures described in Example 120: $^1$H NMR (500 MHz, Solvent) δ 0.90-1.01 (m, 2H), 1.18-1.24 (m, 2H), 1.42-1.50 (m, 1H), 1.50-1.62 (m, 2H), 1.68-1.79 (m, 2H), 2.00-2.09 (m, 1H), 2.71 (d, J=7.15 Hz, 2H), 2.94 (dd, J=13.00, 8.80 Hz, 2H), 3.02 (dd, J=13.00, 6.04 Hz, 2H), 3.13 (dd, J=15.12, 10.17 Hz, 1H), 4.57-4.65 (m, 1H), 7.18-7.23 (m, 1H), 7.26-7.30 (m, 4H), 7.47 (d, J=9.90 Hz, 1H), 7.74 (s, 1H) 7.89 (s, 1H), 7.97 (d, J=8.25 Hz, 1H). HRMS (ES$^+$): Calcd for $C_{27}H_{33}N_7O$: 471.2747, Found: 472.2839 (M+H).

Tables 1-6 below summarize the prepared examples of compounds in the present invention.

TABLE 1

| Ex # | A | R$^3$ | R$^{11}$ | Mass spec (m/z) (M + H)$^+$ |
|---|---|---|---|---|
| 1 | 4-(H$_2$N-C(=NH))-phenyl | 4-Ph-imidazol-2-yl | benzyl | 410.20 |
| 14 | 4-(H$_2$NCH$_2$)-cyclohexyl | 4-Ph-imidazol-2-yl | phenethyl | 417.27 |
| 15 | 4-(H$_2$NCH$_2$)-cyclohexyl | 4-(3-Br-phenyl)-imidazol-2-yl | benzyl | 483.07, 481.07 |
| 25 | 4-(H$_2$NCH$_2$)-cyclohexyl | 4-(4-(CH$_2$CO$_2$Et)-phenyl)-imidazol-2-yl | benzyl | 489.29 |
| 26 | 4-(H$_2$NCH$_2$)-cyclohexyl | 4-(4-(CH$_2$CO$_2$H)-phenyl)-imidazol-2-yl | benzyl | 461.26 |

TABLE 1-continued

| Ex # | A | R³, R⁴ | R¹¹ | Mass spec (m/z) (M + H)⁺ |
|---|---|---|---|---|
| 27 | 4-(aminomethyl)cyclohexyl | 2-[4-(carbamoylmethyl)phenyl]-1H-imidazol-4-yl | benzyl | 460.27 |
| 75 | trans-4-(aminomethyl)cyclohexyl | 4-phenyl-1H-imidazol-2-yl | benzyl | 403.2 |
| 76 | cis-4-(aminomethyl)cyclohexyl | 4-phenyl-1H-imidazol-2-yl | benzyl | 403.1 |
| 82 | trans-4-(aminomethyl)cyclohexyl | 5-bromo-4-(4-carbamoylphenyl)-1H-imidazol-2-yl | benzyl | 526.1, 524.1 |
| 83 | phenyl | 4-(4-carbamimidoylphenyl)-1H-imidazol-2-yl | benzyl | 410.2 |
| 84 | 4-carbamoylphenyl | 4-(4-carbamimidoylphenyl)-1H-imidazol-2-yl | benzyl | 453.2 |

TABLE 1-continued

| Ex # | A | R³/R⁴ imidazole | R¹¹ | Mass spec (m/z) (M + H)⁺ |
|---|---|---|---|---|
| 86 | 4-sulfamoylphenyl | 4-(4-carbamimidoylphenyl)-1H-imidazol-2-yl | phenyl | 489.2 |
| 106 | trans-4-(aminomethyl)cyclohexyl | 4,5-bis(3-amino-1H-indazol-6-yl)-1H-imidazol-2-yl | phenyl | 589.5 |
| 107 | trans-4-(aminomethyl)cyclohexyl | 4-(4-carbamoylphenyl)-5-trifluoromethyl-1H-imidazol-2-yl | phenyl | 514.2 |
| 108 | phenyl | 4-(4-carbamimidoylphenyl)-1H-imidazol-2-yl | phenyl | 410.2 |
| 112 | 4-(aminomethyl)phenyl | 4-phenyl-1H-imidazol-2-yl | phenyl | 397.4 |

TABLE 1-continued
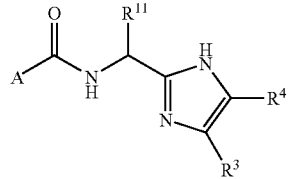
| Ex # | A | | R11 | Mass spec (m/z) (M + H)+ |
|---|---|---|---|---|
| 113 | cyclohexyl-CH2NH2 | imidazole-6-(3-amino-1H-indazol)-Br | benzyl | 538.4 |
| 114 | cyclohexyl-CH2NH2 | imidazole-phenyl-CONH2, CO2Me | benzyl | 504.4 |
| 115 | cyclohexyl-CH2NH2 | imidazole-phenyl-CONH2 | 2-OCF3-benzyl | 530.2 |
| 116 | cyclohexyl-CH2NH2 | imidazole-phenyl-CONH2 | 3-OCF2H-benzyl | 512.3 |
| 117 | phenyl-CH2NH2 | imidazole-phenyl-CONH2 | benzyl | 440.2 |
| 118 | 3-F-phenyl-CH2NH2 | imidazole-phenyl-CONH2 | benzyl | 458.2 |

TABLE 1-continued
| Ex # | A | R³, R⁴ | R¹¹ | Mass spec (m/z) (M + H)⁺ |
|---|---|---|---|---|
| 119 | 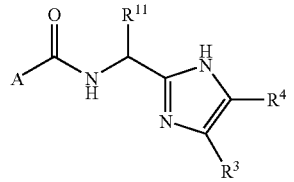 | 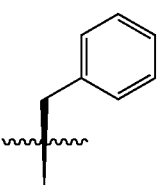 | 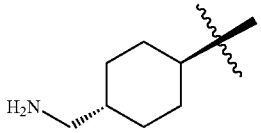 | 491.2 |
| 120 | 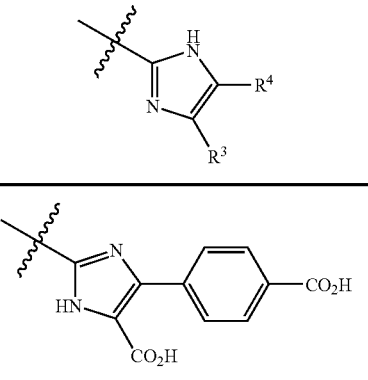 | 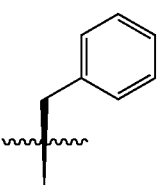 | 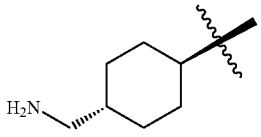 | 492.4 |
| 121 | 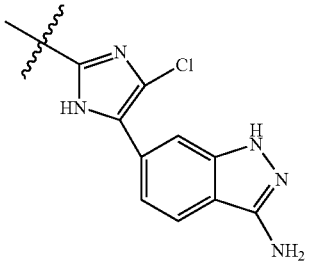 | 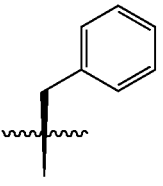 | 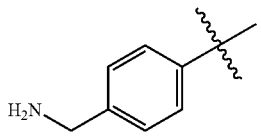 | 486.3 |
| 122 | 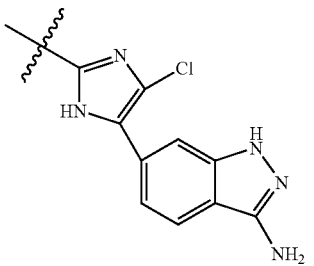 | 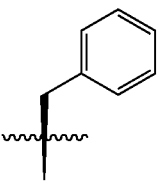 | 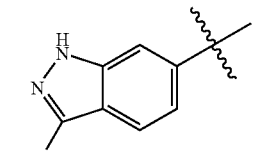 | 510.3 (M − H+)− |

TABLE 1-continued
| Ex # | A | R³ | R¹¹ | Mass spec (m/z) (M + H)⁺ |
|---|---|---|---|---|
| 123 | 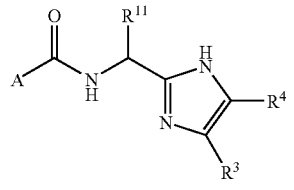 | 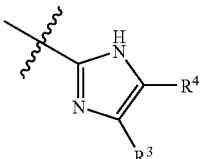 | 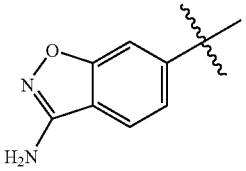 | 513.1 |
| 124 | 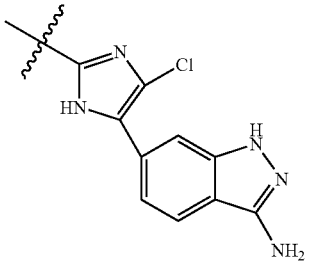 | 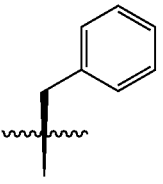 | 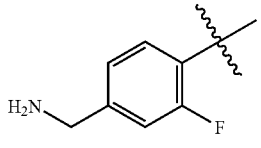 | 504.1 |
| 128 | 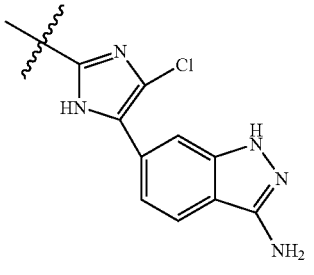 | 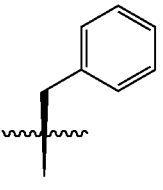 | 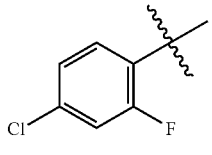 | 509.3 |
| 129 | 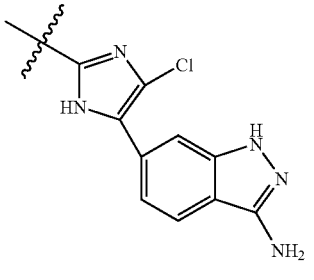 | 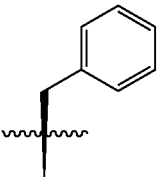 | 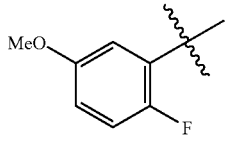 | 505.3 |

TABLE 1-continued

| Ex # | A | R³ | R¹¹ | Mass spec (m/z) (M + H)⁺ |
|---|---|---|---|---|
| 130 | 4-(aminomethyl)cyclohexyl | 5-chloro-4-(4-carbamoylphenyl)-1H-imidazol-2-yl | benzyl | 480.4 |
| 131 | 4-carbamoylcyclohexyl | 5-chloro-4-(4-carbamoylphenyl)-1H-imidazol-2-yl | benzyl | 506.2 |
| 132 | 4-carbamoylphenyl | 5-chloro-4-(4-carbamoylphenyl)-1H-imidazol-2-yl | benzyl | 500.1 |
| 133 | 4-(aminomethyl)cyclohexyl | 4-(3-amino-1H-indazol-6-yl)-1H-imidazol-2-yl | (2,2-dimethyl-1,3-benzodioxol-4-yl)methyl | 530.3 |
| 134 | 4-(aminomethyl)cyclohexyl | 4-(4-carbamoylphenyl)-1H-imidazol-2-yl | 3-(difluoromethoxy)benzyl | 512.1 |
| 135 | 4-(aminomethyl)cyclohexyl | 4-(4-carbamoyl-2-phenylphenyl)-1H-imidazol-2-yl | benzyl | 522.4 |

TABLE 1-continued
| Ex # | A | | R[11] | Mass spec (m/z) (M + H)+ |
|---|---|---|---|---|
| 136 | 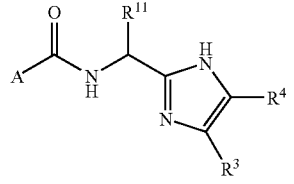 | 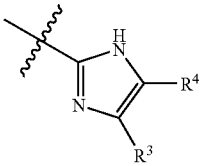 | 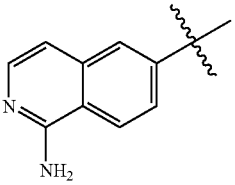 | 523.2 |
| 137 | 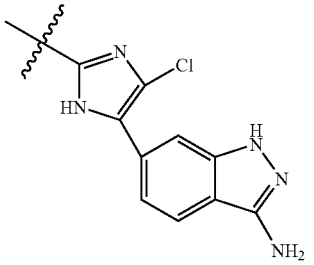 | 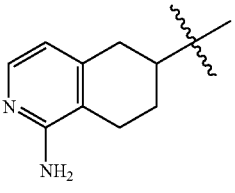 | 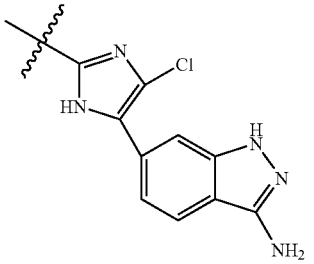 | 527.3 |
| 140 | 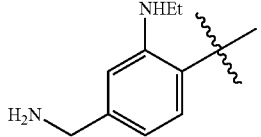 | 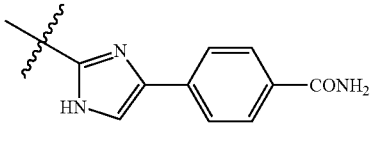 | 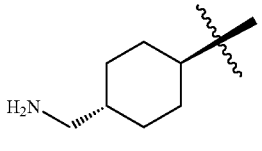 | 483.4 |
| 141 | 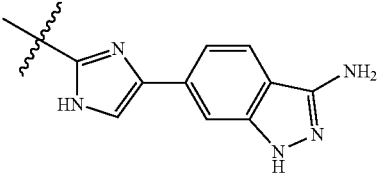 | 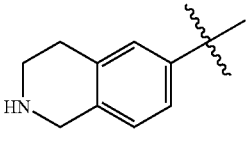 | 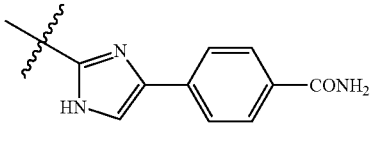 | 550.3 |
| 142 | | | | 466.2 |

TABLE 1-continued

| Ex # | A | R³, R⁴ (imidazole) | R¹¹ | Mass spec (m/z) (M + H)⁺ |
|---|---|---|---|---|
| 143 | 3-ethyl-4-(aminomethyl)phenyl | 4-(4-carbamoylphenyl)-1H-imidazol-2-yl | phenyl (benzyl) | 468.4 |
| 144 | 1-methyl-3-amino-1H-indazol-6-yl | 4-chloro-5-(3-amino-1H-indazol-6-yl)-1H-imidazol-2-yl | phenyl (benzyl) | 526.3 |
| 145 | 4-(aminomethyl)cyclohexyl | 5-(3-fluoro-5-cyanophenyl)-1H-imidazol-2-yl | phenyl (benzyl) | 446.3 |
| 146 | 4-(aminomethyl)cyclohexyl | 5-(3-amino-1H-indazol-6-yl)-1H-imidazol-2-yl | 2-OPh-phenyl | 550.2 |
| 147 | 1-amino-5,6,7,8-tetrahydroisoquinolin-6-yl | 4-chloro-5-(3-amino-1H-indazol-6-yl)-1H-imidazol-2-yl | phenyl (benzyl) | 527.3 |

TABLE 1-continued
| Ex # | A | | R[11] | Mass spec (m/z) (M + H)+ |
|---|---|---|---|---|
| 155 | 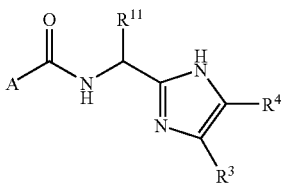 | 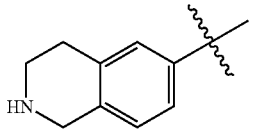 | 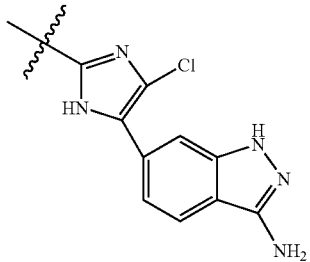 | 512.2 |
| 157 | 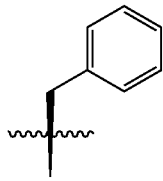 | 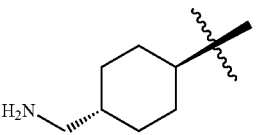 | 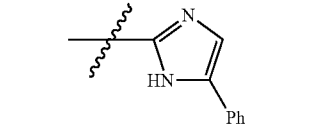 | 530.3 |
| 158 | 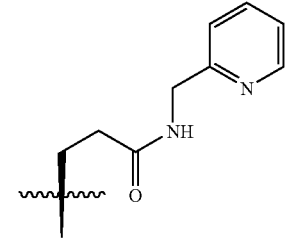 | 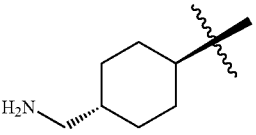 | 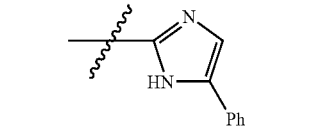 | 461.3 |
| 160 | 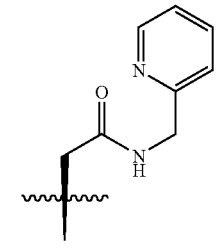 | 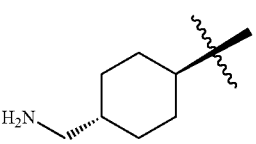 | 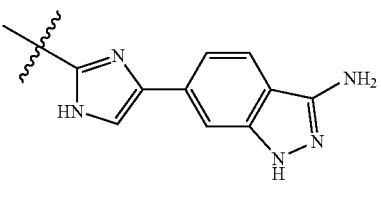 | 620.3 |

TABLE 1-continued
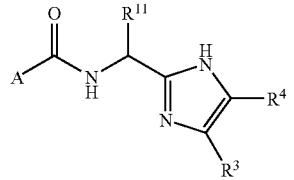
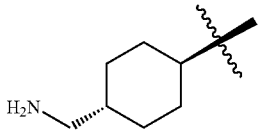
| Ex # | A | | R[11] | Mass spec (m/z) (M + H)+ |
|---|---|---|---|---|
| 161 | 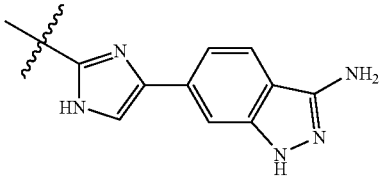 | 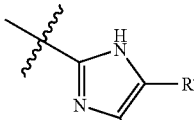 | 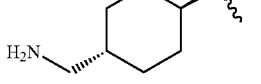 | 620.3 |
| 162 | 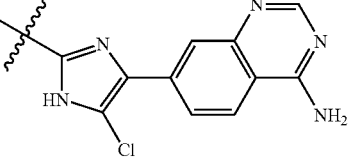 | 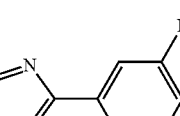 | 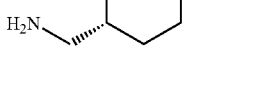 | 504.2 |
| 165 | 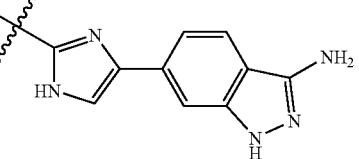 | 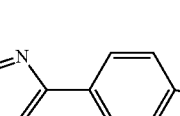 | 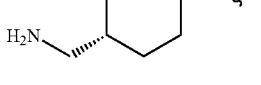 | 564.0 |
| 171 | 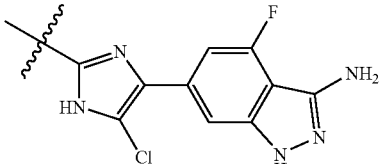 | 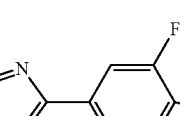 | 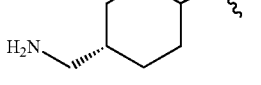 | 510.3 |
| 172 | 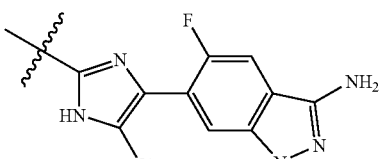 | 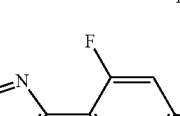 | 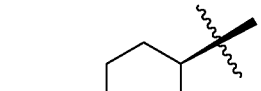 | 510.3 |
| 173 | 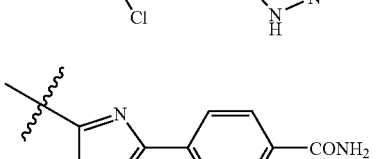 | 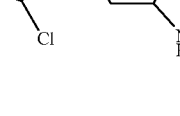 | | 504.1 |

TABLE 1-continued
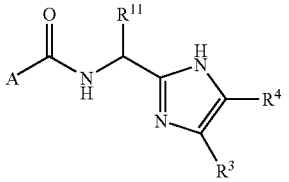
| Ex # | A | R³ R⁴ | R¹¹ | Mass spec (m/z) (M + H)⁺ |
|---|---|---|---|---|
| 174 | 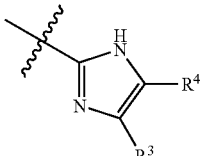 | 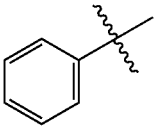 | 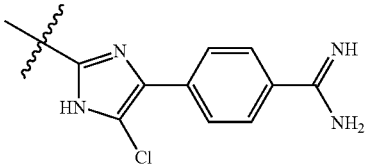 | 442.2 |
| 175 | 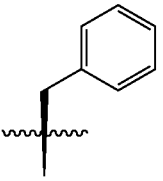 | 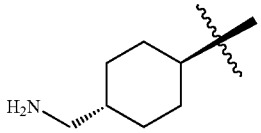 | 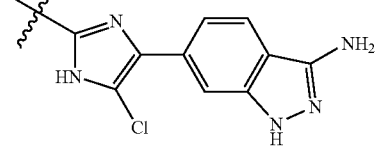 | 558.2 |
| 176 | 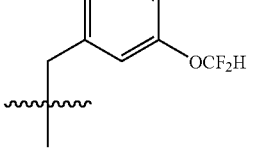 | 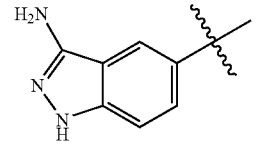 | 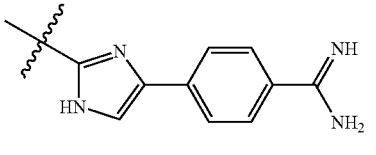 | 465.0 |
| 177 | 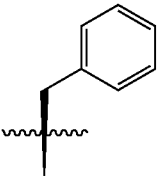 | 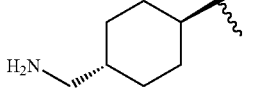 | 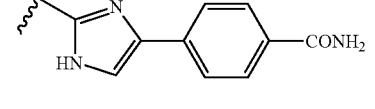 | 490.0 |
| 178 | 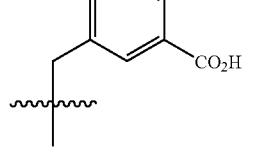 | 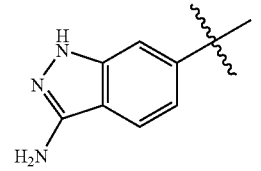 | 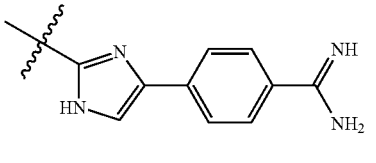 | 465.0 |
| 179 | 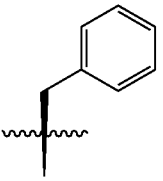 | 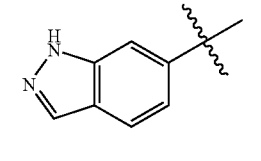 | 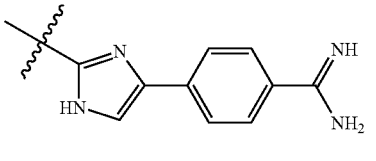 | 450.0 |

TABLE 1-continued

| Ex # | A | R³, R⁴ | R¹¹ | Mass spec (m/z) (M + H)⁺ |
|---|---|---|---|---|
| 180 | benzodiazepinedione | imidazole-phenyl-amidine | benzyl | 508.0 |
| 181 | indole | imidazole-phenyl-amidine | benzyl | 449.0 |
| 183 | 3-fluoro-4-carbamoylphenyl | imidazole-phenyl-amidine | benzyl | 471.1 |
| 187 | 4-sulfamoylphenyl | imidazole-phenyl-amidine | benzyl | 489.0 |
| 188 | 3-fluoro-4-carbamoylphenyl | chloro-imidazole-(3-aminoindazol-6-yl) | benzyl | 518.2 |
| 189 | 3-fluoro-4-carbamoylphenyl | chloro-imidazole-(4-aminoquinazolin-7-yl) | benzyl | 530.0 |

TABLE 1-continued
| Ex # | A | R³ R⁴ | R¹¹ | Mass spec (m/z) (M + H)⁺ |
|---|---|---|---|---|
| 190 | 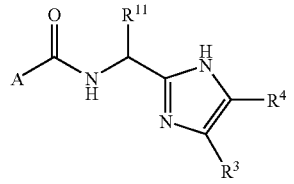 | 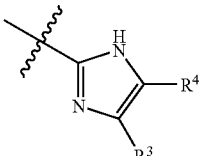 | 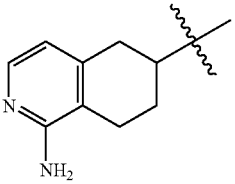 | 527.2 |
| 191 | 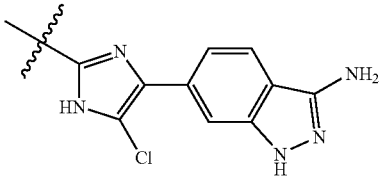 | 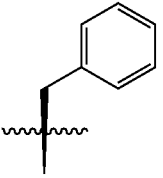 | 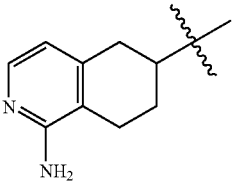 | 539.2 |
| 192 | 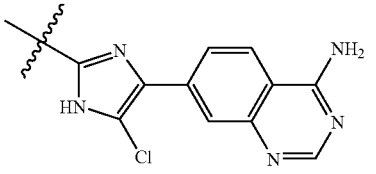 | 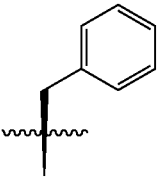 | 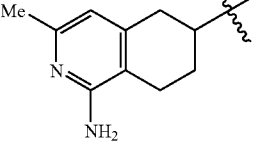 | 537.0 |
| 194 | 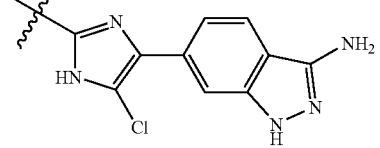 | 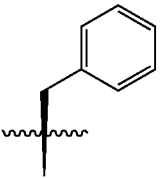 | 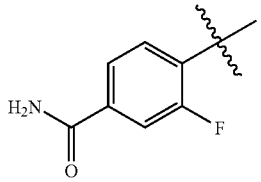 | 531.06 |
| 195 | 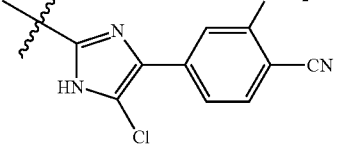 | 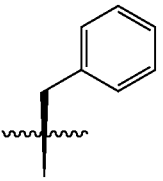 | 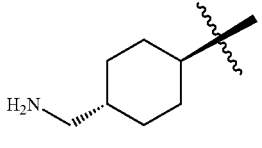 | 557.32 |
| 196 | 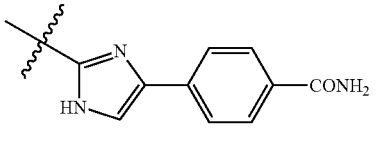 | 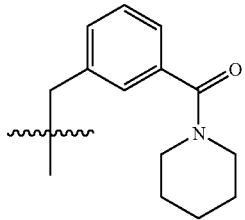 | 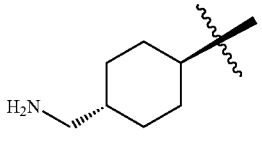 | 579.33 |

TABLE 1-continued
| Ex # | A | R³ | R¹¹ | Mass spec (m/z) (M + H)⁺ |
|---|---|---|---|---|
| 197 | 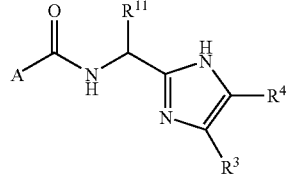 | 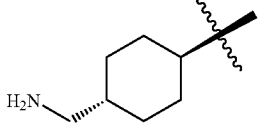 | 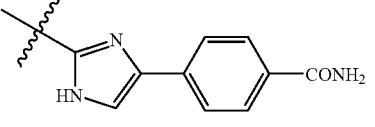 | 579.31 |
| 198 | 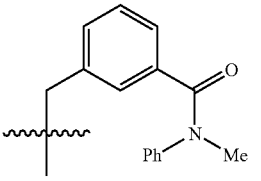 | 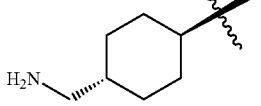 | 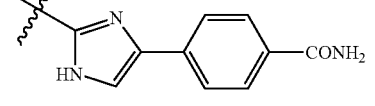 | 579.35 |
| 199 | 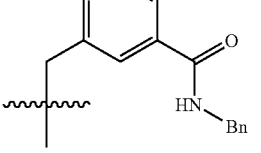 | 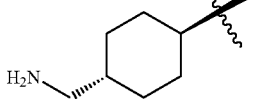 | 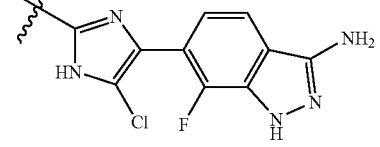 | 510.3 |
| 203 | 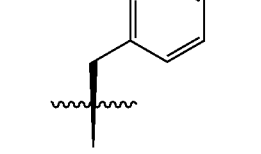 | 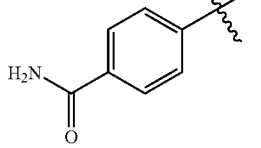 | 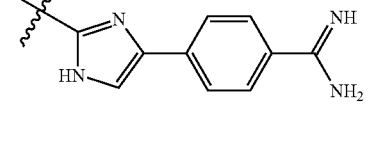 | 453.0 |
| 213 | 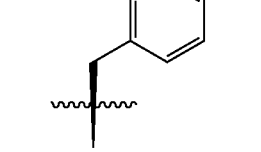 | 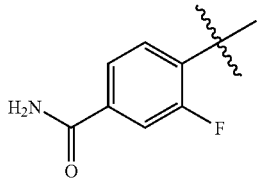 | 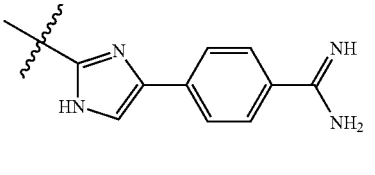 | 471.03 |
| 214 | 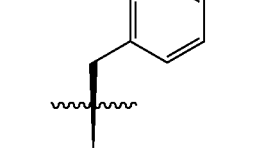 | 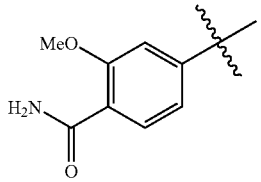 | 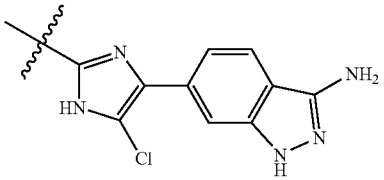 | 530.17 |

TABLE 1-continued

| Ex # | A | R³/R⁴ imidazole | R¹¹ | Mass spec (m/z) (M + H)⁺ |
|---|---|---|---|---|
| 215 | 4-carbamoyl-2-methoxyphenyl | 5-chloro-4-(3-amino-1H-indazol-6-yl)-1H-imidazol-2-yl | benzyl | 530.17 |
| 217 | trans-4-(aminomethyl)cyclohexyl | 4-(4-carbamoylphenyl)-1H-imidazol-2-yl | 3-(i-Bu-carbamoyl)benzyl | 545.3 |
| 218 | trans-4-(aminomethyl)cyclohexyl | 4-(4-carbamoylphenyl)-1H-imidazol-2-yl | 3-(isopentylcarbamoyl)benzyl | 559.32 |
| 219 | trans-4-(aminomethyl)cyclohexyl | 4-(4-carbamoylphenyl)-1H-imidazol-2-yl | 3-(t-Bu-carbamoyl)benzyl | 545.4 |
| 220 | trans-4-(aminomethyl)cyclohexyl | 4-(4-carbamoylphenyl)-1H-imidazol-2-yl | 3-(4-chlorobenzylcarbamoyl)benzyl | 613.3 |

TABLE 1-continued
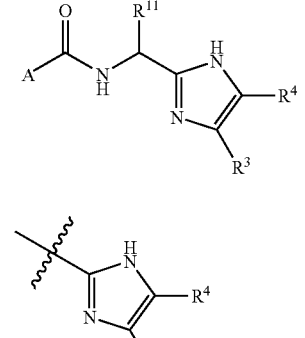
| Ex # | A | 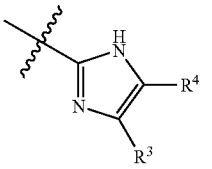  R³ | R¹¹ | Mass spec (m/z) (M + H)⁺ |
|---|---|---|---|---|
| 221 | 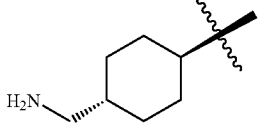 | 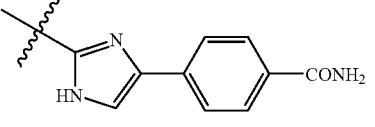 | 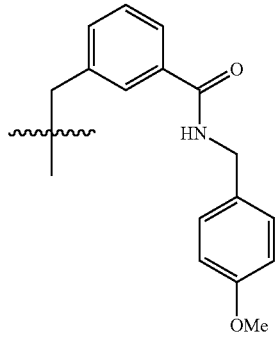 | 609.32 |
| 222 | 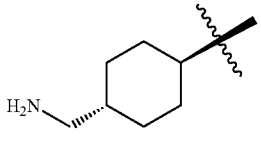 | 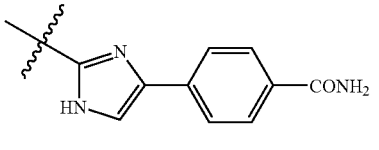 | 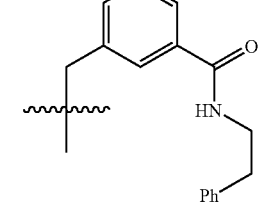 | 593.35 |
| 223 | 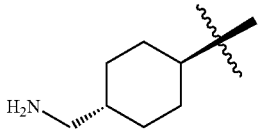 | 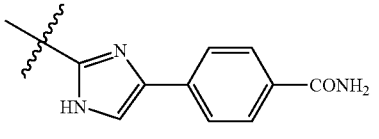 | 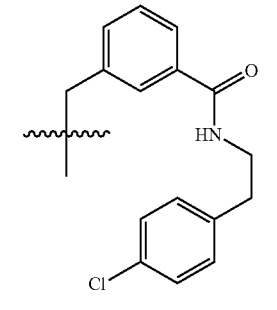 | 627.25 |
| 224 | 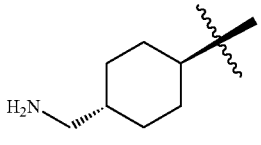 | 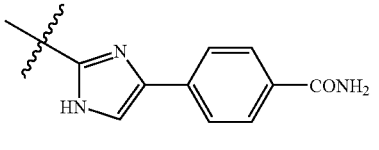 | 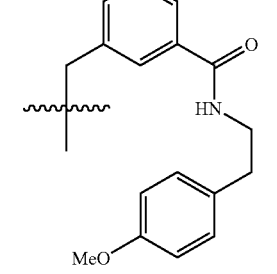 | 623.38 |

TABLE 1-continued
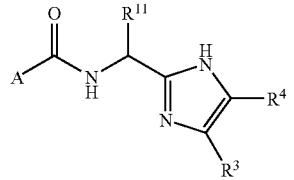
| Ex # | A | | R11 | Mass spec (m/z) (M + H)+ |
|---|---|---|---|---|
| 225 | 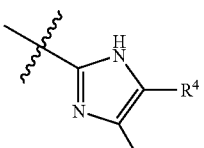 | 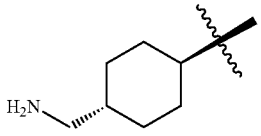 | 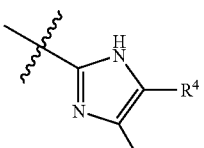 | 607.39 |
| 226 | 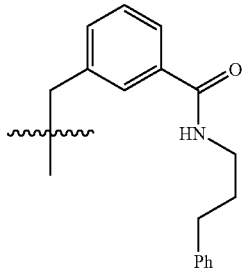 | 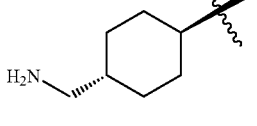 | 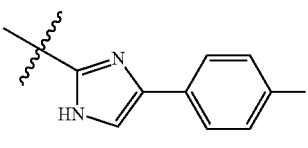 | 593.33 |
| 227 | 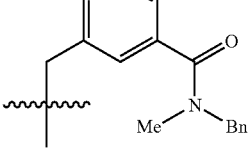 | 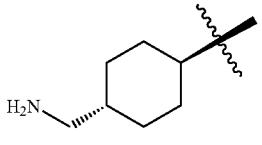 | 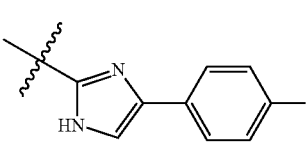 | 607.38 |
| 228 | 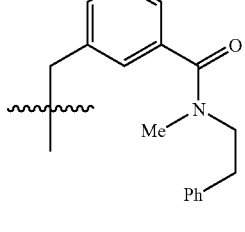 | 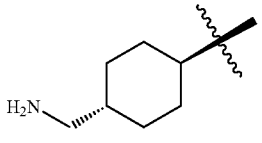 | 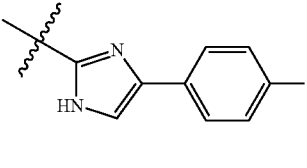 | 579.3 |
| 229 | 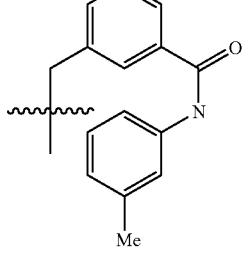 | 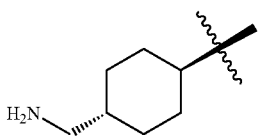 | 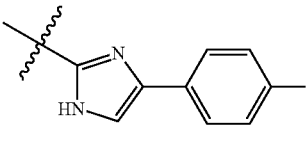 | 579.36 |

TABLE 1-continued
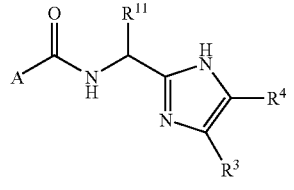
| Ex # | A | | R[11] | Mass spec (m/z) (M + H)+ |
|---|---|---|---|---|
| 230 | 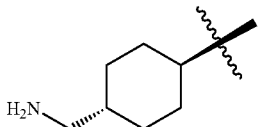 | 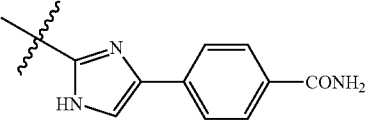 | 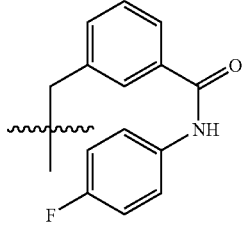 | 583.31 |
| 231 | 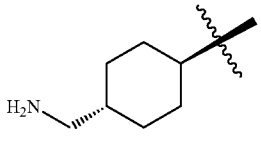 | 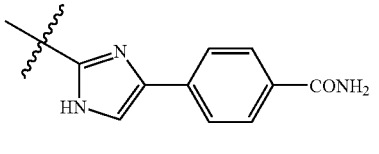 | 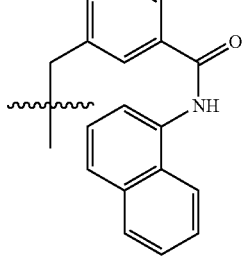 | 615.36 |
| 232 | 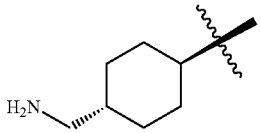 | 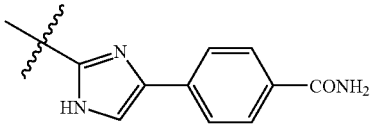 | 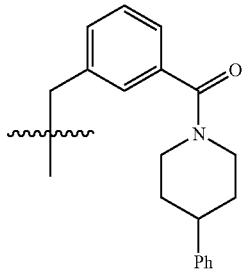 | 633.45 |
| 233 | 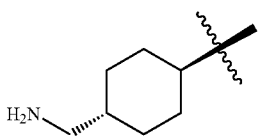 | 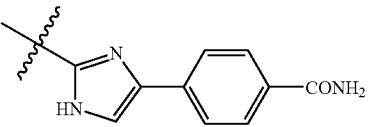 | 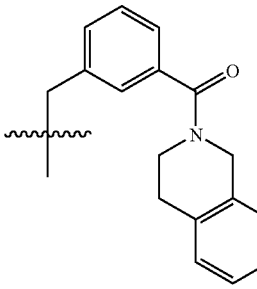 | 605.38 |

TABLE 1-continued
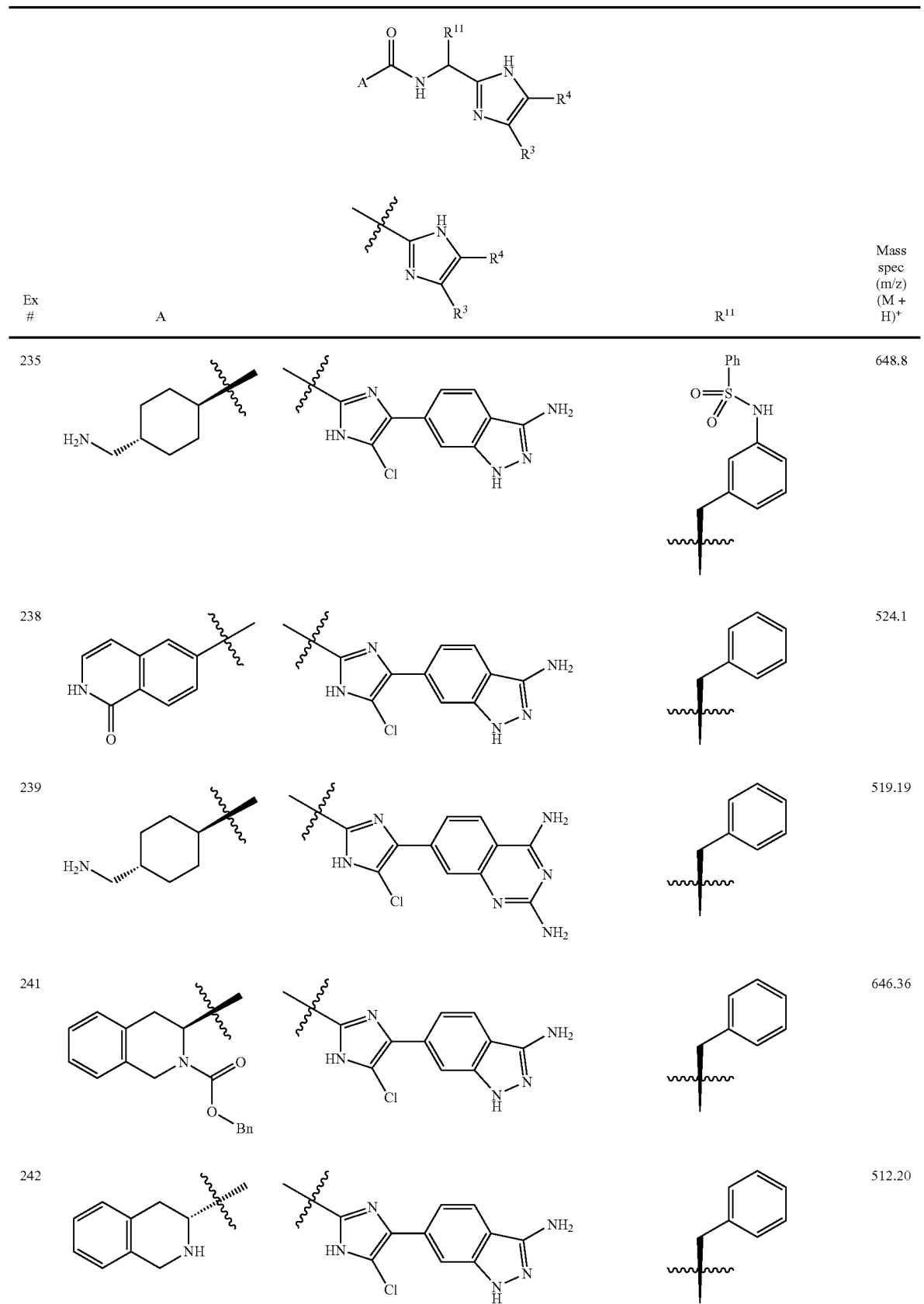

TABLE 1-continued

| Ex # | A | R³, R⁴ (imidazole) | R¹¹ | Mass spec (m/z) (M + H)⁺ |
|---|---|---|---|---|
| 243 | 1,2,3,4-tetrahydroisoquinolin-3-yl (NH in ring) | 5-(3-amino-1H-indazol-6-yl)-4-chloro-1H-imidazol-2-yl | benzyl | 512.20 |
| 244 | 3-amino-1H-indazol-5-yl | 5-(3-amino-1H-indazol-6-yl)-4-chloro-1H-imidazol-2-yl | benzyl | 512.01 |
| 248 | trans-4-(aminomethyl)cyclohexyl | 5-(4-carbamoyl-3-fluorophenyl)-4-bromo-1H-imidazol-2-yl | benzyl | 542.2 |
| 249 | trans-4-(aminomethyl)cyclohexyl | 5-(4-carbamoyl-3-fluorophenyl)-4-chloro-1H-imidazol-2-yl | benzyl | 498.3 |
| 250 | 1-oxo-1,2,3,4-tetrahydroisoquinolin-6-yl | 5-(3-amino-1H-indazol-6-yl)-4-chloro-1H-imidazol-2-yl | benzyl | 526.2 |
| 251 | trans-4-(aminomethyl)cyclohexyl | 4-methyl-5-phenyl-1H-imidazol-2-yl | benzyl | 417.4 |

TABLE 1-continued

| Ex # | A | R³ | R¹¹ | Mass spec (m/z) (M + H)⁺ |
|---|---|---|---|---|
| 252 | 4-(aminomethyl)cyclohexyl | 2-imidazolyl-4-(4-carbamoylphenyl)-5-Me | benzyl | 460.3 |
| 253 | 4-(methoxycarbonyl)cyclohexyl | 2-imidazolyl-4-(3-amino-1H-indazol-6-yl)-5-Cl | benzyl | 521.2 |
| 254 | 2-benzoyl-1,2,3,4-tetrahydroisoquinolin-3-yl | 2-imidazolyl-4-(3-amino-1H-indazol-6-yl)-5-Cl | benzyl | 616.2 |
| 255 | 1,2,3,4-tetrahydronaphthalen-2-yl | 2-imidazolyl-4-(3-amino-1H-indazol-6-yl)-5-Cl | benzyl | 511.2 |
| 256 | 4-(aminomethyl)cyclohexyl | 2-imidazolyl-4-(3-amino-1H-indazol-6-yl)-5-Me | benzyl | 472.4 |
| 257 | 4-(aminomethyl)cyclohexyl | 2-imidazolyl-4-(4-cyano-3-fluorophenyl)-5-Me | benzyl | 460.4 |

TABLE 1-continued
| Ex # | A | R³ R⁴ | R¹¹ | Mass spec (m/z) (M + H)⁺ |
|---|---|---|---|---|
| 261 | 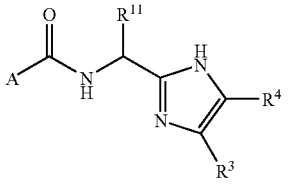 | 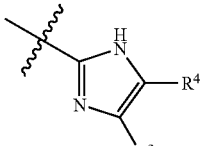 | 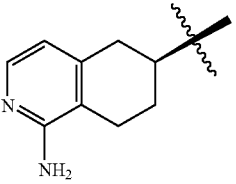 | 516.2 |
| 262 | 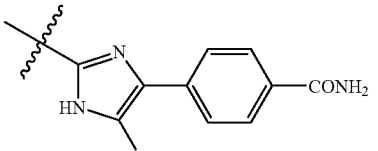 | 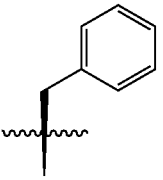 | 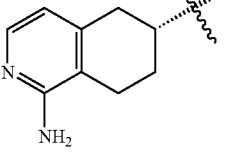 | 516.2 |
| 263 | 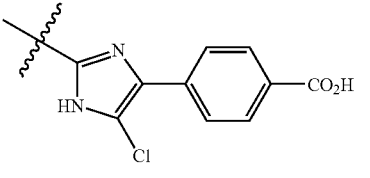 | 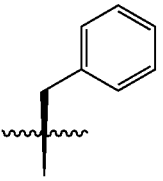 | 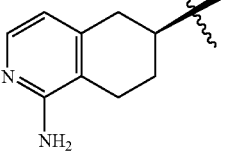 | 515.2 |
| 264 | 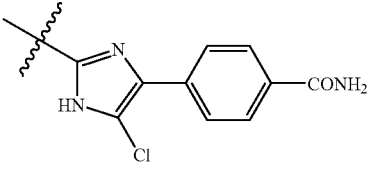 | 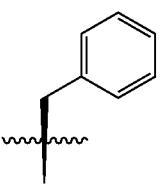 | 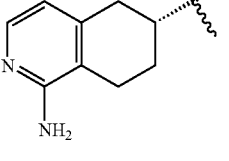 | 515.3 |
| 265 | 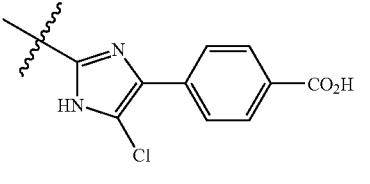 | 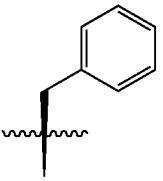 | 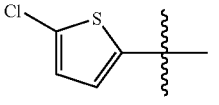 | 497.1 |
| 266 | 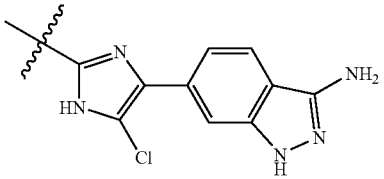 | 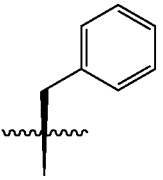 | 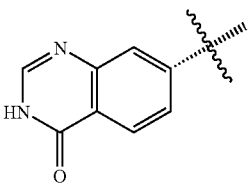 | 525.2 |

TABLE 1-continued
| Ex # | A | R³ | R¹¹ | Mass spec (m/z) (M + H)⁺ |
|---|---|---|---|---|
| 267 | 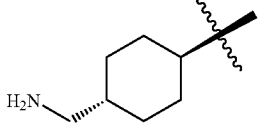 | 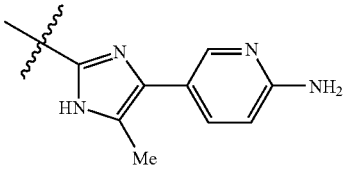 | 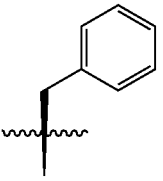 | 433.3 |
| 268 | 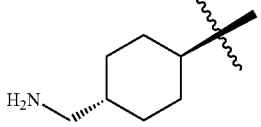 | 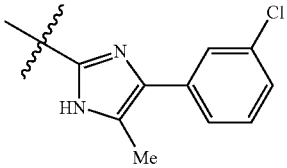 | 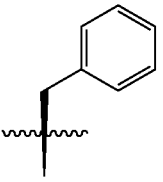 | 451.3 |
| 269 | 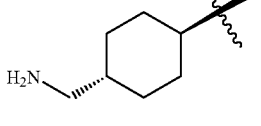 | 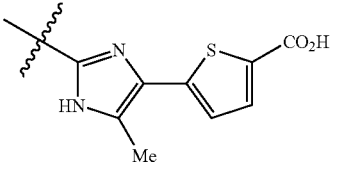 | 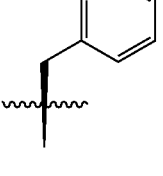 | 467.2 |
| 270 | 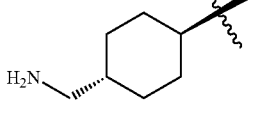 | 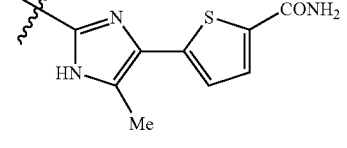 | 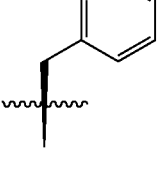 | 466.3 |
| 271 | 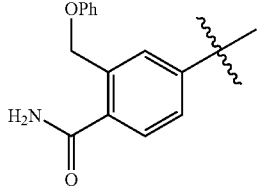 | 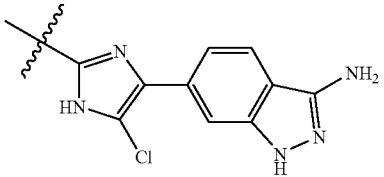 | 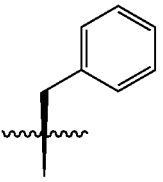 | 606.1 |
| 272 | 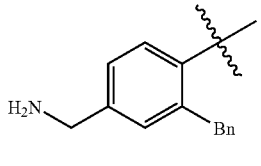 | 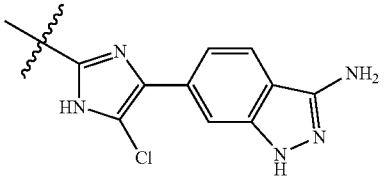 | 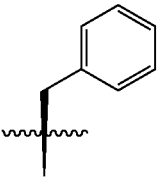 | 579.2 |

TABLE 1-continued

| Ex # | A | | R11 | Mass spec (m/z) (M + H)+ |
|---|---|---|---|---|
| 273 | 1-amino-tetrahydroisoquinoline | 4-cyanophenyl-chloro-imidazole | benzyl | 497.2 |
| 274 | 1-amino-tetrahydroisoquinoline | 4-cyanophenyl-chloro-imidazole | benzyl | 497.2 |
| 275 | 4-methylphenyl | 3-aminoindazol-6-yl-chloro-imidazole | benzyl | 471.3 |
| 276 | phenyl | 3-aminoindazol-6-yl-chloro-imidazole | benzyl | 457.3 |
| 277 | 3-methoxyphenyl | 3-aminoindazol-6-yl-chloro-imidazole | benzyl | 487.3 |
| 278 | 4-(aminomethyl)cyclohexyl | 4-carbamoylphenyl-chloro-imidazole | 3-acetamidobenzyl | 537.2 |

US 8,101,778 B2
175                                                                    176
TABLE 1-continued
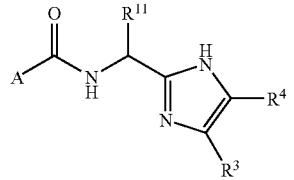
| Ex # | A | | R[11] | Mass spec (m/z) (M + H)+ |
|---|---|---|---|---|
| 279 | 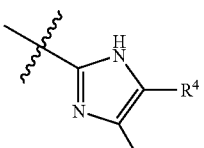 | 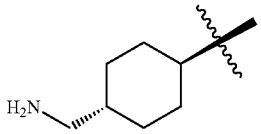 | 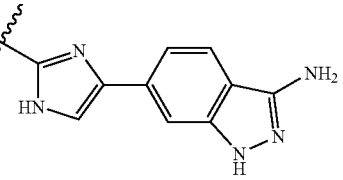 | 545.3 |
| 280 | 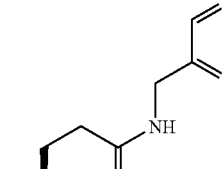 | 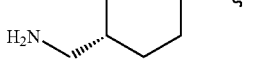 | 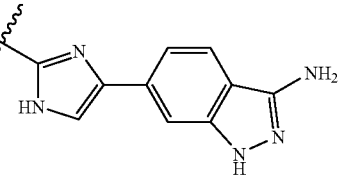 | 543.3 |
| 281 | 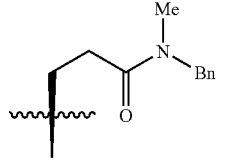 | 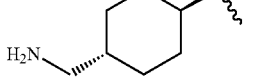 | 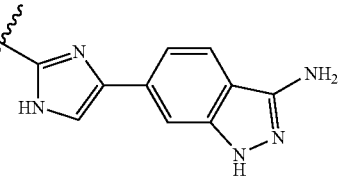 | 529.3 |
| 282 | 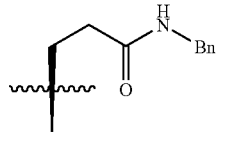 | 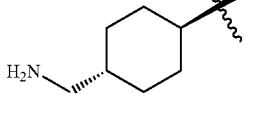 | 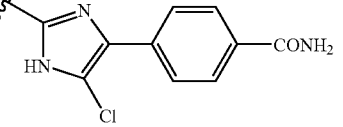 | 565.4 |
| 283 | 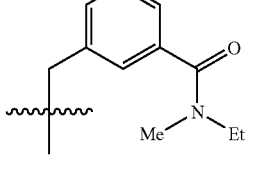 | 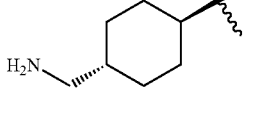 | 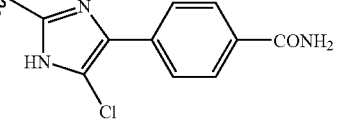 | 579.4 |
| 284 | 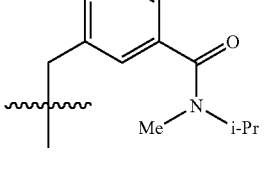 | 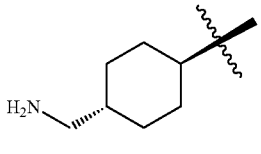 | 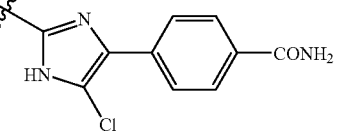 | 593.4 |

TABLE 1-continued
| Ex # | A | R³ | R¹¹ | Mass spec (m/z) (M + H)⁺ |
|---|---|---|---|---|
| 285 | 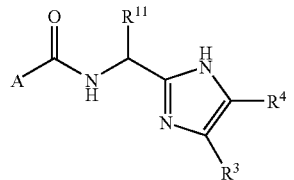 | 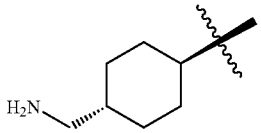 | 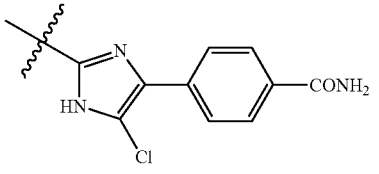 | 613.4 |
| 286 | 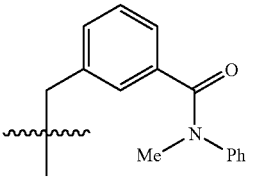 | 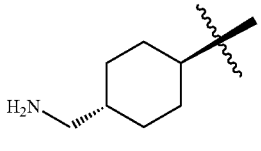 | 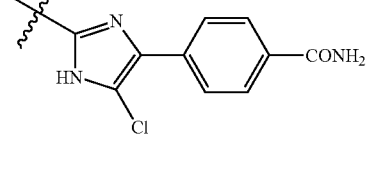 | 627.4 |
| 287 | 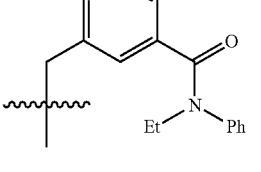 | 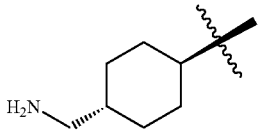 | 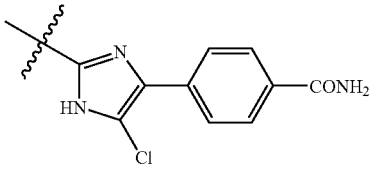 | 627.4 |
| 288 | 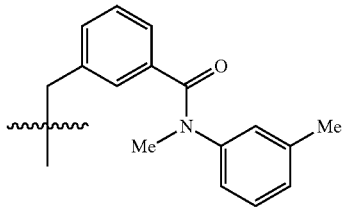 | 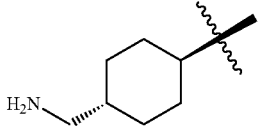 | 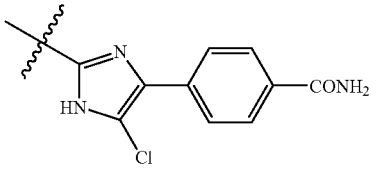 | 627.4 |
| 289 | 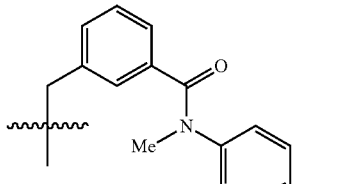 | 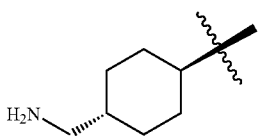 | 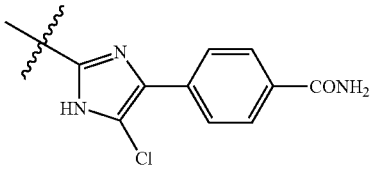 | 661.4 |
| 290 | 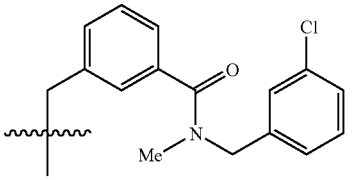 | 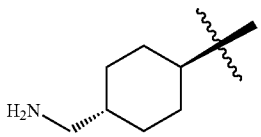 | 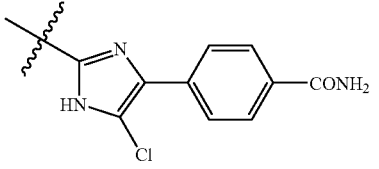 | 661.4 |

TABLE 1-continued
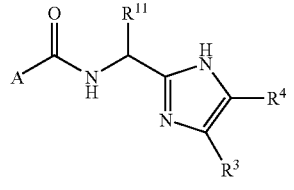
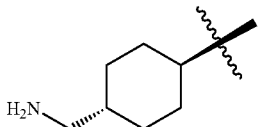
| Ex # | A | R³ R⁴ | R¹¹ | Mass spec (m/z) (M + H)⁺ |
|---|---|---|---|---|
| 291 | 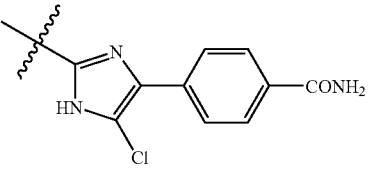 | 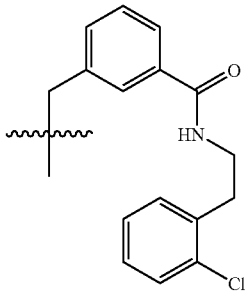 | 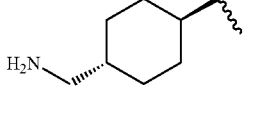 | 661.4 |
| 292 | 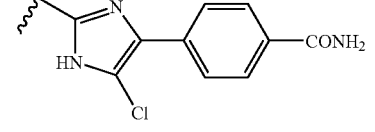 | 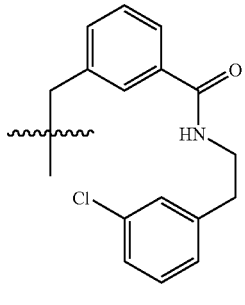 | 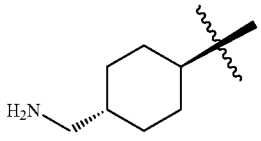 | 661.4 |
| 293 | 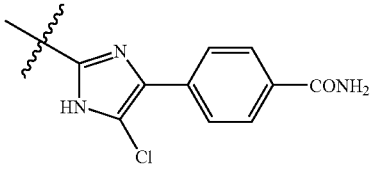 | 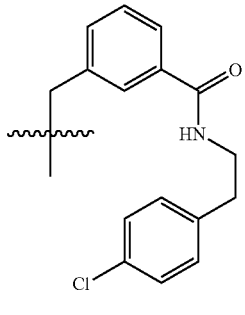 | 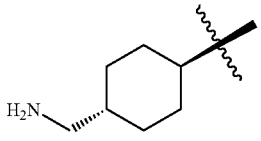 | 661.4 |
| 294 | 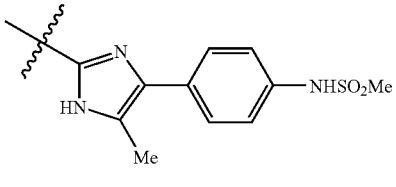 | 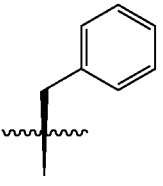 | | 510.3 |

TABLE 1-continued
| Ex # | A | | R11 | Mass spec (m/z) (M + H)+ |
|---|---|---|---|---|
| 295 | 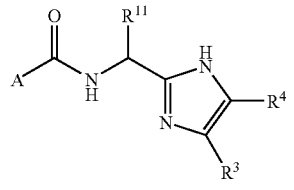 | 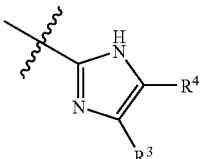 | 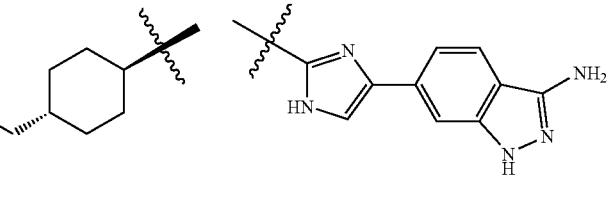 | 493.4 |
| 296 | 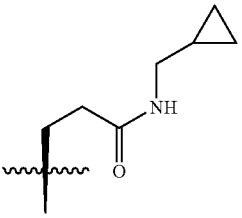 | 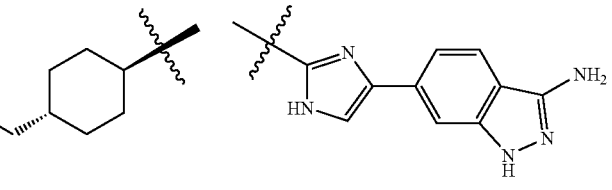 | 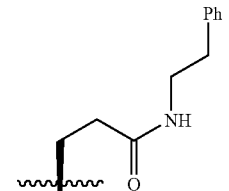 | 543.4 |
| 297 | 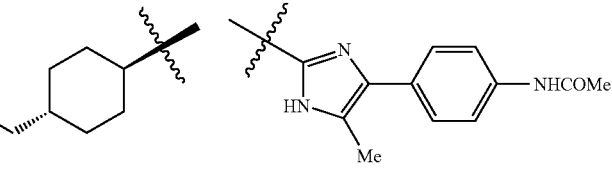 | 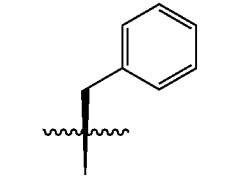 | 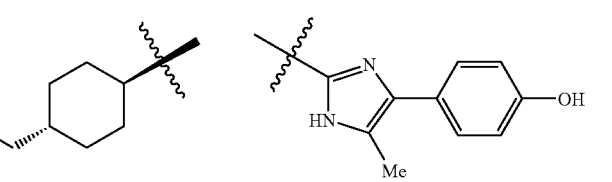 | 474.3 |
| 298 | 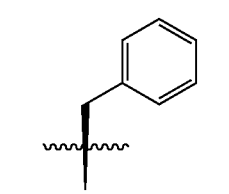 | 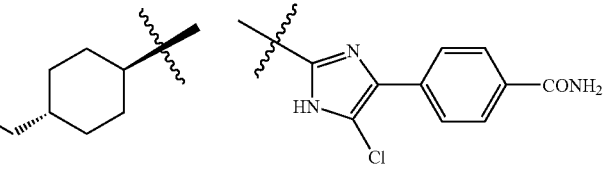 | 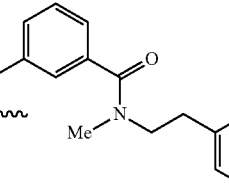 | 433.3 |
| 299 |  |  |  | 642.5 |

US 8,101,778 B2
183                                                                                       184
TABLE 1-continued
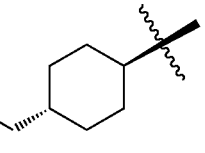
| Ex # | A | | R[11] | Mass spec (m/z) (M + H)+ |
|---|---|---|---|---|
| 300 | 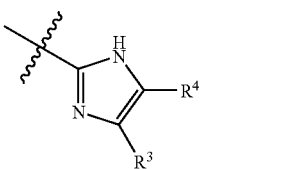 | 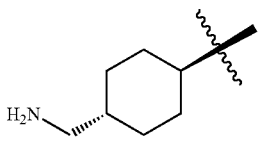 | 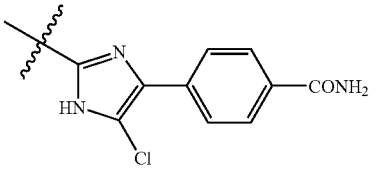 | 625.4 |
| 301 | 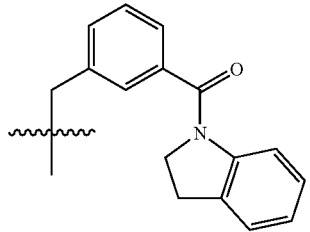 | 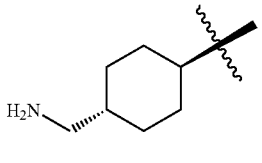 | 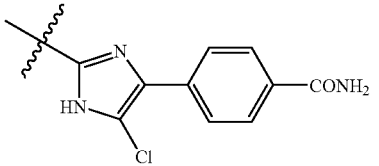 | 625.4 |
| 302 | 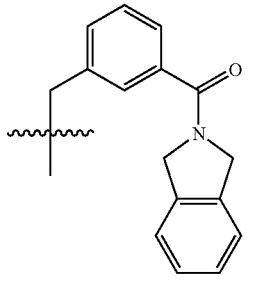 | 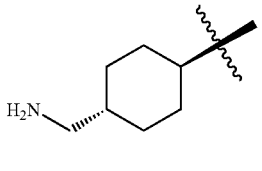 | 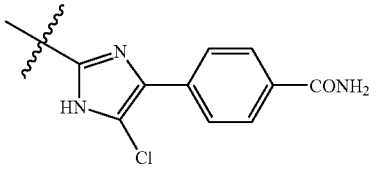 | 641.4 |
| 303 | 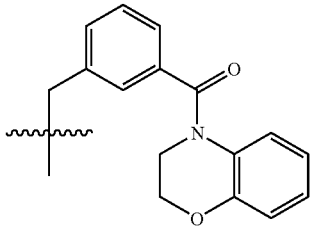 | 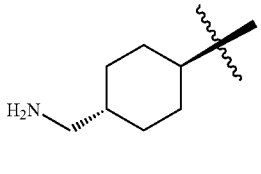 | 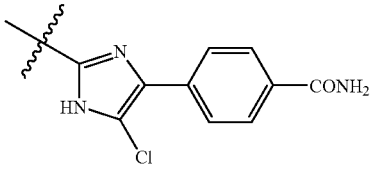 | 653.5 |
| 304 | 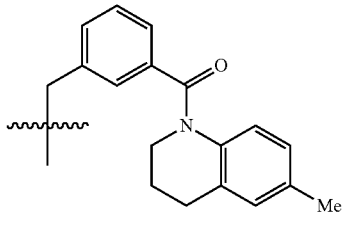 | 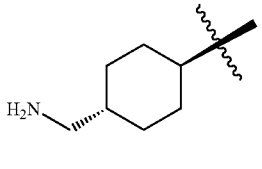 | 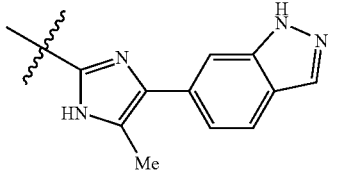 | 457.3 |

TABLE 1-continued

| Ex # | A | R³, R⁴ (imidazole) | R¹¹ | Mass spec (m/z) (M + H)⁺ |
|---|---|---|---|---|
| 305 | 1-amino-tetrahydroisoquinolin-6-yl | 7-fluoro-3-amino-1H-indazol-6-yl imidazole with Cl | phenyl (benzyl) | 545.3 |
| 306 | 4-(aminomethyl)cyclohexyl | 3-(NHSO₂Me)phenyl imidazole with Me | phenyl (benzyl) | 510.3 |
| 307 | 4-(aminomethyl)cyclohexyl | 3-(NHCOMe)phenyl imidazole with Me | phenyl (benzyl) | 474.4 |
| 308 | 4-(aminomethyl)cyclohexyl | 5-(CO₂H)thiophen-2-yl imidazole with Cl | phenyl (benzyl) | 487.2 |
| 309 | 4-carbamoyl-2-chlorophenyl | 3-amino-1H-indazol-6-yl imidazole with Cl | phenyl (benzyl) | 534.3 |
| 310 | 4-(aminomethyl)cyclohexyl | 3-amino-1H-indazol-6-yl imidazole with Cl | -CH₂CH₂C(O)NH-CH₂-thiazol-2-yl | 558.3 |

TABLE 1-continued
| Ex # | A | | R[11] | Mass spec (m/z) (M + H)+ |
|---|---|---|---|---|
| 311 | | | | 552.3 |
| 312 | | | | 472.3 |
| 313 | | | | 490.3 |
| 314 | | | | 649.2 |
| 315 | | | | 613.3 |
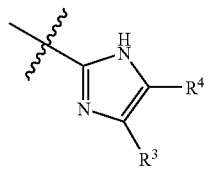

TABLE 1-continued
| Ex # | A | | R[11] | Mass spec (m/z) (M + H)+ |
|---|---|---|---|---|
| 316 | 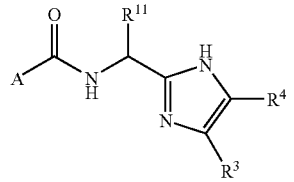 | 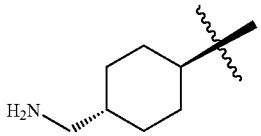 | 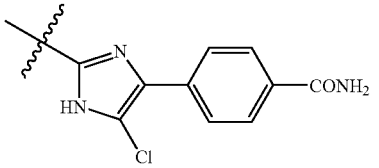 | 649.2 |
| 317 | 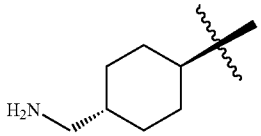 | 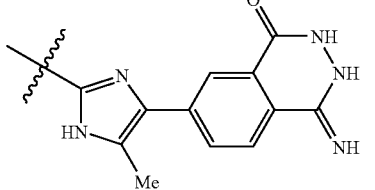 | 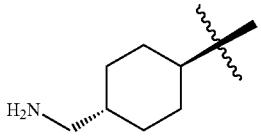 | 500.3 |
| 318 | 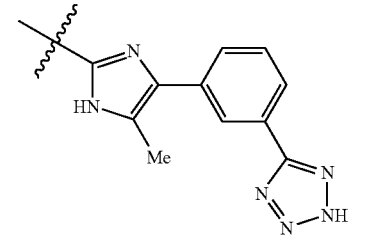 | 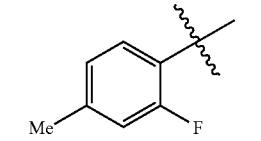 | | 485.3 |
| 319 | | 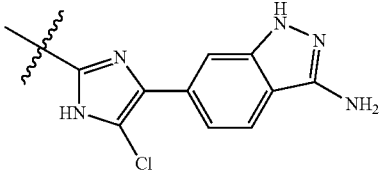 | | 489.3 |

TABLE 2
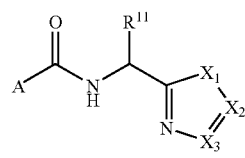
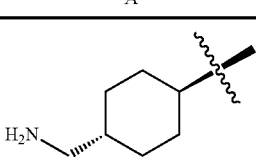
| Ex # | A | | R[11] | Mass spec (m/z) (M + H)+ |
|---|---|---|---|---|
| 48 | 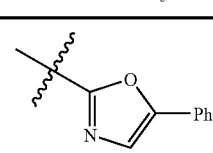 | 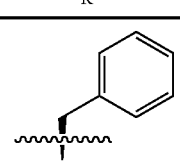 | 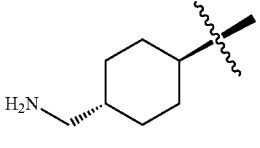 | 404.3 |
| 49 | 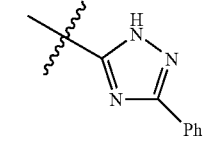 | 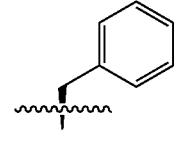 | 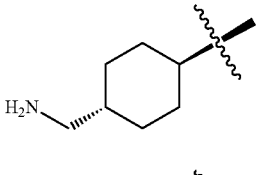 | 404.2 |
| 50 | 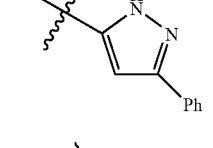 | 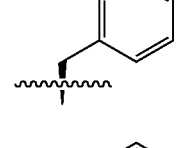 | 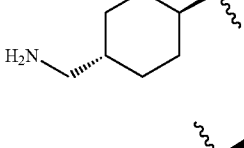 | 403.1 |
| 51 | 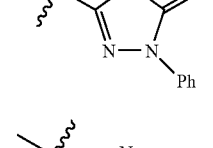 | 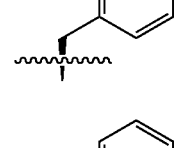 | 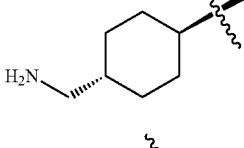 | 420.1 |
| 52 | 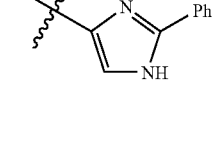 | 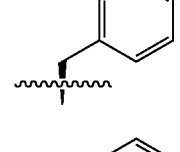 | 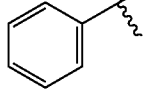 | 403.3 |
| 125 | 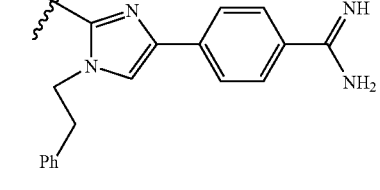 | 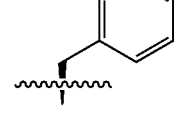 | 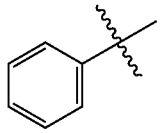 | 514.3 |
| 126 | 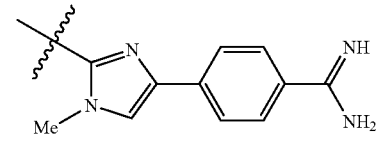 | 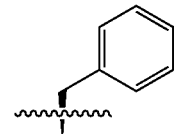 | 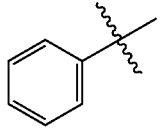 | 424.2 |
| 127 | 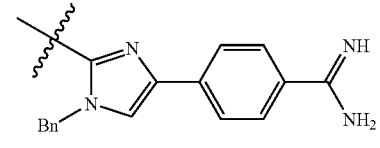 | 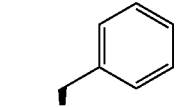 | | 500.2 |

TABLE 2-continued
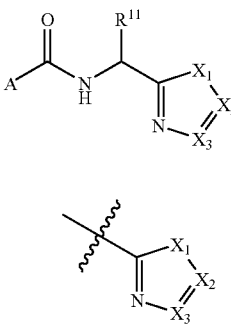
| Ex # | A | [structure] | R¹¹ | Mass spec (m/z) (M + H)⁺ |
|---|---|---|---|---|
| 139 | 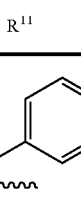 | 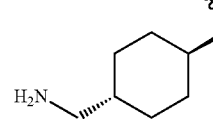 | 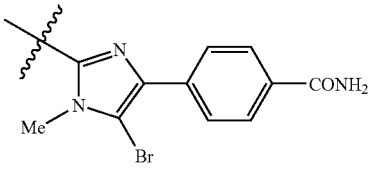 | 538.2 540.2 |
| 182 | 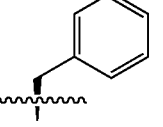 | 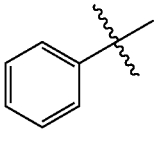 | 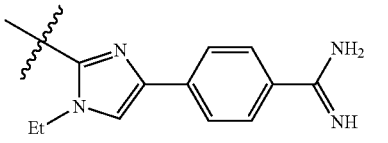 | 450.2 |
TABLE 3
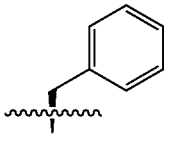
| Ex | R¹¹ | R³ | Mass spec (m/z), (M + H)⁺ |
|---|---|---|---|
| 2 |  | 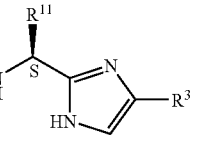 | 403.2 |
| 3 | 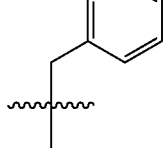 | 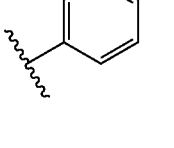 | 428.15 |
| 4 | 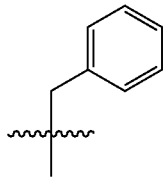 | 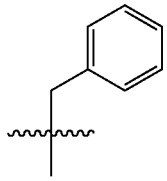 | 481.09 |

TABLE 3-continued

| Ex | R11 | R3 | Mass spec (m/z), (M + H)+ |
|---|---|---|---|
| 5 | benzyl | 4-OMe-phenyl | 433.25 |
| 6 | (1-Bn-imidazol-4-yl)methyl | phenyl | 483.23 |
| 7 | benzyl | 3-CO2Me-phenyl | 461.25 |
| 8 | Me | phenyl | 327.21 |
| 9 | benzyl | phenyl | 417.27 |
| 10 | benzyl | 4-CF3-phenyl | 471.24 |
| 11 | benzyl | 3-CF3-phenyl | 471.24 |

TABLE 3-continued

[Structure: trans-4-(aminomethyl)cyclohexanecarboxamide linked to an (S)-CH(R11)-imidazole bearing R3 at the 4-position]

| Ex | R11 | R3 | Mass spec (m/z), (M + H)+ |
|---|---|---|---|
| 12 | benzyl | 3-fluorophenyl | 421.24 |
| 13 | benzyl | 3-cyanophenyl | 428.30 |
| 16 | 3-chlorobenzyl | phenyl | 437.21 |
| 17 | 4-chlorobenzyl | phenyl | 437.21 |
| 18 | (pyridin-2-yl)methyl | phenyl | 404.25 |
| 19 | (pyridin-3-yl)methyl | phenyl | 404.25 |
| 20 | benzyl | 2-methoxyphenyl | 433.26 |

TABLE 3-continued
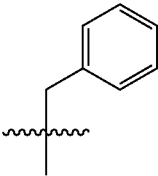
| Ex | R¹¹ | R³ | Mass spec (m/z), (M + H)⁺ |
|---|---|---|---|
| 21 | 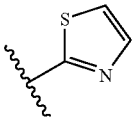 | 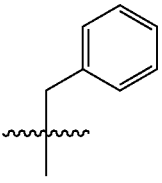 | 432.18 |
| 22 | 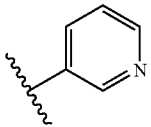 | 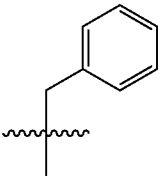 | 404.25 |
| 23 | 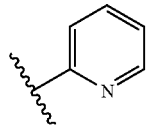 | 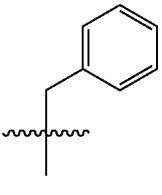 | 404.25 |
| 24 | 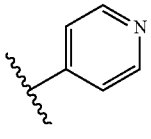 | 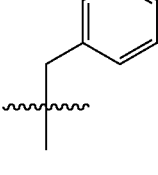 | 404.25 |
| 28 | 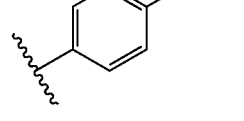 | 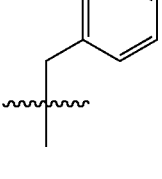 | 446.26 |
| 29 | 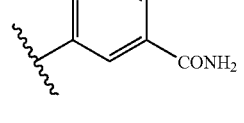 | 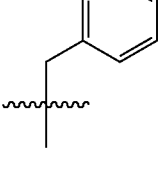 | 446.2 |
| 30 | 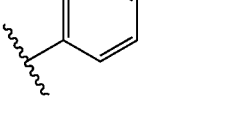 | | 460.27 |

TABLE 3-continued

| Ex | R[11] | R[3] | Mass spec (m/z), (M + H)+ |
|---|---|---|---|
| 31 | benzyl | 4-(CONMe₂)phenyl | 474.29 |
| 32 | benzyl | 1H-benzimidazol-2-yl | 443.25 |
| 33 | benzyl | benzoxazol-2-yl | 444.24 |
| 34 | benzyl | benzothiazol-2-yl | 460.22 |
| 35 | benzyl | 1-methyl-1H-benzimidazol-2-yl | 457.27 |
| 36 | benzyl | 4-(CO₂Me)thiazol-2-yl | 468.21 |
| 37 | benzyl | —CO₂Me | 385.33 |

TABLE 3-continued

| Ex | R11 | R3 | Mass spec (m/z), (M + H)+ |
|---|---|---|---|
| 38 | benzyl | —CO2H | 371.21 |
| 39 | benzyl | —CONHCH2CO2Et | 478.24 |
| 40 | benzyl | —CONHCH2CO2H | 428.22 |
| 41 | benzyl | —CONHBn | 460.27 |
| 62 | benzyl | 3-methoxyphenyl | 433.22 |
| 63 | benzyl | 2,4-difluorophenyl | 439.23 |
| 64 | benzyl | 4-fluorophenyl | 421.24 |

TABLE 3-continued

| Ex | R11 | R3 | Mass spec (m/z), (M + H)+ |
|---|---|---|---|
| 65 | benzyl | 4-cyano-3-fluorophenyl | 446.23 |
| 66 | benzyl | 3-carboxyphenyl | 447.24 |
| 67 | benzyl | 4-(methoxycarbonyl)phenyl | 461.26 |
| 68 | benzyl | 4-carboxyphenyl | 447.24 |
| 69 | benzyl | 3-amino-1H-indazol-6-yl | 458.27 |
| 79 | (thiazol-4-yl)methyl | phenyl | 410.2 |
| 80 | (benzothiazol-2-yl)methyl | phenyl | 460.1 |

TABLE 3-continued

| Ex | R11 | R3 | Mass spec (m/z), (M + H)+ |
|---|---|---|---|
| 81 | 4-pyridylmethyl | phenyl | 404.0 |
| 87 | benzyl | 3-(CH2CO2H)phenyl | 461.1 |
| 88 | benzyl | 3-(CH2CONH2)phenyl | 460.2 |
| 89 | benzyl | 4-(SO2NH2)phenyl | 482.1 |
| 90 | benzyl | 3-hydroxyphenyl | 419.2 |
| 91 | benzyl | 3-(CH2CO2Et)phenyl | 489.2 |
| 94 | 4-fluorobenzyl | phenyl | 421.3 |

TABLE 3-continued

| Ex | R11 | R3 | Mass spec (m/z), (M + H)+ |
|---|---|---|---|
| 95 | 4-NO2-benzyl | phenyl | 448.2 |
| 96 | 4-CF3-benzyl | phenyl | 471.3 |
| 97 | 4-Ph-benzyl | phenyl | 479.3 |
| 98 | 4-OBn-benzyl | phenyl | 509.3 |
| 99 | 4-OMe-benzyl | phenyl | 433.3 |
| 100 | 4-(C(O)Ph)-benzyl | phenyl | 507.5 |
| 101 | 3-CF3-benzyl | phenyl | 471.4 |

TABLE 3-continued
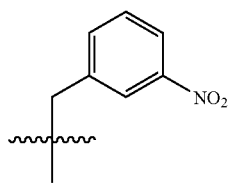
| Ex | R[11] | R[3] | Mass spec (m/z), (M + H)+ |
|---|---|---|---|
| 102 | 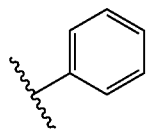 | 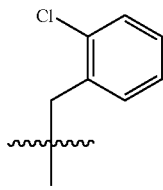 | 448.2 |
| 103 | 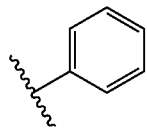 | 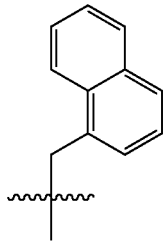 | 437.4 |
| 104 | 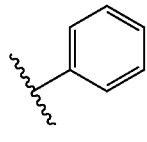 | 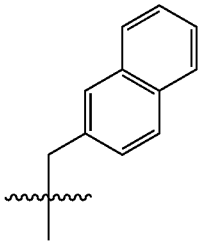 | 453.5 |
| 105 | 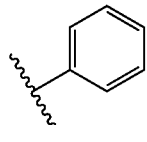 | 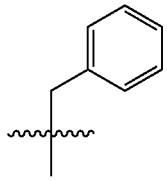 | 453.4 |
| 109 | 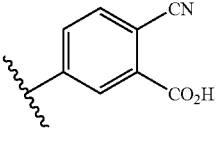 | 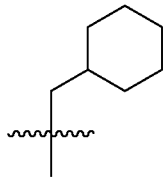 | 472.3 |
| 110 | 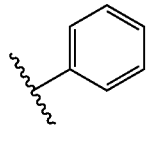 |  | 409.4 |

TABLE 3-continued
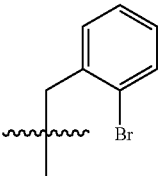
| Ex | R[11] | R[3] | Mass spec (m/z), (M + H)+ |
|---|---|---|---|
| 111 | 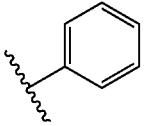 | 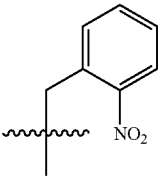 | 481.3 |
| 148 | 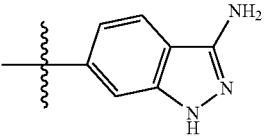 | 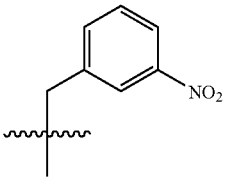 | 503.2 |
| 149 | 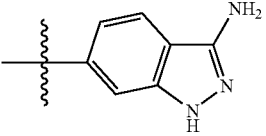 | 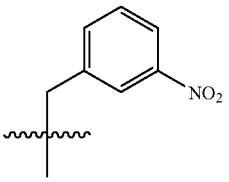 | 503.1 |
| 150 | 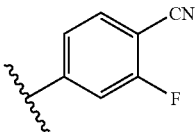 | 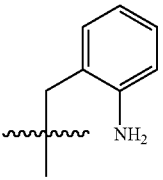 | 491.0 |
| 151 | 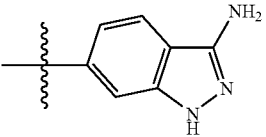 | 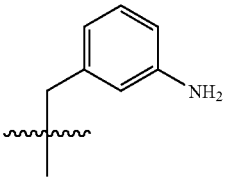 | 473.3 |
| 152 | 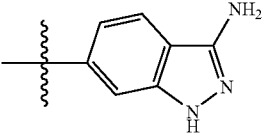 | 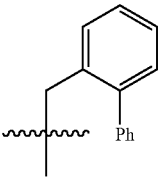 | 473.2 |
| 153 | 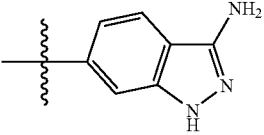 |  | 534.3 |

TABLE 3-continued

| Ex | R11 | R3 | Mass spec (m/z), (M + H)+ |
|---|---|---|---|
| 154 | 3-Ph-benzyl | 6-(3-amino-1H-indazolyl) | 534.3 |
| 156 | 3-(NHSO2Ph)-benzyl | 6-(3-amino-1H-indazolyl) | 613.1 |
| 159 | 2-(NHCOBn)-benzyl | 6-(3-amino-1H-indazolyl) | 591.3 |
| 163 | 2-(NHCOCH2CH2Ph)-benzyl | 6-(3-amino-1H-indazolyl) | 605.3 |
| 164 | 2-(NHSO2Ph)-benzyl | 6-(3-amino-1H-indazolyl) | 613.2 |
| 166 | 2-(NHCOPh)-benzyl | 6-(3-amino-1H-indazolyl) | 577.3 |
| 167 | 2-Br-benzyl | 6-(3-amino-1H-indazolyl) | 537.9 |

TABLE 3-continued

| Ex | R¹¹ | R³ | Mass spec (m/z), (M + H)⁺ |
|---|---|---|---|
| 168 | -CH₂-C(CH₃)₃ (neopentyl, t-Bu-CH₂-) | 6-(3-amino-1H-indazolyl) | 438.1 |
| 169 | -CH₂-O-CH₂-Ph (benzyloxymethyl) | 6-(3-amino-1H-indazolyl) | 488.1 |
| 170 | -CH₂-S-CH₂-Ph (benzylthiomethyl) | 6-(3-amino-1H-indazolyl) | 504.1 |
| 201 | -CH₂-CH₂-Ph (phenethyl) | 6-(3-amino-1H-indazolyl) | 457.9 |
| 202 | -CH₂-CH₂-Ph (phenethyl) | 5-(3-hydroxy-1H-indazolyl) | 459.2 |
| 207 | -CH₂-CH₂-Ph (phenethyl) | 3-biphenyl | 479.3 |

TABLE 3-continued

| Ex | R¹¹ | R³ | Mass spec (m/z), (M + H)⁺ |
|---|---|---|---|
| 208 | benzyl | quinolin-8-yl | 454.3 |
| 209 | benzyl | 4-phenylphenyl | 479.3 |
| 210 | benzyl | benzo[1,3]dioxol-5-yl | 447.3 |
| 211 | benzyl | naphthalen-2-yl | 453.2 |
| 212 | benzyl | naphthalen-1-yl | 453.3 |
| 216 | benzyl | 3-aminophenyl (NH₂) | 418.3 |
| 234 | benzyl | 3-(dimethylamino)phenyl (NMe₂) | 446.3 |

TABLE 3-continued

| Ex | R11 | R3 | Mass spec (m/z), (M + H)+ |
|---|---|---|---|
| 236 | benzyl | 4-(OBn)phenyl | 509.3 |
| 237 | benzyl | 4-(CH2O-t-Bu)phenyl | 489.3 |
| 240 | benzyl | 4-(SO2Me)phenyl | 481.2 |
| 245 | benzyl | quinolin-5-yl | 454.3 |
| 246 | benzyl | quinolin-6-yl | 454.3 |

TABLE 3-continued

[Structure: trans-4-(aminomethyl)cyclohexanecarboxamide linked to (S)-CH(R¹¹)-imidazole with R³ at 4-position of imidazole]

| Ex | R¹¹ | R³ | Mass spec (m/z), (M + H)⁺ |
|---|---|---|---|
| 247 | benzyl (CH₂Ph) | isoquinolin-5-yl | 454.3 |
| 258 | benzyl | 4-chlorophenyl | 437.3 |
| 259 | benzyl | 4-(2-oxopiperidin-1-yl)phenyl | 500.3 |
| 260 | benzyl | 1-oxo-1,2-dihydroisoquinolin-6-yl | 470.3 |

TABLE 4

[Structure: trans-4-(aminomethyl)cyclohexanecarboxamide linked to (S)-CH(CH₂Ph)-benzimidazole with R³ᵃ substituent]

| Ex # | R³ᵃ | Mass spec (m/z) (M + H)⁺ |
|---|---|---|
| 42 | $CO_2Et$ | 435.3 |
| 43 | $CO_2H$ | 421.2 |
| 44 | $CONH_2$ | 420.2 |
| 45 | —$CH_2CO_2Et$ | 463.4 |

TABLE 4-continued

[Structure: same as above]

| Ex # | R³ᵃ | Mass spec (m/z) (M + H)⁺ |
|---|---|---|
| 46 | —$CH_2CO_2H$ | 435.4 |
| 47 | —$CH_2CONH_2$ | 434.3 |

TABLE 5
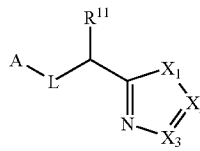
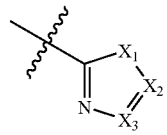
| Ex # | A | L | | R[11] | Mass spec (m/z) (M + H)+ |
|---|---|---|---|---|---|
| 53 | 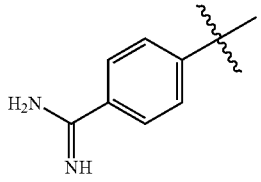 | —NHCO— | 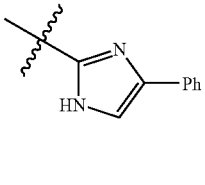 | 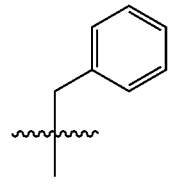 | 410.20 |
| 54 | 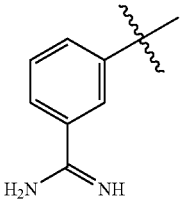 | —NHCO— | 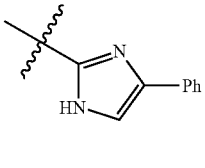 | 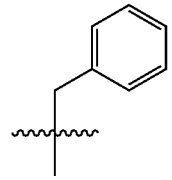 | 410.20 |
| 55 | 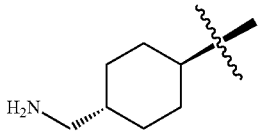 | —NHCO— | 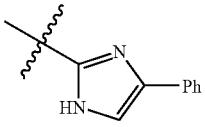 | 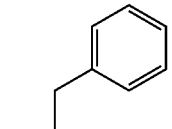 | 410.20 |
| 56 |  | —NHCO— | 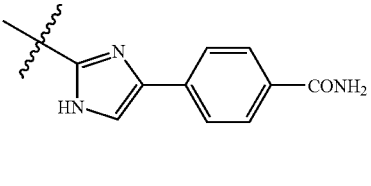 | 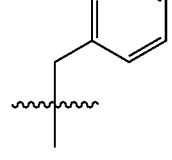 | 453.20 |
| 57 | 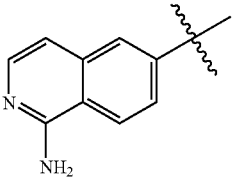 | —NHCO— | 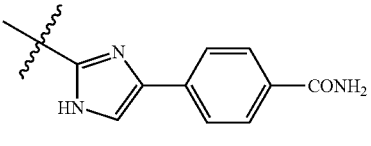 | 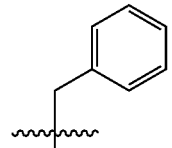 | 477.3 |
| 58 | 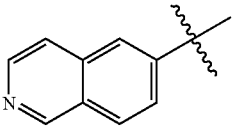 | —NHCO— | 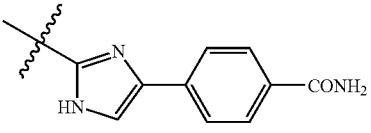 | 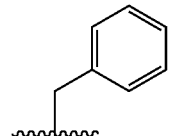 | 462.19 |

TABLE 5-continued

| Ex # | A | L | | R[11] | Mass spec (m/z) (M + H)+ |
|---|---|---|---|---|---|
| 59 | 4-(H2NOC)-phenyl | —NHCO— | 2-(4-amidinophenyl)-1H-imidazol-4-yl | benzyl | 453.4 |
| 61 | 4-amidinophenyl | —NHCOCH2— | 4-phenyl-1H-imidazol-2-yl | benzyl | 424.21 |
| 77 | trans-4-(aminomethyl)cyclohexyl | NHCONH | 4-phenyl-1H-imidazol-2-yl | benzyl | 418.1 |
| 92 | 3-(H2NOC)-phenyl | —NHCO— | 2-(4-amidinophenyl)-1H-imidazol-4-yl | benzyl | 453.2 |
| 93 | phenyl | —NHCO— | 2-(4-amidinophenyl)-1H-imidazol-4-yl | benzyl | 410.2 |

TABLE 5-continued

| Ex # | A | L | [structure] | R[11] | Mass spec (m/z) (M + H)+ |
|---|---|---|---|---|---|
| 138 | 3-amino-1H-indazol-6-yl | —CH₂CONH— | 6-(3-amino-1H-indazolyl)-5-chloro-1H-imidazol-2-yl | benzyl | 526.3 |
| 184 | 3-amino-1H-indazol-5-yl | —SO₂NH— | 4-(4-carbamimidoylphenyl)-1H-imidazol-2-yl | benzyl | 501.5 |
| 185 | 3-carbamoylphenyl | —SO₂NH— | 4-(4-carbamimidoylphenyl)-1H-imidazol-2-yl | benzyl | 489.0 |

TABLE 6

| Ex # | R[10] | Mass spec (m/z) (M + H)+ |
|---|---|---|
| 70 | Bn | 493.20 |
| 71 | —CH₂CH₂Ph | 507.31 |
| 72 | —CH₂CH₂CO₂Et | 489.62 |
| 74 | —CH₂CH₂CONH₂ | 474.62 |

TABLE 6-continued

| Ex # | R[10] | Mass spec (m/z) (M + H)+ |
|---|---|---|
| 85 | —CH₂CH₂C(O)NHCH₂CH₂Ph | 578.4 |

Using combinations of the above described synthetic routes and experimental procedures along with methods known to one skilled in the art of organic synthesis, additional compounds of this invention as shown below in Table 6 can be prepared.

TABLE 7
| Ex # | A | | R11 |
|---|---|---|---|
| 1001 | 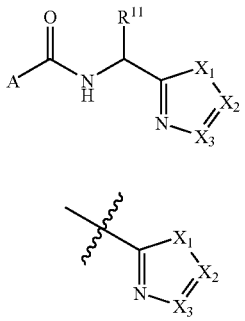 | 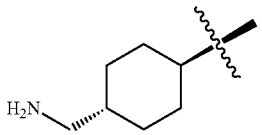 | 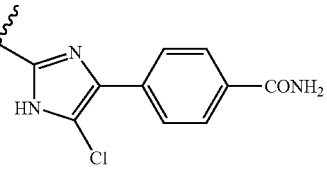 |
| 1002 | 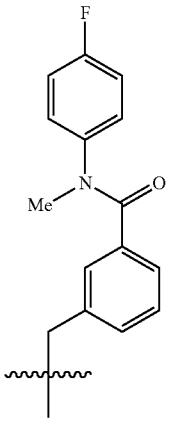 | 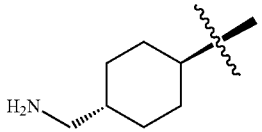 | 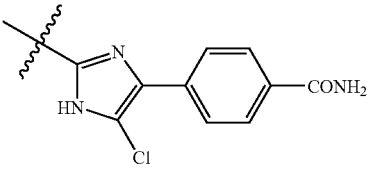 |
| 1003 | 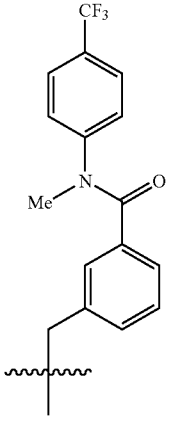 | 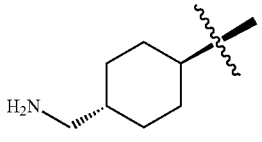 | 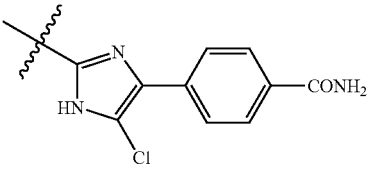 |

TABLE 7-continued
| Ex # | A | | R[11] |
|---|---|---|---|
| 1004 | 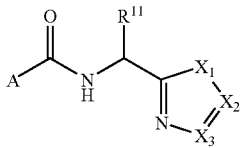 | 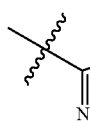 | 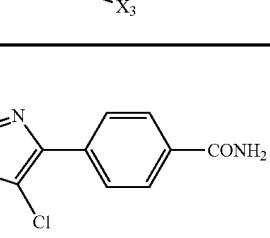 |
| 1005 |  | 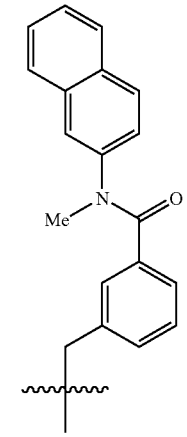 | 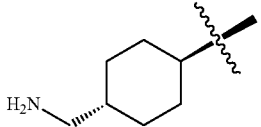 |
| 1006 | 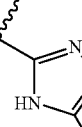 |  | 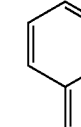 |

TABLE 7-continued
| Ex # | A | | $R^{11}$ |
|---|---|---|---|
| 1007 | 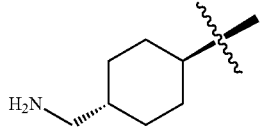 | 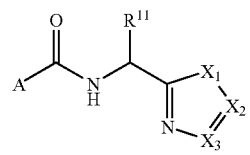 | 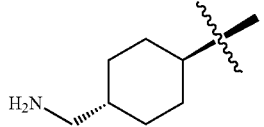 |
| 1008 | 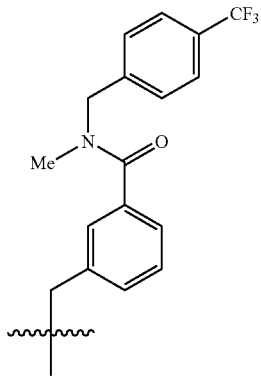 | 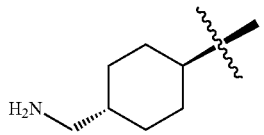 | 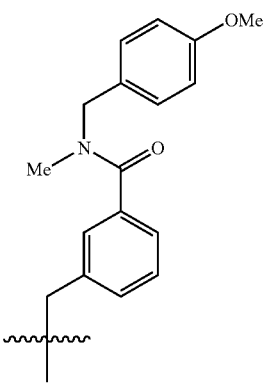 |
| 1009 | | | |
(Structures for examples 1007, 1008, 1009 shown in the table)

TABLE 7-continued
| Ex # | A | | R[11] |
|---|---|---|---|
| 1010 | 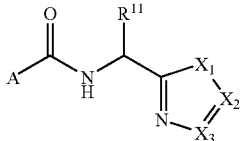 | 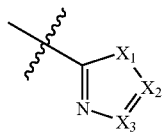 | 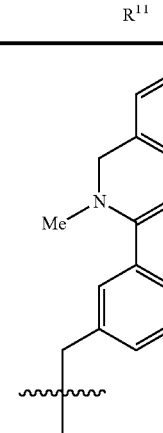 |
| 1011 | 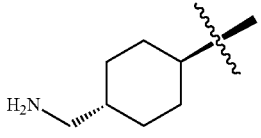 | 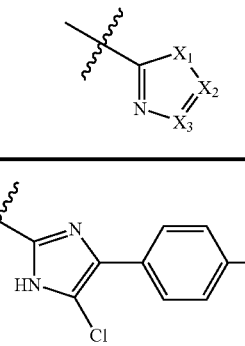 | 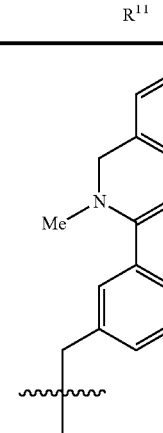 |
| 1012 | 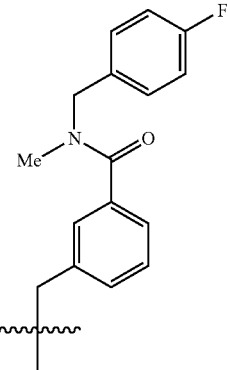 | 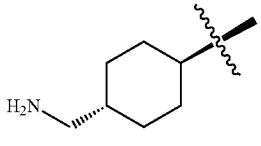 | 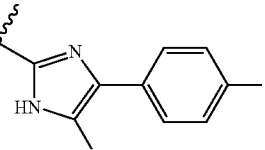 |

TABLE 7-continued

| Ex # | A | | R[11] |
|---|---|---|---|
| 1013 | aminomethyl cyclohexyl | 4-chloro-5-(4-carbamoylphenyl)-1H-imidazol-2-yl | N-methyl-N-(pyridin-4-ylmethyl)-3-benzamide |
| 1014 | aminomethyl cyclohexyl | 4-chloro-5-(4-carbamoylphenyl)-1H-imidazol-2-yl | N,N-dimethyl-3-benzamide |
| 1016 | aminomethyl cyclohexyl | 4-chloro-5-(4-carbamoylphenyl)-1H-imidazol-2-yl | N-(cyclohexylmethyl)-N-methyl-3-benzamide |

TABLE 7-continued
| Ex # | A | | R[11] |
|---|---|---|---|
| 1017 | 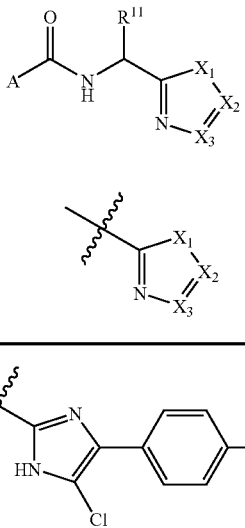 | 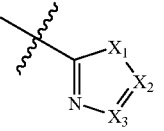 | 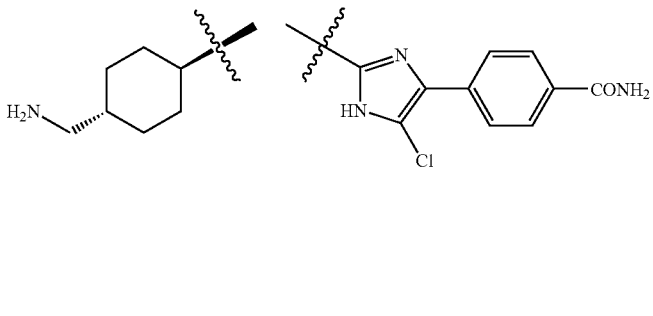 |
| 1018 | 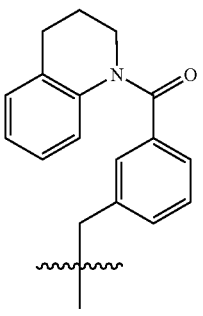 | 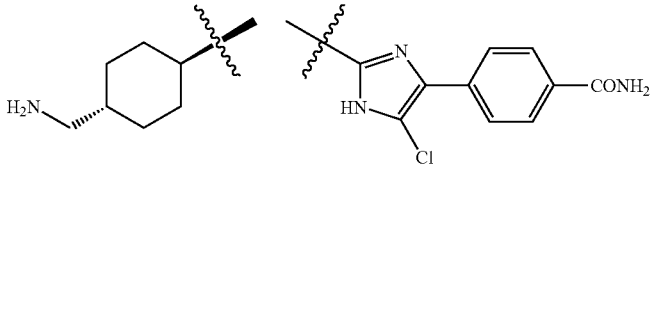 | 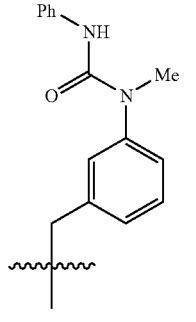 |
| 1019 | 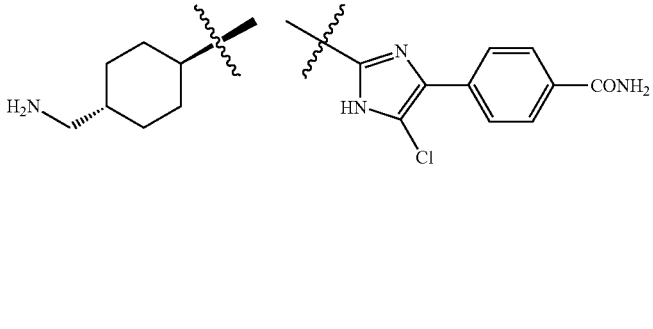 | 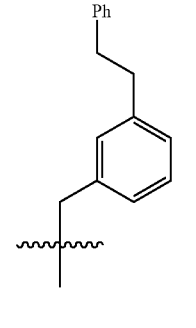 | 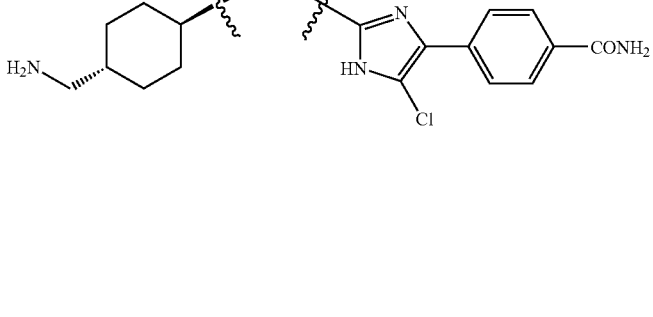 |
| 1020 | 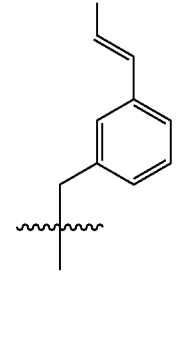 | | |

TABLE 7-continued

| Ex # | A | | R[11] |
|---|---|---|---|
| 1021 | 4-(aminomethyl)cyclohexyl | 2-[4-(aminocarbonyl)phenyl]-5-chloro-1H-imidazol-4-yl | N-methyl-N-(3-methylphenyl)acetamide (Me, Me on N, acetyl) |
| 1022 | 4-(aminomethyl)cyclohexyl | 2-[4-(aminocarbonyl)phenyl]-5-chloro-1H-imidazol-4-yl | N-methyl-N-(3-methylphenyl)benzamide (Bn, Me on N) |
| 1024 | 4-(aminomethyl)cyclohexyl | 2-[4-(aminocarbonyl)phenyl]-5-chloro-1H-imidazol-4-yl | N,N-dimethylsulfonamide (Me, Me on N) |
| 1025 | 4-(aminomethyl)cyclohexyl | 2-[4-(aminocarbonyl)phenyl]-5-chloro-1H-imidazol-4-yl | N-benzyl-N-methylsulfonamide (Bn, Me on N) |

TABLE 7-continued

| Ex # | A | | R11 |
|---|---|---|---|
| 1028 | 4-(aminomethyl)cyclohexyl | 2-yl-5-(4-carbamoylphenyl)-4-chloro-1H-imidazole | 3-[N-benzyl-N-methyl-sulfamoyl]phenylmethyl |
| 1029 | 4-(aminomethyl)cyclohexyl | 2-yl-5-(4-carbamoylphenyl)-4-chloro-1H-imidazole | 3-(phenylsulfamoyl)phenylmethyl |
| 1030 | 4-(aminomethyl)cyclohexyl | 2-yl-5-(4-carbamoylphenyl)-4-chloro-1H-imidazole | 3-(N-methylsulfamoyl)phenylmethyl |
| 1031 | 4-(aminomethyl)cyclohexyl | 2-yl-5-(4-carbamoylphenyl)-4-chloro-1H-imidazole | 3-(N-benzylsulfamoyl)phenylmethyl |

TABLE 7-continued
| Ex # | A | | R[11] |
|------|---|---|-------|
| 1032 | 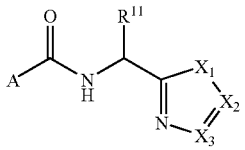 | 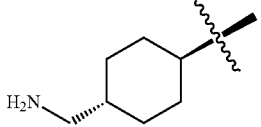 | 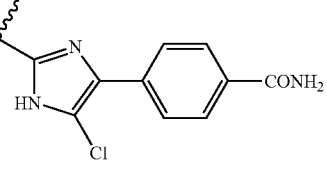 |
| 1033 | 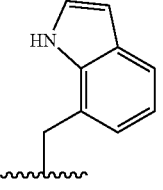 | 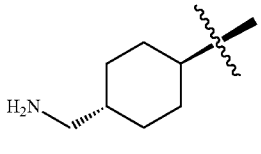 | 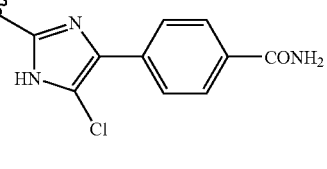 |
| 1034 | 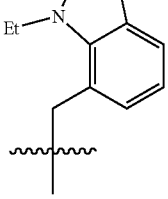 | 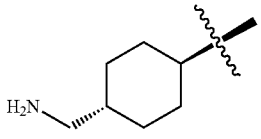 | 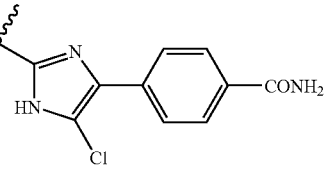 |
| 1035 | 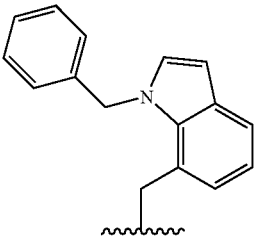 | 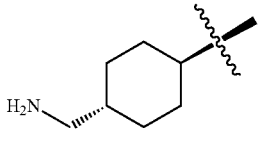 | 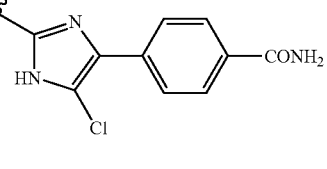 |
| 1036 | 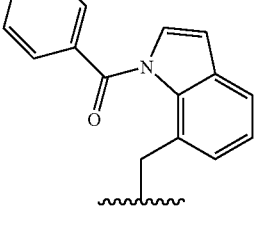 | 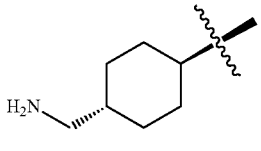 | 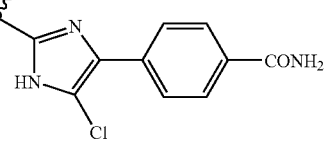 |

TABLE 7-continued
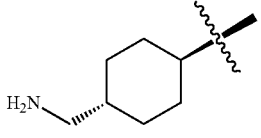
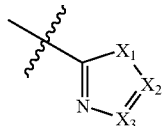
| Ex # | A | | R[11] |
|---|---|---|---|
| 1037 | 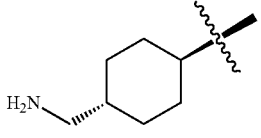 | 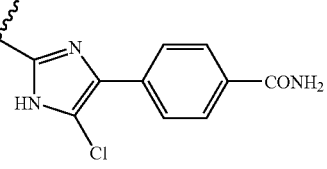 | 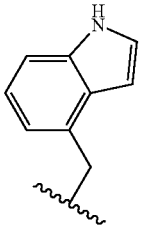 |
| 1038 | 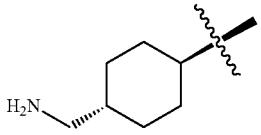 | 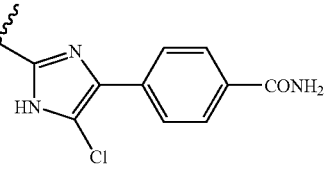 | 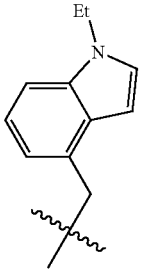 |
| 1039 | 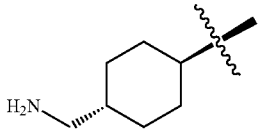 | 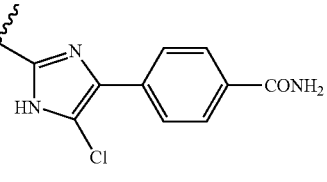 | 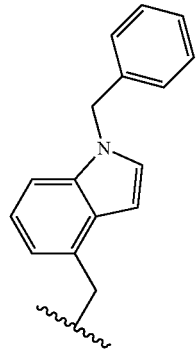 |
| 1040 | 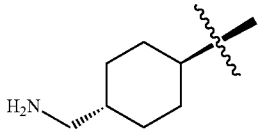 | 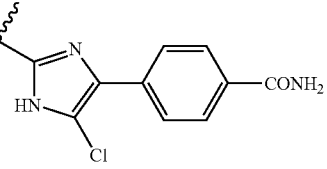 | 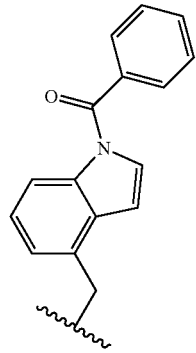 |

TABLE 7-continued
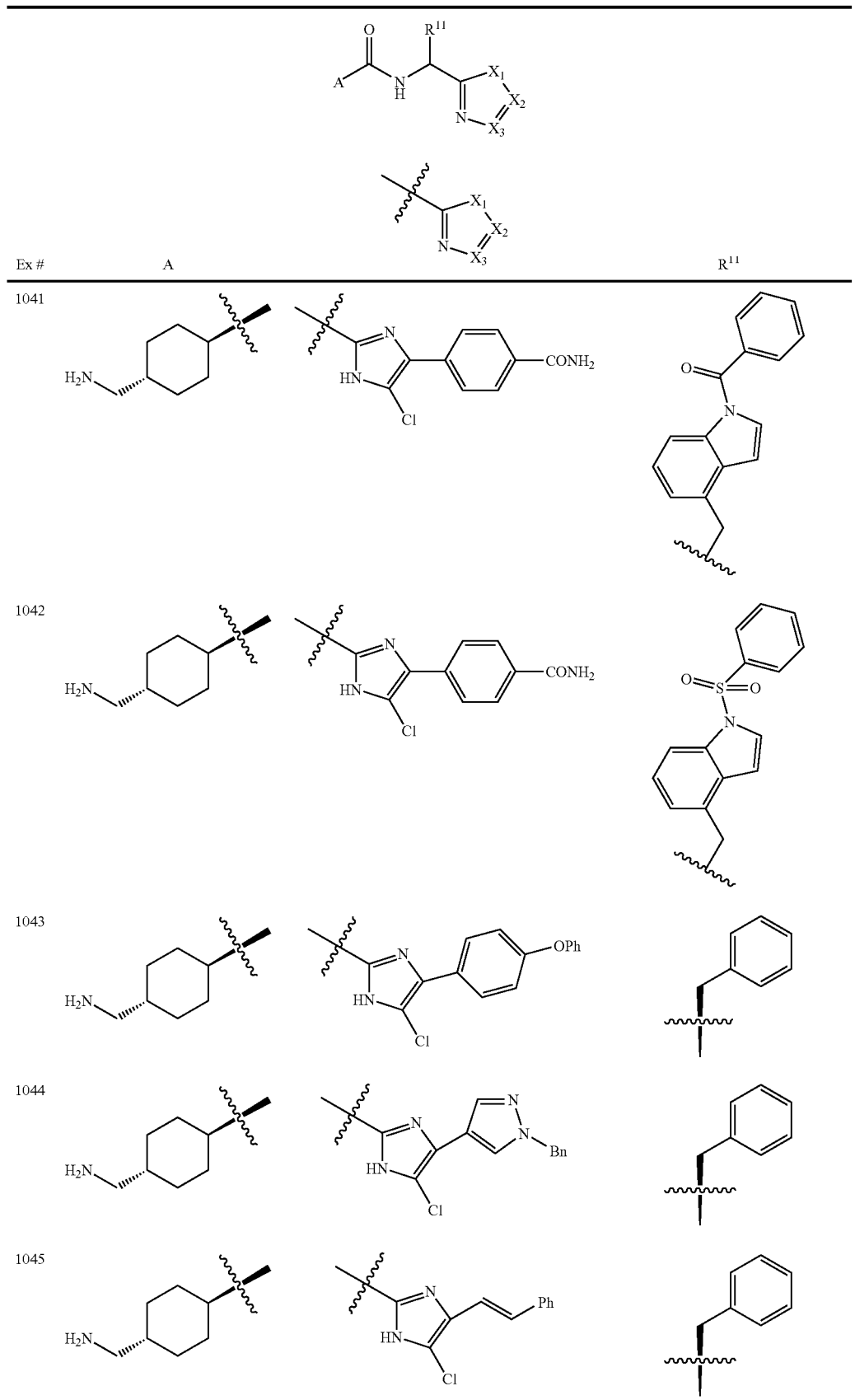

TABLE 7-continued
| Ex # | A | | R[11] |
|---|---|---|---|
| 1046 | 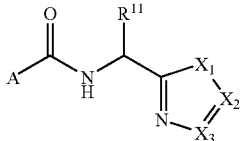 | 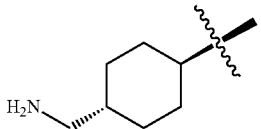 | 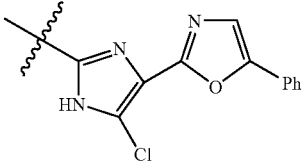 |
| 1047 | 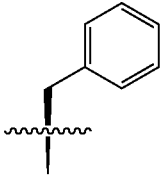 | 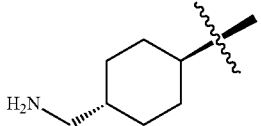 | 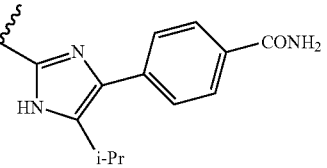 |
| 1048 | 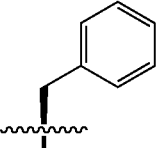 | 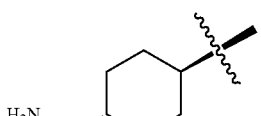 | 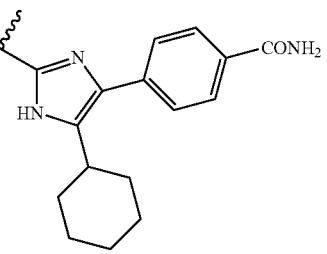 |
| 1049 | 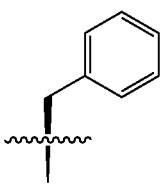 | 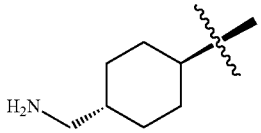 | 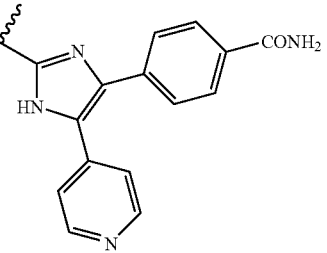 |
| 1050 | 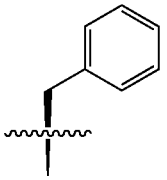 | 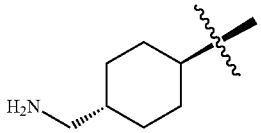 | 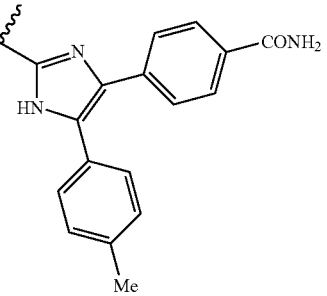 |

TABLE 7-continued
| Ex # | A | | R[11] |
|---|---|---|---|
| 1051 | 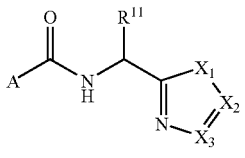 | 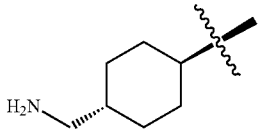 | 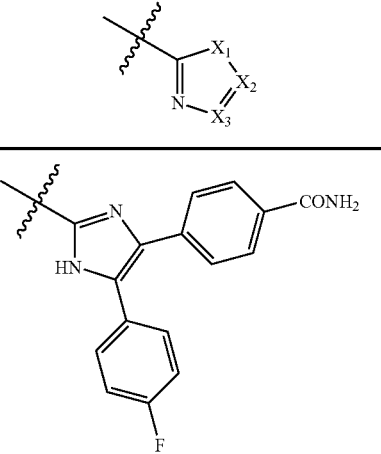 |
| 1052 | 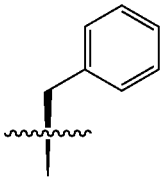 | 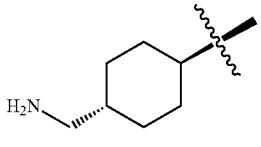 | 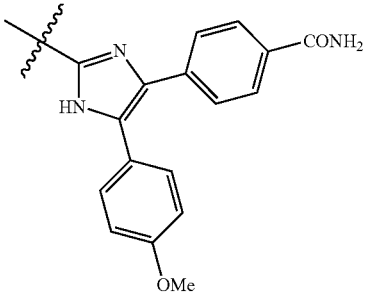 |
| 1053 | 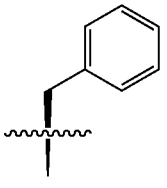 | 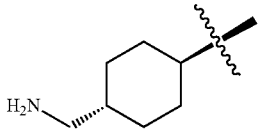 | 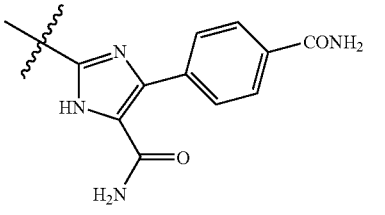 |
| 1054 | 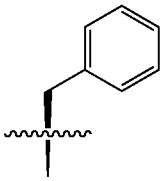 | 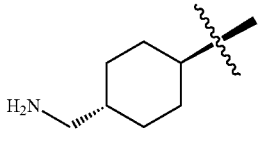 | 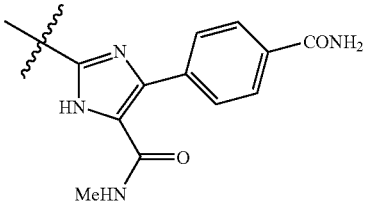 |
| 1055 | 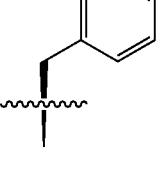 | 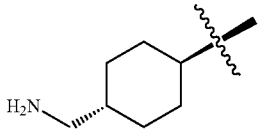 | 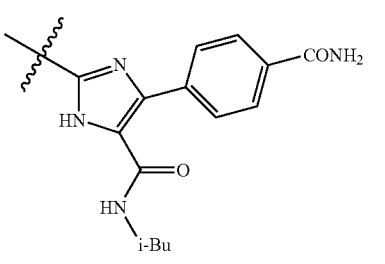 |

TABLE 7-continued
| Ex # | A | | R[11] |
|------|---|---|-------|
| 1056 | 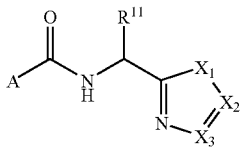 | 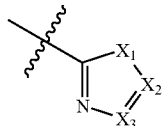 | 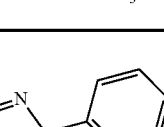 |
| 1057 | 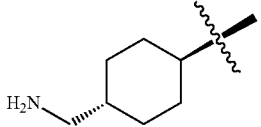 | 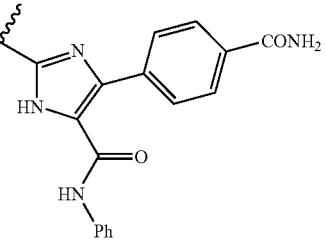 | 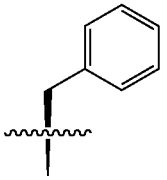 |
| 1058 | 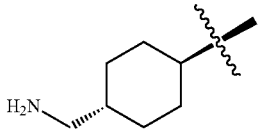 | 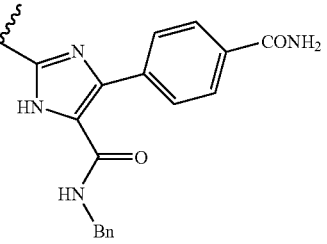 | 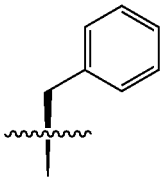 |
| 1059 | 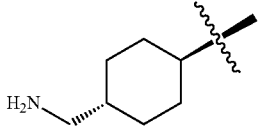 | 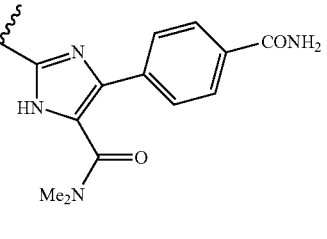 | 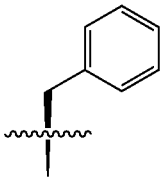 |
| 1060 | 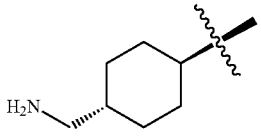 | 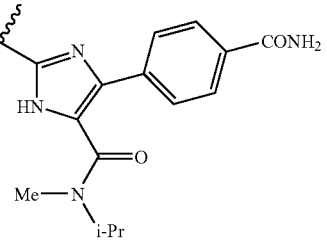 | 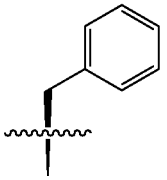 |

TABLE 7-continued
| Ex # | A | | R11 |
|---|---|---|---|
| 1061 | 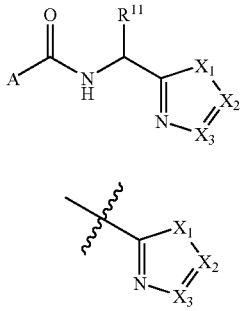 | 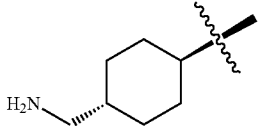 | 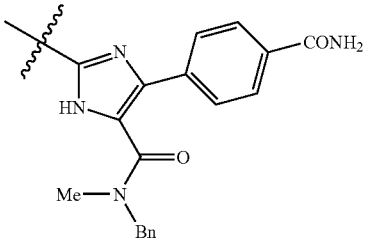 |
| 1062 | 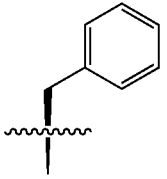 | 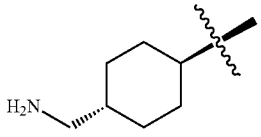 | 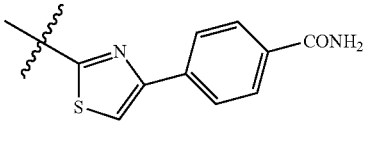 |
| 1063 | 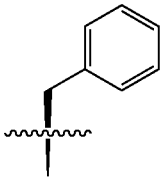 | 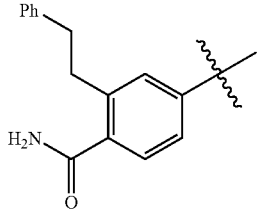 | 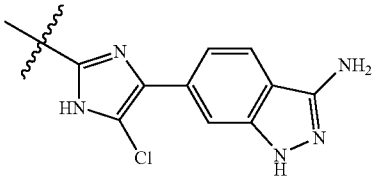 |
| 1064 | 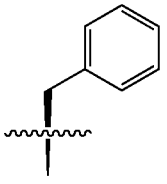 | 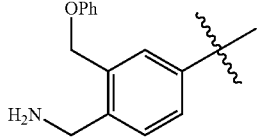 | 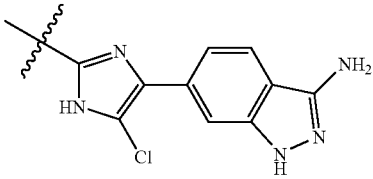 |
| 1065 | 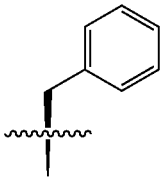 | 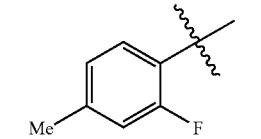 | 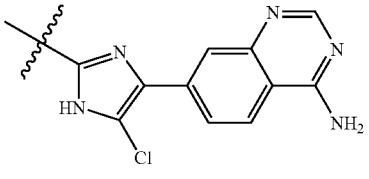 |

TABLE 7-continued
| Ex # | A | | R11 |
|---|---|---|---|
| 1066 | 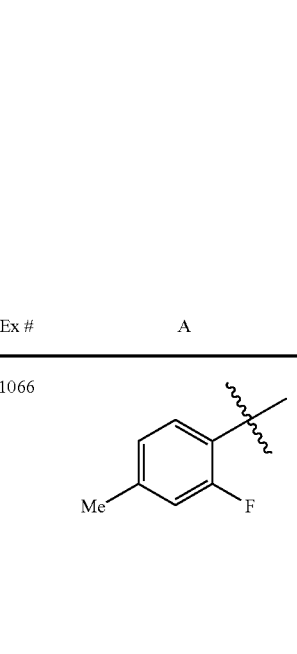 | 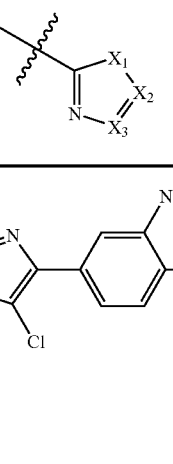 | 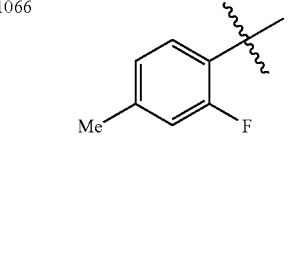 |
| 1067 | 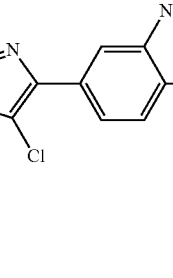 | 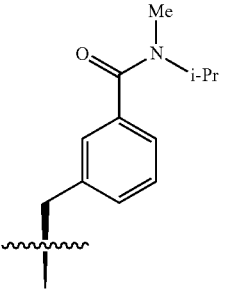 | 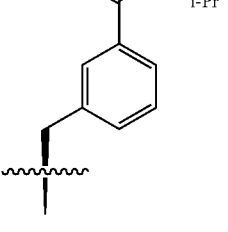 |
| 1068 | 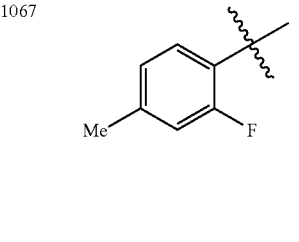 | 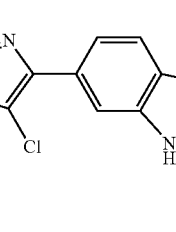 | 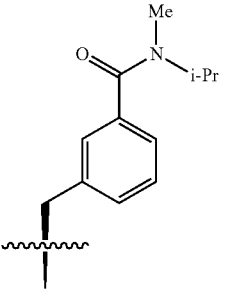 |
| 1069 | 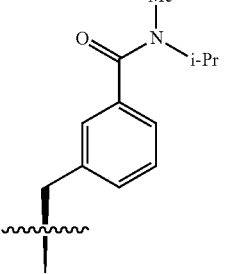 | 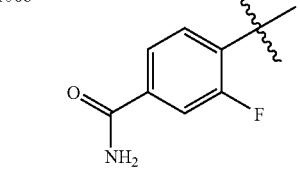 | 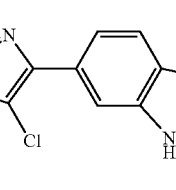 |

TABLE 7-continued

| Ex # | A | | R[11] |
|---|---|---|---|
| 1070 | trans-4-(aminomethyl)cyclohexyl | 2-yl-5-chloro-4-(3-amino-1H-indazol-6-yl)-1H-imidazole | 3-[N-methyl-N-cyclopropyl-carbamoyl]benzyl |
| 1071 | trans-4-(aminomethyl)cyclohexyl | 2-yl-5-chloro-4-(4-carbamoylphenyl)-1H-imidazole | 3-[N-methyl-N-cyclopropyl-carbamoyl]benzyl |
| 1072 | 1-amino-5,6,7,8-tetrahydroisoquinolin-6-yl | 2-yl-5-chloro-4-(4-carbamoylphenyl)-1H-imidazole | 3-[N-methyl-N-isopropyl-carbamoyl]benzyl |
| 1073 | 1-amino-5,6,7,8-tetrahydroisoquinolin-6-yl | 2-yl-5-chloro-4-(4-aminoquinazolin-7-yl)-1H-imidazole | 3-[N-methyl-N-isopropyl-carbamoyl]benzyl |

TABLE 7-continued

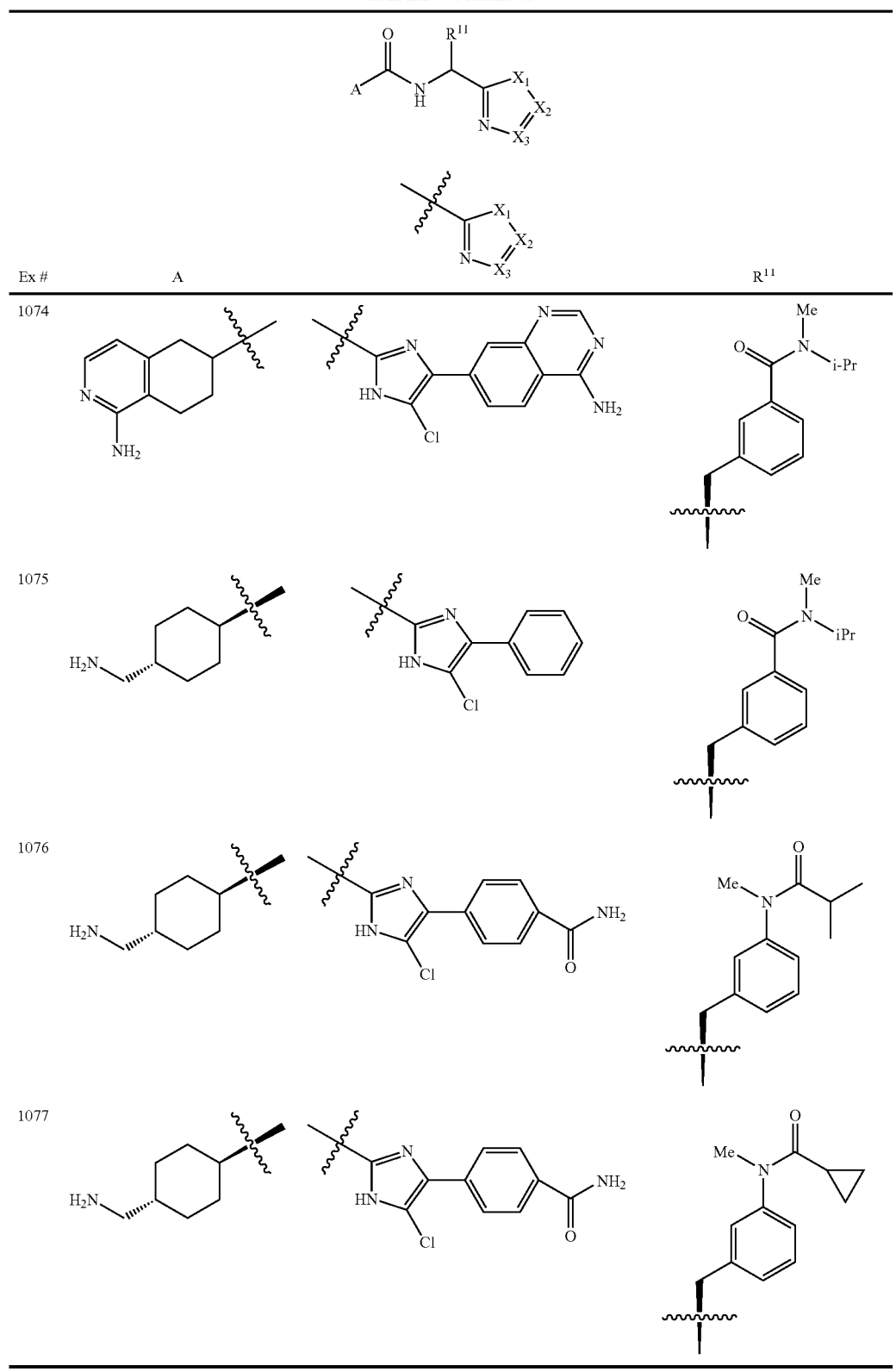

UTILITY

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory distress syndrome, hereditary angioedema or other inherited or acquired deficiencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, preferred compounds of the present invention, such as the particular compounds disclosed in the above examples, have been identified to be active and exhibit $K_i$'s of equal to or less than 15 µM in the Factor XIa assay, thereby demonstrating the utility of the compounds of the present invention as especially effective inhibitors of coagulation Factor XIa. More preferred compounds have $K_i$'s of equal to or less than 5 µM, preferably equal to or less than 1 µM, more preferably equal to or less than 0.5 µM.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, compounds tested in the Factor VIIa assay are considered to be active if they exhibit a $K_i$ of equal to or less than 15 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, Compounds tested in the plasma kallikrein assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

In general, preferred compounds of the present invention have demonstrated $K_i$ values of equal to or less than 15 µM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s = I/(K_i(1+S/K_m)) \text{ for a competitive inhibitor with one binding site; or}$$

$$v_s/v_o = A+((B-A)/1+((IC_{50}/(I)^n))) \text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The effectiveness of compounds of the present invention as inhibitors of the coagulation factors XIa, VIa, IXa, Xa, or thrombin, can be determined using relevant in vivo thrombosis models, including In Vivo Electrically-induced Carotid Artery Thrombosis Models and In Vivo Rabbit Arteriovenous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d. c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin.

Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), aprotinin, synthetic pentasaccharide, direct acting thrombin inhibitors including hirudin and argatroban, as well as other factor VIa, VIIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/ glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat and aP2 inhibitors (such as those disclosed in WO00/ 59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIa, IXa, Xa, XIa, and/or plasma kallikrein. XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIa, IXa, Xa, XIa, and/or plasma kallikrein. For example, the presence of thrombin, Factor VIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:
1. A compound selected from:
   (S)-4-carbamimidoyl-N-(2-phenyl-1-(4-phenyl-1H-imidazol-2-yl)ethyl)benzamide,
   (S)-4-(aminomethyl)-N-(2-phenyl-1-(4-phenyl-1H-imidazol-2-yl)ethyl)-trans-cyclohexanecarboxamide,
   (S)-4-(aminomethyl)-N-{1-[4-(4-cyano-phenyl)-1H-imidazol-2-yl]-2-phenyl-ethyl}-trans-cyclohexanecarboxamide,

(S)-4-(aminomethyl)-N-{1-[4-(4-bromo-phenyl)-1H-imidazol-2-yl]-2-phenyl-ethyl}-trans-cyclohexanecarboxamide,
(S)-4-(aminomethyl)-N-{1-[4-(4-methoxy-phenyl)-1H-imidazol-2-yl]-2-phenyl-ethyl}-trans-cyclohexanecarboxamide,
(S)-4-(aminomethyl)-N-[2-(1-benzyl-1H-imidazol-4-yl)-1-(4-phenyl-1H-imidazol-2-yl)-ethyl]-trans-cyclohexanecarboxamide,
(S)-3-(2-{1-[trans-(4-Aminomethyl)-cyclohexanecarboxamido]-2-phenyl-ethyl}-1H-imidazol-4-yl)-benzoic acid methyl ester,
(S)-4-(aminomethyl)-N-{1-[4-(3-fluoro-phenyl)-1H-imidazol-2-yl]-2-phenyl-ethyl}-trans-cyclohexanecarboxamide,
(S)-4-(aminomethyl)-N-{1-[4-(3-bromo-phenyl)-1H-imidazol-2-yl]-2-phenyl-ethyl}-trans-cyclohexanecarboxamide,
(S)-4-(aminomethyl)-N-[2-(3-chlorophenyl)-1-(4-phenyl-1H-imidazol-2-yl)ethyl]-trans-cyclohexanecarboxamide,
(S)-4-(aminomethyl)-N-[2-(4-chlorophenyl)-1-(4-phenyl-1H-imidazol-2-yl)ethyl]-trans-cyclohexanecarboxamide,
(S)-4-(aminomethyl)-N-[1-(4-phenyl-1H-imidazol-2-yl)-2-(2-pyridyl)ethyl]-trans-cyclohexanecarboxamide,
(S)-[4-(2-{1-[trans-(4-aminomethyl)-cyclohexanecarboxamido]-2-phenyl-ethyl}-1H-imidazol-4-yl)-phenyl]acetic acid,
(S)-4-(aminomethyl)-N-{1-[(4-carbamoylmethyl-phenyl)-1H-imidazol-2-yl]-2-phenyl-ethyl}-trans-cyclohexanecarboxamide,
(S)-[4-(2-{1-[(4-aminomethyl)-cyclohexanecarboxamido]-2-phenyl-ethyl}-1H-imidazol-4-yl)]-benzamide,
(S)-[3-(2-{1-[(4-aminomethyl)-cyclohexanecarboxamido]-2-phenyl-ethyl}-1H-imidazol-4-yl)]-benzamide,
(S)-4-(2-(1-trans-(4-aminomethyl)-cyclohexanecarboxamido)-2-phenylethyl)-1H-imidazol-4-yl)-N,N-dimethylbenzamide,
(S)-2-(1-trans-(4-aminomethyl)-cyclohexanecarboxamido)-2-phenylethyl)-1H-benzo[d]imidazole-5-carboxamide,
N-(4-carbamimidoylphenyl)-3-phenyl-2-(4-phenyl-1H-imidazol-2-yl)propanamide,
4-(2-(1-(4-carbamimidoylphenylamino)-1-oxo-3-phenyl-propan-2-yl)-1H-imidazol-4-yl)benzamide,
4-(2-(1-(1-aminoisoquinolin-6-ylamino)-1-oxo-3-phenyl-propan-2-yl)-1H-imidazol-4-yl)benzamide,
4-(2-(4-(4-carbamimidoylphenyl)-1H-imidazol-2-yl)-3-phenylpropanamido)benzamide,
(S)-4-(aminomethyl)-N-{1-[4-(2,4-difluoro-phenyl)-1H-imidazol-2-yl]-2-phenyl-ethyl}-trans-cyclohexanecarboxamide,
(S)-4-(aminomethyl)-N-{1-[4-(4-fluoro-phenyl)-1H-imidazol-2-yl]-2-phenyl-ethyl}-trans-cyclohexanecarboxamide,
(S)-3-(2-(1-trans-(4-aminomethyl)-cyclohexanecarboxamido)-2-phenylethyl)-1H-imidazol-4-yl)-benzoic acid,
4-[2-[1-[4-[4-(carbamimidoylphenyl]-1H-imidazol-2-yl]-2-phenylethyl]-1H-imidazol-4-yl]-benzamide,
(S)-4-(aminomethyl)-N-[1-(4-phenyl-1H-imidazol-2-yl)-2-(4-pyridinyl)ethyl]-trans-cyclohexanecarboxamide,
(S)-4-[2-[1-[4-(aminomethyl)cyclohexanecarboxamido] amino]-2-phenylethyl]-4-(bromo-1H-imidazol-5-yl)-benzamide,
(S)-3-[2-[1-[4-(aminomethyl)cyclohexanecarboxamido]-2-phenylethyl]-1H-imidazol-4-yl]-phenylacetic acid,
(S)-3-[2-[1-[4-(aminomethyl)cyclohexanecarboxamido]-2-phenylethyl]-1H-imidazol-4-yl]-phenylacetamide,
(S)-4-(aminomethyl)-N-[1-[4-(3-hydroxyphenyl)-1H-imidazol-2-yl]-2-phenylethyl]-trans-cyclohexanecarboxamide,
(S)-3-[2-[1-[4-(aminomethyl)cyclohexanecarboxamido]-2-phenylethyl]-1H-imidazol-4-yl]-phenylacetic acid, ethyl ester,
2-[4-(4-carbamimidoyl-phenyl)-1H-imidazol-2-yl]-3,N-diphenyl-propionamide,
(S)-4-(aminomethyl)-N-[2-(4-fluorophenyl)-1-(4-phenyl-1H-imidazol-2-yl)ethyl]-trans-cyclohexanecarboxamide,
(S)-4-(aminomethyl)-N-[2-[4-(benzyloxy)phenyl]-1-(4-phenyl-1H-imidazol-2-yl)ethyl]-trans-cyclohexanecarboxamide,
(S)-4-(aminomethyl)-N-[2-(4-benzoylphenyl)-1-(4-phenyl-1H-imidazol-2-yl)ethyl]-trans-cyclohexanecarboxamide,
(S)-4-(aminomethyl)-N-[1-(4-phenyl-1H-imidazol-2-yl)-2-[3-(trifluoromethyl)phenyl]ethyl]-trans-cyclohexanecarboxamide,
(S)-4-(aminomethyl)-N-[-2-(3-nitrophenyl)-1-(4-phenyl-1H-imidazol-2-yl)ethyl]-trans-cyclohexanecarboxamide,
(S)-4-(aminomethyl)-N-[2-(2-chlorophenyl)-1-(4-phenyl-1H-imidazol-2-yl)ethyl]-trans-cyclohexanecarboxamide,
(S)-4-(aminomethyl)-N-[2-(1-naphthalenyl)-1-(4-phenyl-1H-imidazol-2-yl)ethyl]-trans-cyclohexanecarboxamide,
(S)-4-(aminomethyl)-N-[2-(2-naphthalenyl)-1-(4-phenyl-1H-imidazol-2-yl)ethyl]-trans-cyclohexanecarboxamide,
(S)-4-[2-[(1-[4-(aminomethyl)cyclohexanecarboxamido]-2-phenylethyl]-4-(trifluoromethyl)-1H-imidazol-5-yl]-benzamide,
(S)-N-[1-[4-[4-(carbamimidoyl)phenyl]-1H-imidazol-2-yl]-2-phenylethyl]-benzamide,
(S)-4-(aminomethyl)-N-[2-(2-bromophenyl)-1-(4-phenyl-1H-imidazol-2-yl)ethyl]-trans-cyclohexanecarboxamide,
(S)-5-[4-(carbamoylphenyl]-2-[1-[4-(aminomethyl)cyclohexanecarboxamido]-2-phenylethyl]-1H-imidazole-4-carboxylic acid, methyl ester,
4-[2-[1-[4-(aminomethyl)cyclohexanecarboxamido]-2-[2-(trifluoromethoxy)phenyl]ethyl]-1H-imidazol-4-yl]-benzamide,
4-[2-[1-[4-(aminomethyl)cyclohexanecarboxamido]-2-[2-(difluoromethoxy)phenyl]ethyl]-1H-imidazol-4-yl]-benzamide,
(S)-N-[1-[4-[4-(carbamoyl)phenyl]-1H-imidazol-2-yl]-2-phenylethyl]-4-(aminomethyl)-benzamide,
(S)-N-[1-[4-[4-(carbamoyl)phenyl]-1H-imidazol-2-yl]-2-phenylethyl]-4-(aminomethyl)-2-fluoro-benzamide,
(S)-N-[1-[4-(3-amino-1H-indazol-6-yl)-5-chloro-1H-imidazol-2-yl]-2-phenylethyl]-4-(aminomethyl)-benzamide,
(S)-N-[1-[4-(3-amino-1H-indazol-6-yl)-5-chloro-1H-imidazol-2-yl]-2-phenylethyl]-4-(aminomethyl)-2-fluoro-benzamide,
(S)-N-[1-[4-[4-(carbamimidoyl)phenyl]-1-(2-phenyl-ethyl)-1H-imidazol-2-yl]-2-phenylethyl]-benzamide,
(S)-N-[1-[4-[4-(carbamimidoyl)phenyl]-1-methyl-1H-imidazol-2-yl]-2-phenylethyl]-benzamide, (S)-N-[1-[4-(3-amino-1H-indazol-6-yl)-5-chloro-1H-imidazol-2-yl]-2-phenylethyl]-2-fluoro-5-methoxy-benzamide,
(S)-4-[2-[1-[4-(aminomethyl)cyclohexanecarboxamido]-2-phenylethyl]-4-chloro-1H-imidazol-5-yl]-benzamide,
(S)-N-[1-[4-(3-amino-1H-indazol-6-yl)-5-chloro-1H-imidazol-2-yl]-2-phenylethyl]-1,4-benzenedicarboxamide,
4-[2-[1-[4-(aminomethyl)cyclohexanecarboxamido]-2-[3-(difluoromethoxy)phenyl]ethyl]-1H-imidazol-4-yl-]benzamide,
(S)-4-[2-[1-[4-(aminomethyl)cyclohexanecarboxamido]-2-phenylethyl]-4-phenyl-1H-imidazol-5-yl]-benzamide,
N-[1-[4-(3-amino-1H-indazol-6-yl)-1H-imidazol-2-yl]-2-[(2S)-2-methyl-2-(2-phenylethyl)-1,3-benzodioxol-4-yl]ethyl]-4-(aminomethyl)-trans-cyclohexanecarboxamide,
N-[1-[4-(3-amino-1H-indazol-6-yl)-1H-imidazol-2-yl]-2-[(2R)-2-methyl-2-(2-phenylethyl)-1,3-benzodioxol-4-yl]ethyl]-4-(aminomethyl)-trans-cyclohexanecarboxamide,
N-[2-[(2S)-2-[4-(3-amino-1H-indazol-6-yl)-1H-imidazol-2-yl]-2-trans-4-(aminomethyl)cyclohexanecarboxamdno]ethyl]phenyl]-benzamide,
(R)-N-[1-[4-(3-amino-1H-indazol-6-yl)-1H-imidazol-2-yl]-2-(phenylmethoxy)ethyl]-4-(aminomethyl)-trans-cyclohexanecarboxamide,
(R)-N-[1-[4-(3-amino-1H-indazol-6-yl)-1H-imidazol-2-yl]-2-[(phenylmethyl)thio]ethyl]-4-(aminomethyl)-trans-cyclohexanecarboxamide,
3-[2-[4-[4-(aminocarbonyl)phenyl]-1H-imidazol-2-yl]-2-trans-4-(aminomethyl)cyclohexanecarboxamido]ethyl]-benzoic acid, methyl ester,
(S)-3-amino-N-[1-[4-[4-(carbamimidoyl)phenyl]-1H-imidazol-2-yl]-2-phenylethyl]-1H-indazole-5-carboxamide,
3-[2-[4-[4-(aminocarbonyl)phenyl]-1H-imidazol-2-yl]-2-trans-4-(aminomethyl)cyclohexanecarboxamido]ethyl]-benzoic acid,
(S)-N-{1-[4-(4-carbamimidoyl-phenyl)-1-ethyl-1H-imidazol-2-yl]-2-phenyl-ethyl}-benzamide,
$N^1$-{(S)-1-[4-(3-amino-1H-indazol-6-yl)-5-chloro-1H-imidazol-2-yl]-2-phenyl-ethyl}-2-fluoro-terephthalamide,
$N^1$-{(S)-1-[4-(4-amino-quinazolin-7-yl)-5-chloro-1H-imidazol-2-yl]-2-phenyl-ethyl}-2-fluoro-terephthalamide,
4-(2-{1-[(4-aminomethyl-trans-cyclohexanecarboamido]-2-[3-(piperidine-1-carbonyl)-phenyl]-ethyl}-1H-imidazol-4-yl)-benzamide,
4-(2-{1-[(4-aminomethyl-trans-cyclohexanecarboamido]-2-[3-(o-tolylcarbamoyl)-phenyl-ethyl}-1H-imidazol-4-yl)-benzamide,
4-(2-{1-[(4-aminomethyl-trans-cyclohexanecarboamido]-2-[3-(methyl-phenyl-carbamoyl)-phenyl]-ethyl}-1H-imidazol-4-yl)-benzamide,
4-(2-{1-[(4-aminomethyl-trans-cyclohexanecarboamido]-2-[3-(benzylcarbamoyl)-phenyl]-ethyl}-1H-imidazol-4-yl)-benzamide,
(S) 4-aminomethyl-N-[1-(4-biphenyl-4-yl-1H-imidazol-2-yl)-2-phenyl-ethyl]-trans-cyclohexanecarboxamide,
(S)-4-aminomethyl-N-[1-(4-naphthalen-2-yl-1H-imidazol-2-yl)-2-phenyl-ethyl]-trans-cyclohexanecarboxamide,
$N^4$-{(S)-1-[4-(3-amino-1H-indazol-6-yl)-5-chloro-1H-imidazol-2-yl]-2-phenyl-ethyl}-2-methoxy-terephthalamide,
(S)-4-aminomethyl-N-{1-[4-(3-amino-phenyl)-1H-imidazol-2-yl]-2-phenyl-ethyl}-cyclohexanecarboxamide,
4-(2-{1-[(4-aminomethyl-trans-cyclohexanecarboamido]-2-[3-isobutyl-carbamoyl-phenyl]-ethyl}-1H-imidazol-4-yl)-benzamide,
4-(2-{1-[(4-aminomethyl-trans-cyclohexanecarboamido]-2-[3-(3-methyl-butylcarbamoyl)-phenyl]-ethyl}-1H-imidazol-4-yl)-benzamide,
4-(2-{1-[(4-aminomethyl-trans-cyclohexanecarboamido]-2-[3-tert-butylcarbamoyl-phenyl]-ethyl}-1H-imidazol-4-yl)-benzamide,
4-(2-{1-[(4-aminomethyl-trans-cyclohexanecarboamido]-2-[3-(4-chloro-benzylcarbamoyl)-phenyl]-ethyl}-1H-imidazol-4-yl)-benzamide,
4-(2-{1-[(4-aminomethyl-trans-cyclohexanecarboamido]-2-[3-(4-methoxy-benzylcarbamoyl)-phenyl]-ethyl}-1H-imidazol-4-yl)-benzamide,
4-(2-{1-[(4-aminomethyl-trans-cyclohexanecarboamido]-2-[3-phenethylcarbamoyl-phenyl]-ethyl}-1H-imidazol-4-yl)-benzamide,
4-(2-{1-[(4-aminomethyl-trans-cyclohexanecarboamido]-2-[3-[2-(4-chloro-phenyl)-ethylcarbamoyl]-phenyl]-ethyl}-1H-imidazol-4-yl)-benzamide,
4-(2-{1-[(4-aminomethyl-trans-cyclohexanecarboamido]-2-[3-[2-(4-methoxy-phenyl)-ethylcarbamoyl]-phenyl]-ethyl}-1H-imidazol-4-yl)-benzamide,
4-(2-{1-[(4-aminomethyl-trans-cyclohexanecarboamido]-2-[3-(3-phenyl-propylcarbamoyl)-phenyl]-ethyl}-1H-imidazol-4-yl)-benzamide,
4-(2-{1-[(4-aminomethyl-trans-cyclohexanecarboamido]-2-[3-(benzyl-methyl-carbamoyl)-phenyl]-ethyl}-1H-imidazol-4-yl)-benzamide,
4-(2-{1-[(4-aminomethyl-trans-cyclohexanecarboamido]-2-[3-(methyl-phenethyl-carbamoyl)-phenyl]-ethyl}-1H-imidazol-4-yl)-benzamide,
4-(2-{1-[(4-aminomethyl-trans-cyclohexanecarboamido]-2-[3-m-tolyl-carbamoyl-phenyl]-ethyl}-1H-imidazol-4-yl)-benzamide,
4-(2-{1-[(4-aminomethyl-trans-cyclohexanecarboamido]-2-[3-p-tolyl-carbamoyl-phenyl]-ethyl}-1H-imidazol-4-yl)-benzamide,
4-(2-{1-[(4-aminomethyl-trans-cyclohexanecarboamido]-2-[3-(4-fluoro-phenylcarbamoyl)-phenyl]-ethyl}-1H-imidazol-4-yl)-benzamide,
4-(2-{1-[(4-aminomethyl-trans-cyclohexanecarboamido]-2-[3-(naphthalene-1-ylcarbamoyl)-phenyl]-ethyl}-1H-imidazol-4-yl)-benzamide,
4-(2-{1-[(4-aminomethyl-trans-cyclohexanecarboamido]-2-[3-(4-phenyl-piperidine-1-carbonyl)-phenyl]-ethyl}-1H-imidazol-4-yl)-benzamide,
4-(2-{1-[(4-aminomethyl-trans-cyclohexanecarboamido]-2-[3-(3,4-dihydro-1H-isoquinoline-2-carbonyl)-phenyl]-ethyl}-1H-imidazol-4-yl)-benzamide,
(S)-N-{1-[4-(4-benzyloxy-phenyl)-1H-imidazol-2-yl]-2-phenyl-ethyl}-4-aminomethyl-trans-cyclohexanecarboxamide,
4-(2-{(S)-1-[(4-aminomethyl-trans-cyclohexanecarbonyl)-amino]-2-phenyl-ethyl}-5-bromo-1H-imidazol-4-yl)-2-fluoro-benzamide,
4-(2-{(S)-1-[(4-aminomethyl-trans-cyclohexanecarbonyl)-amino]-2-phenyl-ethyl}-5-chloro-1H-imidazol-4-yl)-2-fluoro-benzamide, (S)-N-[1-(5-methyl-4-phenyl-1H-imidazol-2-yl)-2-phenyl-ethyl]-4-aminomethyl-trans-cyclohexanecarboxamide,
4-(2-{(S)-1-[(4-aminomethyl-trans-cyclohexanecarbonyl)-amino]-2-phenyl-ethyl}-5-methyl-1H-imidazol-4-yl)-benzamide,
1-amino-N-{(S)-1-[4-(4-carbamoyl-phenyl)-5-chloro-1H-imidazol-2-yl]-2-phenyl-ethyl}-5,6,7,8-tetrahydro-isoquinoline-6-carboxylic acid,
4-aminomethyl-N-{(S)-1-[4-(3-chloro-phenyl)-5-methyl-1H-imidazol-2-yl]-2-phenyl-ethyl}-trans-cyclohexanecarboxamide,
$N^4$-{(S)-1-[4-(3-amino-1H-indazol-6-yl)-5-chloro-1H-imidazol-2-yl]-2-phenyl-ethyl}-2-phenoxymethyl-terephthalamide,
N-{(S)-1-[4-(3-amino-1H-indazol-6-yl)-5-chloro-1H-imidazol-2-yl]-2-phenyl-ethyl}-4-aminomethyl-2-benzyl-benzamide,
N-{(S)-1-[4-(3-amino-1H-indazol-6-yl)-5-chloro-1H-imidazol-2-yl]-2-phenyl-ethyl}-4-methyl-benzamide,
4-(2-{(S)-2-(3-acetylamino-phenyl)-1-[(4-aminomethyl-cyclohexanecarboxamido]-ethyl}-5-chloro-1H-imidazol-4-yl)-benzamide,
4-aminomethyl-N-{(S)-1-[5-(3-amino-1H-indazol-6-yl)-1H-imidazol-2-yl]-3-[(5-methyl-pyrazin-2-ylmethyl)-carbamoyl]-propyl}-cyclohexanecarboxamide,
4-aminomethyl-N-[(S)-1-[5-(3-amino-1H-indazol-6-yl)-1H-imidazol-2-yl]-3-(benzyl-methyl-carbamoyl)-propyl]-cyclohexanecarboxamide,
4-aminomethyl-N-[(S)-1-[5-(3-amino-1H-indazol-6-yl)-1H-imidazol-2-yl]-3-(benzyl-carbamoyl)-propyl]-cyclohexanecarboxamide,
4-(2-{1-[(4-aminomethyl-cyclohexanecarboxamido]-2-[3-(ethyl-methyl-carbamoyl)-phenyl]-ethyl}-5-chloro-1H-imidazol-4-yl)-benzamide,
4-(2-{1-[(4-aminomethyl-cyclohexanecarboxamido]-2-[3-(isopropyl-methyl-carbamoyl)-phenyl]-ethyl}-5-chloro-1H-imidazol-4-yl)-benzamide,
4-(2-{1-[(4-aminomethyl-cyclohexanecarboxamido]-2-[3-(isobutyl-methyl-carbamoyl)-phenyl]-ethyl}-5-chloro-1H-imidazol-4-yl)-benzamide,
4-(2-{1-[(4-aminomethyl-cyclohexanecarboxamido]-2-[3-(methyl-phenyl-carbamoyl)-phenyl]-ethyl}-5-chloro-1H-imidazol-4-yl)-benzamide,
4-(2-{1-[(4-aminomethyl-cyclohexanecarboxamido]-2-[3-(ethyl-phenyl-carbamoyl)-phenyl]-ethyl}-5-chloro-1H-imidazol-4-yl)-benzamide,
4-(2-{1-[(4-aminomethyl-cyclohexanecarboxamido]-2-[3-(methyl-m-toluoyl-carbamoyl)-phenyl]-ethyl}-5-chloro-1H-imidazol-4-yl)-benzamide,
4-(2-{1-[(4-aminomethyl-cyclohexanecarboxamido]-2-[3-(methyl-p-toluoyl-carbamoyl)-phenyl]-ethyl}-5-chloro-1H-imidazol-4-yl)-benzamide,
4-[2-(1-[(4-aminomethyl-cyclohexanecarboxamido]-2-{3-[(3-chloro-benzyl)-methyl-carbamoyl]-phenyl}-ethyl)-5-chloro-1H-imidazol-4-yl]-benzamide,
4-[2-(1-[(4-aminomethyl-cyclohexanecarboxamido]-2-{3-[4(4-chloro-benzyl)-methyl-carbamoyl]-phenyl}-ethyl)-5-chloro-1H-imidazol-4-yl]-benzamide,
4-[2-(1-[(4-aminomethyl-cyclohexanecarboxamido]-2-{3-[2-(2-chloro-phenyl)ethylcarbamoyl]-phenyl}-ethyl)-5-chloro-1H-imidazol-4-yl]-benzamide,
4-[2-(1-[(4-aminomethyl-cyclohexanecarboxamido]-2-{3-[2-(3-chloro-phenyl)ethylcarbamoyl]-phenyl}-ethyl)-5-chloro-1H-imidazol-4-yl]-benzamide,
4-[2-(1-[(4-aminomethyl-cyclohexanecarboxamido]-2-{3-[2-(4-chloro-phenyl)ethylcarbamoyl]-phenyl}-ethyl)-5-chloro-1H-imidazol-4-yl]-benzamide,
4-aminomethyl-N-{(S)-1-[4-(4-methanesulfonylamino-phenyl)-5-methyl-1H-imidazol-2-yl]-2-phenyl-ethyl}-trans-cyclohexanecarboxamide,
4-aminomethyl-N-[(S)-1-[5-(3-amino-1H-indazol-6-yl)-1H-imidazol-2-yl]-3-(cyclopropylmethyl-carbamoyl)-propyl]-trans-cyclohexanecarboxamide,
4-aminomethyl-N-[(S)-1-[5-(3-amino-1H-indazol-6-yl)-1H-imidazol-2-yl]-3-(2-(phenyl)ethyl-carbamoyl)-propyl]-trans-cyclohexanecarboxamide,
4-aminomethyl-N-{(S)-1-[4-(4-acetylamino-phenyl)-5-methyl-1H-imidazol-2-yl]-2-phenyl-ethyl}-trans-cyclohexanecarboxamide,
4-aminomethyl-N-{(S)-1-[4-(4-hydroxy-phenyl)-5-methyl-1H-imidazol-2-yl]-2-phenyl-ethyl}-trans-cyclohexanecarboxamide,
4-[2-(1-[(4-aminomethyl-cyclohexanecarboxamido]-2-{3-[methyl-(2-pyridin-2-yl-ethyl)-carbamoyl]-phenyl}-ethyl)-5-chloro-1H-imidazol-4-yl]-benzamide,
4-(2-{1-[(4-aminomethyl-cyclohexanecarboxamido]-2-[3-(2,3-dihydro-indole-1-carbonyl)-phenyl]-ethyl}-5-chloro-1H-imidazol-4-yl)-benzamide,
4-(2-{1-[(4-aminomethyl-cyclohexanecarboxamido]-2-[3-(1,3-dihydro-isoindole-2-carbonyl)-phenyl]-ethyl}-5-chloro-1H-imidazol-4-yl)-benzamide,
4-(2-{1-[(4-aminomethyl-cyclohexanecarboxamido]-2-[3-(2,3-dihydro-1,4-benzoxazine-4-carbonyl)-phenyl]-ethyl}-5-chloro-1H-imidazol-4-yl)-benzamide,
4-(2-{1-[(4-aminomethyl-cyclohexanecarboxamido]-2-[3-(6-methyl-3,4-dihydro-2H-quinoline-1-carbonyl)-phenyl]-ethyl}-5-chloro-1H-imidazol-4-yl)-benzamide,
4-aminomethyl-N-{1-[4-(3-acetylamino-phenyl)-5-methyl-1H-imidazol-2-yl]-2-phenyl-ethyl}-trans-cyclohexanecarboxamide,
N1-{1-[4-(3-amino-1H-indazol-6-yl)-5-chloro-1H-imidazol-2-yl]-2-phenyl-ethyl}-2-chloro-terephthalamide,
4-aminomethyl-N-{1-[4-(3-amino-1H-indazol-6-yl)-5-chloro-1H-imidazol-2-yl]-3-[(thiazol-2-ylmethyl)-carbamoyl]-propyl}-trans-cyclohexanecarboxamide,
4-aminomethyl-N-{1-[4-(3-amino-1H-indazol-6-yl)-5-chloro-1H-imidazol-2-yl]-3-[(pyridin-2-ylmethyl)-carbamoyl]-propyl}-trans-cyclohexanecarboxamide,
[4-(2-{1-[trans-4-aminomethyl-cyclohexanecarboxamido]-2-phenyl-ethyl}-5-methyl-1H-imidazol-4-yl)-phenyl]-carbamic acid methyl ester,
4-(2-{1-[trans-4-aminomethyl-cyclohexanecarboxamido]-2-[3-(methyl-phenyl-sulfamoyl)-phenyl]-ethyl}-5-chloro-1H-imidazol-4-yl)-benzamide,
4-{2-[1-[trans-4-aminomethyl-cyclohexanecarboxamido]-2-(3-benzenesulfonyl-methyl-amino-phenyl)-ethyl]-5-chloro-1H-imidazol-4-yl}-benzamide,
4-(2-{1-[trans-4-aminomethyl-cyclohexanecarboxamido]-2-[3-(benzoyl-methyl-amino)-phenyl]-ethyl}-5-chloro-1H-imidazol-4-yl)-benzamide,
4-aminomethyl-N-(1-{5-methyl-4-[3-(2H-tetrazol-5-yl)-phenyl]-1H-imidazol-2-yl}-2-phenyl-ethyl)-trans-cyclohexanecarboxamide, and
N-{1-[4-(3-amino-1H-indazol-6-yl)-5-chloro-1H-imidazol-2-yl]-2-phenyl-ethyl}-2-fluoro-4-methyl-benzamide, or stereoisomers, tautomers, or pharmaceutically acceptable salts thereof.

2. A pharmaceutical composition, comprising: a pharmaceutically acceptable carrier and a therapeutically effective amount of a compound of claim 1.

* * * * *